(12) United States Patent
Laurent et al.

(10) Patent No.: US 10,752,615 B2
(45) Date of Patent: Aug. 25, 2020

(54) SPIROCYCLIC CONTAINING COMPOUNDS AND PHARMACEUTICAL USES THEREOF

(71) Applicant: GB005, Inc., San Diego, CA (US)

(72) Inventors: Alain Laurent, Lachine (CA); Stephen J. Morris, Beaconsfield (CA)

(73) Assignee: GB005, Inc., San Diego, CA (US)

( * ) Notice: Subject to any disclaimer, the term of this patent is extended or adjusted under 35 U.S.C. 154(b) by 0 days.

(21) Appl. No.: 16/326,082

(22) PCT Filed: Aug. 16, 2017

(86) PCT No.: PCT/CA2017/050970
§ 371 (c)(1),
(2) Date: Feb. 15, 2019

(87) PCT Pub. No.: WO2018/032104
PCT Pub. Date: Feb. 22, 2018

(65) Prior Publication Data
US 2019/0263790 A1    Aug. 29, 2019

(30) Foreign Application Priority Data

| Aug. 17, 2016 | (CA) | 2939286 |
| Feb. 27, 2017 | (CA) | 2959055 |
| May 2, 2017 | (CA) | 2965813 |

(51) Int. Cl.

| C07D 401/14 | (2006.01) |
|---|---|
| C07D 403/04 | (2006.01) |
| C07D 403/14 | (2006.01) |
| C07D 409/14 | (2006.01) |
| C07D 413/14 | (2006.01) |
| C07D 407/14 | (2006.01) |
| A61P 25/28 | (2006.01) |
| A61K 31/4184 | (2006.01) |
| A61K 31/422 | (2006.01) |
| A61K 31/427 | (2006.01) |
| A61K 31/437 | (2006.01) |
| A61K 31/4439 | (2006.01) |
| A61K 31/497 | (2006.01) |
| A61K 31/506 | (2006.01) |
| A61K 45/06 | (2006.01) |
| C07D 417/14 | (2006.01) |
| C07D 471/04 | (2006.01) |

(52) U.S. Cl.
CPC ........ *C07D 409/14* (2013.01); *A61K 31/4184* (2013.01); *A61K 31/422* (2013.01); *A61K 31/427* (2013.01); *A61K 31/437* (2013.01); *A61K 31/4439* (2013.01); *A61K 31/497* (2013.01); *A61K 31/506* (2013.01); *A61K 45/06* (2013.01); *A61P 25/28* (2018.01); *C07D 401/14* (2013.01); *C07D 403/04* (2013.01); *C07D 403/14* (2013.01); *C07D 413/14* (2013.01); *C07D 417/14* (2013.01); *C07D 471/04* (2013.01)

(58) Field of Classification Search
CPC .. C07D 401/14; C07D 403/04; C07D 403/14; C07D 409/14; C07D 413/14; C07D 417/14
See application file for complete search history.

(56) References Cited

FOREIGN PATENT DOCUMENTS

| WO | WO-2013/184766 A1 * | 12/2013 | ........... C07D 401/12 |
| WO | 2014/036016 A1 | 3/2014 | |
| WO | 2017/049401 A1 | 3/2017 | |

OTHER PUBLICATIONS

Golub et al., Science, vol. 286, Oct. 15, 1999, pp. 531-537. (Year: 1999).*

* cited by examiner

*Primary Examiner* — Laura L Stockton
(74) *Attorney, Agent, or Firm* — Seed IP Law Group LLP

(57) ABSTRACT

The present invention relates to a novel family of covalent kinases inhibitors, compounds of this class have been found to have inhibitory activity against members of the TEC kinase family, particularly ITK and/or TXK, BTK, TEC and/or combinations thereof. The present invention is directed to a compound of Formula I or pharmaceutically acceptable salt, solvate, solvates of salt, stereoisomer, tautomer, isotope, prodrug, complex or biologically active metabolite thereof, for use in therapy.

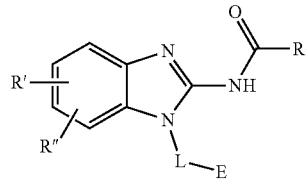

Formula I

13 Claims, 1 Drawing Sheet

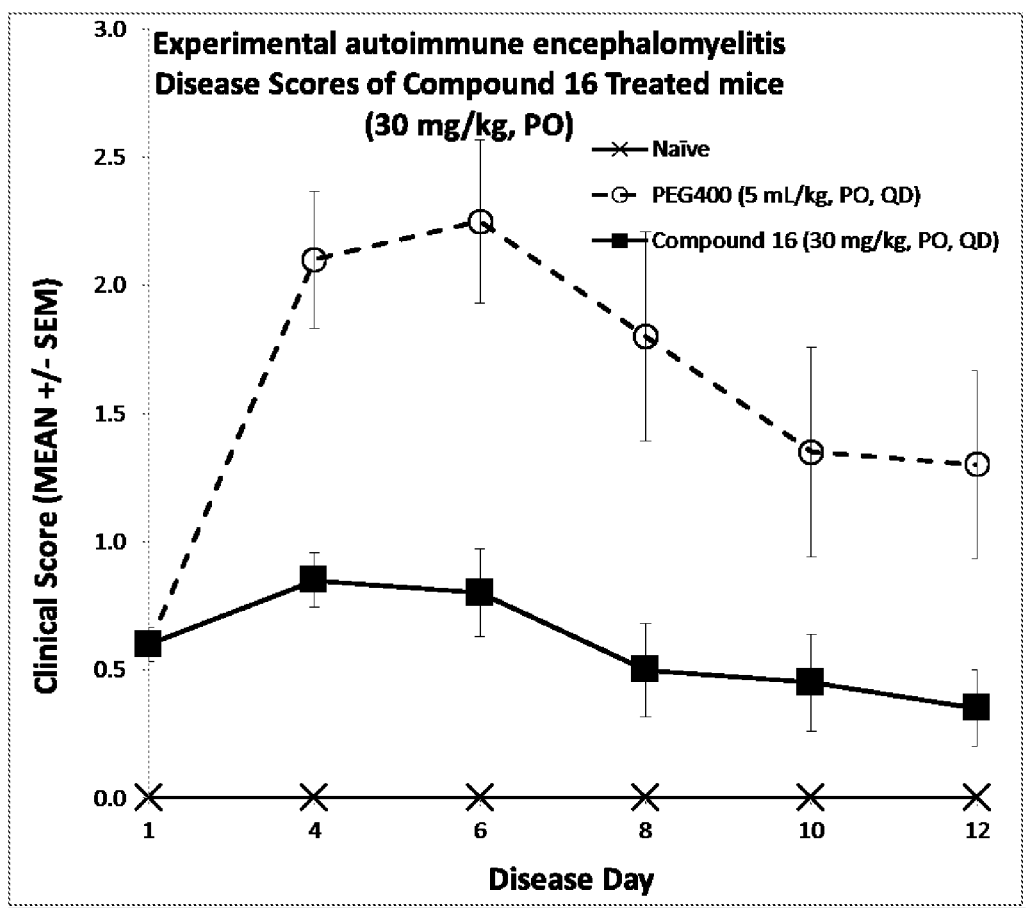

SPIROCYCLIC CONTAINING COMPOUNDS AND PHARMACEUTICAL USES THEREOF

FIELD OF INVENTION

The present invention relates to a novel family of protein kinase inhibitors, their pharmaceutically acceptable salts, to pharmacological compositions that contain them and to their use of the inhibitors to treat or prevent diseases, disorders and conditions associated with kinase function.

BACKGROUND OF THE INVENTION

Protein kinases are a large group of intracellular and transmembrane signalling proteins in eukaryotic cells (Manning G. et al, (2002) Science, 298: 1912-1934). Phosphorylation of specific amino acid residues in target proteins by protein kinases can modulate their activity leading to profound changes in cellular signalling and metabolism. Kinases play key roles in the regulation of cellular proliferation, survival, differentiation and function. Many kinases have been implicated in disease and, as such, are attractive therapeutic targets.

The Tec-kinase-family of kinases consists of Tyrosine kinase expressed in hepatocellular carcinoma (TEC), Interleukin-2 inducible T-cell kinase (ITK, also known as Tsk and Emt), Resting lymphocyte kinase (RLK, also known as TXK for Tyrosine Protein Kinase), Bruton's tyrosine kinase (BTK), Bone marrow kinase on the X-chromosome (BMX, also known as Etk) (Bradshaw J M Cell Signal. 2010; 22(8):1175-84). These intracellular kinases play important roles in the development and function of lymphocytes and myeloid cells (Horwood et al. Int. Rev. Immunol. 2012; 31(2):87-103, Felices Metal. Adv. Immunol. 2007; 93:145-84). Additionally, selected Tec-family members such as ITK, TEC and BMX are expressed in cancerous cells where they may play a role in cancer cell survival and malignancy (Carson C C et al. Clin Cancer Res. 2015; 21(9):2167-76, Mano H. et al. Oncogene. 1990; 5(12):1781-6, Cenni B et al. Int. Rev. Immunol. 2012; 31(2):166-73).

ITK is an important component of T-cell signaling function and differentiation. ITK is activated upon stimulation of T-cell receptors and initiates a signaling cascade that results in cellular activation, cytokine release and rapid proliferation. ITK is important in T-helper (Th) cell development and function including Th1, Th2, Th9, Th17 and T-regulatory cell development (Fowell D J et al. 1999 Immunity 11:399-409; Gomez-Rodriguez J. et al. 2014 J. Exp. Med 211:529-543, Gomez-Rodriguez J. et al 2016 Nat Commun. 2016; 7: 10857). For example, ITK −/− CD4+ T cells show significant reduction in the production of Th1 and Th17 cytokines and exhibit skewed T effector/Treg cell ratios with a bias towards FoxP3+ Treg (Kannan A et al 2015. J Neurosci. 35:221-233, Gomez-Rodriguez J. et al. 2014 J. Exp. Med. 211:529-543). Furthermore, specific inhibition of an allele-sensitive ITK mutant shows that ITK is important in Th1, Th2, Th17, and iNKT-cell cytokine production (Kannan A et al Eur. J. Immunol. 2015. 45: 2276-2285). Consequently, ITK is a promising target for prevention or treatment of diseases involving Th cytokines or where modulation of immunosuppressive Treg cells is desired. Furthermore, polymorphisms in the ITK promoter that increase ITK expression in humans have been linked to increased asthma incidence (Lee, S. H. et al. 2011 Ann Hum Genet 75:359-369) and ITK preferentially regulates the secretion of the Th2 cytokines IL-5 and IL-13 in models of allergic asthma suggesting that ITK inhibitors may be useful in the treatment of asthma (Muller C et al. 2003 J Immunol. 170:5056-63). Also, ITK is upregulated in lesioned skin from patients with allergic contact dermatitis, atopic dermatitis and psoriasis (von Bonin A et al. 2010. Exp. Derm; 20, 41-47).

TXK (RLK) is another Tec-kinase-family member that is expressed in T-cells (Hu Q et al. 1995 J. Biol Chem. 270:1928-1934). TXK (RLK) and ITK regulate Th cell-mediated responses via their differential expression in Th1 and Th2 cells, respectively (Sahu N et al. J. Immunol. 2008, 181:6125-6131). Furthermore, while ITK −/− mice have impaired in NKT cell generation this defect is exacerbated in the absence of both TXK and ITK (Felices M. et al. 2008, J Immunol. 180:3007-3018). Increased expression of TXK has been reported in patients with Behcet's disease, an inflammatory disorder associated with increased inflammation and Th1 cytokine production (Suzuki N et al. 2006 Clin. Med. Res. 4:147-151). Knockout of both ITK and TXK produces stronger effects on T-cell function than knockout of either kinase alone (Schaeffer et al. 1999 Science 284:638-641; Felices et al. 2008 J. Immunol. 180:3007-3018).

TEC kinase, after which the family of related kinases is known, was first shown to be expressed in hepatocellular carcinoma (Mano et al. 1990 Oncogene. 5:1781-6). TEC kinase is also expressed in normal B and T-cells and is up-regulated upon T-cell activation in Th1 and Th2 cells (Tomlinson M G et al 2004 Mol. Cell. Biol., 24:2455-2466). TEC may have different roles from either ITK or TXK. TEC has a unique subcellular distribution differential protein interactions compared with ITK and TXK (Tomlinson M G et al 2004 Mol. Cell. Biol., 24:2455-2466) and TEC, but not TXK or ITK, is a tyrosine kinase of c-Maf leading to enhancement of c-Maf-dependent IL-4 promoter activity (Liu C C et al. 2015 PLoS One. 10:e0127617). Lastly, TEC controls assembly of the non-canonical caspase 8 inflammasome involved in fungal sepsis and TEC-deficient mice are highly resistant to candidiasis (Zwolanek F et al. 2014 PLoS Pathog 10, e1004525).

BTK is important in B-cell receptor signaling and regulation of B-cell development and activation (W. N. Khan et al. Immunity, 1995, 3:283-299 and Satterthwaite A B et al. Immunol. Rev. 2000, 175: 120-127). Mutation of the gene encoding BTK in humans leads to X-linked agammaglobulinemia which is characterized by reduced immune function, including impaired maturation of B-cells, decreased levels of immunoglobulin and peripheral B cells, diminished T-cell independent immune response (Rosen F S et al., N Engl. J. Med., 1995, 333:431-440; and Lindvall J M et al. Immunol. Rev. 2005, 203:200-215). BTK is activated by Src-family kinases and phosphorylates PLC gamma leading to effects on B-cell function and survival. Additionally, BTK is important for cellular function of mast cells, macrophage and neutrophils suggesting that BTK inhibition would be effective in treatment of diseases mediated by these and related cells including inflammation, bone disorders, and allergic disease (Kawakami Y. et al., J Leukoc Biol. 1999; 65(3): 286-90). BTK inhibition is also important in survival of lymphoma cells (Herman S E M. Blood, 2011, 117:6287-6289) suggesting that inhibition of BTK may be useful in the treatment of lymphomas and other cancers (Uckun F M, Int Rev Immunol. 2008; 27(1-2):43-69). As such, inhibitors of BTK and related kinases are of great interest as anti-inflammatory as well as anti-cancer agents. BTK is also important for platelet function and thrombus formation suggesting that BTK-selective inhibitors may prove to be useful antithrombotic agents (Liu J. Blood, 2006, 108:2596-603). Furthermore, BTK is required for inflammasome activation (Ito M. et al. Nat Commun. 2015 Jun. 10; 6:7360) and inhibition of BTK may be useful in treatment of inflammasome-related disorders including; stroke, gout, type 2 diabetes, obesity-induced insulin resistance, atherosclerosis amyotrophic Lateral sclerosis, Parkinson's disease, and Muckle-Wells syndrome. BTK is expressed in CNS microglia and activated in infiltrating macrophages and neutrophils in models of stroke and inhibition of BTK suppresses neurological damage in a mouse model of stroke (Ito M. et al. Nat Commun. 2015 Jun. 10; 6:7360). In addition BTK is expressed in HIV infected T-cells and treatment with BTK inhibitors sensitizes infected cells to apoptotic death and results in decreased virus production (Guendel I et al. J Neurovirol. 2015; 21:257-75). Accordingly, BTK inhibitors may be useful in the treatment of HIV-AIDS and other viral infections.

Experimental data using Tec-kinase-family null animals supports the therapeutic benefit of kinase inhibition in human disease. ITK modulates neuroinflammation due to experimental autoimmune encephalomyelitis (EAE), the animal model of multiple sclerosis (MS). ITK−/− mice exhibit reduced disease severity, and transfer of ITK−/− CD4+T cells into T cell-deficient mice results in lower EAE disease severity (Kannan A k et al. J. Neurosci, 2015; 35:221-233). ITK −/− mice exhibit decreased inflammatory response in contact hypersensitivity models (Von Bonin et al. Experimental Dermatology, 2010; 20, 41-47) and secretion of the Th2 cytokines IL-5 and IL-13 is decreased in models of allergic asthma in ITK −/− mice (Mueller C et al. J Immunol. 2003; 170(10):5056-63).

Data obtained with inhibitors of selected Tec-kinase-family members suggests that inhibitors of these kinases may be useful in the treatment of disease. Inhibitors of ITK, TXK and other Tec-kinase-family members may be useful in the prevention or treatment of T-cell related diseases such as multiple sclerosis, asthma, atopic dermatitis, psoriasis and inflammatory bowel diseases well as viral infections. For example, a small molecule inhibitor of ITK and TXK has shown efficacy in the mouse adoptive T-cell transfer model of colitis (Cho H-S et al. 2015; J. Immunol. 195: 4822-31).

Also, a selective ITK inhibitor blocked leukocyte lung infiltration following ovalbumin challenge in a rat model of asthma (Lin T A et al. 2004 Biochemistry. 43:11056-11062). Additionally, an ITK inhibitor was effective in mouse models of skin contact hypersensitivity (von Bonin A et al. 2010. Exp. Derm; 20, 41-47). Furthermore, ITK inhibitors can alter the HIV replication at various stages of viral life cycle including viral entry, gp120-induced actin reorganization, transcription from viral long terminal repeats (LTR) and virion assembly release from T cells (Readinger J A et al. Proc Natl Acad Sci USA. 2008; 105(18):6684-9). Similarly ITK inhibition alleviates T-cell activation and murine myocardial inflammation associated with Coxsackie virus CVB3 infection (He F et al. Mol Immunol. 2014; 59(1):30-8) and ITK is required for efficient replication of influenza virus in infected T-cells (Fan K et al. J Gen Virol. 2012; 93(Pt 5):987-97). These data suggest that inhibitors of the Tec-kinase-family may be useful in the treatment of a variety of human and animal diseases.

SUMMARY OF THE INVENTION

The present invention relates to a novel family of covalent kinases inhibitors. Compounds of this class have been found to have inhibitory activity against members of the Tec kinase family, particularly ITK and/or RLK (TXK), and/or TEC.

One aspect of the present invention is directed to a compound of Formula I:

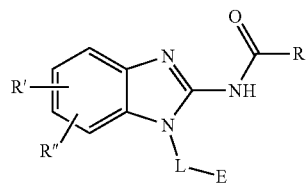

Formula I or a pharmaceutically acceptable salt, solvate, solvate of salt, stereoisomer, tautomer, isotope, prodrug, complex or biologically active metabolite thereof, wherein
R is selected from substituted or unsubstituted aryl or substituted or unsubstituted heteroaryl;
L is selected from

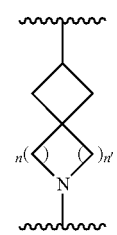

wherein n is an integer from 1 to 3; and n' is an integer from 1 to 3;
E is selected from the group:

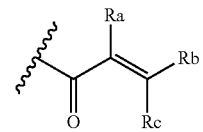

wherein Ra, Rb and Rc are independently selected from hydrogen, halogen, —CN, substituted or unsubstituted alkyl, substituted or unsubstituted heteroalkyl, substituted or unsubstituted cycloalkyl, or substituted or unsubstituted heterocyclyl; or Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or Rb and Rc taken together with the carbon atom to which they are attached form a 3- to 8-membered substituted or unsubstituted cycloalkyl ring or form a 3- to 8-membered heterocyclic ring and Ra is selected as above; or Ra and Rb taken together with the carbon atoms to which they are attached form a triple bond and Rc is selected as above;

provided L-E is

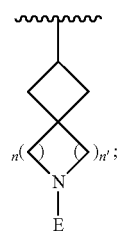

R' and R" are independently selected from —X—Y wherein
X is selected from alkylene, -(alkylene)-NR$^1$—, -(alkylene)-NR$^2$—, -(alkylene)-O—, —O—, —S—, —S(O)$_m$—, —NR$^1$—, —NR$^2$—, —C(O)—, —C(O)O—, —C(O)NR$^1$—, —C(O)ONR$^1$—, or —S(O)$_m$NR$^1$—;
R$^1$ is selected from hydrogen, lower alkyl or lower cycloalkyl;
R$^2$ is selected from —C(O)R$^3$, —C(O)OR$^3$ or —S(O)$_m$R$^3$;
R$^3$ is selected from lower alkyl or lower cycloalkyl;
m is an integer from 1 to 2; or
X is a bond; and
Y is selected from hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or
R' and R" taken together with the carbon atoms to which they are attached form a 3- to 8-membered substituted or unsubstituted cycloalkyl ring, or a 3- to 8-membered substituted or unsubstituted heterocyclyl ring.

In another aspect provided herein a pharmaceutical composition comprising a compound of Formula I disclosed herein, and/or a pharmaceutically acceptable salt, solvate, solvate of salt, stereoisomer, tautomer, isotope, prodrug, complex or biologically active metabolite thereof; and at least one pharmaceutically acceptable carrier or excipient.

The pharmaceutical composition of the present invention comprising a compound of Formula I and/or a pharmaceutically acceptable salt, solvate, solvate of salt, stereoisomer, tautomer, isotope, prodrug, complex or biologically active metabolite thereof suitable for use in therapy, preferably wherein a subject is suffering of a disease, disorder or condition in which one or more Tec kinase family member activity is implicated and can be treated by kinase inhibition.

In another aspect, the present invention relates to the use of a compound of Formula I, as defined herein, or a pharmaceutically acceptable salt or solvate thereof, in the manufacture of a medicament for use in a subject for the prevention or treatment of protein kinase mediated diseases or conditions selected from cancer, autoimmune diseases, allergic diseases, inflammatory diseases, graft-versus-host disease, thromboembolic diseases, neurological disorders, viral infections, bone-related diseases, stroke, Alzheimer's disease, Huntington's disease, amyotrophic Lateral Sclerosis, and thereof.

In another aspect, the present invention provides a pharmaceutical combination comprising a compound of Formula I disclosed herein or a pharmaceutically acceptable salt, solvate, solvate of salt, stereoisomer, tautomer, isotope, prodrug, complex or biologically active metabolite thereof and at least one additional active pharmaceutical ingredient for the treatment or prevention of cancer, autoimmune diseases, allergic diseases, inflammatory diseases or viral infection in combination therapy.

Another aspect of the present invention provides a pharmaceutical composition comprising the compound disclosed herein, or a pharmaceutically acceptable salt solvate, solvate of a salt, stereoisomer, tautomer, isotope, prodrug, complex or biologically active metabolite thereof, for use in treatment with at least one additional active pharmaceutical ingredient for the treatment of cancer, autoimmune diseases, allergic diseases, inflammatory diseases or viral infection wherein: said additional active pharmaceutical ingredient is appropriate for the disease being treated; and said additional active pharmaceutical ingredient is administered together with said composition as a single dosage form or separately from said composition as part of a multiple dosage form.

In another aspect, the present invention provides a pharmaceutical combination comprising a compound of Formula I disclosed herein or a pharmaceutically acceptable salt, solvate, solvate of salt, stereoisomer, tautomer, isotope, prodrug, complex or biologically active metabolite thereof and at least one additional active pharmaceutical ingredient for the treatment or prevention of cancer, autoimmune diseases, allergic diseases, inflammatory diseases or viral infection in combination therapy.

Another aspect of the present invention provides the synthetic methods used to prepare compounds of Formula I of the present invention and are not intended to be limiting.

Another aspect of the present invention provides a method for treating a subject suffering from a protein kinase mediated disease or condition, preferably mediated by a protein kinase, comprising administering to the subject a therapeutically effective amount of the compound disclosed herein, or a pharmaceutically acceptable salt solvate, solvate of a salt, stereoisomer, tautomer, isotope, prodrug, complex or biologically active metabolite thereof in combination with at least one pharmaceutically acceptable carrier.

In yet another aspect, provided herein are methods of preventing or treating a disease treatable by inhibition of ITK in a patient which comprises administering to the patient a pharmaceutical composition consisting of a compound disclosed herein and or a pharmaceutically acceptable salt thereof in a therapeutically effective amount and one or more pharmaceutically acceptable excipients. In one embodiment of this aspect the patient suffers from a disease or disorder that may be treated by kinase inhibition. The compound disclosed herein and/or pharmaceutically acceptable salt thereof may inhibit one or more kinases including but not limited to ITK, RLK (also known as TXK), BMX, BTK, and/or TEC.

Another aspect of the present invention provides a method of modulating kinase activity in a subject comprising administering a therapeutically effective amount of the compound disclosed herein, or a pharmaceutically acceptable salt solvate, solvates of a salt, stereoisomer, tautomer, isotope, prodrug, complex or biologically active metabolite thereof.

Another aspect of the present invention provides a method of inhibiting protein kinase in a cell or tissue comprising contacting the cell or tissue with the compound disclosed herein, or a pharmaceutically acceptable salt solvate, solvates of a salt, stereoisomer, tautomer, isotope, prodrug, complex or biologically active metabolite thereof.

Another aspect of the present invention provides a method of inhibiting protein kinase activity and/or modulating target kinase function, in a subject, comprising administering a therapeutically effective amount of the compound disclosed herein, or a pharmaceutically acceptable salt solvate, solvates of a salt, stereoisomer, tautomer, isotope, prodrug, complex or biologically active.

Another embodiment of the present invention provides a method of treating a subject suffering from cancer, autoimmune diseases, allergic diseases, inflammatory diseases, neurological diseases, viral infection or combinations thereof, wherein the enzymatic activity of ITK, TXK, TEC, BTK or a combination thereof are reduced by administering to the subject a therapeutically effective amount of the compound disclosed herein or a pharmaceutically acceptable salt solvate, solvate of a salt, stereoisomer, tautomer, isotope, prodrug, complex or biologically active metabolite thereof. In an aspect of the present invention the enzymatic activity of the protein kinase is inhibited or modulated in B-cells, T-cells, NK/T cells, microglia and/or mast cells in the subject.

In one embodiment, the present invention provides a method of treatment wherein further comprising administering of a therapeutically effective amount of at least one additional active pharmaceutical ingredient for the treatment of cancer, autoimmune diseases, allergic diseases, inflammatory diseases, neurological disorders or viral infection in combination therapy. The additional active pharmaceutical ingredient is administered together with the compounds of Formula I or a pharmaceutically acceptable salt, solvate, solvate of salt, stereoisomer, tautomer, isotope, prodrug, complex or biologically active metabolite thereof, as a single dosage form or separately, as part of a multiple dosage form. The additional active pharmaceutical ingredient is selected from the group comprising: steroids, leukotriene antagonists, anti-histamines, anti-cancer, anti-viral, anti-biotic agents, sodium channel blockers, glutamate antagonists, protein kinase inhibitors or combinations thereof.

Another aspect of the present invention provides a probe comprising the compound of Formula I as disclosed therein, which is covalently conjugated to a detectable label or affinity tag for said compound. The probe, wherein the detectable label is selected from the group consisting of: a fluorescent moiety, a chemiluminescent moiety, a paramagnetic contrast agent, a metal chelate, a radioactive isotope containing moiety and biotin.

The administration of a compound of the present invention may be by any appropriate means known in the field, including systemic and localized administration. Prior to administration, the compounds may be formulated as compositions suitable for pharmaceutical or clinical use. Such compositions may comprise appropriate carriers or excipients, such as those for topical, inhalation, or systemic administration. The compound of the present invention may be administered alone or in combination with one or more pharmaceutically acceptable active for the treatment or prevention of a protein kinase mediated condition.

All publications, patent applications, patents and other references mentioned herein are incorporated by references in their entirety.

Other features, objects, and advantages of the invention disclosed herein there are apparent from the description and drawings, and from the claims.

BRIEF DESCRIPTION OF THE DRAWINGS

The FIGURE represents the efficacy of compound 16 that was evaluated in experimental autoimmune encephalomyelitis (EAE), a mouse model of multiple sclerosis.

DETAILED DESCRIPTION OF THE INVENTION

The present invention relates to a novel covalent kinase inhibitor of Formula I

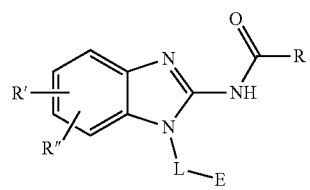

Formula I or pharmaceutically acceptable salt, solvate, solvate of salt, stereoisomer, tautomer, isotope, prodrug, complex or biologically active metabolite thereof, wherein R is selected from substituted or unsubstituted aryl or substituted or unsubstituted heteroaryl;

L is selected from

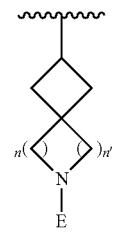

wherein n is an integer from 1 to 3; and n' is an integer from 1 to 3;

E is selected from the group:

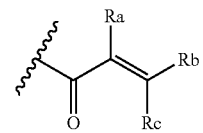

wherein Ra, Rb and Rc are independently selected from hydrogen, halogen, —CN, substituted or unsubstituted alkyl, substituted or unsubstituted heteroalkyl, substituted or unsubstituted cycloalkyl, or substituted or unsubstituted heterocyclyl; or Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or Rb and Rc taken together with the carbon atom to which they are attached form a 3- to 8-membered substituted or unsubstituted cycloalkyl ring or form a 3- to 8-membered heterocyclic ring and Ra is selected as above; or Ra and Rb taken together with the carbon atoms to which they are attached form a triple bond and Rc is selected as above;

provided L-E is

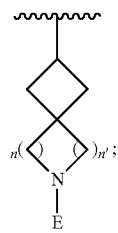

R' and R" are independently selected from —X—Y wherein X is selected from alkylene, -(alkylene)-NR$^1$—, -(alkylene)-NR$^2$—, -(alkylene)-O—, —O—, —S—, —S(O)$_m$—, —NR$^1$—, —NR$^2$—, —C(O)—, —C(O)O—, —C(O)NR$^1$—, —C(O)ONR$^1$—, or —S(O)$_m$NR$^1$—;

where

R$^1$ is selected from hydrogen, C$_1$-C$_6$ alkyl or 3- to 8-membered cycloalkyl ring;

$R^2$ is selected from —C(O)$R^3$, —C(O)O$R^3$ or —S(O)$_m R^3$;

$R^3$ is selected from $C_1$-$C_6$ alkyl or 3- to 8-membered cycloalkyl ring;

m is an integer from 1 to 2; or

X is a bond and;

Y is selected from hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or R' and R" taken together with the carbon atoms to which they are attached form a 3- to 8-membered substituted or unsubstituted cycloalkyl ring, or a 3- to 8-membered substituted or unsubstituted heterocyclyl ring.

An embodiment includes compounds of Formula I, where Ra, Rb and Rc are independently selected from the group consisting of hydrogen, —CN, halogen, and $C_1$ to $C_3$ substituted or unsubstituted alkyls.

An embodiment includes compounds of Formula I, where E is

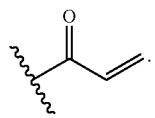 [SMILES: *C(=O)C=C]

An embodiment includes compounds of Formula I, where L-E is selected from

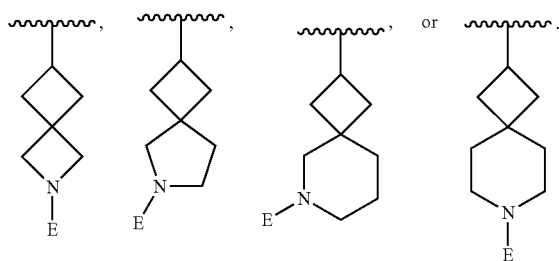

An embodiment includes compounds of Formula I, where L-E is selected from

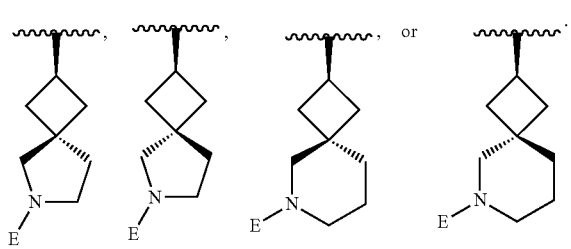

An embodiment includes compounds of Formula I, where L-E is

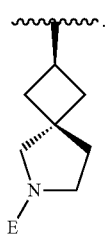

An alternate embodiment includes compounds of Formula I, where L-E is

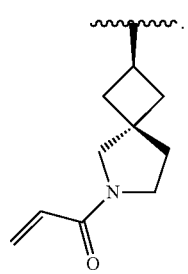 [SMILES: *[C@H]1C[C@@]2(CCN(C(=O)C=C)C2)C1]

An embodiment includes compounds of Formula I, where R is a substituted or unsubstituted aryl.

An embodiment includes compounds of Formula I, where R is a substituted or unsubstituted heteroaryl.

An embodiment includes compounds of Formula I, where R' is selected from —$CH_2$—NH—Y wherein Y is as defined above and R" is hydrogen.

An embodiment includes compounds of Formula I, where R' is selected from —$CH_2$—Y wherein Y is as defined above and R" is hydrogen.

An embodiment includes compounds of Formula I where X—Y is selected from —$NR^2C(O)$—Y wherein $R^2$ and Y are as defined above and R" is hydrogen.

An embodiment includes compounds of Formula I, where R' and R" are both hydrogen.

An embodiment includes compounds of Formula I, where R' is halogen and R" is hydrogen.

An embodiment includes compounds of Formula I, where n=1.

An embodiment includes compounds of Formula I, where n=2.

An embodiment includes compounds of Formula I, where n=3.

An embodiment includes compounds of Formula I, where n'=1.

An embodiment includes compounds of Formula I, where n'=2.

An embodiment includes compounds of Formula I, where n'=3;

Compounds of Formula I may exist as tautomers. For example, compounds of Formula I may exist in the following tautomeric form:

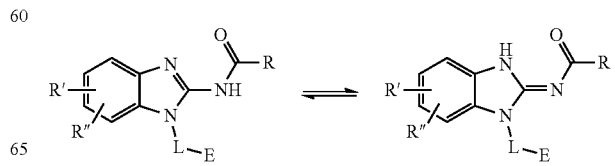

wherein R, R', R", L and E are as defined herein.

The compounds of the present invention may have activity as inhibitors of protein kinases including tyrosine protein kinases. Most particularly, compounds of the present invention may inhibit ITK enzyme and ITK-dependent cellular functions.

In an embodiment of the present invention compounds of Formula I may be formulated into a pharmaceutical composition which comprises an pharmaceutically effective amount of Formula I, or a pharmaceutically acceptable salt or solvate thereof, in association with at least one pharmaceutically acceptable excipient, diluent or carrier.

According to the present invention there is provided a pharmaceutical composition which comprises a compound of Formula I, or a pharmaceutically acceptable salt or solvate thereof, in association with at least one pharmaceutically acceptable excipient, diluent or carrier.

The pharmaceutical compositions may be in a conventional pharmaceutical form suitable for oral administration (e.g., tablets, capsules, granules, powders and syrups), parenteral administration (e.g., injections (intravenous, intramuscular, or subcutaneous)), drop infusion preparations, inhalation, eye lotion, topical administration (e.g., ointment), or suppositories. Regardless of the route of administration selected, the compounds may be formulated into pharmaceutically acceptable dosage forms by conventional methods known to those skilled in the art.

The term "compound" refers also to its pharmaceutically acceptable salt, solvate, solvate of salt, stereoisomer, tautomer, isotope, prodrug, complex or biologically active metabolite thereof.

The term "pharmaceutically effective amount" refers to any amount of the composition for the prevention and treatment of humans that is effective in preventing or treating a disease or condition associated with protein kinase activity.

The term "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein means a pharmaceutically acceptable material, composition, or vehicle, such as a liquid or solid filler, diluent, excipient, solvent or encapsulating material. Each carrier must be acceptable in the sense of being compatible with the other ingredients of the formulation, including the active ingredient, and not injurious or harmful to the patient. Some examples of materials which may serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. For oral formulations, "pharmaceutically acceptable carrier" such as cellulose, calcium silicate, corn starch, lactose, sucrose, dextrose, calcium phosphate, stearic acid, magnesium stearate, calcium stearate, gelatin, talc, surfactants, suspending agents, emulsifiers, diluents, and others may be used. For injectable formulations, "pharmaceutically acceptable carrier" such as water, saline, glucose solution, glucose solution analogs, alcohols, glycols, ethers (e.g., polyethylene glycol 400), oils, fatty acids, fatty acid esters, glycerides, surfactants, suspending agents, emulsifiers, and others may be used.

The term "pharmaceutically acceptable salt" refers to the relatively non-toxic, inorganic and organic acid addition salts of the compound(s). These salts may be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like (See, for example, Berge et al. (1977) "Pharmaceutical Salts", *J. Pharm. Sci.* 66: 1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts may likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The term "spirocycle", as used herein, refers to bicyclic rings system connected through just one atom. The rings may be different or identical. The connecting atom, also called spiroatom, is preferably a quaternary carbon. Spirocycle may be optionally substituted with one or more substituents as defined herein.

The term "alkyl", as used herein, refers to a saturated hydrocarbon chain. Alkyl chains may be straight or branched. Alkyl chains may be optionally substituted with one or more substituents as defined herein. Representative alkyl groups include methyl, ethyl, propyl, (n-propyl and isopropyl) butyl (n-butyl, t-butyl and isobutyl), pentyl (n-pentyl and isopentyl), hexyl and the like. In certain preferred embodiments, alkyl substituents are lower alkyl groups, e.g., having from 1 to 6 carbon atoms or 1 to 3 carbon atoms.

The term "alkenyl", as used herein, refers to an unsaturated hydrocarbon chain analogous in length and possible substitution to the "alkyl" described above, but that contain at least one double bond. Representative alkenyl groups include vinyl, propen-2-yl, crotyl, isopenten-2-yl, 1,3-butadien-2-yl, 2,4-pentadienyl, and 1,4-pentadien-3-yl. In certain preferred embodiments, alkenyl substituents are lower alkenyl groups, e.g., having from 2 to 6 carbon atoms.

The term "alkynyl", as used herein, refers to an unsaturated hydrocarbon chain analogous in length and possible substitution to the "alkyl" described above, but that contain at least one triple bond. Representative alkynyl groups include ethynyl, 1- and 3-propynyl, and 3-butynyl. In certain preferred embodiments, alkynyl substituents are lower alkyl groups, e.g., having from 2 to 6 carbon atoms.

The term, "alkylene", as used herein, refers to an alkyl group with two open valences.

The term "heteroalkyl", as used herein, refers to a saturated or partially saturated chain containing one to four heteroatoms selected from the group consisting of O, N and S, and wherein the nitrogen and sulfur atoms may optionally be oxidized and the nitrogen atom may optionally be quaternized. Heteroalkyl chains may be straight or branched. Heteroalkyl chains may be optionally substituted with one or more substituents as defined herein. The heteroatom(s) O, N and S may be placed at any interior position of the heteroalkyl group. Up to two heteroatoms may be consecutive.

The term "cycloalkyl", "carbocycle" or "carbocyclyl" also include polycyclic ring systems having two or more cyclic rings in which two or more carbons are common to two adjoining rings wherein at least one of the rings is cycloalkyl, e.g., the other cyclic rings may be aryl, heteroaryl, and/or heterocyclyl. Representative cycloalkyl rings include cyclopropyl, cyclobutyl, cyclopentyl, cyclohexyl, 1-cyclohexenyl, 3-cyclohexen-1-yl, cycloheptyl, tetrahydronaphthyl, indanyl, adamantly and combinations thereof. Cycloalkyl rings may be optionally substituted with one or more substituents as defined herein. In certain preferred embodiments, cycloalkyl substituents are lower cycloalkyl, e.g., refers to 3- to 8-membered ring, in which each atom of the ring is carbon or; refers to a spirocycle where each ring is a saturated or partially saturated hydrocarbon ring and the spiro atom is carbon.

The term "heterocyclyl" alternatively "heterocyclic", as used herein, refers to non-aromatic ring structures, more preferably 3- to 8-membered rings, whose ring structures include one to four heteroatoms or; refers to a spirocycle where the bicyclic rings system contains 1 to 4 heteroatoms. Heterocyclyl rings may be optionally substituted with one or more substituents as defined herein. The term "heterocyclyl" or "heterocyclic" also include polycyclic ring systems having two or more cyclic rings in which two or more carbons are common to two adjoining rings wherein at least one of the rings is heterocyclic, e.g., the other cyclic rings may be cycloalkyls, aryls and/or heteroaryls. Heterocyclyl groups include, for example, tetrahydrofuran, piperidine, piperazine, pyrrolidine, morpholine, lactones, lactams and combinations thereof.

The term "aryl", as used herein, refers to 5-, 6-, and 7-membered aromatic rings in which each atom of the ring is carbon. Aryl rings may be optionally substituted with one or more substituents as defined herein. The term "aryl" also includes polycyclic ring systems having two or more cyclic rings in which two or more carbons are common to two adjoining rings wherein at least one of the rings is aryl, e.g., the other cyclic rings may be cycloalkyls, heteroaryls, and/or heterocyclyls. Aryl groups include, for example, benzene, naphthalene, phenanthrene, anthracene and combinations thereof.

The term "heteroaryl" or Het, as used herein, refers to 5-, 6-, and 7-membered aromatic rings whose ring structures include one to four heteroatoms. Heteroaryl rings may be optionally substituted with one or more substituents as defined herein. The term "heteroaryl" also includes polycyclic ring systems having two or more cyclic rings in which two or more carbons are common to two adjoining rings wherein at least one of the rings is heteroaryl, e.g., the other cyclic rings may be cycloalkyls, aryls and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and combinations thereof.

The terms "polycyclyl" alternatively "polycyclic", as used herein, refer to two or more rings (e.g., cycloalkyls, aryls, heteroaryls, and/or heterocyclyls) in which two or more carbons are common to two adjoining rings, e.g., the rings are "fused rings". Polycyclyl rings may be optionally substituted with one or more substituents as defined herein.

The term "aralkyl", as used herein, refers to an alkyl group substituted with an aryl group, for example —$(CH_2)_p$—Ar and p is an integer from 1 to 8. The aralkyl may be further substituted with an $C_1$-$C_3$ alkyl group.

The term "heteroaralkyl", as used herein, refers to an alkyl group substituted with a heteroaryl group, for example —$(CH_2)_p$-Het and p is an integer from 1 to 8. The heteroaralkyl may be further substituted with an $C_1$-$C_3$ alkyl group.

The term "alkoxy", as used herein, refers to an alkyl ether substituent, wherein the term alkyl is as defined therein. Representative alkoxy groups include methoxy, ethoxy, propoxy, tert-butoxy and combinations thereof.

The term "ether", as used herein, refers to an oxy group bridging two moieties linked at carbon atoms.

The term "alkoxyalkyl", as used herein, refers to an alkyl group substituted with an alkoxy group, thereby forming ether.

The term "halo" or "halogen", as used herein, refers to fluorine, chlorine, bromine and iodine.

The term "heteroatom", as used herein, refers to an atom of any element other than carbon or hydrogen. Preferred heteroatoms are nitrogen, oxygen, and sulfur.

The term "hydrocarbon", as used herein, refers to a group consisting entirely of carbon and hydrogen.

The term, "haloalkyl", as used herein, refers to an alkyl substituent wherein one or more hydrogens are replaced by a halogen.

The term "carbonyl", as used herein, when alone includes formyl —CH(O) and in combination is a —C(O) group.

The term "carboxyl", alternatively "carboxy", as used herein, refers to —C(O)OH or the corresponding "carboxylate" anion, such as in a carboxylic acid salt.

The term "acyl", as used herein, refers to —C(O)R wherein R is alkyl, heteroalkyl, haloalkyl, cycloalkyl, heterocyclyl, aryl or heteroaryl as defined therein. Representative acyl groups include acetyl, trifluoroacethyl, benzoyl, and combinations thereof.

The term "alkoxycarbonyl", as used herein, refers to —C(O)OR wherein R is alkyl as defined therein. Representative alkoxycarbonyl groups include methoxycarbonyl, ethoxycarbonyl, and combinations thereof.

The term "alkylthio", as used herein, refers to a thioether —SR wherein R is alkyl as defined therein. Representative alkylthio groups include methylthio, ethylthio and combinations thereof.

The term "sulfonate", as used herein, refers to a salt or ester of a sulfonic acid —$OSO_2$R wherein R is alkyl, heteroalkyl, haloalkyl, cycloalkyl, heterocyclyl, aryl or heteroaryl as defined therein. Representative sulfonate groups include mesylate, besylate, tosylate, and combinations thereof.

The term "sulfonyl", as used herein, refers to —SO$_2$R wherein R is alkyl, heteroalkyl, haloalkyl, cycloalkyl, heterocyclyl, aryl or heteroaryl as defined therein. Representative sulfonate groups include methylsufonyl, ethylsulfonyl, and combinations thereof.

The term "sulfamoyl", as used herein, refers to —SO$_2$NH$_2$.

The term "sulfonamido", as used herein, refers to —S(O)$_2$NRR' wherein R and R' are independently selected from alkyl, heteroalkyl, haloalkyl, cycloalkyl, heterocyclyl, aryl and heteroaryl as defined above. R and R' may combine to form a heterocyclyl ring.

The term "amino", as used herein, refers to —NRR' wherein R and R' are independently selected from hydrogen, alkyl, heteroalkyl, haloalkyl, cycloalkyl, heterocyclyl, aryl and heteroaryl as defined therein. R and R' may combine to form a heterocyclyl ring.

The term "amido" alternatively "amide", as used herein, refers to —C(O)NRR' wherein R and R' are independently selected from hydrogen, alkyl, heteroalkyl, haloalkyl, cycloalkyl, heterocyclyl, aryl or heteroaryl as defined therein. R and R' may combine to form an heterocyclyl ring.

The term "substituted" refers to moieties having substituents replacing hydrogen on one or more atoms of the backbone. It may be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms.

Substituents, as used herein, are selected from an alkyl, an alkenyl, an alkynyl, a haloalkyl, a heteroalkyl, a cycloalkyl, a 3 to 8 membered heterocyclyl, an aryl, a heteroaryl, a halogen, a hydroxyl, a carbonyl, carboxyl, an alkoxycarbonyl, a formyl, or an acyl, a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, an aralkyl, or an aromatic or a heteroaromatic moiety; and wherein:

alkyl represents 01-6 alkyl;
alkenyl represents 02-6 alkenyl;
alkynyl represents 02-6 alkynyl; and
aryl includes 5-, 6-, and 7-membered substituted or unsubstituted single-ring aromatic groups in which each atom of the ring is carbon or polycyclic ring systems having two or more cyclic rings in which two or more carbons are common to two adjoining rings wherein at least one of the rings is aromatic;
carbocyclyl includes a non-aromatic substituted or unsubstituted ring in which each atom of the ring is carbon or polycyclic ring systems having two or more cyclic rings in which two or more carbons are common to two adjoining rings wherein at least one of the rings is carbocyclic;
heteroaryl includes substituted or unsubstituted aromatic 5- to 7-membered ring structures whose ring structures include one to four heteroatoms or polycyclic ring systems having two or more cyclic rings in which two or more carbons are common to two adjoining rings wherein at least one of the rings is heteroaromatic;
heterocyclyl includes substituted or unsubstituted non-aromatic 3- to 10-membered ring structures whose ring structures include one to four heteroatoms or polycyclic ring systems having two or more cyclic rings in which two or more carbons are common to two adjoining rings wherein at least one of the rings is heterocyclic; or a pharmaceutically acceptable salt thereof.

It may be understood by those skilled in the art that the substituents may themselves be substituted, if appropriate.

To the extent any indicated substituent groups may be incompatible with the synthetic methods described herein, the substituent may be protected with a suitable protecting group (PG) that is stable to the reaction conditions used in these methods. The protecting group or "Protective Group" is introduced into a molecule by chemical modification of a functional group to obtain chemoselectivity in a subsequent chemical reaction. Common protecting groups are: alcohol protecting groups, amine protecting groups, carbonyl protecting groups, carboxylic acid protecting groups, phosphate protecting groups and terminal alkyne protecting groups. The protecting group PG$^1$, PG$^2$, PG$^3$ and PG$^4$ that are different, may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999). Examples of protecting groups used throughout include, but are not limited to Fmoc, Bn, Boc, CBz and COCF$_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

As used herein, the term "probe" means a compound of the invention which is labeled with either a detectable label or an affinity tag, and which is capable of binding, either covalently or non-covalently, to a protein kinase domain. When, for example, the probe is non-covalently bound, it may be displaced by a test compound. When, for example, the probe is bound covalently, it may be used to form cross-linked adducts, which may be quantified and inhibited by a test compound. As used herein, the term "affinity tag" means a ligand or group, linked either to a compound of the present invention or to a protein kinase domain, that allows the conjugate to be extracted from a solution.

The term "prodrug" denotes a compound that is a drug precursor which, upon administration to a subject, is converted within the body into a compound of Formula I. Prodrugs of compounds of Formula I or pharmaceutically acceptable salts or solvates thereof are within the scope of this disclosure.

The term "subject" or "patient" means a human or an animal subject for prevention or treatment.

In an embodiment the use is ex vivo, for example in vitro, such as an in vitro assay.

The term "combination" within the meaning of this invention includes the simultaneous, sequential or separate use of the components or active pharmaceutical ingredients.

Compounds of the invention also include all isotopes of atoms present in the intermediates and/or final compounds. Isotopes include those atoms having the same atomic number but different mass numbers. For example, compounds of Formula I include those wherein the hydrogen is replaced by deuterium, tritium and combinations thereof.

Therapeutic Uses and Applications

The compounds of the present invention may have potential utility as inhibitors of protein kinase activity and are suitable for use in therapy.

An aspect of the present invention provides a method of inhibiting protein kinase activity in a cell, the method consisting of administering to said cell compound of Formula I as defined herein, or a pharmaceutically acceptable salt, solvate, solvate of salt, stereoisomer, tautomer, isotope, prodrug, complex or biologically active metabolite thereof as defined herein.

In a further aspect, the present invention provides a method of inhibiting protein kinase in vitro or in vivo, said method consisting of contacting a cell with an effective amount of a compound of Formula I, or a pharmaceutically acceptable salt or solvate thereof, as defined herein.

A further aspect of the present invention provides a method of inhibiting protein kinase activity in a human or animal subject for treatment or prevention of protein kinase mediated disease, the method consisting of administering to said subject an effective amount of a compound of Formula I as defined herein, or a pharmaceutically acceptable salt or solvate thereof.

The term "protein kinase mediated disease" is used herein associated with abnormal or undesirable cellular responses triggered or maintained by protein kinase-mediated events. Furthermore, aberrant activation, mutation or excessive expressions of various protein kinases are implicated in the mechanism of multiple diseases and disorders. These diseases include, but are not limited to cancer, autoimmune disease, inflammation, viral infection and neurological disease.

In one embodiment, the protein kinase inhibited by compounds of the present invention is ITK, TXK, BTK or TEC singly or in combination.

The compounds of the present invention may be suitable for use in the treatment of or prevention of diseases that involve ITK, TXK, BTK or TEC, i.e. diseases that involve T-cells, B-cells, microglia and/or NK-cells, for example, cancer, autoimmune diseases, allergic diseases, inflammatory diseases, neurodegeneration, viral infection and combinations thereof.

In one embodiment, a compound disclosed herein and/or pharmaceutically acceptable salt thereof is administered to a patient in need or recognized need thereof to prevent or treat an inflammatory disorder. In another embodiment, a compound disclosed herein and/or pharmaceutically acceptable salt thereof is administered to a patient in need or recognized need thereof to prevent or treat an inflammatory disorder characterized by excessive or undesired cytokine activity or production. In yet another embodiment, a compound and/or pharmaceutically acceptable salt thereof is administered to a patient in need or recognized need thereof to prevent or treat lung inflammation, allergic asthma, pneumonia, psoriasis, atopic dermatitis or a combination thereof. In yet another embodiment a compound and/or pharmaceutically acceptable salt thereof is administered to a patient in need of or recognized need thereof to prevent or treat uveitis or dry eye disease.

Examples of an autoimmune disease in the present invention include arthritis, systemic lupus erythematosus, rheumatoid arthritis, psoriasis, psoriatic arthritis, Still's disease, juvenile arthritis, type I diabetes, inflammatory bowel disease, myasthenia gravis, Hashimoto's thyroiditis, Ord's thyroiditis, Basedow's disease, Sjogren's syndrome, multiple sclerosis, Guillain-Barre syndrome, acute disseminated encephalomyelitis, Addison disease, opsoclonus-myoclonus syndrome, ankylosing spondylitis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu arteritis, temporal arteritis, warm autoimmune hemolytic anemia, Wegener granuloma, alopecia universalis, Burchett disease, chronic fatigue syndrome, dysautonomia, endometriosis, interstitial cystitis, myotonia, vulvodynia, pemphigus, and combinations thereof.

Examples of an allergic disease in the present invention include allergy, anaphylaxis, allergic conjunctivitis, allergic rhinitis, atopic dermatitis and combinations thereof.

Examples of an inflammatory disease in the present invention include asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, epicondylitis, epididymitis, fasciitis, fibrositis, gastritis, gastroenteritis, hepatitis, hidradenitis suppurativa, inflammatory bowel disease, laryngitis, mastitis, meningitis, myelitis, myocarditis, myositis nephritis, oophoritis, orchitis, osteitis, osteoarthritis, pancreatitis, parotitis, pericarditis, peritonitis, pharyngitis, pleuritis, phlebitis, pneumonia, proctitis, prostatitis, pyelonephritis, rhinitis, salpingitis, sinusitis, stomatitis, synovitis, tendinitis, tonsillitis, uveitis, vaginitis, vasculitis, vulvitis, and combinations thereof.

Examples of a viral infection include HIV/AIDS, influenza and combinations thereof.

Examples of neurodegenerative disease include multiple sclerosis, Alzheimer's disease, Huntington's disease, and amyotrophic lateral sclerosis.

Examples of cancer in the present invention include T-cell lymphomas and T-cell leukemias including peripheral T-cell lymphoma, Seazry syndrome/cutaneous T-cell lymphoma, solid tumors, non-Hodgkin's lymphoma, acute lymphoblastic leukemia, and adult T-cell leukemia/lymphoma. Additional examples include NK/T-cell lymphoma, nasal type and aggressive NK-cell leukemia as well as melanoma and hepaptocellular carcinoma.

In one embodiment, the compound of Formula I or pharmaceutically acceptable salt, solvate, solvate of salt, stereoisomer, tautomer, isotope, prodrug, complex, or biologically active metabolite thereof, is acting by inhibiting one or more of the host cell kinases involved in cell proliferation, cell survival, viral replication, autoimmunity, an inflammatory disease or an infectious disease.

In further aspect of the present invention, the compound of Formula I or pharmaceutically acceptable salt, solvate, solvate of salt, stereoisomer, tautomer, isotope, prodrug, complex, or biologically active metabolite thereof, is acting as inhibitor of cell kinases as anti-inflammatory, autoimmune modulators or anti-cancer agents.

In a further aspect of the present invention, the compound of Formula I or pharmaceutically acceptable salt, solvate, solvate of salt, stereoisomer, tautomer, isotope, prodrug, complex, or biologically active metabolite thereof, is acting by inhibiting one or more of the host cell kinases involved in T-cell function proliferation or polarization.

The compounds of Formula I or pharmaceutically acceptable salt, solvate, solvate of salt, stereoisomer, tautomer, isotope, prodrug, complex, or biologically active metabolite thereof and pharmaceutically acceptable compositions of the present invention may be employed in combination therapies, the compounds and pharmaceutically acceptable compositions may have potential utility in combination with other therapies for the treatment of cancer, viral infections, immune, inflammatory, neurological diseases, proliferative and allergic disorders. Example includes but not limited to co-administration with steroids, leukotriene antagonists, anti-histamines, anti-cancer, anti-viral, anti-biotic agents or other protein kinase inhibitors. The anti-cancer agent may be selected from the group consisting of: cell signal transduction inhibitors, mitosis inhibitors, alkylating agents, anti-metabolites, intercalating anticancer agents, topoisomerase inhibitors, immunotherapeutic agents, anti-hormonal agents, and a mixture thereof. The additional active pharmaceutical ingredient used in the combination is appropriate for the disease being treated and said additional active pharmaceutical ingredient is administered together with the compounds of Formula I as a single dosage form or separately as part of a multiple dosage form.

Another aspect of the present invention provides compounds of the present invention may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels, cream or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; rectally such as in the form of suppositories; or liposomally. Dosage unit formulations containing non-toxic, pharmaceutically acceptable vehicles or diluents may be administered. The compounds may be administered in a form suitable for immediate release, extended release, delayed release or controlled release. Immediate release or extended release may be achieved with suitable pharmaceutical compositions or, particularly in the case of extended release, with devices such as subcutaneous implants or osmotic pumps. The compounds may be administered in a form suitable for targeted delivery in which the drug is only active in the target area of the body (for example, in cancerous tissues) and sustained release formulations in which the drug is released over a period of time in a controlled manner from a formulation.

The compounds of the present invention are indicated both in the therapeutic and/or prophylactic treatment of the above-mentioned conditions. For the above-mentioned therapeutic and/or prophylactic uses the dosage administered may vary with the compound employed, the subject, the mode of administration, the treatment desired and the disorder indicated. The daily dosage may be between about 0.01 mg/kg to about 100 mg/kg and preferably from about 1 mg/kg to about 25 mg/kg, of the subject body weight per day, one or more times a day, to obtain the desired therapeutic effect.

The compounds of Formula I or pharmaceutically acceptable salt, solvate, solvate of salt, stereoisomer, tautomer, isotope, prodrug, complex, or biologically active metabolite thereof may be suitable for use in the preparation of a medicament for inhibiting a protein kinase activity selected from ITK, TXK, BTK, TEC or combination thereof in a subject.

A pharmaceutical acceptable composition of the present invention may be obtained by conventional procedures using conventional pharmaceutical excipients, well known in the art. It may typically comprise pharmaceutically acceptable additives, carriers or excipients. The pharmaceutical composition of the present invention may be formulated in accordance with conventional methods, and may be prepared in the form of oral formulations such as tablets, pills, powders, capsules, syrups, emulsions, microemulsions and others, or parenteral formulations such as intramuscular, intravenous or subcutaneous administrations.

For oral formulations, carriers or additives such as cellulose, calcium silicate, corn starch, lactose, sucrose, dextrose, calcium phosphate, stearic acid, magnesium stearate, calcium stearate, gelatin, talc, surfactants, suspending agents, emulsifiers, diluents, and others may be used. Solid dosage forms for oral administration include capsules, tablets, pills, powders, and granules. Liquid dosage forms for oral administration include, but are not limited to, pharmaceutically acceptable emulsions, microemulsions, solutions, suspensions, syrups and elixirs. The liquid dosage forms may contain inert diluents and may also include adjuvants such as wetting agents, emulsifying and suspending agents, sweetening, flavoring, and perfuming agents.

For Injectable formulations, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid are used in the preparation of injectables.

Another aspect of the present invention provides a pharmaceutical composition comprising a compound of Formula I or a pharmaceutically acceptable salt, solvate, solvate of salt, stereoisomer, tautomer, isotope, prodrug, complex or biologically active metabolite thereof, and at least one pharmaceutically acceptable carrier, diluent or excipient.

The pharmaceutical composition of the present invention is for use in prevention or treatment of cancer, autoimmune diseases, allergic diseases, inflammatory diseases, graft-versus-host disease, thromboembolic diseases, neurological disorders, viral infections, bone-related diseases or combinations thereof.

In an embodiment of the present invention a compound of Formula I or a pharmaceutically acceptable salt, solvate, solvate of salt, stereoisomer, tautomer, isotope, prodrug, complex or biologically active metabolite thereof suitable for use in therapy, wherein a subject is suffering of a disease, disorder or condition in which one or more protein kinase family member activity is implicated. In an embodiment, the protein kinase is selected from ITK, TXK, BTK, TEC or combinations thereof.

In an embodiment of the present invention a compound of Formula I or a pharmaceutically acceptable salt, solvate, solvate of salt, stereoisomer, tautomer, isotope, prodrug, complex or biologically active metabolite thereof, is for use in the treatment or prevention of cancer, autoimmune diseases, allergic diseases, inflammatory diseases, neurological disorders, or viral infection in combination therapy. The cancer may include B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, or solid tumors, In an embodiment of the present invention a compound of Formula I or a pharmaceutically acceptable salt, solvate, solvate of salt, stereoisomer, tautomer, isotope, prodrug, complex or biologically active metabolite thereof, is for use in therapy, further comprising at least one additional active pharmaceutical ingredient for the treatment or prevention of cancer, autoimmune diseases, allergic diseases, inflammatory diseases, neurological disorders or viral infection in combination therapy. The additional active pharmaceutical ingredient is selected from the group consisting of: steroids, leukotriene antagonists, anti-histamines, anti-cancer, anti-viral, anti-biotic agents, protein kinase inhibitors, immune modulators, checkpoint inhibitors and a combination thereof, and wherein additional active pharmaceutical ingredient is administered together with the compounds of Formula I or a pharmaceutically acceptable salt, solvate, solvate of salt, stereoisomer, tautomer, isotope, prodrug, complex or biologically active metabolite thereof, as a single dosage form, or separately as part of a multiple dosage form.

In another aspect, the present invention relates to a compound of the invention as defined herein, or a pharmaceutically acceptable salt or solvate thereof, or a pharmaceutical composition as defined herein, for use in therapy or prevention of protein kinase mediated disease.

Compounds of the present invention, in any aspect or embodiment may be used in the treatment or prevention of cancer, autoimmune diseases selected from: rheumatoid arthritis, juvenile rheumatoid arthritis, osteoarthritis, ankylosing spondylitis, psoriatic arthritis, psoriasis vulgaris, pemphigus vulgaris, bullous pemphigoid, Sjogren's syndrome, systemic lupus erythromatosus, discoid SLE, lupus nephritis, antiphospholipidosis, whipple, dermatomyositis, polymyositis, autoimmune thrombocytopenia, idiopathic thrombocytopenia purpura, thrombotic thrombocytopenia purpura, autoimmune (cold) agglutinin disease, autoimmune hemolytic anemia, cryoglobulinemia, autoimmune vasculitis, ANCA-associated vasculitis, scleroderma, systemic sclerosis, multiple sclerosis, chronic focal encephalitis, Guillian-Barre syndrome, chronic fatigue syndrome, mononucleosis, neuromyelitis optica, autoimmune uveitis, Grave's disease, thyroid associated opthalmopathy, granulomatosis with microscopic polyangitis, Wegeners granulomatosis, idiopathic pulmonary fibrosis, sarcoidosis, idiopathic membranous nephropathy, IgA nephropathy, glomerulos clerosis, pancreatitis, type I diabetes or type II diabetes, allergic diseases, inflammatory diseases, neurological disorders or viral infection in combination therapy.

In another aspect, the present invention relates to a compound of the invention as defined herein, or a pharmaceutically acceptable salt or solvate thereof, or a pharmaceutical composition as defined herein, for use in the treatment of subjects suffering from a protein kinase mediated diseases or conditions. In an embodiment, the protein kinase is selected from ITK, TXK, TEC, or combinations thereof.

Another aspect of the present invention provides a use of the compound of Formula I or a pharmaceutically acceptable salt or solvate thereof as an inhibitor of protein kinase an embodiment, the protein kinase is selected from ITK, TXK, TEC, or combinations thereof. In an embodiment, the use is ex vivo, for example in vitro, such as an in vitro assay.

In another aspect, the present invention relates to the use of a compound of the invention as defined herein, or a pharmaceutically acceptable salt or solvate thereof, in the manufacture of a medicament for use in subjects for the treatment or prevention of protein kinase mediated diseases or conditions, for the treatment of cancer, autoimmune diseases, allergic diseases, inflammatory diseases, graft-versus-host disease, thromboembolic diseases, neurological disorders, viral infections, bone-related diseases or combinations thereof. In an embodiment, the protein kinase is selected from ITK, TXK, BTK, TEC, or combinations thereof.

In another aspect, the present invention relates to a method of treating or prevention of a disease or condition associated with protein kinase activity, said method comprising administering to a subject a therapeutically effective amount of a compound of the invention as defined herein, or a pharmaceutically acceptable salt or solvate thereof, or a pharmaceutical composition as defined herein. In an embodiment, the protein kinase is selected from ITK, TXK, BTK, TEC, or combinations thereof.

Another aspect of the present invention provides a compound, or a pharmaceutically acceptable salt or solvate thereof, or a pharmaceutical composition as defined herein, for use in the treatment of or prevention of diseases that involve ITK, BTK, TXK and\or other TEC kinases, i.e. diseases that involve B cells, microglia, T-cells and/or mast cells, for example, cancer, autoimmune diseases, allergic diseases, inflammatory diseases, graft-versus-host disease, thromboembolic diseases, bone-related diseases and the like.

A further aspect of the present invention provides the use of a compound, or a pharmaceutically acceptable salt or solvate thereof, in the manufacture of a medicament for use in the treatment or prevention of diseases that involve ITK, BTK, TXK and\or other TEC kinases, i.e. diseases that involve B cells, microglia, T-cells and mast cells, for example, cancer, autoimmune diseases, allergic diseases, inflammatory diseases, graft-versus-host disease, thromboembolic diseases, bone-related diseases and the like.

In another aspect, the present invention provides a method of treating or preventing a disease or condition, said method comprising administering to a subject a therapeutically effective amount of a compound of Formula I or a pharmaceutically acceptable salt or solvate thereof, or a pharmaceutical composition as defined herein. In a particular embodiment, the disease or conditions include allergic diseases, autoimmune diseases, inflammatory diseases, thromboembolic diseases, bone-related diseases, cancer, graft-versus-host disease, and the like.

Another aspect of the present invention provides a method of modulating kinase function, the method comprising contacting a cell with a compound of the present invention in an amount sufficient to modulate the enzymatic activity of ITK, TXK and\or other TEC kinases, thereby modulating the kinase function. The method may be ex vivo, for example in vitro.

Another aspect of the present invention provides a method of inhibiting cell proliferation or survival in vitro or in vivo, said method comprising contacting a cell with an effective amount of a compound as defined herein, or a pharmaceutically acceptable salt or solvate thereof.

In one embodiment, the present invention provides a method of producing a protein kinase inhibitory effect in a cell or tissue, said method comprising contacting the cell or tissue with an effective amount of a compound of Formula I or a pharmaceutically acceptable salt or solvate thereof.

In other embodiment, the present invention provides a method of producing a protein kinase inhibitory effect in vivo, said method comprising administering to a subject an effective amount of a compound of Formula I, or a pharmaceutically acceptable salt or solvate thereof.

Another aspect of the present invention provides a method of modulating the target kinase function, comprising:
a) contacting a cell or a protein kinase with a compound of the present invention in an amount sufficient of a compound of Formula I, or a pharmaceutically acceptable salt or solvate thereof to modulate the target kinase function, thereby;
b) modulating the target kinase activity and signaling.

In yet another aspect, provided herein are methods of treating a disease treatable by inhibition of protein kinase in a patient which comprises administering to the patient a pharmaceutical composition comprising a compound Formula I disclosed herein and or a pharmaceutically acceptable salt thereof in a therapeutically effective amount and one or more pharmaceutically acceptable excipients. In one embodiment of this aspect the patient suffers from a disease or disorder that may be treated by kinase inhibition. The compound disclosed herein of Formula I or pharmaceutically acceptable salt thereof, may inhibit one or more kinases members of the Tec family of non-receptor protein kinases, including but not limited to ITK, TXK, TEC or combinations thereof.

In another aspect, the present invention provides a pharmaceutical combination comprising a compound of the present invention and at least one additional active pharmaceutical ingredient for the treatment or prevention of cancer, autoimmune diseases, allergic diseases, inflammatory diseases or viral infection in combination therapy.

In one embodiment, the present invention provides a method of treatment wherein further comprising administering of a therapeutically effective amount of at least one additional active pharmaceutical ingredient for the treatment of cancer, autoimmune diseases, allergic diseases, inflammatory diseases, neurological disorders or viral infection in combination therapy. The additional active pharmaceutical ingredient is administered together with the compounds of Formula I as a single dosage form or separately as part of a multiple dosage form. The additional active pharmaceutical ingredient is selected from the group comprising: steroids, leukotriene antagonists, anti-histamines, anti-cancer, anti-viral, anti-biotic agents, protein kinase inhibitors or combinations thereof.

The administration of a compound of the present invention may be by any appropriate means known in the field, including systemic and localized administration. Prior to administration, the compounds may be formulated as compositions suitable for pharmaceutical or clinical use. Such compositions may comprise appropriate carriers or excipients, such as those for topical, inhalation, or systemic administration. The compound of the present invention may be administered alone or in combination with one or more pharmaceutically acceptable active for the treatment or prevention of a protein kinase mediated condition.

The compounds object of the present invention may be administered to a mammal 1 to 4 times a day. A dosage may be between 0.01-100 mg/kg body weight/day of the compound object of the present invention may be administered to a patient receiving these compositions. The dose may vary within wide limits and is to be suited to the individual conditions in each individual case. For the above uses the appropriate dosage may vary depending on the mode of administration, the particular condition to be treated and the effect desired. Preferably a dose of 1 to 50 mg/kg body weight/day may be used.

In an embodiment of the present invention suitable dosage rates for a subject, for example humans, are of the order of from about 10 mg to 3 g/day, administered orally once, or divided doses, such as 2 to 4 times a day, or in sustained release form. For topical delivery, depending on the permeability of the skin, the type and the severity of the disease and dependent on the type of formulation and frequency of application, different concentrations of active compounds within the medicament may be sufficient to elicit a therapeutic effect by topical application. Preferably, the concentration of an active compound pharmaceutically acceptable salts, solvates, solvates of salts, stereoisomers, tautomers, isotopes, prodrugs, complexes or biologically active metabolites thereof, within a medicament according to the present invention is in the range of between 1 μmol/L and 100 mmol/L.

In further aspect of the present invention, the compound of Formula I or pharmaceutically acceptable salts, solvates, solvates of salts, stereoisomers, tautomers, isotopes, prodrugs, complexes, or biologically active metabolites thereof, act as inhibitors of cell kinases as anti-inflammatory, anti-cancer, anti-viral and as antithrombotic agents.

The compounds and/or pharmaceutically acceptable salts of the present invention may be administered in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound and/or pharmaceutically acceptable salt of the present disclosure is used contemporaneously with one or more other drugs, a pharmaceutical composition in unit dosage form containing such other drugs and the compound and/or pharmaceutically acceptable salt of the present disclosure is preferred. However, the combination therapy may also include therapies in which the compound and/or pharmaceutically acceptable salt of the present disclosure and one or more other drugs are administered on different overlapping schedules. It is also contemplated that when used in combination with one or more other active ingredients, the compounds and/or pharmaceutically acceptable salts of the present disclosure and the other active ingredients may be used in lower doses than when each is used singly. Accordingly, the pharmaceutical compositions of the present disclosure also include those that contain one or more other active ingredients, in addition to a compound and/or pharmaceutically acceptable salt of the present disclosure.

The above combinations include combinations of a compound of the present disclosure not only with one other active compound, but also with two or more other active compounds. Likewise, compounds and/or pharmaceutically acceptable salts of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore by those skilled in the art, contemporaneously or sequentially with a compound and/or pharmaceutically acceptable salt of the present disclosure. When a compound and/or pharmaceutically acceptable salt of the present disclosure is used contemporaneously with one or more other drugs, a pharmaceutical composition containing such other drugs in addition to the compound and/or pharmaceutically acceptable salt of the present disclosure is preferred. Accordingly, the pharmaceutical compositions of the present disclosure also include those that also contain one or more other active ingredients, in addition to a compound and/or pharmaceutically acceptable salt of the present disclosure. The weight ratio of the compound and/or pharmaceutically acceptable salt of the present disclosure to the second active ingredient may be varied and may depend upon the effective dose of each ingredient. Generally, an effective dose of each may be used.

The present invention further provides a method of synthesizing a compound of the present invention as defined herein.

Another aspect of the present invention provides a probe, the probe comprising a compound of the present invention labeled with a detectable label or an affinity tag. In other words, the probe comprises a residue of a compound of Formula I or a pharmaceutically acceptable salt or solvate thereof, covalently conjugated to a detectable label. Such detectable labels include, but are not limited to, a fluorescent moiety, a chemiluminescent moiety, a paramagnetic contrast agent, a metal chelate, a radioactive isotope-containing moiety and biotin.

Specific Abbreviations Used
AcOH acetic acid
AIDS Acquired Immune Deficiency Syndrome
ATP Adenosine Triphosphate
Blk B lymphocyte kinase
BMX Bone marrow-expressed kinase
BrCN Cyanogen bromide
BTK Bruton's Tyrosine Kinase
CbzCl benzyl chloroformate
CuI Copper (I) iodide
Cu2O Copper (I) oxide
Cs2CO3 Cesium carbonate
CsF Cesium fluoride
DCM dichloromethane
DIPEA diisopropylethylamine
DMF dimethylformamide
DMSO Dimethyl sulfoxide
EDTA Ethylenediaminetetraacetic acid
EtOAc Ethyl acetate
EtOH ethanol
FCS Fetal Calf serum
HATU (1-[Bis(dimethylamino)methylene]-1H-1,2,3-triazolo[4,5-b]pyridinium 3-oxide hexafluorophosphate)
HIV Human immunodeficiency virus
HBr hydrogen bromide
HCl Hydrogen chloride
Jak3 Janus Kinase 3
ITK Interleukin-2 inducible T-cell kinase
K2CO3 Potassium carbonate
LiOH Lithium hydroxide
LDA Lithium diisopropylamide
LG Leaving Group
MeOH methanol
MgSO4 magnesium sulfate
μl microliter
ml milliliter
mmol millimole
MS mass spectrometry
NaHCO3 sodium bicarbonate
NK/T-cell Natural killer T-cell
NaOH sodium hydroxide
NaBH(OAc)3 sodium triacetoxyborohydride
NMP N-methyl-2-pyrrolidone
PBMC Peripheral blood mononuclear cells
PBS Phosphate buffered saline
PG Protecting Group
RLK/TXK Resting lymphocyte kinase
RPMI Roswell Park Memorial Institute medium
s-Phos 2-Dicyclohexylphosphino-2',6'-dimethoxybiphenyl
TEA triethylamine
TEC Tyrosine kinase expressed in carcinoma
Tec-family kinase The family of Tec-protein-tyrosine kinases (TEC, ITK, RLK, BMX, BTK)
THF tetrahydrofuran
Zn Zinc dust General Synthetic Methods In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, may be selected by a person skilled in the art.

The following section describes general synthetic method(s) which may be useful in the preparation of compounds of the instant invention.

Compounds of Formula I

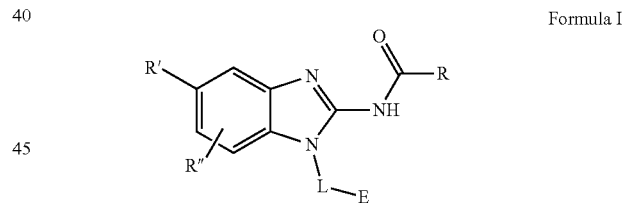

Formula I where L-E is selected from

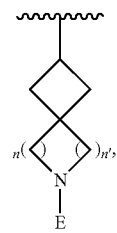

R' is selected from —CH$_2$—NH—Y and R" is hydrogen, are prepared as described below:

Intermediate A3 is obtained by reacting commercially available Intermediate A1 with an amine of formula A2 where n and n' are as defined herein and PG$^1$ is a suitable protecting group. Reductive amination of Intermediate A3 with an amine of formula YNH$_2$ where Y is as defined therein provides Intermediate A4. Protection of the alkyl amino group with a suitable protective group PG$^2$ provides Intermediate A5. Reduction of the nitro group provides Intermediate A6 which is then cyclised to the corresponding aminobenzimidazole Intermediate A7. Coupling of Intermediate A7 with an acid of formula RCO$_2$H under standard coupling conditions or with an activated acid of formula RC(O)LG where R is as defined above and LG is a leaving group provides Intermediate A8. Removal of PG$^1$ protecting group provides Intermediate A9. Compounds of Formula I are then obtained from Intermediate A9 by first coupling Intermediate 9 with an acid of formula

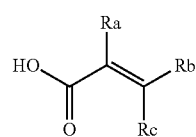

under standard coupling conditions or with an activated acid of formula

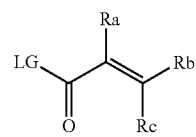

where R$^a$, R$^b$ and R$^c$ are as defined above and LG is a leaving group followed by removal of PG$^2$ protective group (see Scheme A) that is different from PG$^1$.

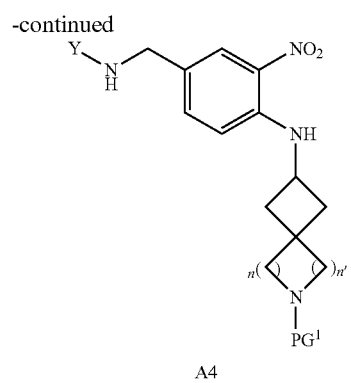

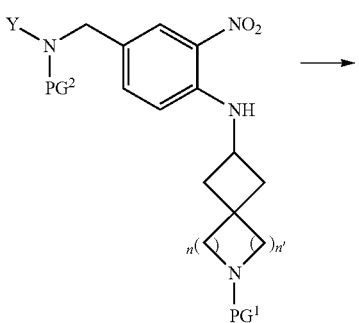

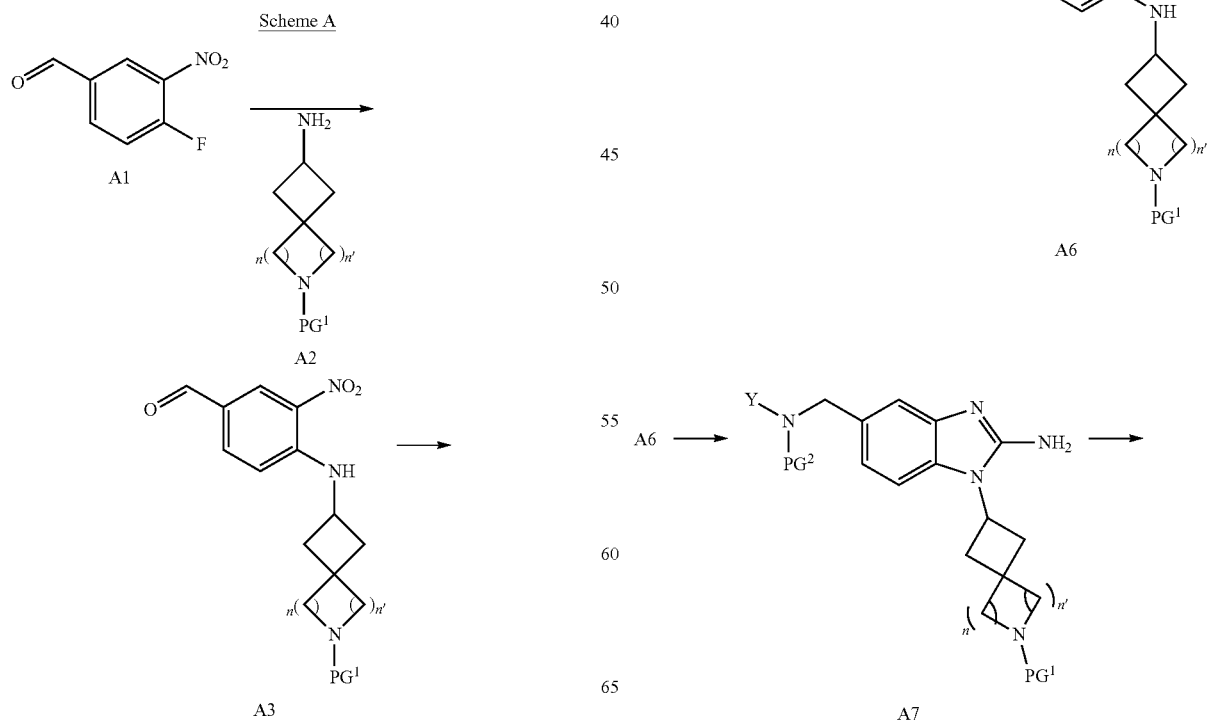

-continued

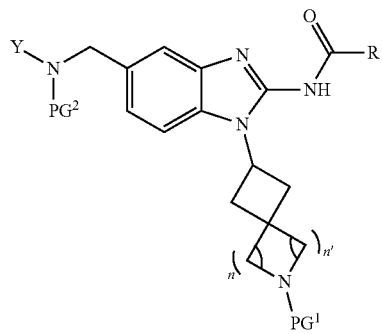

A8

A8 →
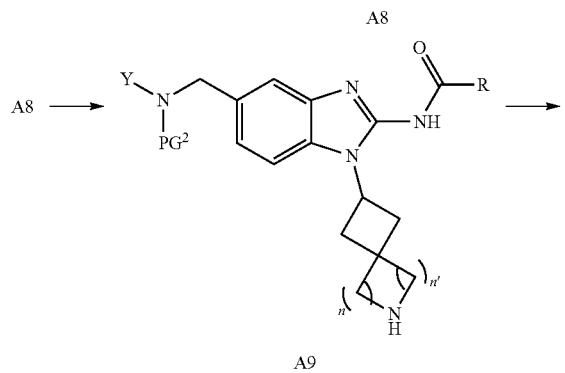

A9

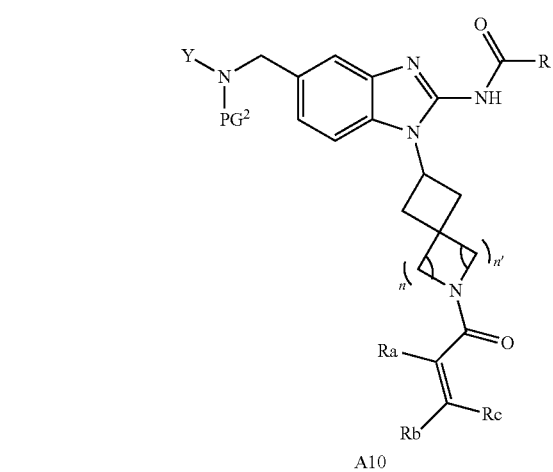

A10

A10 →
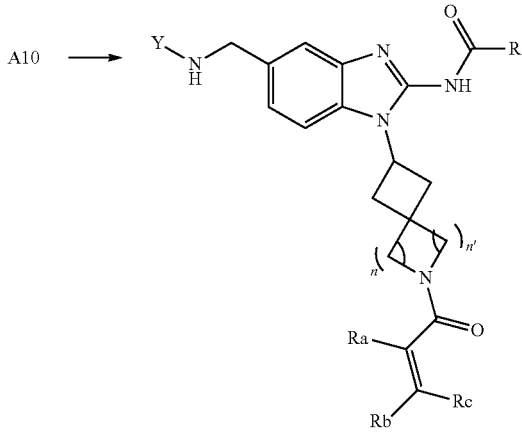

Formula I

In an alternative method, compounds of Formula I

Formula I where L-E is selected from

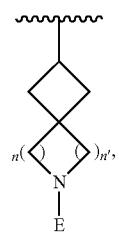

R' is selected from —CH$_2$—NH—Y and R" is hydrogen, are prepared as described below (see Scheme B):

Reduction of Intermediate A3 provides Intermediate B1. Protection of the alcohol group with a suitable protective group PG$^3$ provides Intermediate B2. Reduction of the nitro group provides Intermediate B3 which is then cyclized to the corresponding aminobenzimidazole Intermediate B4. Coupling of Intermediate B4 with an acid of formula RCO$_2$H under standard coupling conditions or with an activated acid of formula RC(O)LG where R is as defined above and LG is a leaving group provides Intermediate B5. Removal of PG$^1$ and PG$^3$ protecting groups provides Intermediate B6. Coupling of Intermediate B6 with an acid of formula

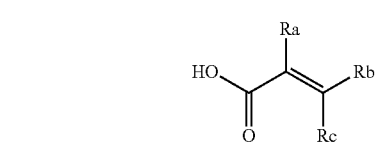

under standard coupling conditions or with an activated acid of formula

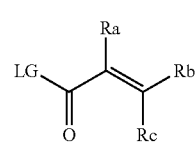

where R$^a$, R$^b$ and R$^c$ are as defined above and LG is a leaving group provides Intermediate B7 which is oxidized to provide Intermediate B8. Reductive amination of Intermediate B8 with an amine of formula Y—NH$_2$ where Y is as defined above provides compounds of Formula I.

Scheme B
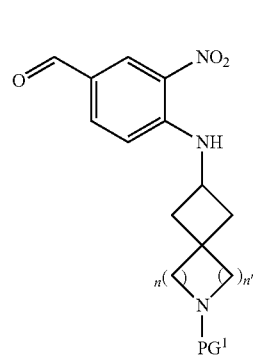
A3
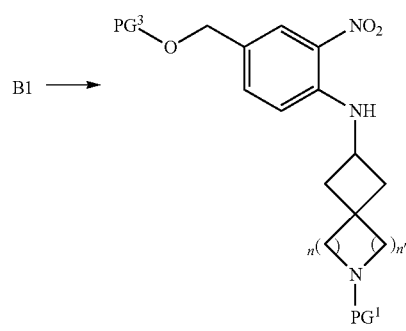
B1
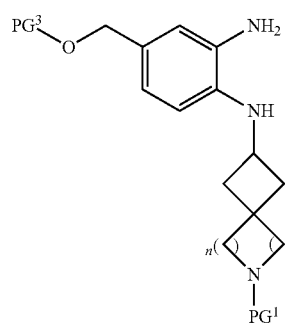
B2
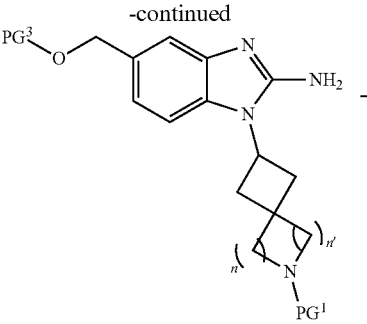
B3
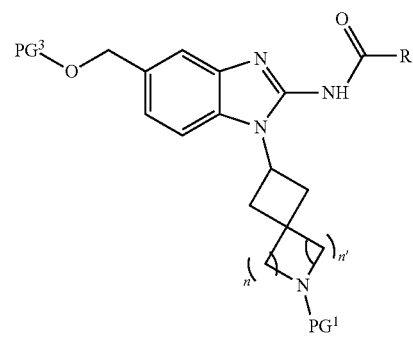
B4
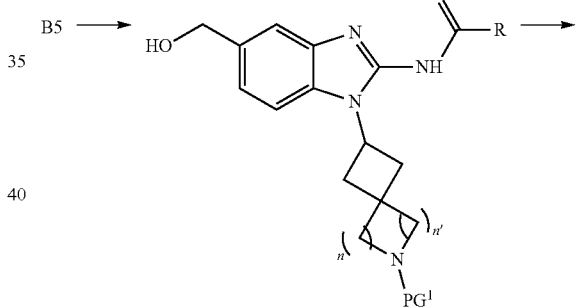
B5
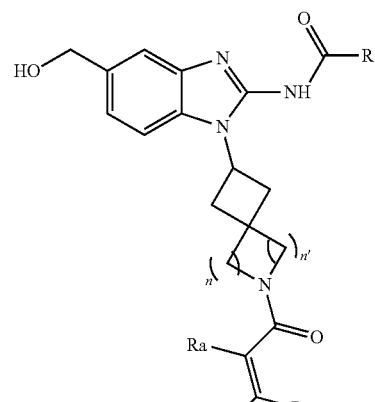
B6
B7

-continued

B7 →
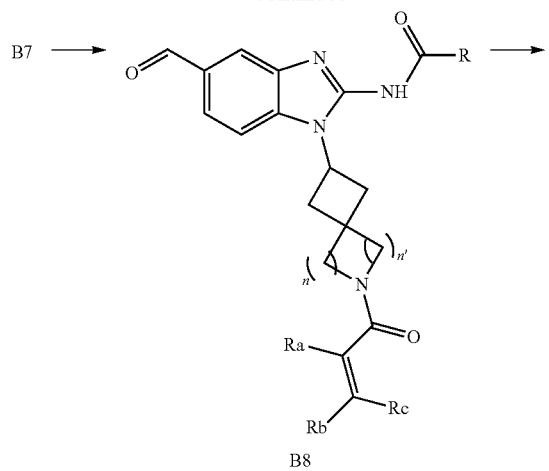
B8

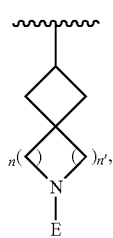
Formula I

Compounds of Formula I

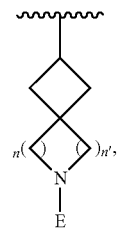
Formula I where L-E is selected from

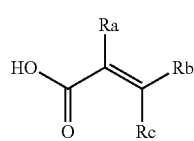

R' is selected from —CH₂—NH—Y and R" is hydrogen, are prepared in a similar manner by replacing

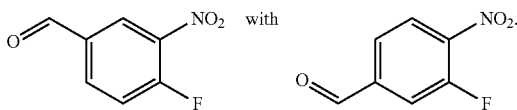 [SMILES: O=Cc1ccc(F)c([N+](=O)[O-])c1 ; O=Cc1ccc([N+](=O)[O-])c(F)c1]

Compounds of Formula I

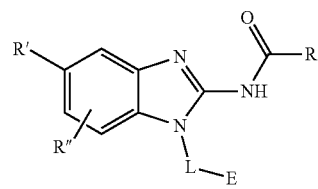
Formula I where L-E is selected from

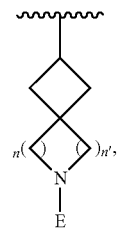

R' is selected from —NR¹C(O)Y and R" is hydrogen, are prepared as described below:

Protection of commercially available Intermediate C1 with a suitable protective group provides Intermediate C2. Alkylation of Intermediate C2 with an Intermediate of formula R¹LG where R¹ is as defined above and LG is a leaving group provides Intermediate C3.

Intermediate C4 is obtained by reacting Intermediates C3 with an amine of formula A2 where n and n' are as defined above and PG¹ is a suitable protecting group. Reduction of the nitro group provides Intermediate C5 which is then cyclized to the corresponding aminobenzimidazole Intermediate C6. Coupling of Intermediate C6 with an acid of formula RCO₂H under standard coupling conditions or with an activated acid of formula RC(O)LG where R is as defined above and LG is a leaving group provides Intermediate C7. Removal of PG¹ protecting group provides Intermediate C8. Intermediate C9 is obtained by coupling Intermediate C8 with an acid of formula

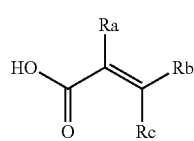

under standard coupling conditions or with an activated acid of formula

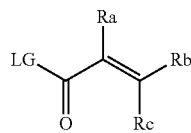

where $R^a$, $R^b$ and $R^c$ are as defined above and LG is a leaving group. Removal of $PG^4$ protecting group provides Intermediate C10. Coupling of Intermediate C10 with an acid of formula $YCO_2H$ under standard coupling conditions or with an activated acid of formula $YC(O)LG$ where Y is as defined above and LG is a leaving group provides compounds of Formula I.

Scheme C

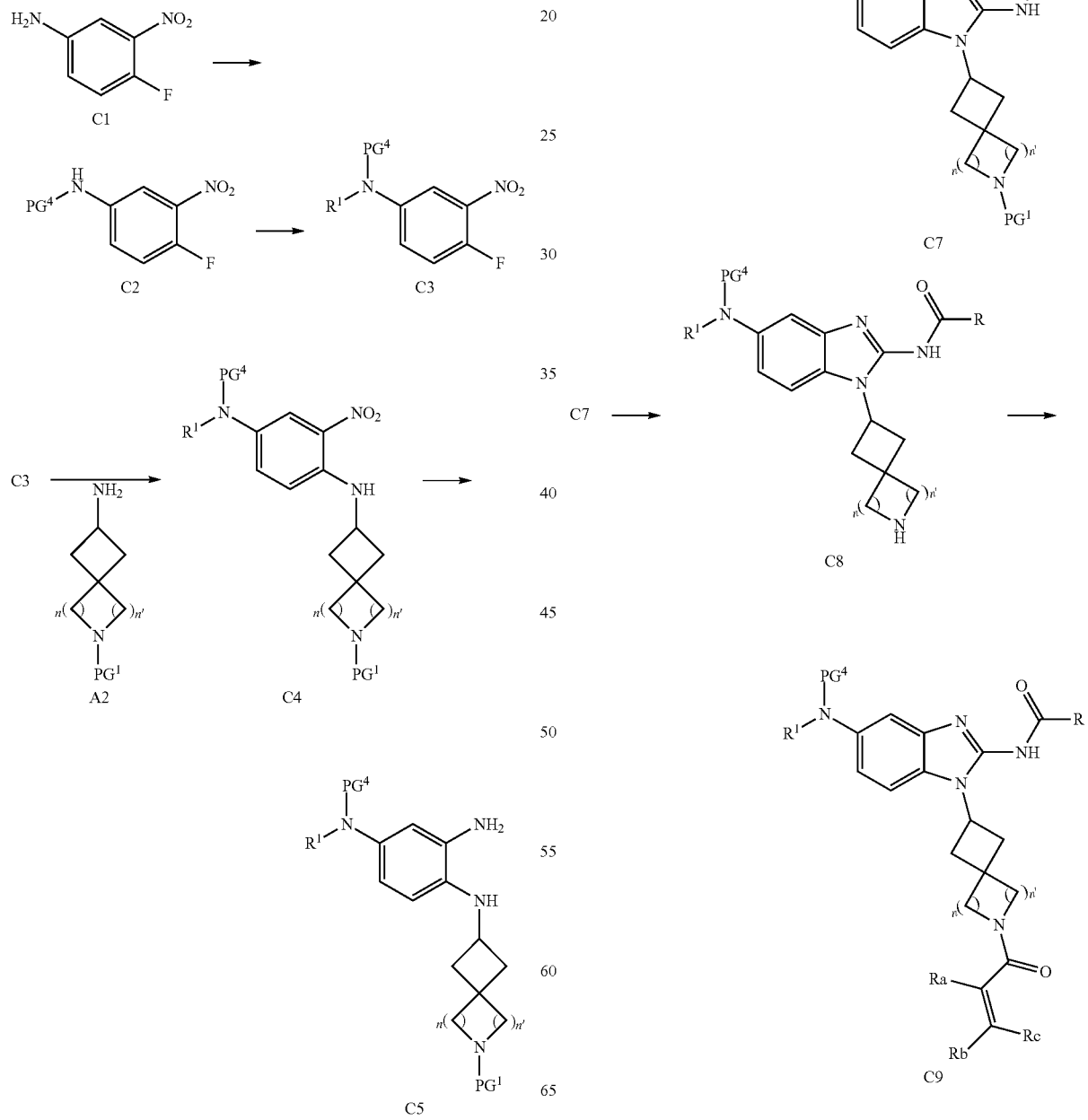

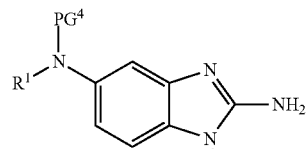

-continued

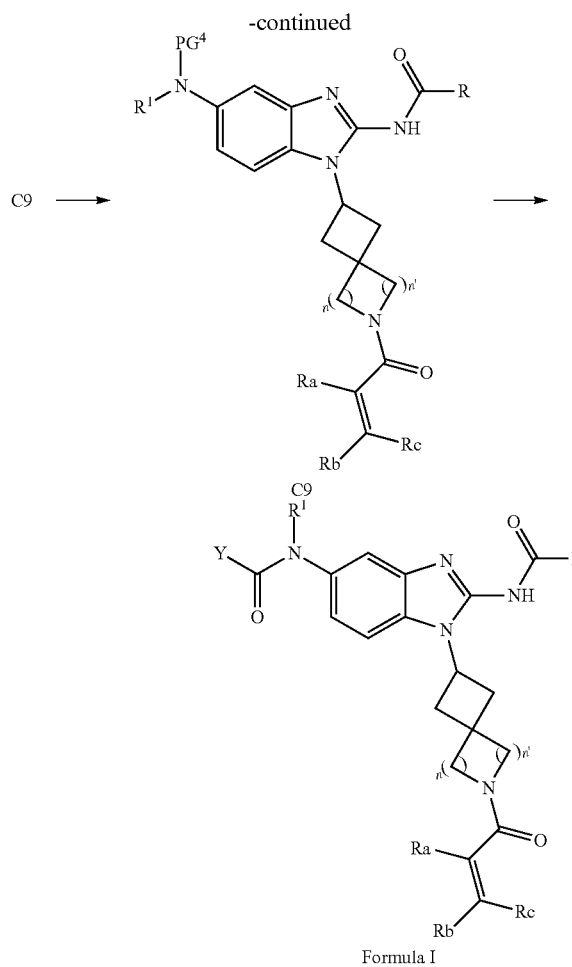

Formula I

In an alternative method, compounds of Formula I

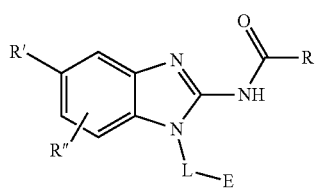

Formula I where L-E is selected from

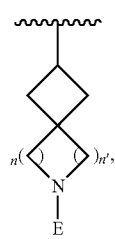

R' is selected from —NR¹C(O)Y and R" is hydrogen, are prepared as described below:

Intermediate D2 is obtained in a 2 steps sequence, from Intermediate C7, by first removing PG⁴ protective group to provide Intermediate D1, followed by reacting Intermediate D1 with an acid of formula YCO₂H under standard coupling conditions or with an activated acid of formula YC(O)LG, where Y is as defined above and LG is a leaving group, to provide Intermediate D2. Removal of PG¹ protecting group provides Intermediate D3. Compounds of Formula I are then obtained from Intermediate D3 by coupling Intermediate D3 with an acid of formula

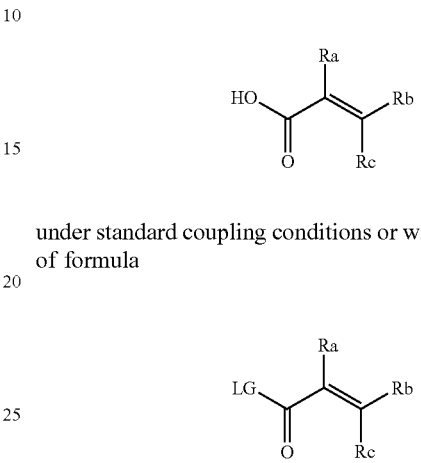

under standard coupling conditions or with an activated acid of formula where $R^a$, $R^b$ and $R^c$ are as defined above and LG is a leaving group.

Scheme D

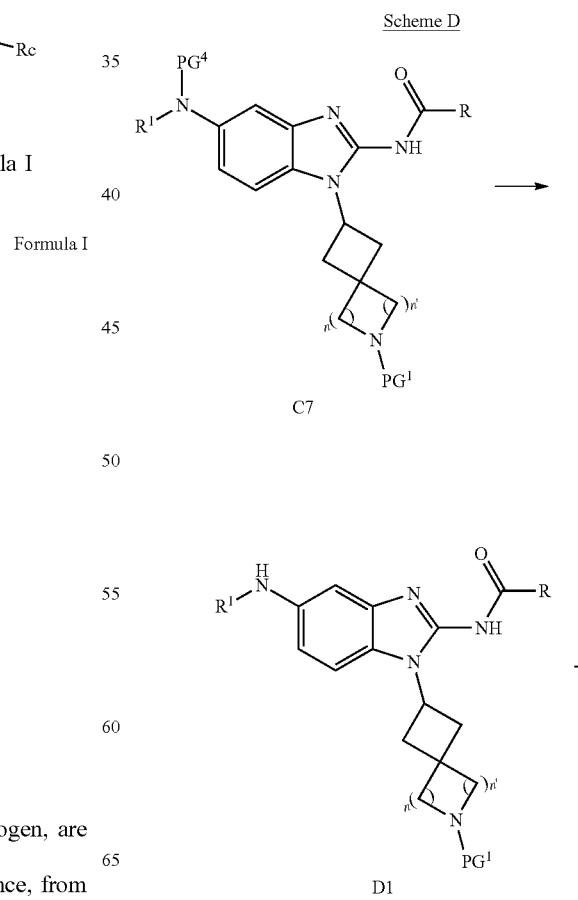

-continued

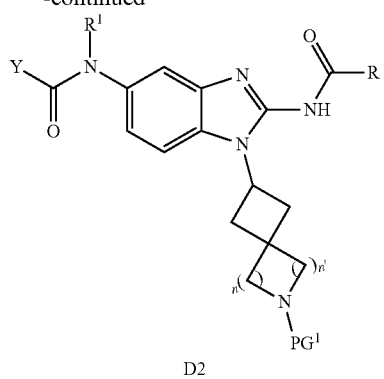

D2

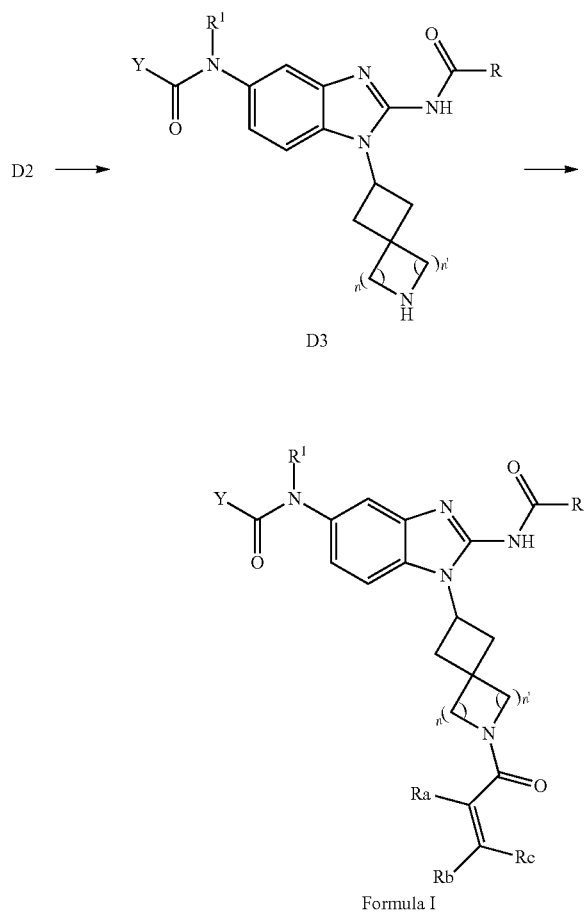

Compounds of Formula I

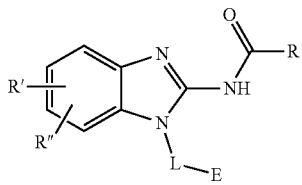

Formula I where L-E is selected from

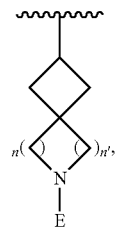

R' is selected from hydrogen, halogen, —OMe and R" is hydrogen, are prepared as described below:

Intermediate E2 is obtained by reacting commercially available Intermediate E1 with an amine of formula A2 where n and n' are as defined therein and $PG^1$ is a suitable protecting group. Reduction of the nitro group provides Intermediate E3 which is then cyclised to the corresponding aminobenzimidazole Intermediate E4. Coupling of Intermediate E4 with an acid of formula $RCO_2H$ under standard coupling conditions or with an activated acid of formula RC(O)LG where R is as defined above and LG is a leaving group provides Intermediate E5. Removal of $PG^1$ protecting group provides Intermediate E6. Compounds of Formula I are then obtained from Intermediate E6 by coupling Intermediate E6 with an acid of formula $$\underset{O}{\overset{HO}{\underset{\|}{C}}}\underset{R_c}{\overset{R_a}{=}}R_b$$

under standard coupling conditions or with an activated acid of formula $$\underset{O}{\overset{LG}{\underset{\|}{C}}}\underset{R_c}{\overset{R_a}{=}}R_b$$

where $R^a$, $R^b$ and $R^c$ are as defined above and LG is a leaving group.

Scheme E

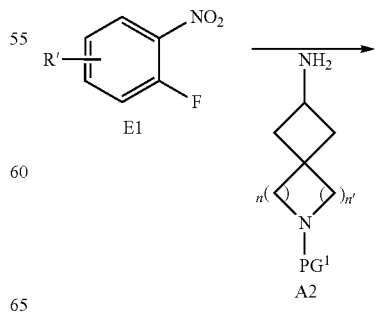

-continued

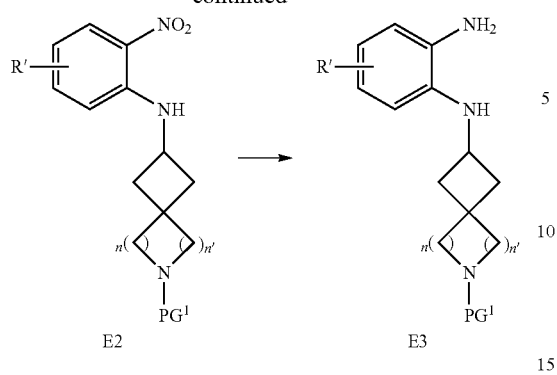

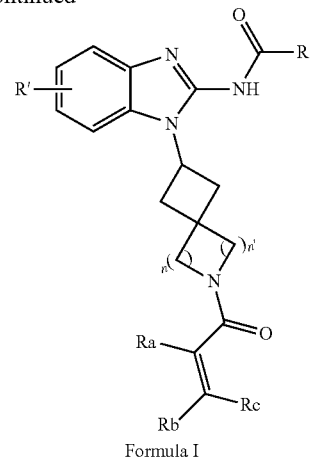

Formula I

Synthesis of Intermediates 1-c and 1-c'

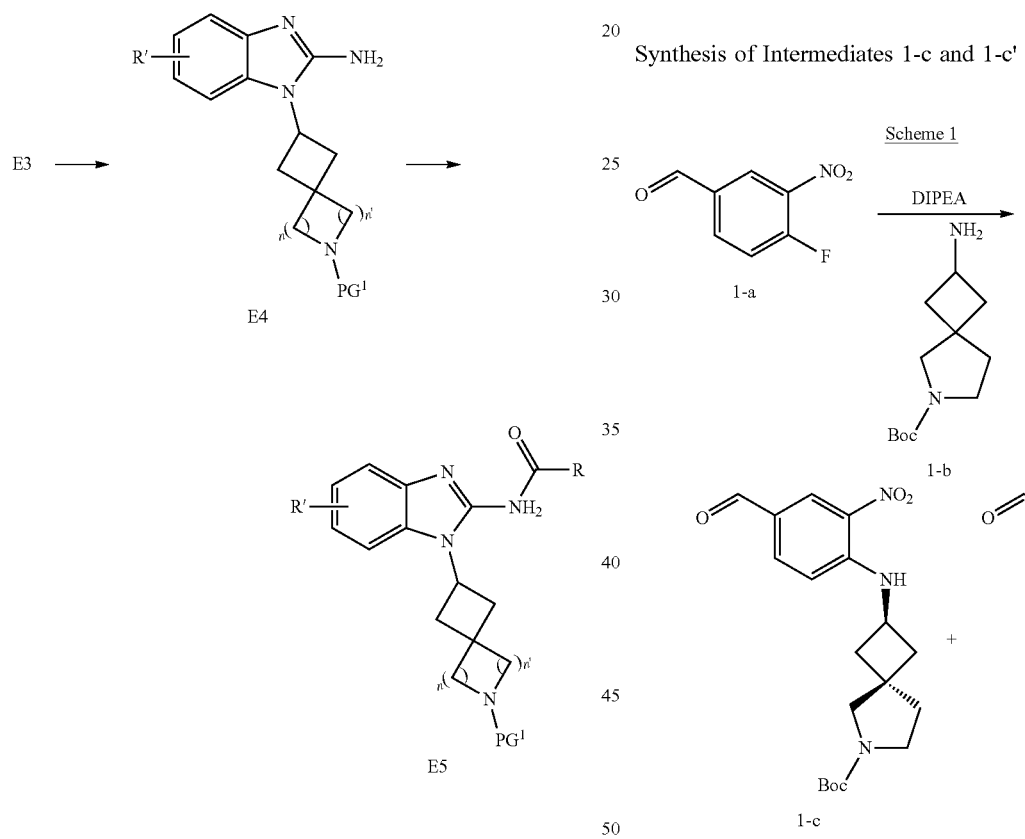

Step 1: Intermediates 1-c and 1-c'

To a solution of 4-fluoro-3-nitrobenzaldehyde 1-a (1.0 g, 6.2 mmol) and DIPEA (3.2 ml, 18.7 mmol) in acetonitrile was added a solution of Intermediate 1-b (1.5 g, 6.5 mmol) in acetonitrile. After the addition was completed, the reaction was stirred overnight at room temperature. Volatiles were removed under reduced pressure. A saturated aqueous solution of ammonium chloride and dichloromethane were added to the residue, the organic layer was separated, and the aqueous phase was extracted twice with dichloromethane. The combined organic extracts were dried over MgSO$_4$, filtered and concentrated under reduced pressure. Separation by silica gel chromatography eluting with an ethyl acetate/hexane gradient provided intermediates isomers 1-c as a yellow solid and 1-c' as a yellow solid.

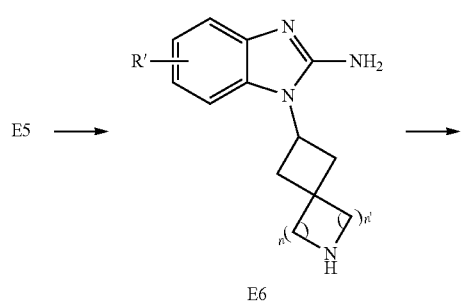

Synthesis of Intermediate 2-d

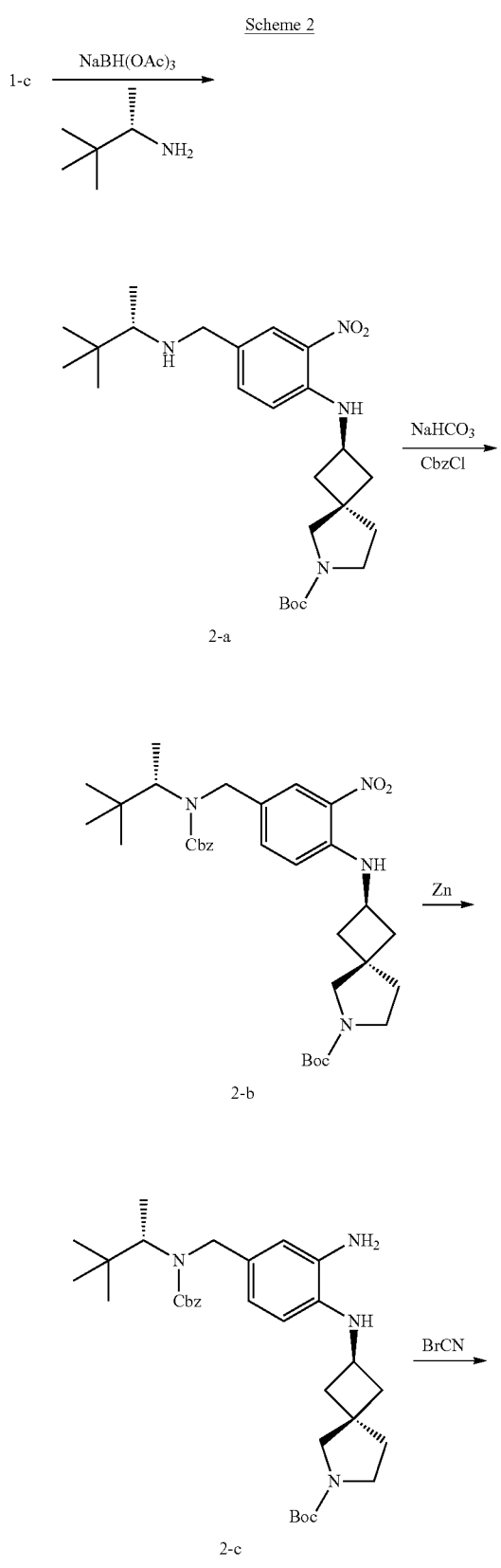

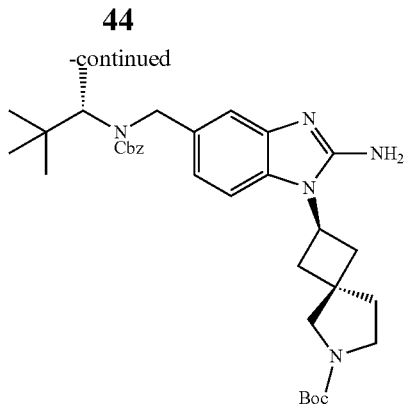

Step 1: Intermediate 2-a

To a solution of Intermediate 1-c (400 mg, 1.0 mmol) and (S)-3,3-dimethylbutan-2-amine (119 mg, 1.2 mmol) in 1,2-dichloroethane was added sodium triacetoxyborohydride (339 mg, 1.6 mmol) and the reaction was stirred overnight at room temperature. A saturated aqueous solution of NaHCO$_3$ and dichloromethane were then added, the organic layer was separated, and the aqueous phase was extracted twice with dichloromethane. The combined organic extracts were washed with brine, dried over MgSO$_4$, filtered and concentrated under reduced pressure to provide Intermediate 2-a as a yellow solid.

Step 2: Intermediate 2-b

To a solution of Intermediate 2-a (490 mg, 1.1 mmol) in dichloromethane (9.0 ml) were sequentially added a saturated aqueous solution of sodium bicarbonate (9.0 ml) and benzyl chloroformate (170 µl, 1.2 mmol) and the reaction was then stirred for 2 hours at room temperature. The organic layer was separated, and the aqueous phase was extracted twice with dichloromethane. The combined organic extracts were washed with brine, dried over MgSO$_4$, filtered and concentrated under reduced pressure. Purification by silica gel chromatography provided Intermediate 2-b as a yellow solid.

Step 3: Intermediate 2-c

To a solution of Intermediate 2-b (600 mg, 1.0 mmol) in MeOH (9.7 ml) were sequentially added ammonium chloride (1.6 g) and zinc dust (330 mg, 5.0 mmol). The reaction was stirred until completion at room temperature and then filtered over celite. The filtrate was concentrated under reduced pressure. A saturated aqueous solution of NaHCO$_3$ and ethyl acetate were added to the residue, the organic layer was separated, washed with brine, dried over MgSO$_4$, filtered and concentrated under reduced pressure to provide Intermediate 2-c as a beige solid.

Step 4: Intermediate 2-d

To a solution of Intermediate 2-c (570 mg, 1.0 mmol) in EtOH (10 ml) was added cyanogen bromide (107 mg, 1.0 mmol) and the reaction was stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 2-d as a purple solid.

Synthesis of Intermediate 3-d

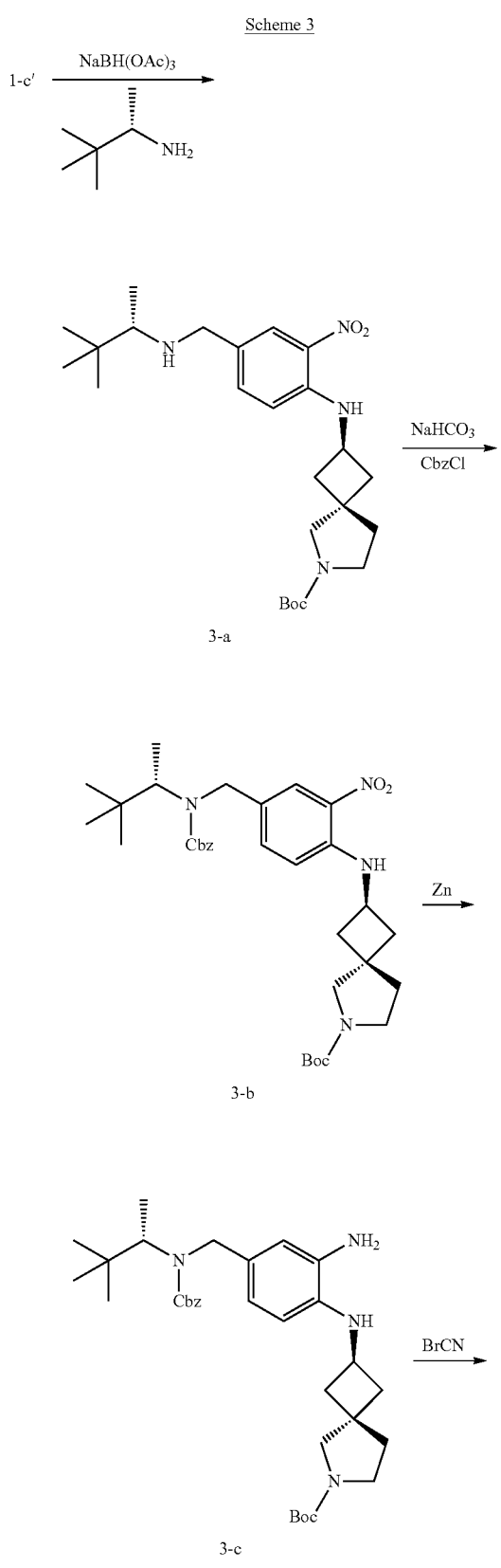

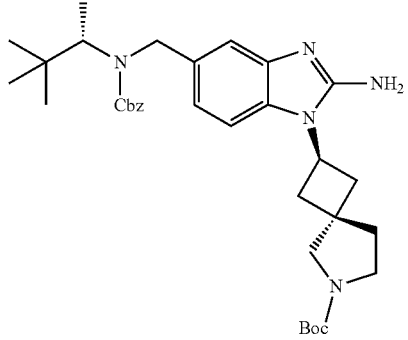

Step 1: Intermediate 3-a

To a solution of Intermediate 1-c' (680 mg, 1.8 mmol) and (S)-3,3-dimethylbutan-2-amine (202 mg, 1.9 mmol) in 1,2-dichloroethane was added sodium triacetoxyborohydride (580 mg, 2.7 mmol) and the reaction was stirred overnight at room temperature. A saturated aqueous solution of NaHCO$_3$ and dichloromethane were then added, the organic layer was separated, and the aqueous phase was extracted twice with dichloromethane. The combined organic extracts were washed with brine, dried over MgSO$_4$, filtered and concentrated under reduced pressure to provide Intermediate 3-a as a yellow solid.

Step 2: Intermediate 3-b

To a solution of Intermediate 3-a (834 mg, 1.8 mmol) in dichloromethane (9.0 ml) were sequentially added a saturated aqueous solution of sodium bicarbonate (9.0 ml) and benzyl chloroformate (638 µl, 4.5 mmol) and the reaction was then stirred until completion at room temperature. The organic layer was separated, and the aqueous phase was extracted twice with dichloromethane. The combined organic extracts were washed with brine, dried over MgSO$_4$, filtered and concentrated under reduced pressure. Purification by silica gel chromatography provided Intermediate 3-b as a yellow solid.

Step 3: Intermediate 3-c

To a solution of Intermediate 3-b (700 mg, 1.2 mmol) in MeOH (9.7 ml) was added ammonium chloride (1.8 g, 36.0 mmol) and zinc dust (385 mg, 5.9 mmol). The reaction was stirred until completion at room temperature and then filtered over celite. The filtrate was concentrated under reduced pressure. A saturated aqueous solution of NaHCO$_3$ and ethyl acetate were added to the residue, the organic layer was separated, washed with brine, dried over MgSO$_4$, filtered and concentrated under reduced pressure to provide Intermediate 3-c as a beige solid.

Step 4: Intermediate 3-d

To a solution of Intermediate 3-c (650 mg, 1.2 mmol) in EtOH (24 ml) was added cyanogen bromide (146 mg, 1.4 mmol) and the reaction was stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 3-d as a purple solid.

Synthesis of Intermediate 4-c

Synthesis of Compound 3

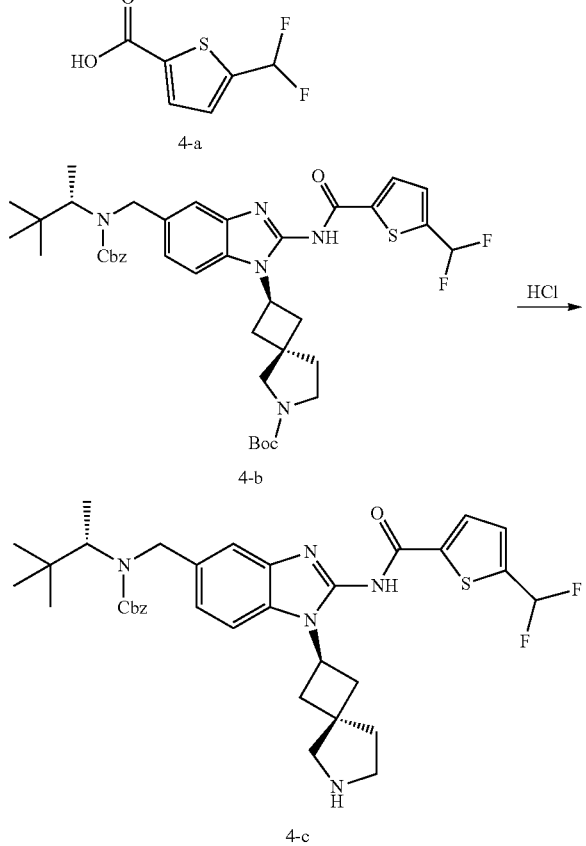

Scheme 4

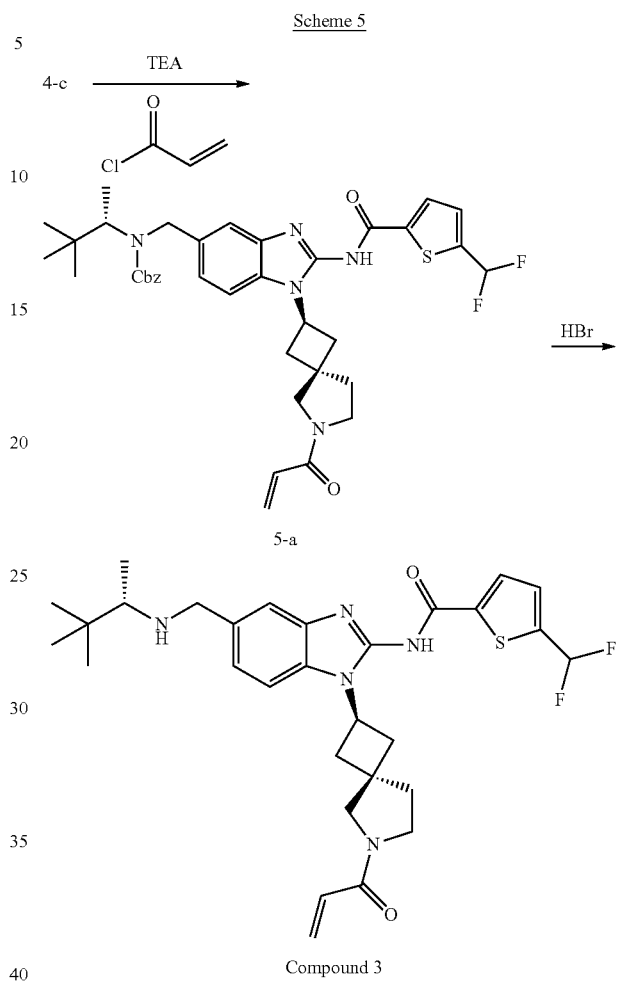

Scheme 5

Step 1: Intermediate 4-b

To a solution of 5-(difluoromethyl)thiophene-2-carboxylic acid 4-a (42 mg, 0.23 mmol) in DMF (3.5 ml) was added HATU (105 mg, 0.28 mmol) and after stirring for 30 minutes a solution of Intermediate 2-d (125 mg, 0.21 mmol) and DIPEA (111 μl, 0.64 mmol) in DMF was added. The reaction was then stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided Intermediate 4-b as a beige solid.

Step 2: Intermediate 4-c

To a solution of Intermediate 4-b (110 mg, 0.15 mmol) in MeOH (1.0 ml) was added a solution of 4N hydrogen chloride in 1,4-dioxane (5 ml, 20.0 mmol). The reaction was stirred for 1 hour at room temperature. Volatiles were removed under reduced pressure to provide Intermediate 4-c.HCl as a beige solid.

Step 1: Intermediate 5-a

To a solution of Intermediate 4-c.HCl (91 mg, 0.14 mmol) in THF (2 ml) cooled to 0° C. were sequentially added DIPEA (122 μl, 0.7 mmol) and acryloyl chloride (14 μL, 0.17 mmol) and the solution was stirred for 30 minutes at 0° C. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 5-a as beige solid.

Step 2: Compound 3

To a solution of Intermediate 5-a (99 mg, 0.14 mmol) in dichloromethane (1.5 ml) cooled to 0° C. was added a solution of 33% HBr in AcOH (1.0 ml) and the solution was then stirred until completion at 0° C. Diethyl ether was added, a precipitate formed and was collected by filtration, washed with diethyl ether and dried under vacuum. Purification by silica gel chromatography provided Compound 3 as a white solid.

Compounds 5 and 11 were prepared starting from Intermediate 2-d, in a similar manner to Compound 3, by replacing

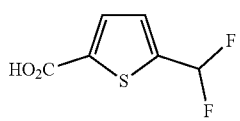 [SMILES: O=C(O)c1ccc(C(F)F)s1]

for the synthesis of Intermediate 4-b with

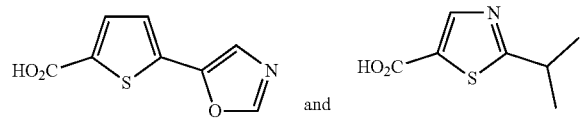

respectively.
Synthesis of Intermediate 6-b

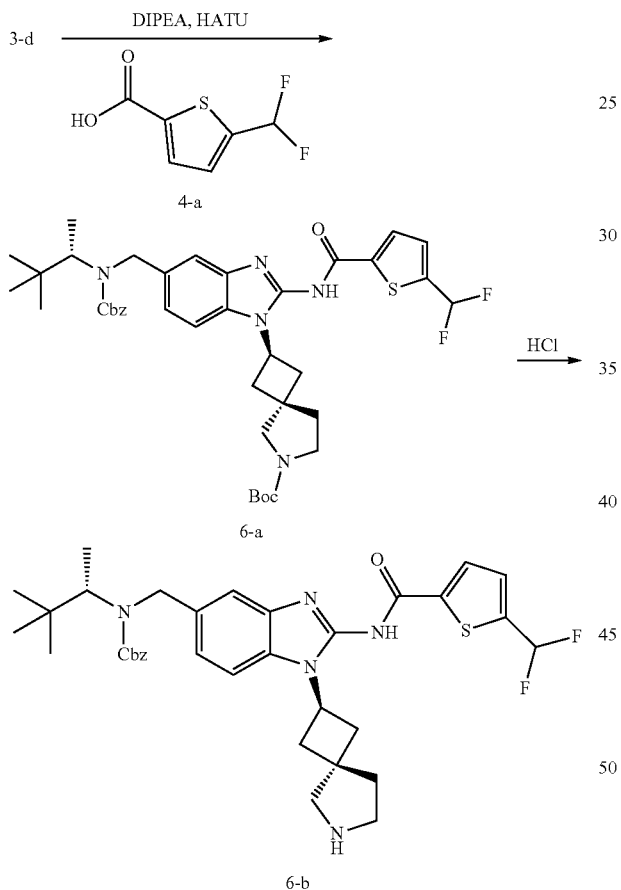

Step 1: Intermediate 6-a

To a solution of Intermediate 5-(difluoromethyl)thiophene-2-carboxylic acid 4-a (58 mg, 0.33 mmol) in DMF (3.5 ml) was added HATU (147 mg, 0.9 mmol) and after stirring for 30 minutes a solution of intermediate 3-d (175 mg, 0.3 mmol) and DIPEA (155 μl, 0.9 mmol) in DMF was added. The reaction was then stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided Intermediate 6-a as a beige solid Step 2: Intermediate 6-b To a solution of Intermediate 6-a (170 mg, 0.23 mmol) in MeOH (1 ml), was added a solution of 4N hydrogen chloride in 1,4-dioxane (5 ml, 20.0 mmol). The reaction was stirred for 1 hour at room temperature. Volatiles were removed under reduced pressure to provide Intermediate 6-b.HCl as a beige solid.

Synthesis of Compound 2

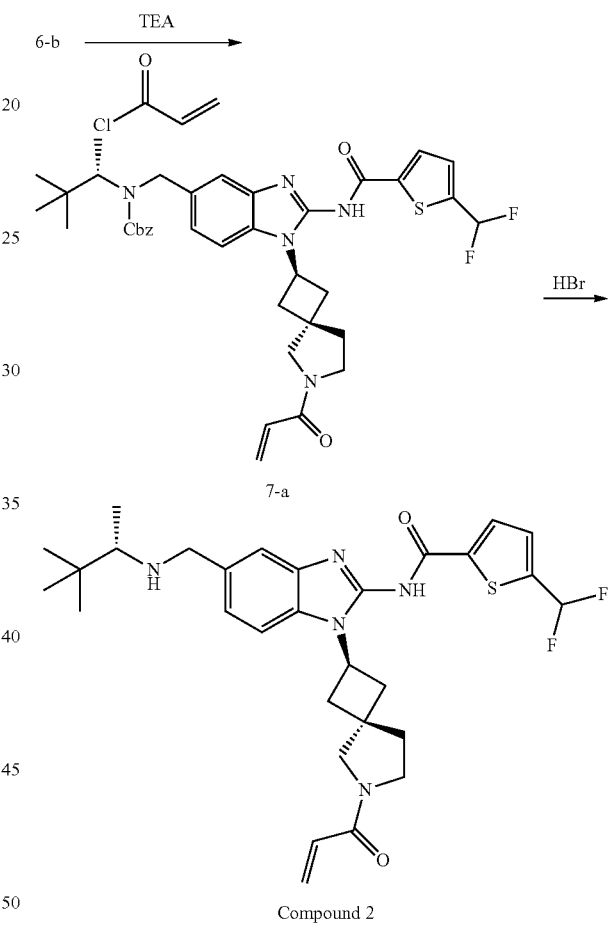

Step 1: Intermediate 7-a

To a solution of Intermediate 6-b.HCl (155 mg, 0.24 mmol) in THF (2 ml) cooled to 0° C. were sequentially added DIPEA (122 μl, 0.7 mmol) and acryloyl chloride (24 μL, 0.30 mmol) and the solution was stirred for 30 minutes at 0° C. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 7-a as a beige solid Step 2: Compound 2

To a solution of Intermediate 7-a (135 mg, 0.19 mmol) in dichloromethane (1.5 ml) cooled to 0° C. was added a solution of 33% HBr in AcOH (2.0 ml) and the solution was then stirred until completion at 0° C. Diethyl ether was added, a precipitate formed and was collected by filtration, washed with diethyl ether and dried under vacuum. Purification by reverse phase chromatography provided Compound 2 as a white solid.

Compounds 4, 6, 7, 8, 13, 14, 19, 20, 21, 22, 23, 24, 25, 26, 32, 33, 38 and 39 were prepared starting from Intermediate 3-d, in a similar manner to Compound 2, by replacing

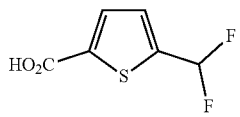

for the synthesis of Intermediate 6-a with

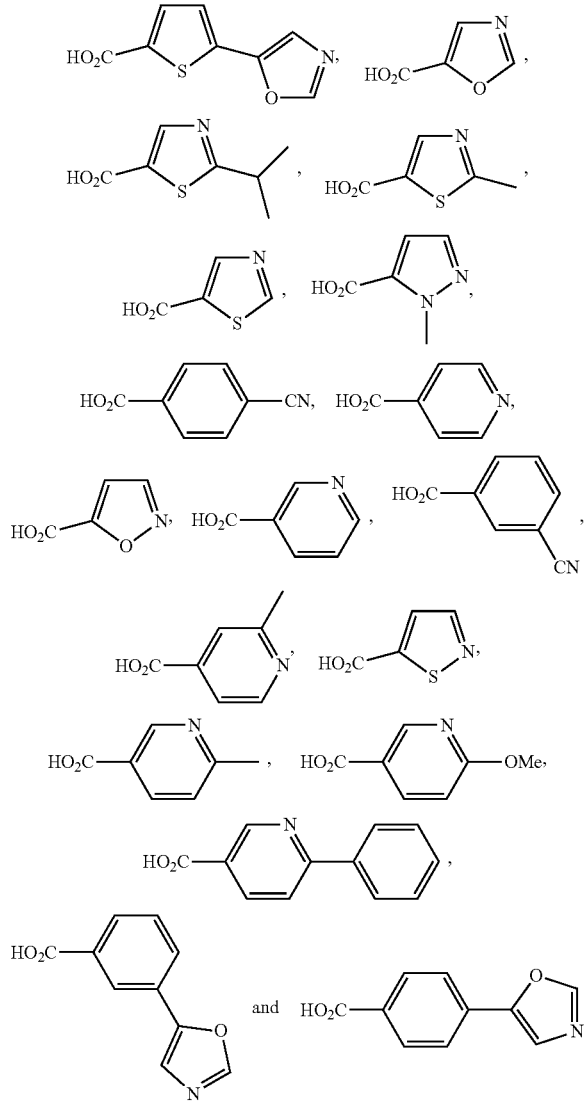

and respectively.

Synthesis of Intermediates 8-b and 8-b'

Scheme 8

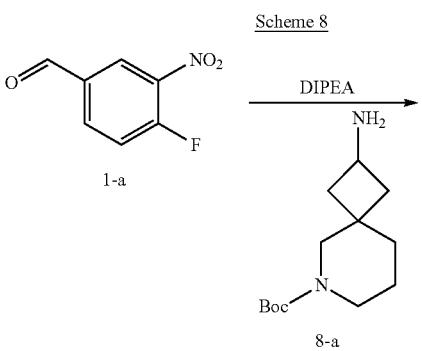

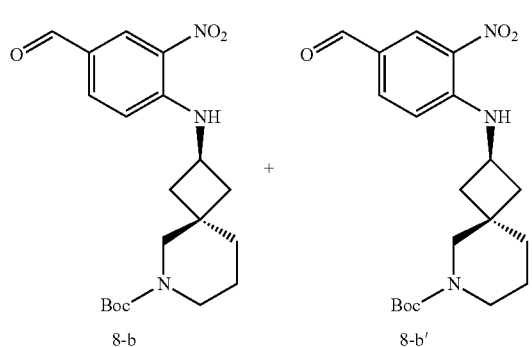

Step 1: Intermediates 8-b and 8-b'

To a solution of 4-fluoro-3-nitrobenzaldehyde 1-a (211 mg, 1.3 mmol) and DIPEA (2.5 ml, 14.4 mmol) in acetonitrile was added a solution of Intermediate 8-a (300 mg, 1.3 mmol) in acetonitrile. After the addition was completed, the reaction was stirred overnight at room temperature. Volatiles were removed under reduced pressure. A saturated aqueous solution of ammonium chloride and dichloromethane were added to the residue, the organic layer was separated, and the aqueous phase was extracted twice with dichloromethane. The combined organic extracts were washed with brine, dried over MgSO$_4$, filtered and concentrated under reduced pressure. Separation by silica gel chromatography eluting with an ethyl acetate/hexanes gradient provided Intermediates isomer 8-b as a yellow solid and 8-b' as a yellow solid.

Synthesis of Intermediate 9-d

Scheme 9

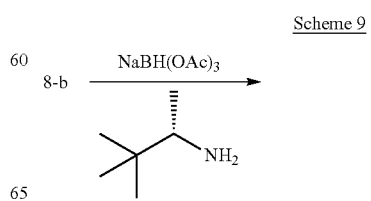

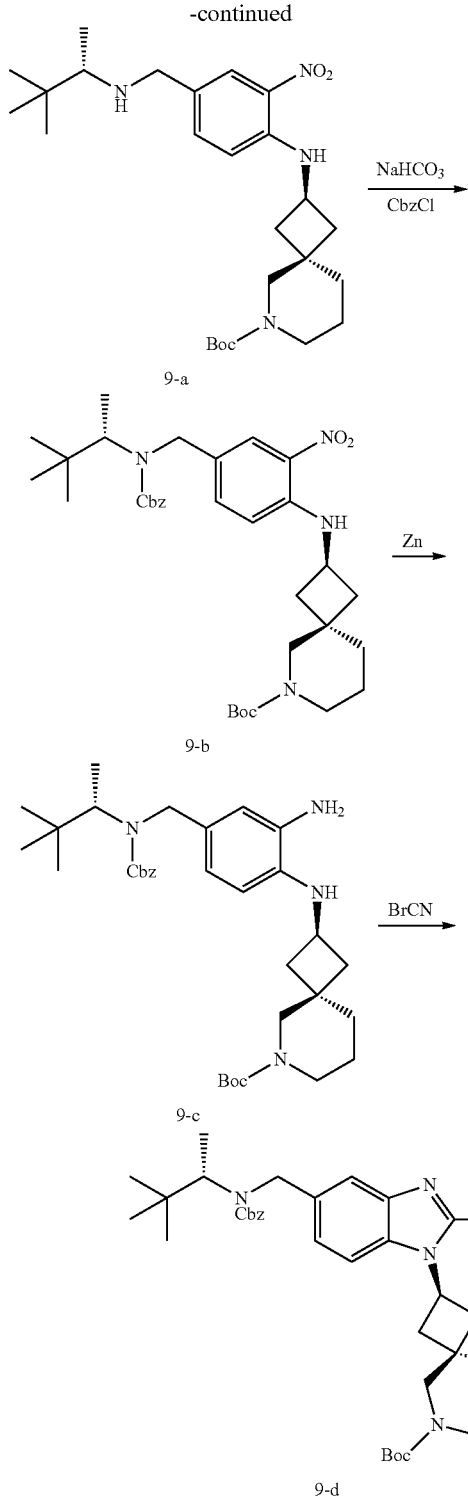

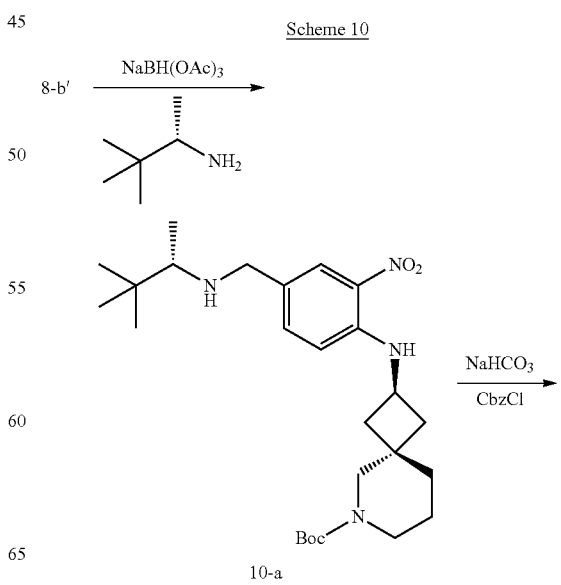

were washed with brine, dried over MgSO₄, filtered and concentrated under reduced pressure to provide Intermediate 9-a as a yellow solid.

Step 2: Intermediate 9-b

To a solution of Intermediate 9-a (1.1 g, 2.3 mmol) in dichloromethane (9.0 ml) were sequentially added a saturated aqueous solution of sodium bicarbonate (9.0 ml) and benzyl chloroformate (364 μl, 2.5 mmol) and the reaction was then stirred until completion at room temperature. The organic layer was separated, and the aqueous phase was extracted twice with dichloromethane. The combined organic extracts were washed with brine, dried over MgSO₄, filtered and concentrated under reduced pressure. Purification by silica gel chromatography provided Intermediate 9-b as a yellow solid.

Step 3: Intermediate 9-c

To a solution of Intermediate 9-b (610 mg, 1.0 mmol) was added ammonium chloride (1.6 g, 30.0 mmol) and zinc dust (328 mg, 5.0 mmol). The reaction was then stirred until completion at room temperature and then filtered over celite. The filtrate was concentrated under reduced pressure. A saturated aqueous solution of NaHCO₃ and ethyl acetate were added to the residue, the organic layer was separated, washed with brine, dried over MgSO₄, filtered and concentrated under reduced pressure to provide Intermediate 9-c as a beige solid.

Step 4: Intermediate 9-d

To a solution of Intermediate 9-c (475 mg, 0.8 mmol) in EtOH (10.0 ml) was added cyanogen bromide (109 mg, 1.0 mmol) and the reaction was stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO₄, filtered and concentrated under reduced pressure to provide Intermediate 9-d as a purple solid.

Synthesis of Intermediate 10-d

Scheme 10

Step 1: Intermediate 9-a

To a solution of Intermediate 8-b (900 mg, 2.3 mmol) and (S)-3,3-dimethylbutan-2-amine (380 mg, 2.8 mmol) in 1,2-dichloroethane was added sodium triacetoxyborohydride (735 mg, 3.5 mmol) and the reaction was stirred at room temperature overnight. A saturated aqueous solution of NaHCO₃ and dichloromethane were then added, the organic layer was separated, and the aqueous phase was extracted twice with dichloromethane. The combined organic extracts -continued

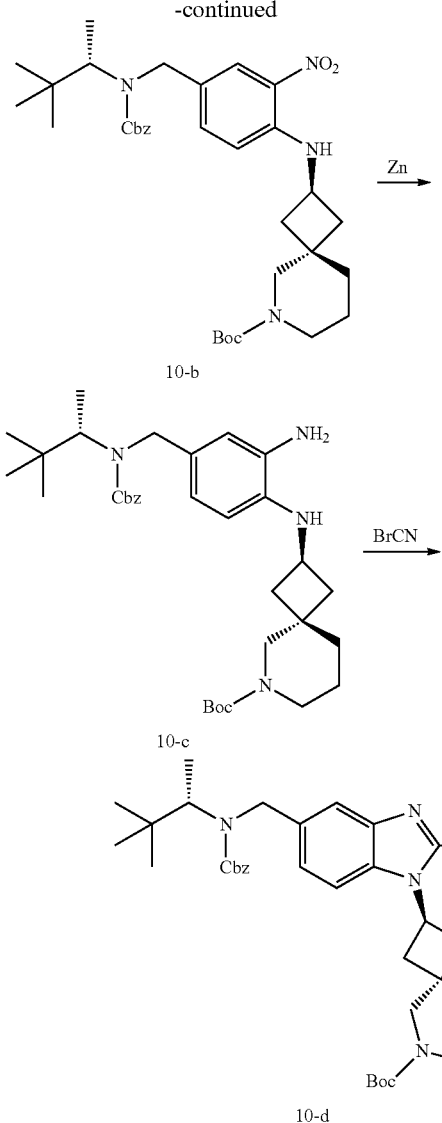

Step 1: Intermediate 10-a

To a solution of Intermediate 8-b' (450 mg, 1.2 mmol) and (S)-3,3-dimethylbutan-2-amine 2-a (140 mg, 1.4 mmol) in 1,2-dichloroethane was added sodium triacetoxyborohydride (367 mg, 1.7 mmol) and the reaction was stirred overnight at room temperature. A saturated aqueous solution of NaHCO$_3$ and dichloromethane were then added, the organic layer was separated, and the aqueous phase was extracted twice with dichloromethane. The combined organic extracts were washed with brine, dried over MgSO$_4$, filtered and concentrated under reduced pressure to provide Intermediate 10-a as a yellow solid.

Step 2: Intermediate 10-b

To a solution of Intermediate 10-a (550 mg, 1.2 mmol) in dichloromethane (9.0 ml) were sequentially added a saturated aqueous solution of sodium bicarbonate (9.0 ml) and benzyl chloroformate (182 µl, 1.3 mmol) and the reaction was then stirred until completion at room temperature. The organic layer was separated, and the aqueous phase was extracted twice with dichloromethane. The combined organic extracts were washed with brine, dried over MgSO$_4$, filtered and concentrated under reduced pressure. Purification by silica gel chromatography provided Intermediate 10-b as a yellow solid.

Step 3: Intermediate 10-c

To a solution of Intermediate 10-b (500 mg, 0.8 mmol) were sequentially added ammonium chloride (1.3 g, 25.0 mmol) and zinc dust (270 mg, 4.1 mmol). The reaction was then stirred until completion at room temperature and then filtered over celite. The filtrate was concentrated under reduced pressure. Ethyl acetate and a saturated aqueous solution of NaHCO$_3$ were added to the residue, the organic layer was separated, washed with brine, dried over MgSO$_4$, filtered and concentrated under reduced pressure to provide Intermediate 10-c as a beige foam.

Step 4: Intermediate 10-d

To a solution of Intermediate 10-c (1.3 g, 2.4 mmol) in EtOH (10.0 ml) was added cyanogen bromide (302 mg, 2.8 mmol) and the reaction was stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 10-d as a purple solid.

Synthesis of Intermediate 11-b

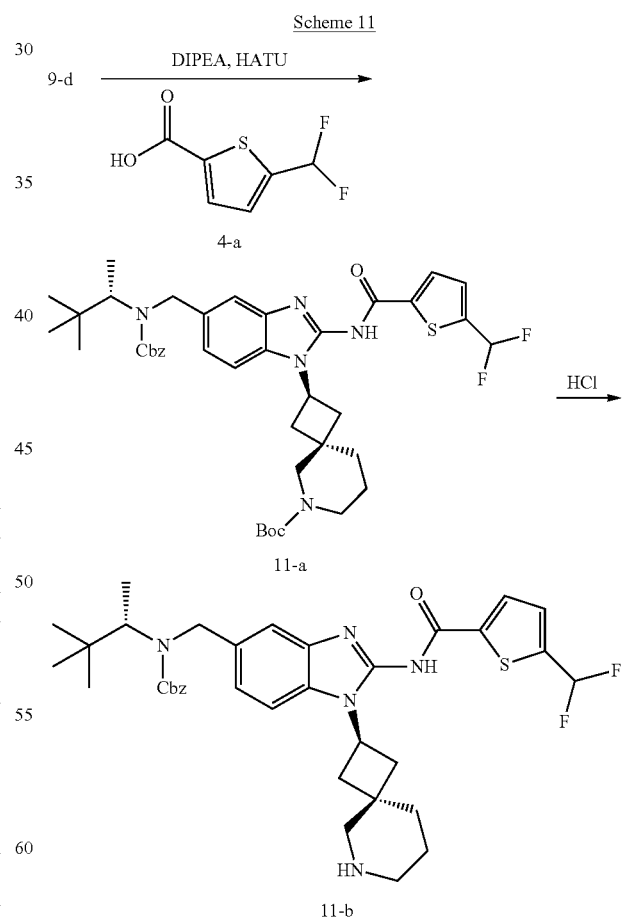

Step 1: Intermediate 11-a

To a solution of 5-(difluoromethyl)thiophene-2-carboxylic acid 4-a (49 mg, 0.27 mmol) in DMF (3.5 ml) was added HATU (123 mg, 0.323 mmol) and after stirring for 30 minutes a solution of Intermediate 9-d (150 mg, 0.25 mmol) and DIPEA (130 µl, 0.74 mmol) in DMF was added. The reaction was then stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO₄, filtered and concentrated under reduced pressure. Purification by silica gel chromatography provided Intermediate 11-a as a beige solid.

Step 2: Intermediate 11-b

To a solution of Intermediate 11-a (150 mg, 0.2 mmol) in MeOH (1 ml), was added a solution of 4N hydrogen chloride in 1,4-dioxane (5.0 ml, 20.0 mmol). The reaction was stirred for 1 hour. Volatiles were removed under reduced pressure to provide Intermediate 11-b.HCl as a beige solid.

Synthesis of Compound 10

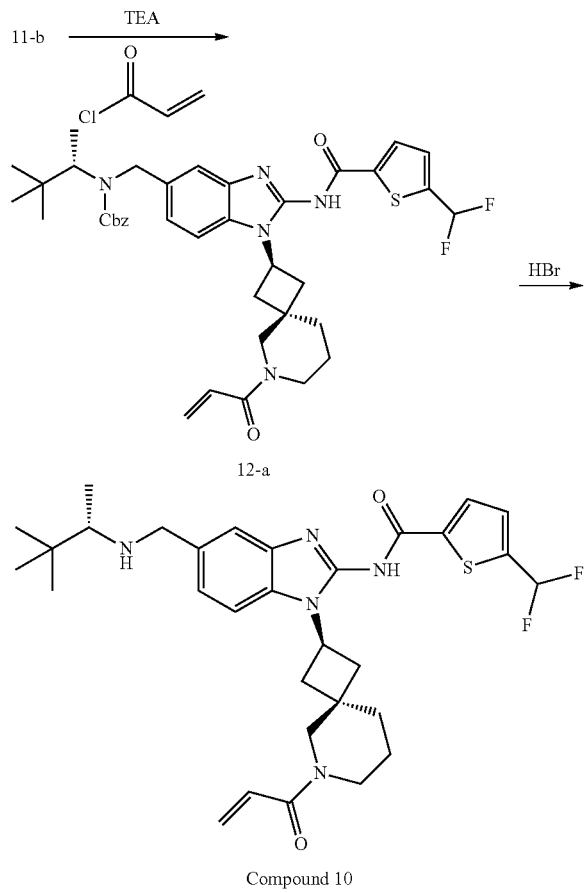

Step 2: Compound 10

To a solution of Intermediate 12-a (100 mg, 0.14 mmol) in dichloromethane (1.5 ml) cooled to 0° C. was added a solution of 33% HBr in AcOH (2 ml) and the solution was then stirred until completion at 0° C. Diethyl ether was added, a precipitate formed and was collected by filtration, washed with diethyl ether and dried under vacuum. Purification by reverse phase chromatography provided Compound 10 as a white solid.

Synthesis of Intermediate 13-b

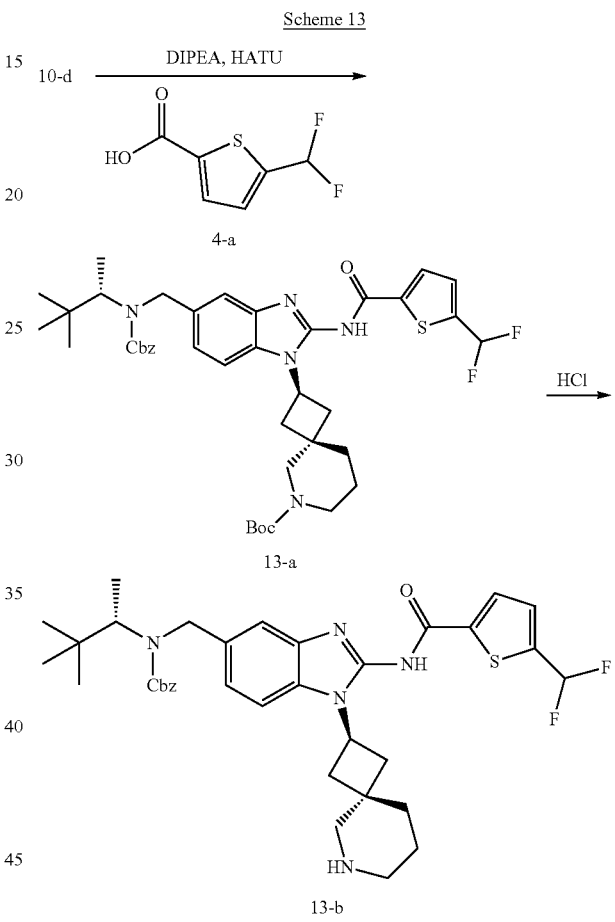

Step 1: Intermediate 13-a

To a solution of 5-(difluoromethyl)thiophene-2-carboxylic acid 4-a (49 mg, 0.27 mmol) in DMF (3.5 ml) was added HATU (123 mg, 0.32 mmol), after stirring for 30 minutes a solution of Intermediate 10-d (150 mg, 0.25 mmol) and DIPEA (130 µl, 0.74 mmol) in DMF was added. The reaction was then stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO₄, filtered and concentrated under reduced pressure. Purification by silica gel chromatography provided Intermediate 13-a as a beige solid.

Step 2: Intermediate 13-b

To a solution of Intermediate 13-a (110 mg, 0.14 mmol) in MeOH (1 ml), was added a solution of 4N hydrogen chloride in 1,4-dioxane (5.0 ml, 20.0 mmol). The reaction Step 1: Intermediate 12-a To a solution of Intermediate 11-b.HCl (100 mg, 0.14 mmol) in THF (2 ml) cooled to 0° C. were sequentially added DIPEA (122 µl, 0.7 mmol) and acryloyl chloride (14 µL, 0.17 mmol) and the solution was stirred for 30 minutes at 0° C. A saturated aqueous solution of ammonium chloride and ethyl acetate were then added, the organic layer was separated, and the aqueous phase was extracted twice with ethyl acetate. The combined organic extracts were washed with brine, dried over MgSO₄, filtered and concentrated under reduced pressure to provide Intermediate 12-a as a white foam.

Synthesis of Compound 9

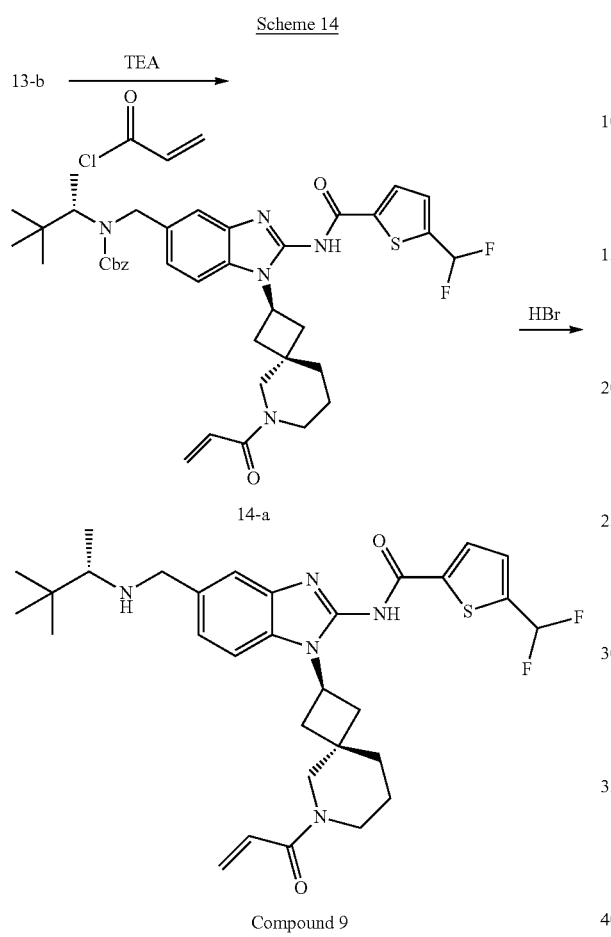

Synthesis of Intermediate 15-b

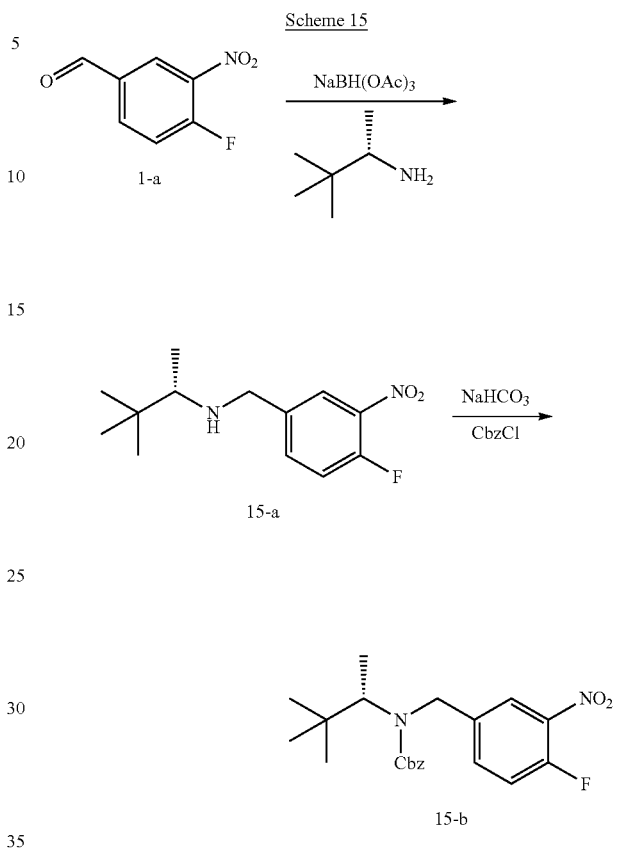

Step 1: Intermediate 14-a

To a solution of Intermediate 13-b.HCl (100 mg, 0.14 mmol) in THF (2 ml) cooled to 0° C. were sequentially added DIPEA (122 μl, 0.7 mmol) and acryloyl chloride (14 μL, 0.17 mmol) and the solution was stirred at 0° C. for 15 minutes. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 14-a as a beige foam.

Step 2: Compound 9

To a solution of Intermediate 14-a (100 mg, 0.14 mmol)) in dichloromethane (1.5 ml) cooled to 0° C. was added a solution of 33% HBr in AcOH (2 ml) and the solution was then stirred until completion at 0° C. Diethyl ether was added, a precipitate formed and was collected by filtration, washed with diethyl ether and dried under vacuum. Purification by reverse phase chromatography provided Compound 9 as a white solid.

Step 1: Intermediate 15-a

To a solution of Intermediate 1-a (1.0 g, 5.9 mmol) and (S)-3,3-dimethylbutan-2-amine (600 mg, 5.9 mmol) in 1,2-dichloroethane was added sodium triacetoxyborohydride (1.8 g, 8.9 mmol) and the reaction was stirred at room temperature overnight. A saturated aqueous solution of NaHCO$_3$ and dichloromethane were then added, the organic layer was separated, and the aqueous phase was extracted twice with dichloromethane. The combined organic extracts were washed with brine, dried over MgSO$_4$, filtered and concentrated under reduced pressure to provide Intermediate 15-a as a yellow solid.

Step 2: Intermediate 15-b

To a solution of Intermediate 15-a (1.46 g, 5.74 mmol) in dichloromethane (15.0 ml) were sequentially added a saturated aqueous solution of sodium bicarbonate (8.0 ml) and benzyl chloroformate (1.2 ml, 8.6 mmol) and the reaction was then stirred until completion. The organic layer was separated, and the aqueous phase was extracted twice with dichloromethane. The combined organic extracts were washed with brine, dried over MgSO$_4$, filtered and concentrated under reduced pressure. Purification by silica gel chromatography provided Intermediate 15-b as a yellow solid.

Synthesis of Intermediate 16-d

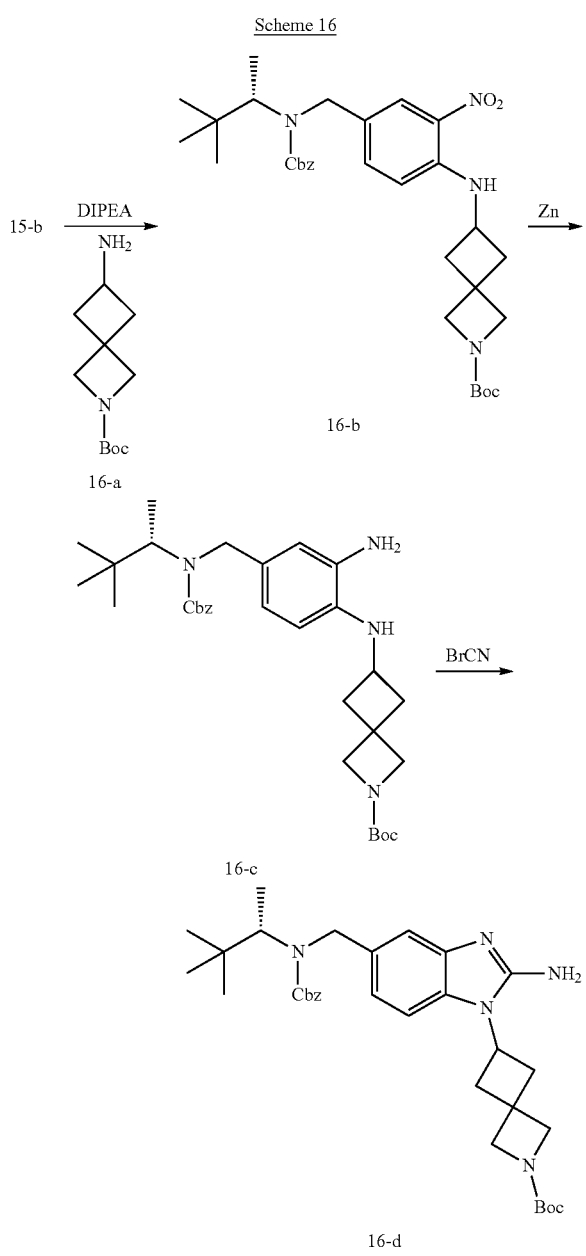

Step 1: Intermediate 16-b

To a solution of Intermediate 15-b (1.24 g, 3.2 mmol) and DIPEA (2.0 g, 16.0 mmol) in acetonitrile (20 ml) was added a solution of Intermediate 16-a (680 mg, 3.2 mmol) in acetonitrile (10 ml). After the addition was completed, the reaction was refluxed for 48 hours and then cooled to room temperature. Volatiles were removed under reduced pressure. A saturated aqueous solution of ammonium chloride and dichloromethane were added to the residue, the organic layer was separated, and the aqueous phase was extracted twice with dichloromethane. The combined organic extracts were washed with brine, dried over MgSO$_4$, filtered and concentrated under reduced pressure. Purification by silica gel chromatography provided Intermediate 16-b as a yellow solid.

Step 2: Intermediate 16-c

To a solution of Intermediate 16-b (860 mg, 1.5 mmol) in MeOH were sequentially added ammonium chloride (1.3 g, 25.0 mmol) and zinc dust (484 mg, 7.4 mmol). The reaction was then stirred until completion at room temperature and then filtered over celite. The filtrate was concentrated under reduced pressure. A saturated aqueous solution of NaHCO$_3$ and ethyl acetate were added to the residue, the organic layer was separated, washed with brine, dried over MgSO$_4$, filtered and concentrated under reduced pressure to provide Intermediate 16-c as a beige foam.

Step 3: Intermediate 16-d

To a solution of Intermediate 16-c (718 mg, 1.3 mmol) in EtOH (10 ml) was added cyanogen bromide (166 mg, 1.6 mmol) and the reaction was stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 16-d as a purple solid.

Synthesis of Intermediate 17-b

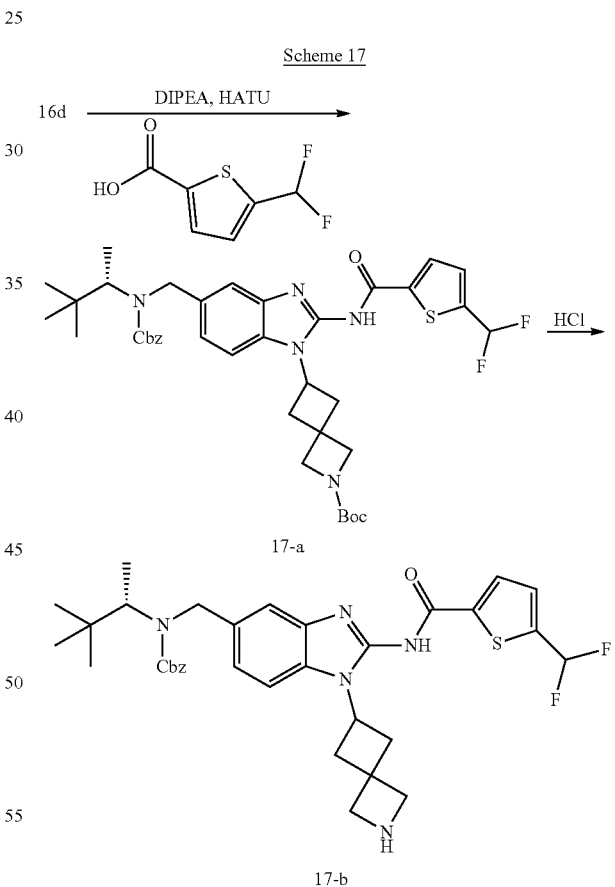

Step 1: Intermediate 17-a

To a solution of 5-(difluoromethyl)thiophene-2-carboxylic acid 4-a (267 mg, 1.5 mmol) in DMF (3.5 ml) was added HATU (618 mg, 1.6 mmol) and after stirring for 30 minutes a solution of Intermediate 16-d (720 mg, 1.25 mmol) and DIPEA (655 µl, 3.0 mmol) in DMF was added. The reaction was then stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided Intermediate 17-a as a beige solid.

Step 2: Intermediate 17-b

To a solution of Intermediate 17-a (910 mg, 1.25 mmol) in MeOH (1 ml), was added a solution of 4N hydrogen chloride in 1,4-dioxane (5.0 ml, 20.0 mmol). The reaction was stirred for 1 hour. Volatiles were removed under reduced pressure to provide Intermediate 17-b.HCl as a white solid.

Synthesis of Compound 1

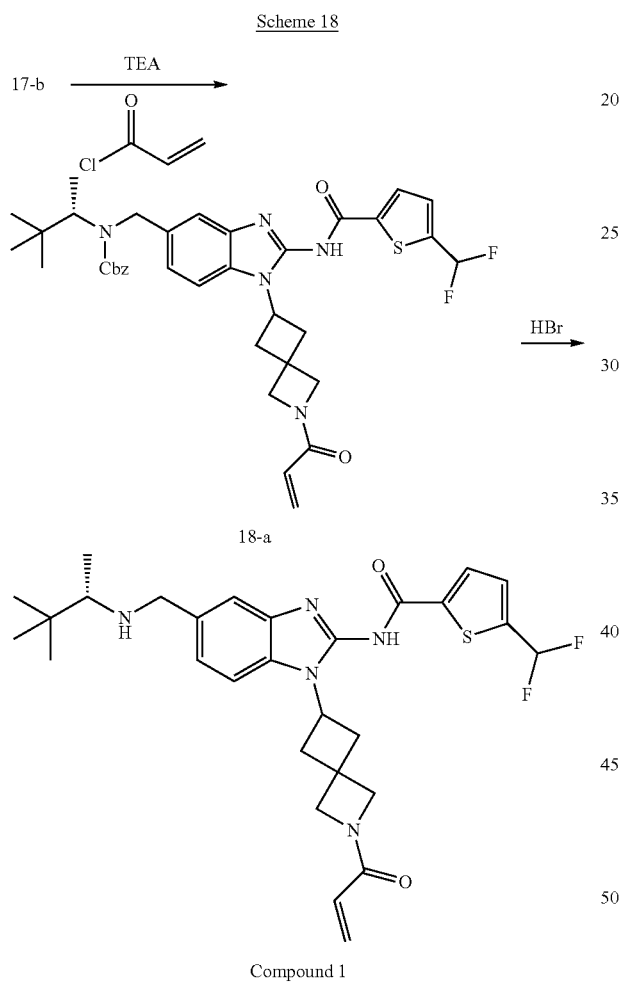

Step 1: Intermediate 18-a

To a solution of Intermediate 17-b.HCl (937 mg, 1.4 mmol) in THF (14 ml) cooled to 0° C. were sequentially added TEA (2.0 ml, 14.7 mmol) and acryloyl chloride (179 µL, 2.2 mmol) and the solution was stirred for 15 minutes at 0° C. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 18-a as a beige foam.

Step 2: Compound 1

To a solution of Intermediate 18-a (940 mg, 1.4 mmol) in dichloromethane (3 ml) cooled to 0° C. was added a solution of 33% HBr in AcOH (5 ml) and the solution was then stirred until completion at 0° C. Diethyl ether was added, a precipitate formed and was collected by filtration, washed with diethyl ether and dried under vacuum. Purification by reverse phase chromatography provided Compound 1 as a white solid.

Synthesis of Intermediate 19-b

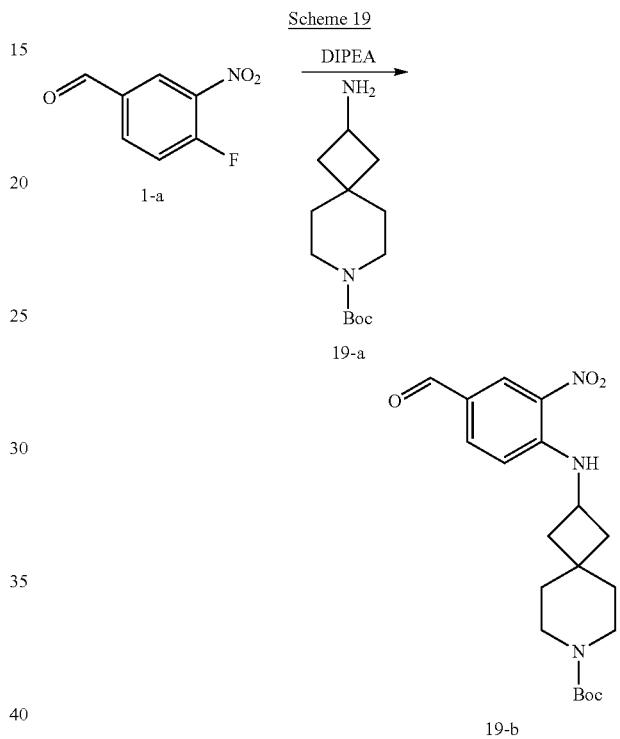

To a solution of 4-fluoro-3-nitrobenzaldehyde 1-a (600 mg, 3.6 mmol) and DIPEA (2.5 ml, 14.4 mmol) in acetonitrile was added a solution of 19-a (700 mg, 2.9 mmol) in acetonitrile. After the addition was completed, the reaction was stirred overnight at room temperature. Volatiles were removed under reduced pressure. A saturated aqueous solution of ammonium chloride and dichloromethane were added to the residue, the organic layer was separated, and the aqueous phase was extracted twice with dichloromethane. The combined organic extracts were washed with brine, dried over MgSO$_4$, filtered and concentrated under reduced pressure. Purification by silica gel chromatography provided Intermediate 19-b as a yellow solid.

Synthesis of Intermediate 20-d

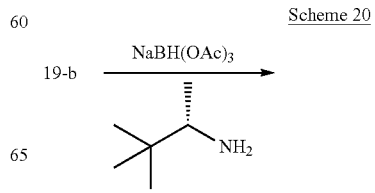

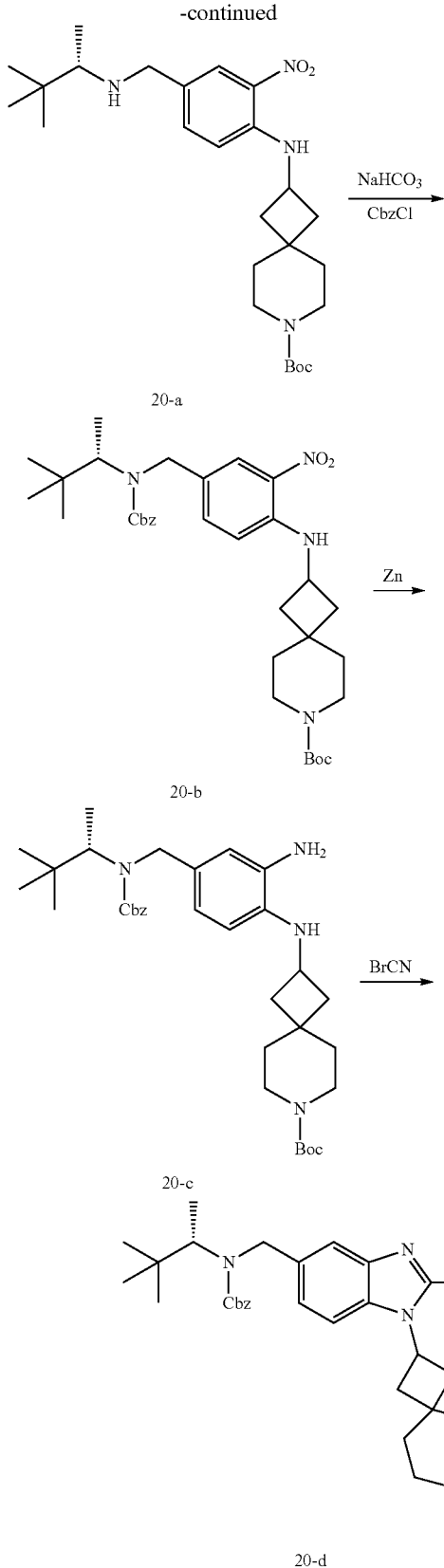

1,2-dichloroethane was added sodium triacetoxyborohydride (570 mg, 2.7 mmol) and the reaction was stirred overnight at room temperature. A saturated aqueous solution of NaHCO₃ and dichloromethane were then added, the organic layer was separated, and the aqueous phase was extracted twice with dichloromethane. The combined organic extracts were washed with brine, dried over MgSO₄, filtered and concentrated under reduced pressure to provide Intermediate 20-a as a yellow solid.

Step 2: Intermediate 20-b

To a solution of Intermediate 20-a (850 mg, 1.8 mmol) in dichloromethane (10 ml) were sequentially added a saturated aqueous solution of sodium bicarbonate (10 ml) and benzyl chloroformate (280 μl, 2.0 mmol) and the reaction was then stirred until completion at room temperature. The organic layer was separated, and the aqueous phase was extracted twice with dichloromethane. The combined organic extracts were washed with brine, dried over MgSO₄, filtered and concentrated under reduced pressure. Purification by silica gel chromatography provided Intermediate 20-b as a yellow solid.

Step 3: Intermediate 20-c

To a solution of Intermediate 20-b (900 mg, 1.5 mmol) in MeOH were sequentially added ammonium chloride (2.4 g, 44.4 mmol) and zinc dust (484 mg, 7.4 mmol). The reaction was stirred until completion at room temperature and then filtered over celite. The filtrate was concentrated under reduced pressure. A saturated aqueous solution of NaHCO₃ and ethyl acetate were added to the residue, the organic layer was separated, washed with brine, dried over MgSO₄, filtered and concentrated under reduced pressure to provide Intermediate 20-c as a beige foam.

Step 4: Intermediate 20-d

To a solution of Intermediate 20-c (850 mg, 1.5 mmol) in EtOH (10 ml) was added cyanogen bromide (1.9 mg, 1.8 mmol) and the reaction was stirred until completion at room temperature. A saturated aqueous solution of sodium bicarbonate and ethyl acetate were then added, the organic layer was separated, and the aqueous phase was extracted twice with ethyl acetate. The combined organic extracts were washed with brine, dried over MgSO₄, filtered and concentrated under reduced pressure to provide Intermediate 20-d as a purple solid.

Synthesis of Intermediate 21-b

Scheme 21

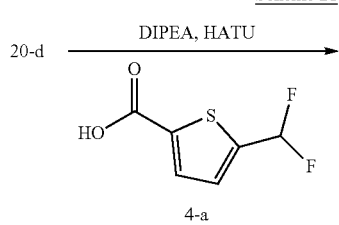

Step 1: Intermediate 20-a

To a solution of Intermediate 19-b (700 mg, 1.8 mmol) and (S)-3,3-dimethylbutan-2-amine (220 mg, 2.2 mmol) in

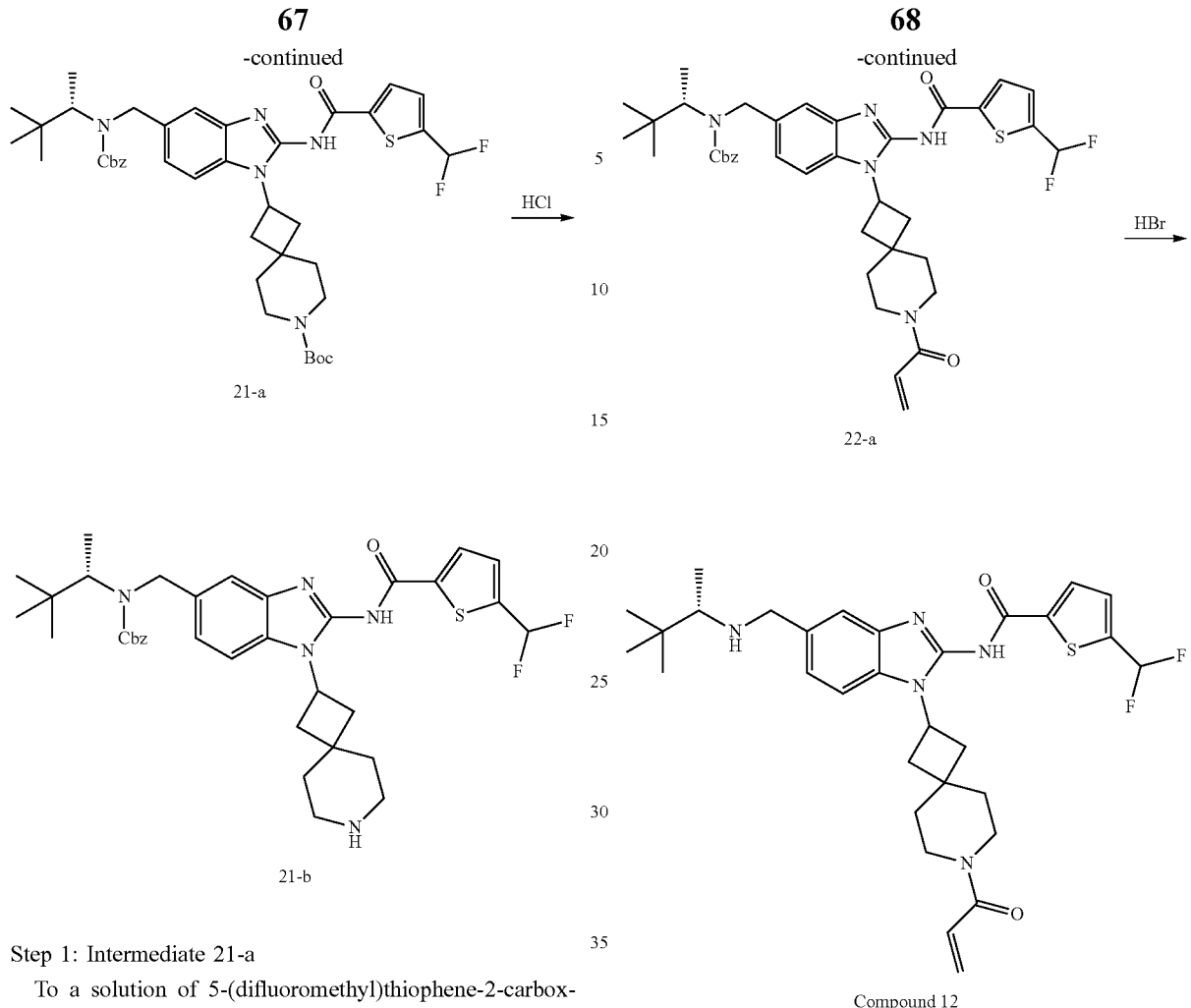

Step 1: Intermediate 21-a

To a solution of 5-(difluoromethyl)thiophene-2-carboxylic acid 4-a (50 mg, 0.27 mmol) in DMF (1.5 ml) was added HATU (123 mg, 0.323 mmol) and after stirring for 30 minutes a solution of Intermediate 20-d (150 mg, 0.25 mmol) and DIPEA (130 µl, 0.75 mmol) in DMF was added. The reaction was then stirred until completion at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided Intermediate 21-a as a beige solid.

Step 2: Intermediate 21-b

To a solution of Intermediate 21-a (155 mg, 0.20 mmol) in MeOH (1 ml), was added a solution of 4N hydrogen chloride in 1,4-dioxane (5.0 ml, 20.0 mmol). The reaction was stirred for 1 hour. Volatiles were removed under reduced pressure to provide Intermediate 21-b.HCl as a white solid.

Synthesis of Compound 12

Scheme 22

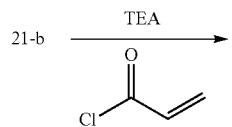

Step 1: Intermediate 22-a

To a solution of Intermediate 21-b.HCl (133 mg, 0.2 mmol) in THF (2 ml) cooled to 0° C. were sequentially added DIPEA (170 µl, 1.0 mmol) and acryloyl chloride (19 µL, 0.24 mmol) and the solution was stirred for 15 minutes at 0° C. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 22-a as a beige foam.

Step 2: Compound 12

To a solution of Intermediate 22-a (144 mg, 0.20 mmol)) in dichloromethane (1.5 ml) cooled to 0° C. was added a solution of 33% HBr in AcOH (2 ml) and the solution was then stirred until completion at 0° C. Diethyl ether was added, a precipitate formed and was collected by filtration, washed with diethyl ether and dried under vacuum. Purification by reverse phase chromatography provided Compound 12 as a white solid.

Synthesis of Intermediate 23-d

Scheme 23

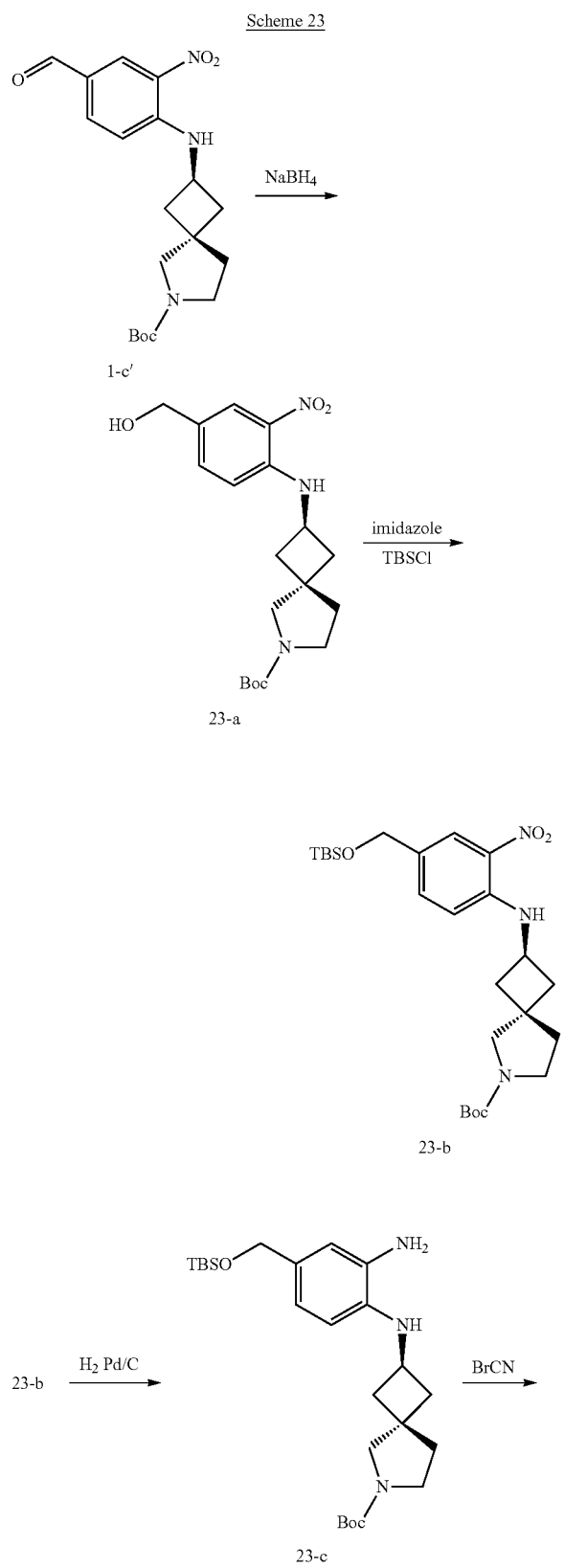

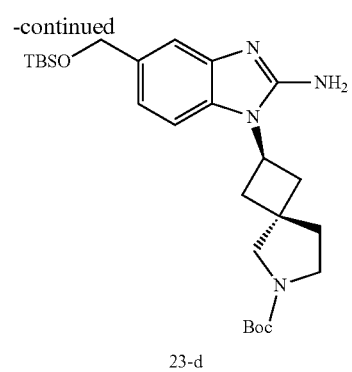

Step 1: Intermediate 23-a

To a solution of Intermediate 1-c' (2.0 g, 5.3 mmol) in ethanol (200 ml) was added sodium borohydride (302 mg, 8.0 mmol) and the reaction was stirred at room temperature for 1 hour. A saturated aqueous solution of $NaHCO_3$ was slowly added and after stirring for 15 minutes volatiles were removed under reduced pressure. Ethyl acetate was added, the organic layer was separated, washed with a saturated aqueous solution of $NaHCO_3$ and brine, dried over $MgSO_4$, filtered and concentrated under reduced pressure to provide Intermediate 23-a as a beige foam.

Step 2: Intermediate 23-b

To a solution of Intermediate 23-a (2.0 g, 5.3 mmol) in dichloromethane (26 ml) cooled to 0° C. were sequentially added imidazole (433 mg, 6.4 mmol) and tert-butylchlorodimethylsilane (879 mg, 5.8 mmol). The reaction was then warmed to room temperature and stirred overnight. A saturated aqueous solution of ammonium chloride and ethyl acetate were added, the organic layer was separated, washed with a saturated aqueous solution of ammonium chloride and brine, dried over $MgSO_4$, filtered and concentrated under reduced pressure to provide Intermediate 23-b as beige oil.

Step 3: Intermediate 23-c

To a solution of Intermediate 23-b (2.6 g, 5.3 mmol) in methanol and stirred under nitrogen was added 10% Pd/C (1.1 g, 0.6 mmol). The reaction mixture was purged with $H_2$ and stirred for 24 hours under $H_2$. The reaction was then filtered through celite and the filtrate was concentrated under reduced pressure to provide Intermediate 23-c as a beige solid.

Step 4: Intermediate 23-d

To a solution of Intermediate 23-c (850 mg, 1.8 mmol) in EtOH (19 ml) was added cyanogen bromide (244 mg, 2.3 mmol) and the reaction was stirred overnight at room temperature. Volatiles were removed under reduced pressure. A saturated aqueous solution of sodium bicarbonate and ethyl acetate were then added to the residue, the organic layer was separated, washed with a saturated aqueous solution of $NaHCO_3$ and brine, dried over $MgSO_4$, filtered and concentrated under reduced pressure to provide Intermediate 23-d as a beige solid.

Synthesis of Intermediate 24-b

Synthesis of Intermediate 25-a

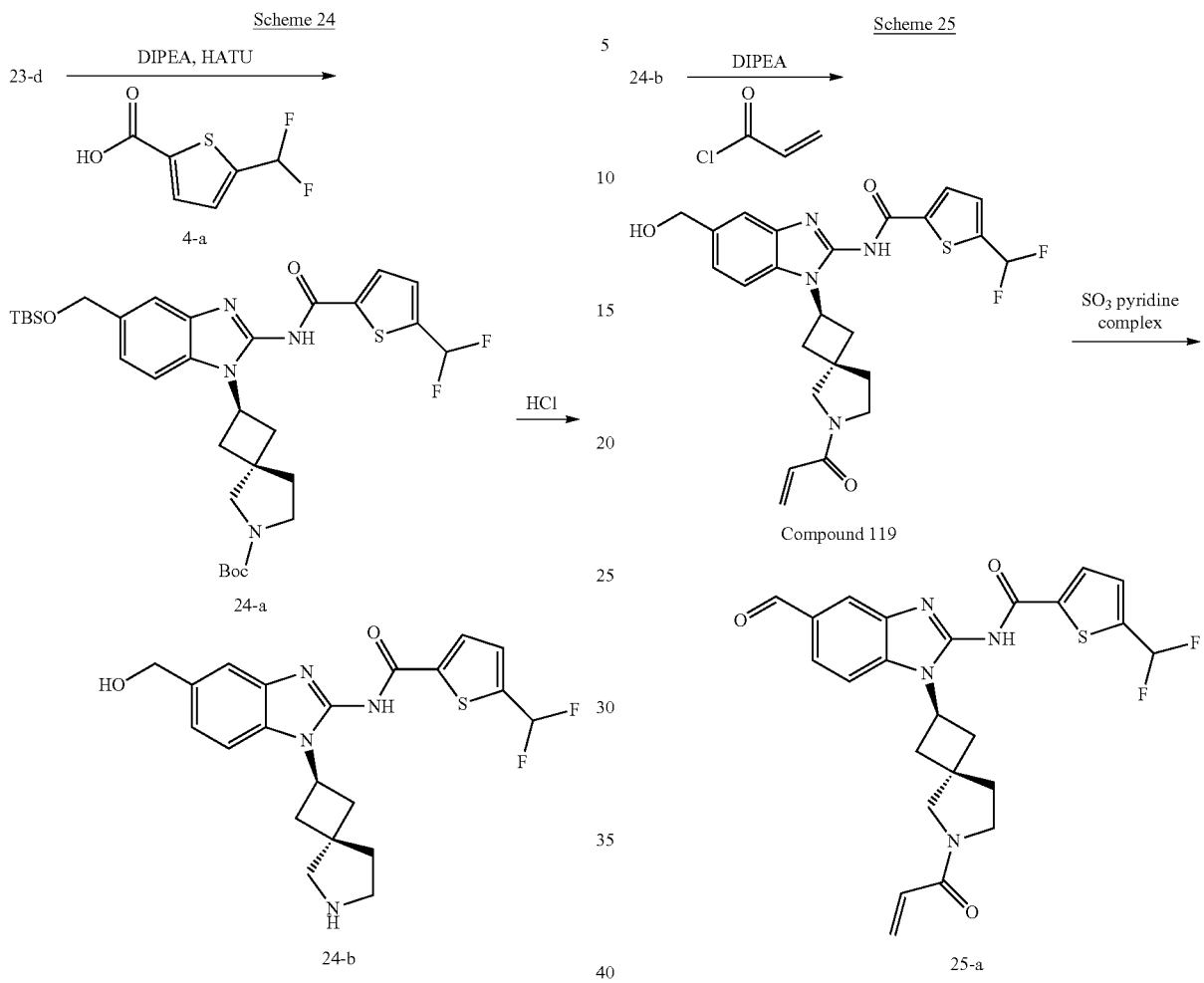

Step 1: Intermediate 24-a

To a solution of 5-(difluoromethyl)thiophene-2-carboxylic acid 4-a (143 mg, 0.8 mmol) in DMF (3.0 ml) cooled to 0° C. was added HATU (328 mg, 0.8 mmol) and after stirring for 30 minutes a solution of intermediate 23-d (300 mg, 0.6 mmol) and DIPEA (323 µl, 1.8 mmol) in DMF was added. The reaction was then stirred at room temperature overnight. A saturated aqueous solution of ammonium chloride and ethyl acetate were then added, the organic layer was separated, washed with a saturated aqueous solution of $NaHCO_3$ and brine, dried over $MgSO_4$, filtered and concentrated under reduced pressure. Purification by silica gel chromatography provided Intermediate 24-a as a purple solid.

Step 2: Intermediate 24-b

To a solution of Intermediate 24-a (207 mg, 0.3 mmol) in MeOH (1 ml) was added 4N HCl in 1,4-dioxane (5.0 ml, 20.0 mmol) and the solution was stirred at room temperature overnight. Volatiles were removed under reduced pressure and diethyl ether was added to the residue. A precipitate formed and was collected by filtration, dried under vacuum to provide Intermediate 24-b.HCl as a purple solid.

Step 1: Compound 119

To a solution of Intermediate 24-b.HCl (150 mg, 0.3 mmol) in tetrahydrofuran (2.0 ml) cooled to −78° C. were sequentially added DIPEA (279 µl, 1.6 mmol) and acryloyl chloride (26 µl, 0.3 mmol) and the reaction was stirred at −78° C. for 15 minutes. Water (20 mL) and ethyl acetate (20 mL) were added; the organic layer was separated, washed with a saturated aqueous solution of $NaHCO_3$ and brine, dried over anhydrous $MgSO_4$, filtered and concentrated under reduced pressure. Purification by reverse phase chromatography provided Compound 119 as a white solid.

Step 2: Intermediate 25-a

To a solution of Compound 119 (150 mg, 0.3 mmol) in THF (3.1 ml) and DMSO (219 µl) cooled to 0° C. were sequentially added DIPEA (215 µl, 1.2 mmol) and a solution of $SO_3$ pyridine complex (147 mg, 0.9 mmol) in DMSO (1.0 mL). The mixture was stirred at 0° C. until completion. Volatiles were removed under reduced pressure, water was added, a precipitate formed and was collected by filtration, washed with water and dried under vacuum to provide Intermediate 25-a as a beige solid.

Synthesis of Compound 27

Scheme 26

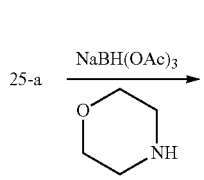

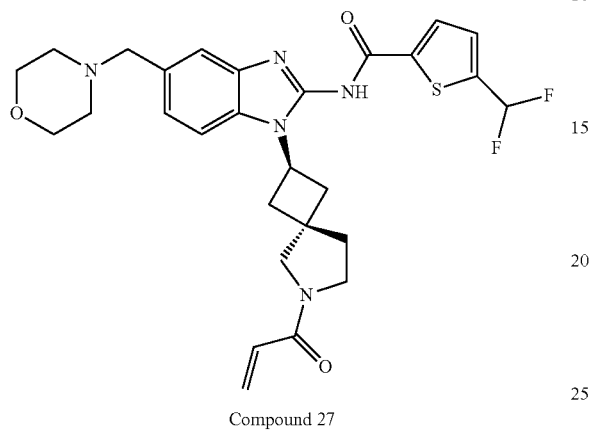

Compound 27

To a solution of Intermediate 25-a (250 mg, 0.5 mmol) and morpholine (45 µl, 0.5 mmol) in THF (2.0 ml) were sequentially added acetic acid (15 µl, 0.2 mmol) and sodium triacetoxyborohydride (164 mg, 0.7 mmol) and the reaction was stirred at room temperature overnight. Volatiles were removed under reduced pressure. Purification by reverse phase chromatography provided Compound 27 as a white solid.

Compounds 34, 35, 36 and 37 were prepared starting from Intermediate 25-a, in a similar manner to Compound 27, by replacing

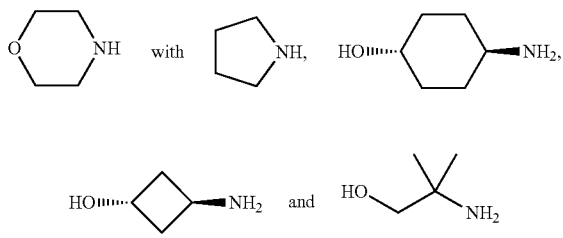

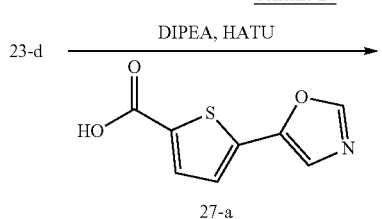

respectively.

Synthesis of Intermediate 27-c

Scheme 27

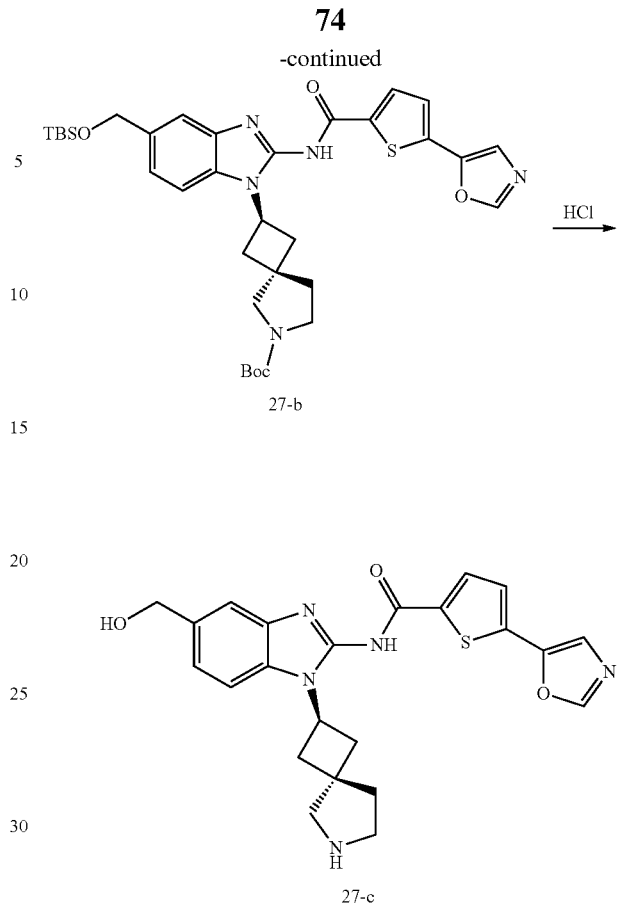

Step 1: Intermediate 27-b

To a solution of 5-(oxazol-5-yl)thiophene-2-carboxylic acid 27-a (385 mg, 1.9 mmol) in DMF (3.0 ml) cooled to 0° C. was added HATU (975 mg, 2.5 mmol) and after stirring for 30 minutes a solution of intermediate 23-d (960 mg, 2.0 mmol) and DIPEA (1.0 ml, 5.9 mmol) in DMF was added. The reaction was then stirred at room temperature overnight. A saturated aqueous solution of ammonium chloride and ethyl acetate were then added, the organic layer was separated, washed with a saturated aqueous solution of NaHCO$_3$ and brine, dried over MgSO$_4$, filtered and concentrated under reduced pressure. Purification by silica gel chromatography provided Intermediate 27-b as a beige solid.

Step 2: Intermediate 27-c

To a solution of Intermediate 27-b (470 mg, 0.7 mmol) in MeOH (1 ml), was added a solution of 4N hydrogen chloride in 1,4-dioxane (5.0 ml, 20 mmol). The reaction was stirred for 1 hour. Volatiles were removed under reduced pressure to provide Intermediate 27-c.2HCl as a beige solid.

Synthesis of Intermediate 28-a

Scheme 28

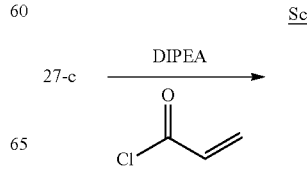

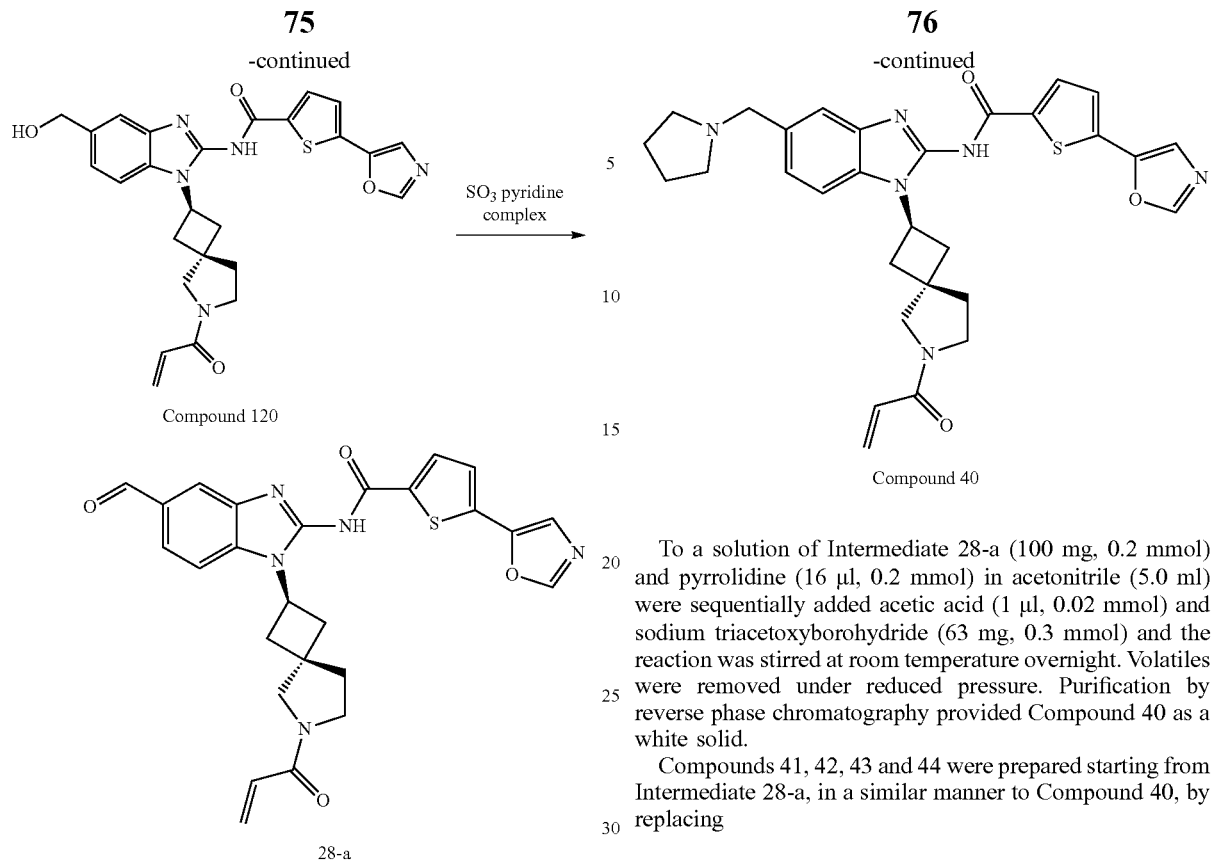

Compound 120

28-a

Step 1: Compound 120

To a solution of Intermediate 27-c.2HCl (393 mg, 0.7 mmol) in tetrahydrofuran (10.0 ml) cooled to −78° C. were sequentially added DIPEA (655 µl, 3.8 mmol) and acryloyl chloride (61 µl, 0.7 mmol) and the reaction was stirred at −78° C. for 15 minutes. Water (20 mL) and ethyl acetate (20 mL) were added; the organic layer was separated, washed with a saturated aqueous solution of NaHCO$_3$ and brine, dried over anhydrous MgSO$_4$, filtered and concentrated under reduced pressure. Purification by reverse phase chromatography provided Compound 120 as a white solid.

Step 2: Intermediate 28-a

To a solution of Compound 120 (380 mg, 0.7 mmol) in THF (7.5 ml) and DMSO (536 µl) cooled to 0° C. were sequentially added DIPEA (526 µl, 3.0 mmol) and a solution of SO$_3$ pyridine complex (360 mg, 2.2 mmol) in DMSO (1.0 mL). The mixture was stirred at 0° C. until completion. Volatiles were removed under reduced pressure, water and ethyl acetate were added to the residue, the organic layer was separated, washed with brine, dried over anhydrous MgSO$_4$, filtered and concentrated under reduced pressure to provide Intermediate 28-a as a beige solid.

Synthesis of Compound 40

Scheme 29

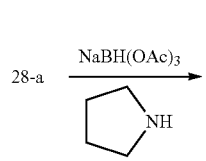

Compound 40

To a solution of Intermediate 28-a (100 mg, 0.2 mmol) and pyrrolidine (16 µl, 0.2 mmol) in acetonitrile (5.0 ml) were sequentially added acetic acid (1 µl, 0.02 mmol) and sodium triacetoxyborohydride (63 mg, 0.3 mmol) and the reaction was stirred at room temperature overnight. Volatiles were removed under reduced pressure. Purification by reverse phase chromatography provided Compound 40 as a white solid.

Compounds 41, 42, 43 and 44 were prepared starting from Intermediate 28-a, in a similar manner to Compound 40, by replacing

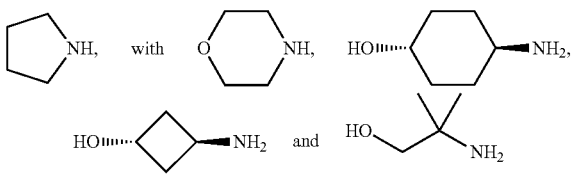

respectively.

Compound 28 was prepared starting from Intermediate 23-d, in a similar manner to Compound 40, by replacing

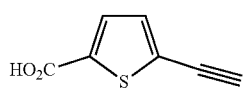

for the synthesis of Intermediate 28-a with

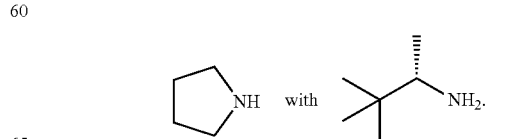

and by replacing

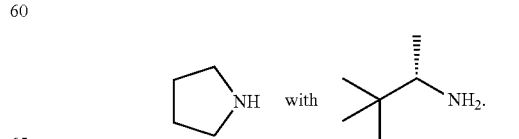

Synthesis of Intermediates 30-c and 30-c'

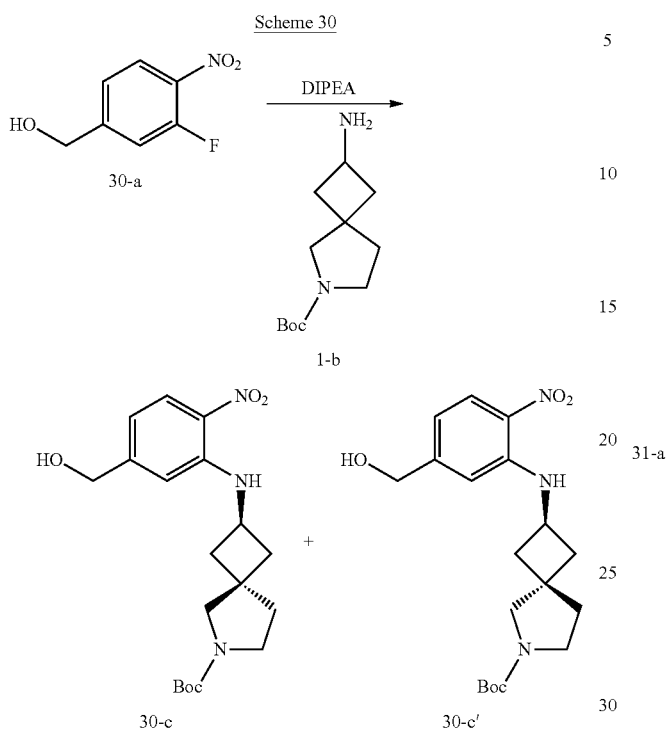

To a solution of Intermediate 30-a (380 mg, 2.2 mmol) and DIPEA (1.2 ml, 6.7 mmol) in DMSO was added Intermediate 1-b (700 mg, 2.4 mmol). The reaction was stirred at 110° C. overnight and then cooled to room temperature. A saturated aqueous solution of ammonium chloride and ethyl acetate were added, the organic layer was separated, and the aqueous phase was extracted twice with ethyl acetate. The combined organic extracts were washed with a saturated aqueous solution of ammonium chloride and brine, dried over MgSO$_4$, filtered and concentrated under reduced pressure. Separation by silica gel chromatography eluting with an ethyl acetate/hexane gradient provided Intermediates isomers 30-c as a yellow solid and 30-c' as a yellow solid.

Synthesis of Intermediate 31-c

Scheme 31

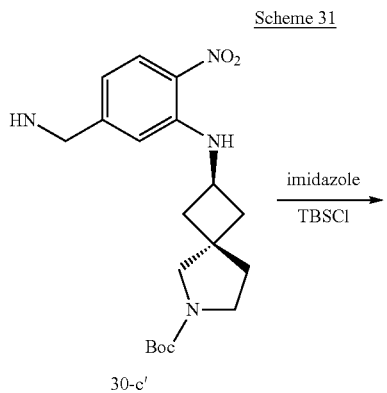

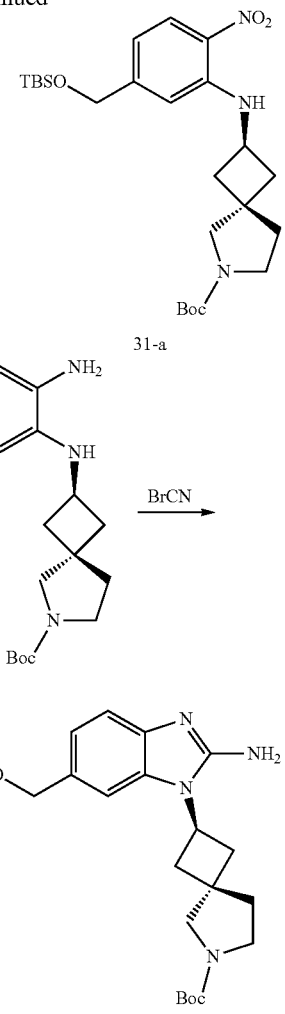

Step 1: Intermediate 31-a

To a solution of Intermediate 30-c' (300 mg, 0.8 mmol) in dichloromethane (4.0 ml) cooled to 0° C. were sequentially added imidazole (114 mg, 1.7 mmol) and tert-butylchlorodimethylsilane (240 mg, 1.6 mmol). The reaction was then warmed to room temperature and stirred overnight. A saturated aqueous solution of ammonium chloride and ethyl acetate were added, the organic layer was separated, washed with a saturated aqueous solution of ammonium chloride and brine, dried over MgSO$_4$, filtered and concentrated under reduced pressure. Purification by silica gel chromatography provided Intermediate 31-a as a beige solid.

Step 2: Intermediate 31-b

To a solution of Intermediate 31-a (400 mg, 0.8 mmol) in methanol (5.4 ml) and water (1 ml) were sequentially added ammonium chloride (1.3 g) and zinc dust (266 mg, 4.1 mmol) and the reaction was stirred at room temperature overnight. Volatiles were removed under reduced pressure. A saturated aqueous solution of sodium bicarbonate and ethyl acetate were added to the residue, the organic layer was separated, and the aqueous phase was extracted twice with ethyl acetate. The combined organic extracts were washed with a saturated aqueous solution of ammonium chloride and brine, dried over MgSO$_4$, filtered and concentrated under reduced pressure to provide Intermediate 31-b as a beige solid.

Step 3: Intermediate 31-c

To a solution of Intermediate 31-b (360 mg, 0.8 mmol) in EtOH (8.0 ml) was added cyanogen bromide (103 mg, 1.0 mmol) and the reaction was stirred overnight at room temperature. Volatiles were removed under reduced pressure. A saturated aqueous solution of sodium bicarbonate and ethyl acetate were then added to the residue, the organic layer was separated, washed with a saturated aqueous solution of NaHCO$_3$ and brine, dried over MgSO$_4$, filtered and concentrated under reduced pressure to provide Intermediate 31-c as a beige solid.

Synthesis of Intermediate 32-b

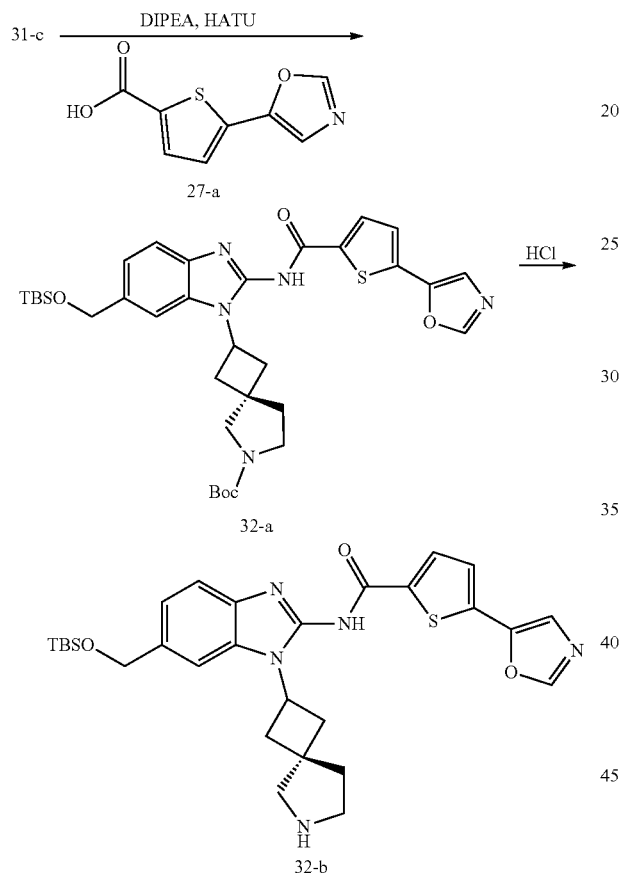

Step 1: Intermediate 32-a

To a solution of 5-(oxazol-5-yl)thiophene-2-carboxylic acid 27-a (229 mg, 1.2 mmol) in DMF (4.0 ml) cooled to 0° C. was added HATU (445 mg, 1.2 mmol) and after stirring for 30 minutes a solution of Intermediate 31-c (380 mg, 0.8 mmol) and DIPEA (409 μl, 2.3 mmol) in DMF was added. The reaction was then stirred at room temperature overnight. A saturated aqueous solution of ammonium chloride and ethyl acetate were then added, the organic layer was separated, washed with a saturated aqueous solution of NaHCO$_3$ and brine, dried over MgSO$_4$, filtered and concentrated under reduced pressure to provide Intermediate 32-a as a beige solid.

Step 2: Intermediate 32-b

To a solution of Intermediate 32-a (445 mg, 0.7 mmol) in MeOH (3.3 ml), was added a solution of 4N hydrogen chloride in 1,4-dioxane (5.0 ml, 20.0 mmol). The reaction was stirred for 1 hour. Volatiles were removed under reduced pressure to provide Intermediate 32-b.2HCl as a beige solid.

Synthesis of Intermediate 33-a

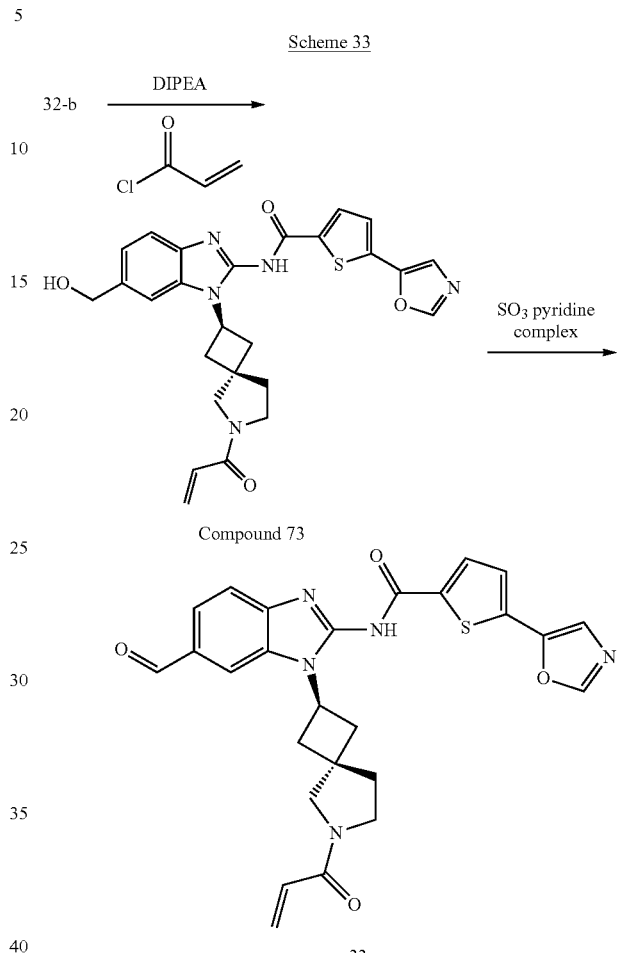

Step 1: Compound 73

To a solution of Intermediate 32-b.2HCl (250 mg, 0.5 mmol) in tetrahydrofuran (5.0 ml) cooled to −78° C. were sequentially added DIPEA (251 μl, 1.4 mmol) and acryloyl chloride (39 μl, 0.5 mmol) and the reaction was stirred at −78° C. for 30 minutes. A saturated aqueous solution of ammonium chloride and ethyl acetate were added; the organic layer was separated, washed with a saturated aqueous solution of NaHCO$_3$ and brine, dried over anhydrous MgSO$_4$, filtered and concentrated under reduced pressure. Purification by reverse phase chromatography provided Compound 73 as a beige solid.

Compound 78 was prepared in a similar manner to Compound 73 starting from Intermediate 30-c.

Step 2: Intermediate 33-a

To a solution of Compound 73 (150 mg, 0.3 mmol) in THF (2.0 ml) and DMSO (1.0 ml) cooled to 0° C. were sequentially added TEA (166 μl, 1.2 mmol) and a solution of SO$_3$ pyridine complex (142 mg, 0.9 mmol) in DMSO (1.0 mL). The mixture was stirred at 0° C. until completion. Volatiles were removed under reduced pressure, water was added. A precipitate formed and was collected by filtration, washed with water and dried under vacuum to provide Intermediate 33-a as a beige solid.

Synthesis of Compound 77

Scheme 34

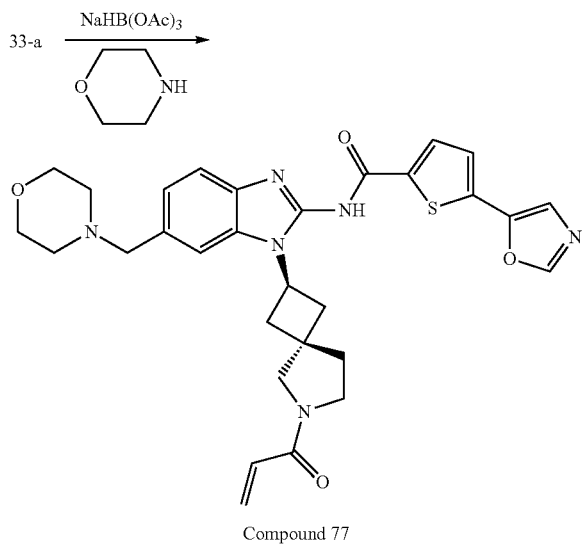

Compound 77

To a solution of Intermediate 33-a (55 mg, 0.1 mmol) and morpholine (9 mg, 0.1 mmol) in acetonitrile (1.0 ml) and dichloroethane (1.0 ml) was added sodium triacetoxyborohydride (35 mg, 0.2 mmol) and the reaction was stirred at room temperature overnight. Volatiles were removed under reduced pressure. Purification by reverse phase chromatography provided Compound 77 as a white solid.

Compound 86 was prepared from Compound 78, in a similar manner to Compound 77 from compound 73, by replacing

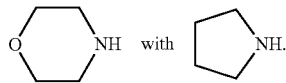

Synthesis of Intermediate 35-c

Scheme 35

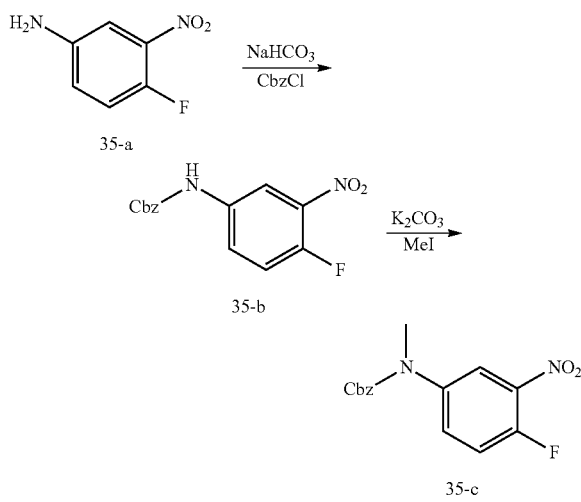

Step 1: Intermediate 35-b

To a solution of 4-fluoro-3-nitroaniline (5.0 g, 32.0 mmol) in dichloromethane (64 ml) were sequentially added a saturated aqueous solution of NaHCO$_3$ (64.1 ml) and benzyl chloroformate (5.5 ml, 38.4 mmol) and the reaction was stirred at room temperature for 2 hours. The organic layer was separated, washed with brine, dried over anhydrous MgSO$_4$, filtered and concentrated under reduced pressure to provide Intermediate 35-b as a beige solid.

Step 2: Intermediate 35-c

To a solution of Intermediate 35-b (6.0 g, 20.7 mmol) in acetonitrile (60 ml) were sequentially added K$_2$CO$_3$ (8.6 g, 62.0 mmol) and methyl iodide (6.5 ml, 103.0 mmol). The reaction was stirred at room temperature overnight and then filtered. The filtrate was concentrated under reduced pressure, a saturated aqueous solution of ammonium chloride and ethyl acetate were then added to the residue, the organic layer was separated, washed with a saturated aqueous solution of ammonium chloride and brine, dried over MgSO$_4$, filtered and concentrated under reduced pressure. Purification by silica gel chromatography provided Intermediate 35-c as a yellow solid.

Synthesis of Intermediates 36-a and 36-a'

Scheme 36

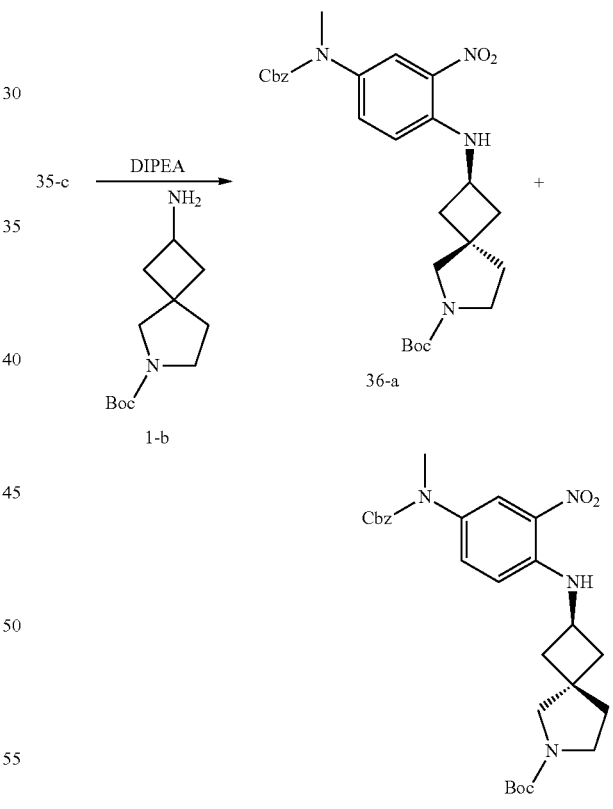

To a solution of Intermediate 35-c (850 mg, 2.8 mmol) and DIPEA (1.5 ml, 8.4 mmol) in DMSO was added Intermediate 1-b.AcOH (880 mg, 3.1 mmol). The reaction was stirred at 110° C. for 3 hours and then cooled to room temperature. A saturated aqueous solution of ammonium chloride and ethyl acetate were added, the organic layer was separated, and the aqueous phase was extracted twice with ethyl acetate. The combined organic extracts were washed with a saturated aqueous solution of ammonium chloride and brine, dried over MgSO$_4$, filtered and concentrated under reduced pressure. Separation by silica gel chromatography eluting with an ethyl acetate/hexane gradient provided Intermediates isomers 36-a as a yellow solid and 36-a' as a yellow solid.

Synthesis of Intermediate 37-b

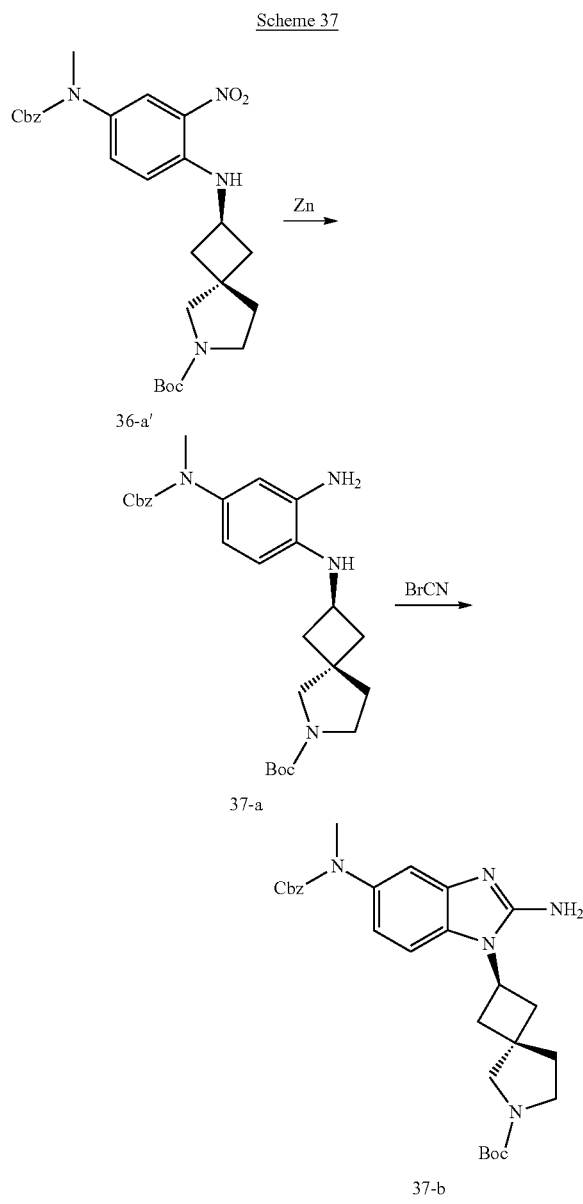

and brine, dried over MgSO$_4$, filtered and concentrated under reduced pressure to provide Intermediate 37-a as a beige solid.

Step 2: Intermediate 37-b

To a solution of Intermediate 37-a (400 mg, 0.8 mmol) in EtOH (8.0 ml) was added cyanogen bromide (110 mg, 1.0 mmol) and the reaction was stirred overnight at room temperature. Volatiles were removed under reduced pressure. A saturated aqueous solution of sodium bicarbonate and ethyl acetate were then added to the residue, the organic layer was separated, washed with a saturated aqueous solution of NaHCO$_3$ and brine, dried over MgSO$_4$, filtered and concentrated under reduced pressure to provide Intermediate 37-b as a beige solid.

Synthesis of Compound 50

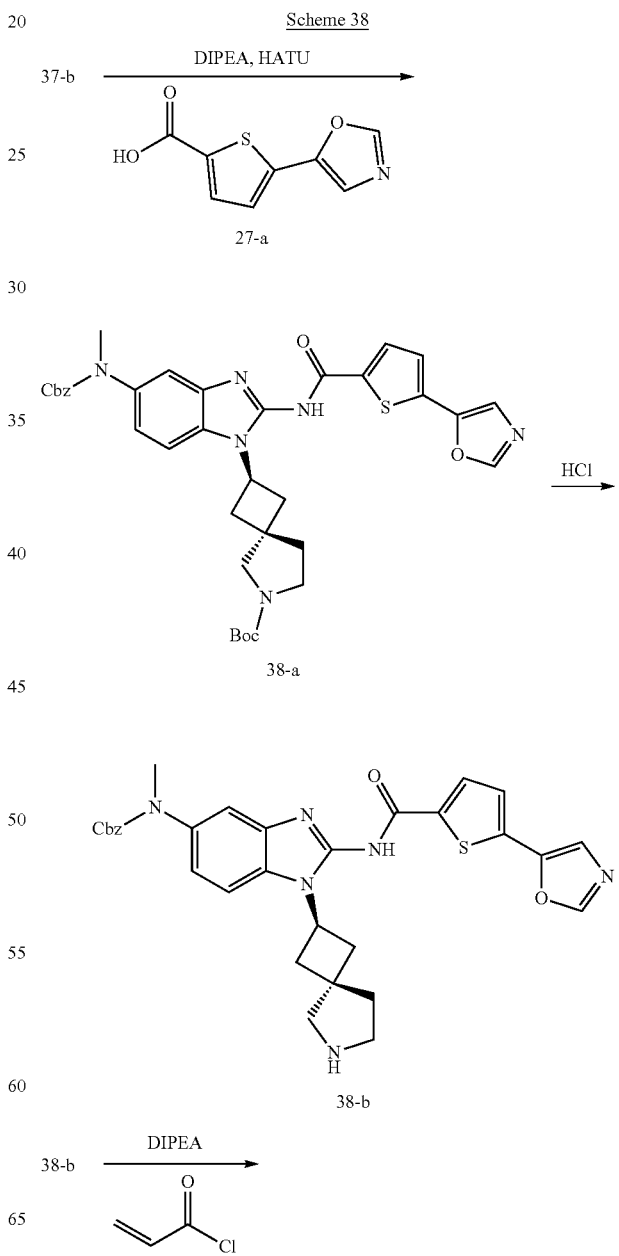

Step 1: Intermediate 37-a

To a solution of Intermediate 36-a' (510 mg, 1.0 mmol) in methanol (6.7 ml) and water (1 ml) were sequentially added ammonium chloride (1.6 g) and zinc dust (327 mg, 5.0 mmol) and the reaction was stirred at room temperature for 1 hour. Volatiles were removed under reduced pressure. A saturated aqueous solution of sodium bicarbonate and ethyl acetate were added to the residue, the organic layer was separated, and the aqueous phase was extracted twice with ethyl acetate. The combined organic extracts were washed with a saturated aqueous solution of ammonium chloride

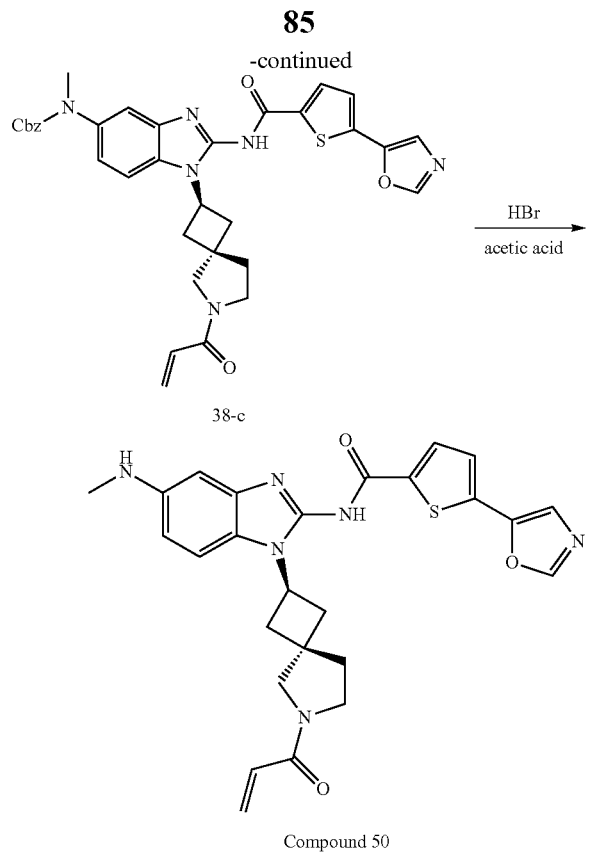

38-c

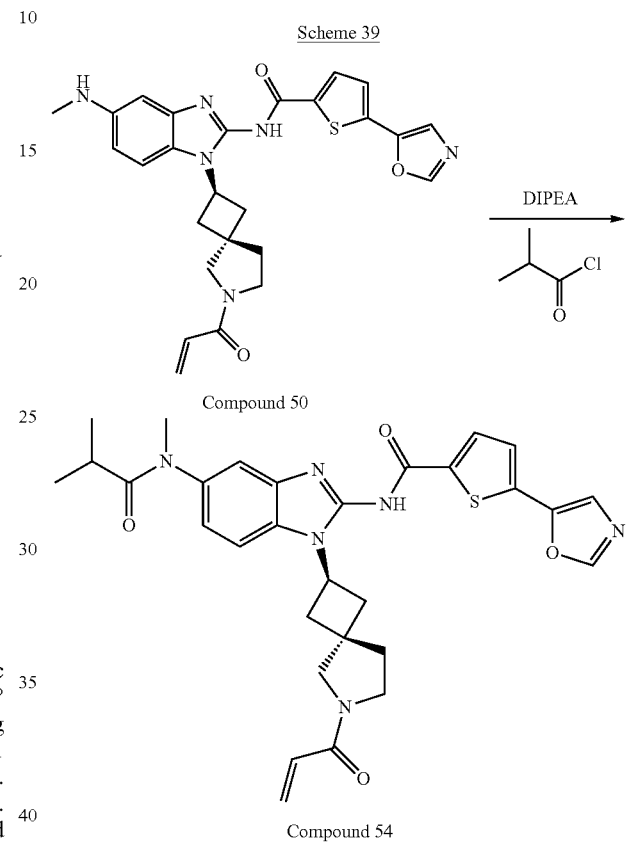

Compound 50

Step 1: Intermediate 38-a

To a solution of 5-(oxazol-5-yl)thiophene-2-carboxylic acid 27-a (229 mg, 1.2 mmol) in DMF (4.0 ml) cooled to 0° C. was added HATU (445 mg, 1.2 mmol) and after stirring for 30 minutes a solution of Intermediate 37-b (540 mg, 1.1 mmol) and DIPEA (560 µl, 3.2 mmol) in DMF was added. The reaction was then stirred at room temperature overnight. A saturated aqueous solution of ammonium chloride and ethyl acetate were then added, the organic layer was separated, washed with a saturated aqueous solution of NaHCO₃ and brine, dried over MgSO₄, filtered and concentrated under reduced pressure.

Purification by silica gel chromatography provided Intermediate 38-a as a beige solid.

Step 2: Intermediate 38-b

To a solution of Intermediate 38-a (600 mg, 0.9 mmol) in MeOH (5.0 ml), was added a solution of 4N hydrogen chloride in 1,4-dioxane (5.0 ml, 20.0 mmol). The reaction was stirred for 2 hours. Volatiles were removed under reduced pressure to provide Intermediate 38-b.2HCl as a beige solid.

Step 3: Intermediate 38-c

To a solution of Intermediate 38-b.2HCl (600 mg, 1.0 mmol) in tetrahydrofuran (2.0 ml) cooled to −78° C. were sequentially added DIPEA (897 µl, 5.1 mmol) and acryloyl chloride (92 µl, 1.1 mmol) and the reaction was stirred at −78° C. for 30 minutes. A saturated aqueous solution of ammonium chloride and ethyl acetate were added; the organic layer was separated, washed with a saturated aqueous solution of NaHCO₃ and brine, dried over anhydrous MgSO₄, filtered and concentrated under reduced pressure. Purification by silica gel chromatography provided Intermediate 38-c as a beige solid.

Step 4: Compound 50

To a solution of Intermediate 38-c (650 mg, 1.0 mmol) in dichloromethane (5 ml) cooled to 0° C. was added a solution of 33% HBr in acetic acid (5 ml, 1.0 mmol) and the reaction was stirred for 1 hour. Water was added; a precipitate formed and was collected by filtration. Purification by reverse phase chromatography provided Compound 50 as a beige solid.

Synthesis of Compound 54

Scheme 39

To a solution of Compound 50 (20 mg, 0.04 mmol) in dichloromethane (1.0 ml) cooled to 0° C. were sequentially added DIPEA (21 µl, 0.1 mmol) and isobutyryl chloride (4 mg, 0.04 mmol) and the reaction was stirred at 0° C. for 30 minutes. A saturated aqueous solution of ammonium chloride and dichloromethane were added; the organic layer was separated, washed with a saturated aqueous solution of NaHCO₃ and brine, dried over anhydrous MgSO₄, filtered and concentrated under reduced pressure. Purification by reverse phase chromatography provided Compound 54 as a beige solid.

Compounds 51, 52, 53 were prepared starting from Compound 50, in a similar manner to Compound 54, by replacing

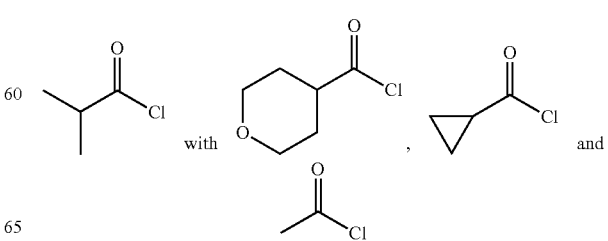

respectively.
Synthesis of Compound 60

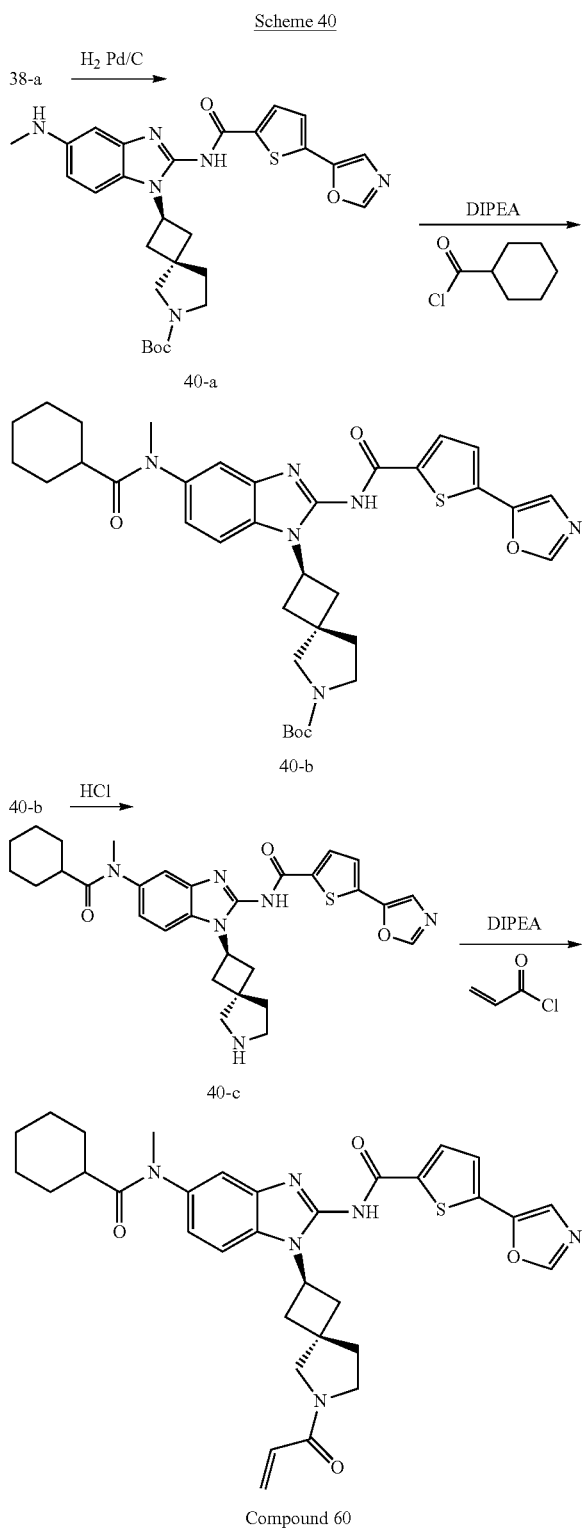

Step 1: Intermediate 40-a
To a solution of Intermediate 38-a (670 mg, 1.0 mmol) in methanol (5 ml) and stirred under nitrogen was added 10% Pd/C (209 mg, 0.1 mmol). The reaction mixture was purged with $H_2$ and stirred for 24 hours under $H_2$. The reaction was then filtered through celite and the filtrate was concentrated under reduced pressure to provide Intermediate 40-a as a beige solid.

Step 2: Intermediate 40-b
To a solution of Intermediate 40-a (75 mg, 0.13 mmol) in dichloromethane (1.0 ml) cooled to 0° C. were sequentially added DIPEA (72 μl, 0.4 mmol) and cyclohexanecarbonyl chloride (22 mg, 0.15 mmol) and the reaction was stirred at room temperature overnight. A saturated aqueous solution of ammonium chloride and dichloromethane were added; the organic layer was separated, washed with a saturated aqueous solution of $NaHCO_3$ and brine, dried over anhydrous $MgSO_4$, filtered and concentrated under reduced pressure. Purification by silica gel chromatography provided Intermediate 40-b as a beige solid.

Step 3: Intermediate 40-c
To a solution of Intermediate 40-b (110 mg, 0.2 mmol) in MeOH (5.0 ml), was added a solution of 4N hydrogen chloride in 1,4-dioxane (3.0 ml, 12.0 mmol). The reaction was stirred for 2 hours. Volatiles were removed under reduced pressure to provide Intermediate 40-c.2HCl as a beige solid.

Step 4: Compound 60
To a solution of Intermediate 40-c.2HCl (95 mg, 0.2 mmol) in DMF (5.0 ml) cooled to −78° C. were sequentially added DIPEA (89 μl, 0.5 mmol) and acryloyl chloride (17 μl, 0.2 mmol) and the reaction was stirred at 0° C. for 30 minutes. A saturated aqueous solution of ammonium chloride and ethyl acetate were added; the organic layer was separated, washed with a saturated aqueous solution of $NaHCO_3$ and brine, dried over anhydrous $MgSO_4$, filtered and concentrated under reduced pressure. Purification by reverse phase chromatography provided Compound 60 as a beige solid.

Compound 59 was prepared starting from Intermediate 40-a, in a similar manner to Compound 60, by replacing

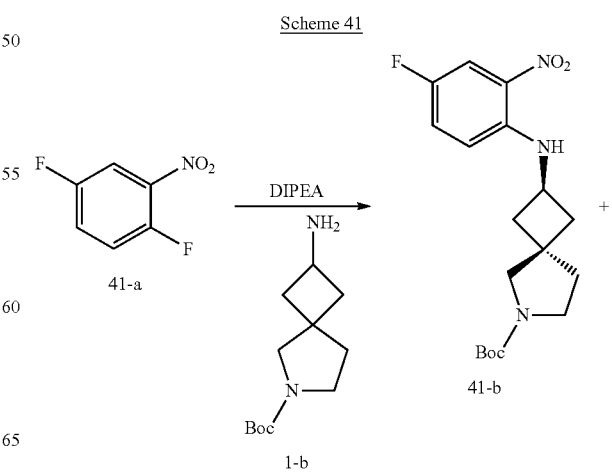

in the presence of HATU and DIPEA.
Synthesis of Intermediates 41-b and 41-b'

-continued

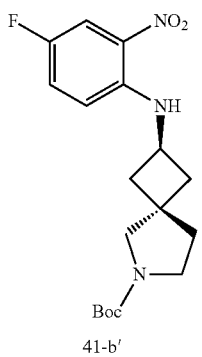

41-b'

To a solution of Intermediate 41-a (500 mg, 3.1 mmol) and DIPEA (1.6 ml, 9.4 mmol) in DMSO was added Intermediate 1-b.AcOH (990 mg, 3.5 mmol). The reaction was stirred at 110° C. for 3 hours and then cooled to room temperature. A saturated aqueous solution of ammonium chloride and ethyl acetate were added, the organic layer was separated, and the aqueous phase was extracted twice with ethyl acetate. The combined organic extracts were washed with a saturated aqueous solution of ammonium chloride and brine, dried over MgSO₄, filtered and concentrated under reduced pressure. Separation by silica gel chromatography eluting with an ethyl acetate/hexane gradient provided Intermediates isomers 41-b as a yellow solid and 41-b' as a yellow solid.

Synthesis of Intermediate 42-b

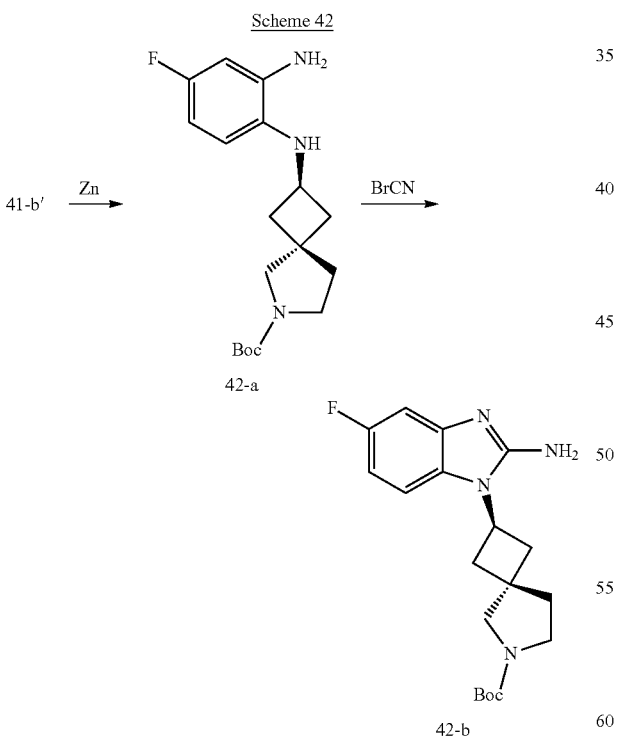

Step 1: Intermediate 42-a

To a solution of Intermediate 41-b' (440 mg, 1.2 mmol) in methanol (8.0 ml) and water (1 ml) were sequentially added ammonium chloride (1.9 g) and zinc dust (394 mg, 6.0 mmol) and the reaction was stirred at room temperature for 1 hour. Volatiles were removed under reduced pressure. A saturated aqueous solution of sodium bicarbonate and ethyl acetate were added to the residue, the organic layer was separated, and the aqueous phase was extracted twice with ethyl acetate. The combined organic extracts were washed with a saturated aqueous solution of ammonium chloride and brine, dried over MgSO₄, filtered and concentrated under reduced pressure to provide Intermediate 42-a as a beige solid.

Step 2: Intermediate 42-b

To a solution of Intermediate 42-a (400 mg, 1.2 mmol) in EtOH (12.0 ml) was added cyanogen bromide (158 mg, 1.5 mmol) and the reaction was stirred overnight at room temperature. Volatiles were removed under reduced pressure. A saturated aqueous solution of sodium bicarbonate and ethyl acetate were then added to the residue, the organic layer was separated, washed with a saturated aqueous solution of NaHCO₃ and brine, dried over MgSO₄, filtered and concentrated under reduced pressure to provide Intermediate 42-b as a purple solid.

Synthesis of Intermediate 43-b

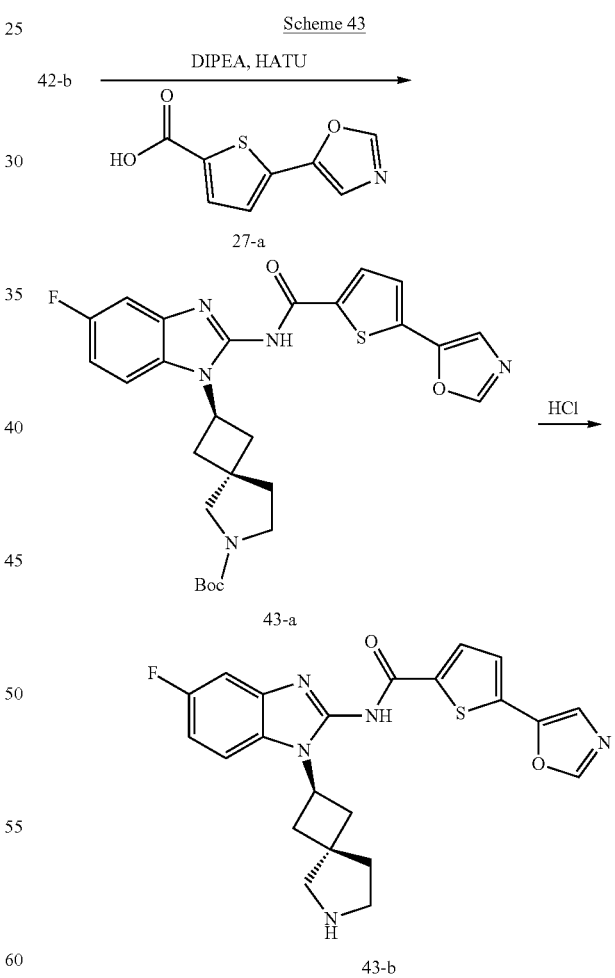

Step 1: Intermediate 43-a

To a solution of 5-(oxazol-5-yl)thiophene-2-carboxylic acid 27-a (341 mg, 1.8 mmol) in DMF (6.0 ml) cooled to 0° C. was added HATU (665 mg, 1.8 mmol) and after stirring for 30 minutes a solution of Intermediate 42-b (420 mg, 1.2 mmol) and DIPEA (611 µl, 3.5 mmol) in DMF was added. The reaction was then stirred at room temperature overnight. A saturated aqueous solution of ammonium chloride and ethyl acetate were then added, the organic layer was separated, washed with a saturated aqueous solution of NaHCO$_3$ and brine, dried over MgSO$_4$, filtered and concentrated under reduced pressure to provide Intermediate 43-a as a beige solid.

Step 2: Intermediate 43-b

To a solution of Intermediate 43-a (340 mg, 0.6 mmol) in MeOH (1.0 ml), was added a solution of 4N hydrogen chloride in 1,4-dioxane (3.0 ml, 12.0 mmol). The reaction was stirred for 2 hours. Volatiles were removed under reduced pressure to provide Intermediate 43-b.2HCl as a beige solid.

Synthesis of Compound 57

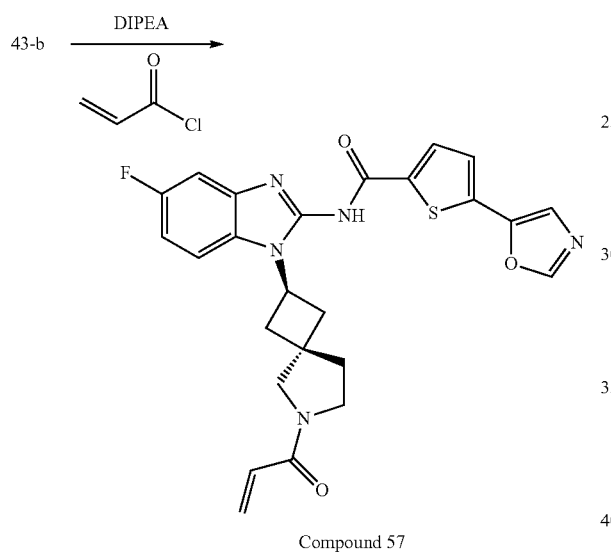

Compound 57

To a solution of Intermediate 43-b.2HCl (300 mg, 0.6 mmol) in DMF (5.0 ml) cooled to 0° C. were sequentially added DIPEA (1.0 ml, 1.5 mmol) and acryloyl chloride (62 µl, 0.8 mmol) and the reaction was stirred at 0° C. for 30 minutes. A saturated aqueous solution of ammonium chloride and ethyl acetate were added; the organic layer was separated, washed with a saturated aqueous solution of NaHCO$_3$ and brine, dried over anhydrous MgSO$_4$, filtered and concentrated under reduced pressure. Purification by reverse phase chromatography provided Compound 57 as a beige solid.

Compound 68 was prepared in a similar manner to Compound 57 starting from Intermediate 41-b.

Compounds 56, 58 and 61 were prepared in a similar manner to Compound 57 by replacing Intermediate

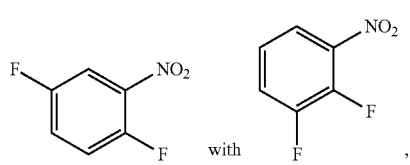

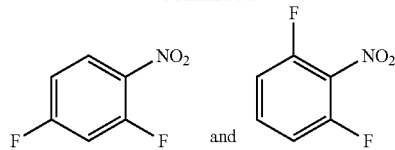

respectively.

Compounds 62, 70 and 67 were prepared in a similar manner to Compound 68 by replacing Intermediate

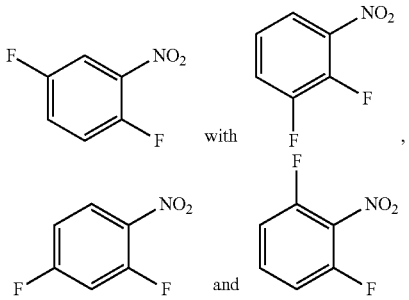

respectively.

Synthesis of Intermediates 45-b and 45-b'

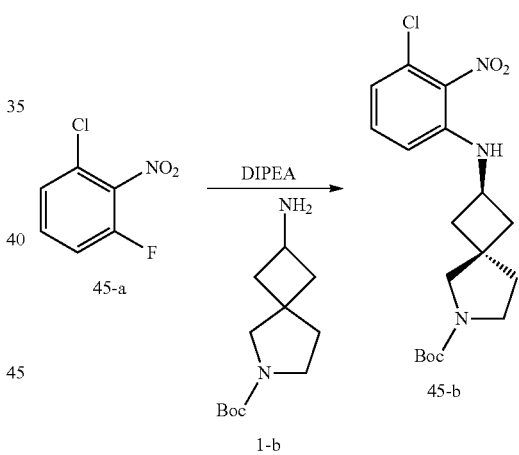

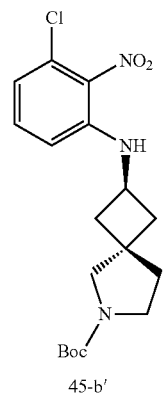

To a solution of Intermediate 45-a (500 mg, 2.8 mmol) and DIPEA (1.5 ml, 8.5 mmol) in DMSO was added intermediate 1-b.AcOH (709 mg, 3.1 mmol). The reaction was stirred at 110° C. for 3 hours and then cooled to room temperature. A saturated aqueous solution of ammonium chloride and ethyl acetate were added, the organic layer was separated, and the aqueous phase was extracted twice with ethyl acetate. The combined organic extracts were washed with a saturated aqueous solution of ammonium chloride and brine, dried over MgSO₄, filtered and concentrated under reduced pressure. Separation by silica gel chromatography eluting with an ethyl acetate/hexane gradient provided Intermediates isomers 45-b as a yellow solid and 45-b' as a yellow solid.

Synthesis of Intermediate 46-b

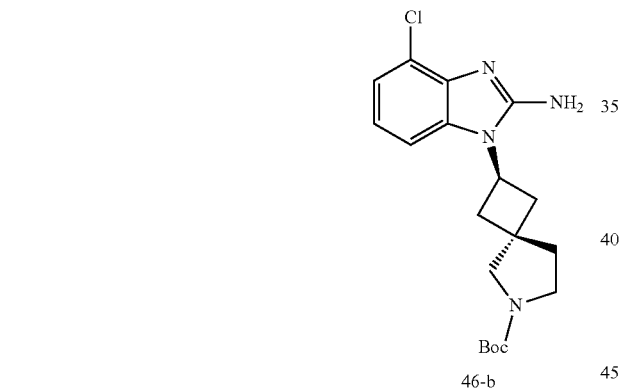

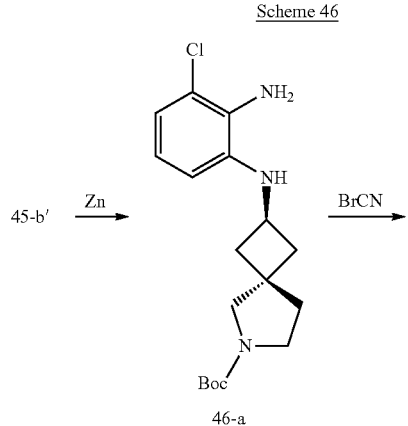

Step 1: Intermediate 46-a

To a solution of Intermediate 45-b' (460 mg, 1.2 mmol) in methanol (8.0 ml) and water (1 ml) were sequentially added ammonium chloride (1.9 g) and zinc dust (394 mg, 6.0 mmol) and the reaction was stirred at room temperature for 1 hour. Volatiles were removed under reduced pressure. A saturated aqueous solution of sodium bicarbonate and ethyl acetate were added to the residue, the organic layer was separated, and the aqueous phase was extracted twice with ethyl acetate. The combined organic extracts were washed with a saturated aqueous solution of ammonium chloride and brine, dried over MgSO₄, filtered and concentrated under reduced pressure to provide Intermediate 46-a as a beige solid.

Step 2: Intermediate 46-b

To a solution of Intermediate 46-a (420 mg, 1.2 mmol) in EtOH (12.0 ml) was added cyanogen bromide (158 mg, 1.5 mmol) and the reaction was stirred overnight at room temperature. Volatiles were removed under reduced pressure. A saturated aqueous solution of sodium bicarbonate and ethyl acetate were then added to the residue, the organic layer was separated, washed with a saturated aqueous solution of NaHCO₃ and brine, dried over MgSO₄, filtered and concentrated under reduced pressure to provide Intermediate 46-b as a purple solid.

Synthesis of Intermediate 47-b

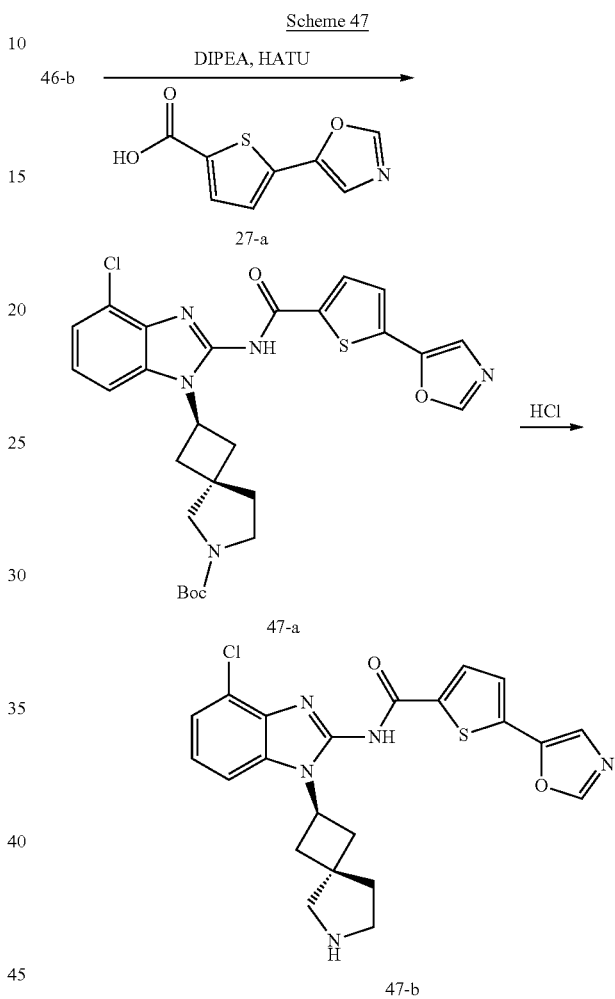

Step 1: Intermediate 47-a

To a solution of 5-(oxazol-5-yl)thiophene-2-carboxylic acid 27-a (233 mg, 1.2 mmol) in DMF (4.0 ml) was added HATU (454 mg, 1.2 mmol) and after stirring for 30 minutes a solution of Intermediate 46-b (300 mg, 0.8 mmol) and DIPEA (417 μl, 2.4 mmol) in DMF was added. The reaction was then stirred at room temperature overnight. A saturated aqueous solution of ammonium chloride and ethyl acetate were then added, the organic layer was separated, washed with a saturated aqueous solution of NaHCO₃ and brine, dried over MgSO₄, filtered and concentrated under reduced pressure to provide Intermediate 47-a as a beige solid.

Step 2: Intermediate 47-b

To a solution of Intermediate 47-a (500 mg, 0.9 mmol) in MeOH (1.0 ml), was added a solution of 4N hydrogen chloride in 1,4-dioxane (3.0 ml, 12.0 mmol). The reaction was stirred for 2 hours. Volatiles were removed under reduced pressure to provide Intermediate 47-b.2HCl as a beige solid.

Synthesis of Compound 64

Scheme 48

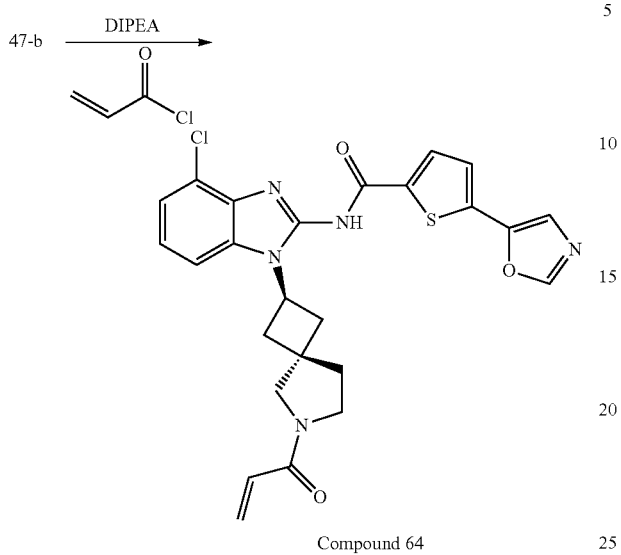

Compound 64

To a solution of Intermediate 47-b.2HCl (250 mg, 0.5 mmol) in DMF (5.0 ml) cooled to 0° C. were sequentially added DIPEA (267 µl, 1.5 mmol) and acryloyl chloride (50 µl, 0.6 mmol) and the reaction was stirred at 0° C. for 30 minutes. A saturated aqueous solution of ammonium chloride and ethyl acetate were added; the organic layer was separated, washed with a saturated aqueous solution of NaHCO$_3$ and brine, dried over anhydrous MgSO$_4$, filtered and concentrated under reduced pressure. Purification by reverse phase chromatography provided Compound 64 as a beige solid.

Compound 72 was prepared in a similar manner to Compound 64 starting from Intermediate 45-b.

Compounds 63 and 65 were prepared in a similar manner to Compound 64 by replacing Intermediate

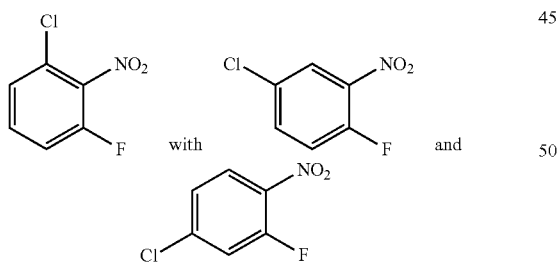

respectively.

Compounds 71 and 69 were prepared in a similar manner to Compound 72 by replacing Intermediate

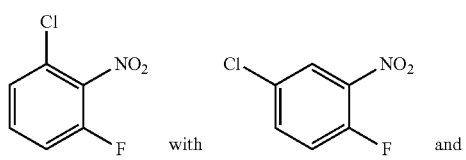

respectively.

Synthesis of Intermediates 49-b and 49-b'

Scheme 49

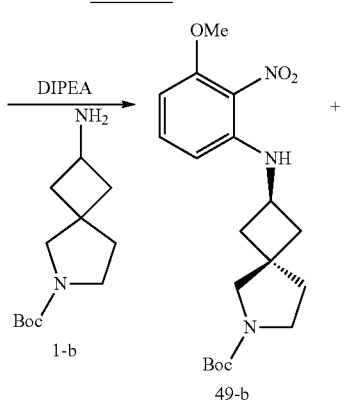

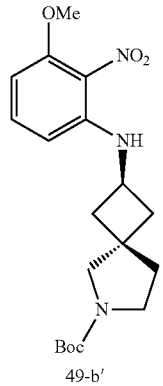

49-b'

To a solution of Intermediate 49-a (500 mg, 2.9 mmol) and DIPEA (1.5 ml, 8.7 mmol) in DMSO was added Intermediate 1-b.AcOH (727 mg, 3.2 mmol). The reaction was stirred at 110° C. for 3 hours and then cooled to room temperature. A saturated aqueous solution of ammonium chloride and ethyl acetate were added, the organic layer was separated, and the aqueous phase was extracted twice with ethyl acetate. The combined organic extracts were washed with a saturated aqueous solution of ammonium chloride and brine, dried over MgSO$_4$, filtered and concentrated under reduced pressure. Separation by silica gel chromatography eluting with an ethyl acetate/hexane gradient provided Intermediates isomers 49-b as a yellow solid and 49-b' as a yellow solid.

Synthesis of Intermediate 50-b

Scheme 50

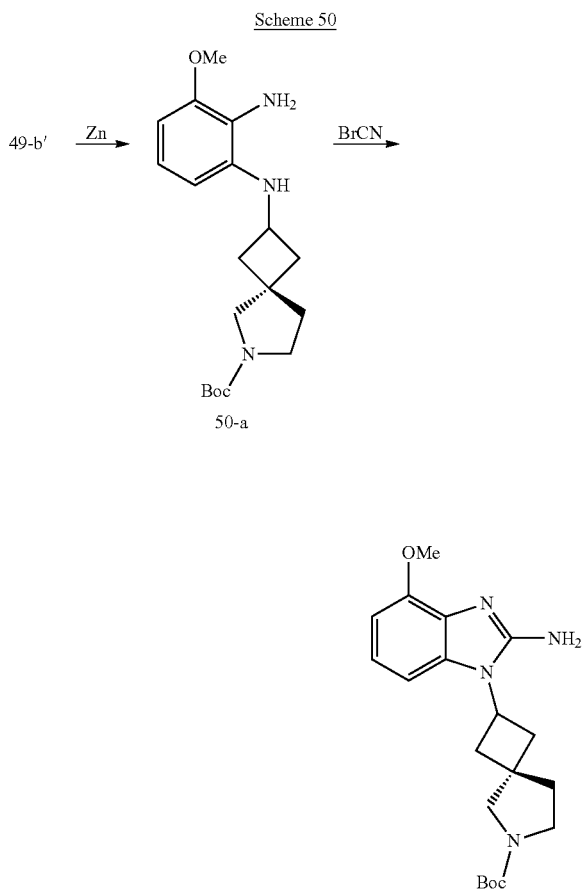

Step 1: Intermediate 50-a

To a solution of Intermediate 49-b' (400 mg, 1.1 mmol) in methanol (7.0 ml) and water (1 ml) were sequentially added ammonium chloride (1.7 g) and zinc dust (346 mg, 5.3 mmol) and the reaction was stirred at room temperature for 1 hour. Volatiles were removed under reduced pressure. A saturated aqueous solution of ammonium chloride and ethyl acetate were added to the residue, the organic layer was separated, and the aqueous phase was extracted twice with ethyl acetate. The combined organic extracts were washed with a saturated aqueous solution of sodium bicarbonate and brine, dried over MgSO$_4$, filtered and concentrated under reduced pressure to provide Intermediate 50-a as a purple solid.

Step 2: Intermediate 50-b

To a solution of Intermediate 50-a (370 mg, 1.1 mmol) in EtOH (10.0 ml) was added cyanogen bromide (141 mg, 1.3 mmol) and the reaction was stirred overnight at room temperature. Volatiles were removed under reduced pressure. A saturated aqueous solution of sodium bicarbonate and ethyl acetate were then added to the residue, the organic layer was separated, washed with a saturated aqueous solution of NaHCO$_3$ and brine, dried over MgSO$_4$, filtered and concentrated under reduced pressure to provide Intermediate 50-b as a beige solid.

Synthesis of Intermediate 51-b

Scheme 51

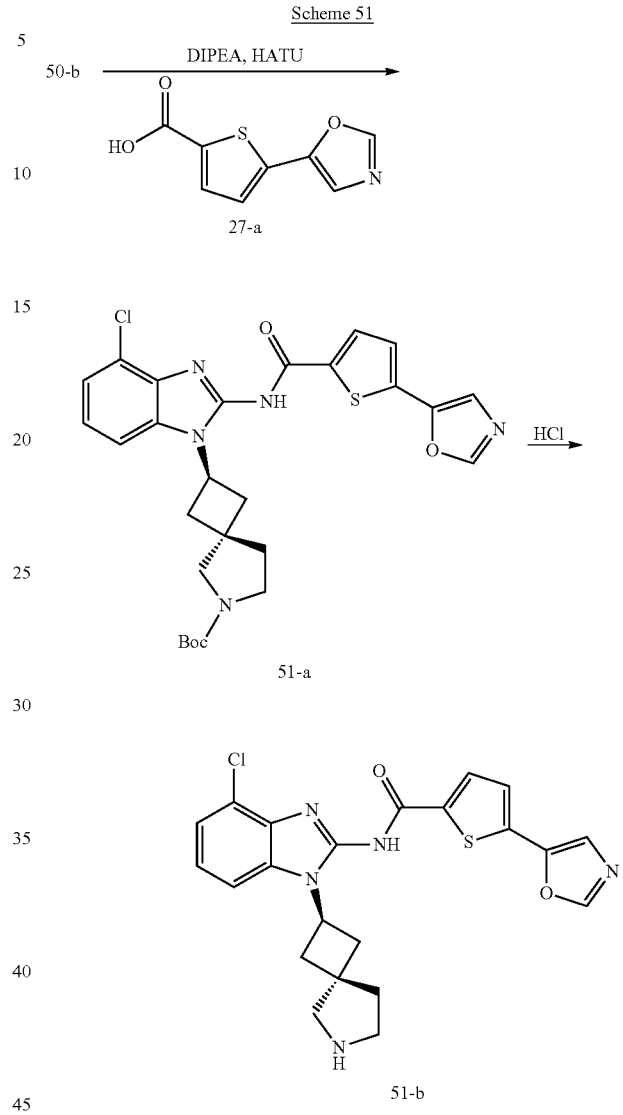

Step 1: Intermediate 51-a

To a solution of 5-(oxazol-5-yl)thiophene-2-carboxylic acid 27-a (207 mg, 1.1 mmol) in DMF (4.0 ml) was added HATU (310 mg, 0.8 mmol) and after stirring for 30 minutes a solution of Intermediate 50-b (370 mg, 0.8 mmol) and DIPEA (428 µl, 2.4 mmol) in DMF was added. The reaction was then stirred at room temperature overnight. A saturated aqueous solution of ammonium chloride and ethyl acetate were then added, the organic layer was separated, washed with a saturated aqueous solution of NaHCO$_3$ and brine, dried over MgSO$_4$, filtered and concentrated under reduced pressure to provide Intermediate 51-a as a beige solid.

Step 2: Intermediate 51-b

To a solution of Intermediate 51-a (450 mg, 0.8 mmol) in MeOH (1.0 ml), was added a solution of 4N hydrogen chloride in 1,4-dioxane (3.0 ml, 12.0 mmol). The reaction was stirred for 2 hours. Volatiles were removed under reduced pressure, diethyl ether was added, a precipitate formed and was collected by filtration, dried under vacuum to provide Intermediate 51-b.2HCl as a beige solid.

Synthesis of Compound 87

Scheme 52

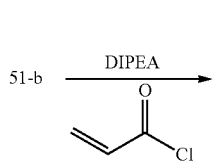

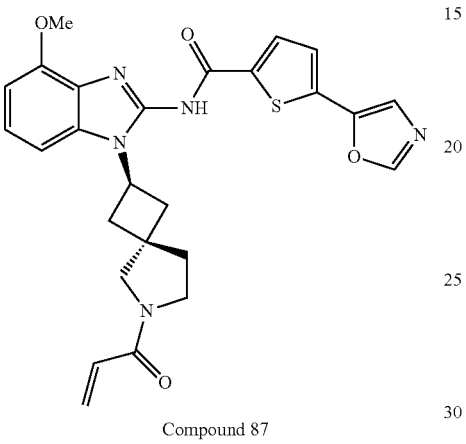

Compound 87

To a solution of Intermediate 51-b.2HCl (400 mg, 0.9 mmol) in DMF (5.0 ml) cooled to 0° C. were sequentially added DIPEA (466 µl, 2.6 mmol) and acryloyl chloride (87 µl, 1.1 mmol) and the reaction was stirred at 0° C. for 30 minutes. A saturated aqueous solution of ammonium chloride and ethyl acetate were added; the organic layer was separated, washed with a saturated aqueous solution of NaHCO₃ and brine, dried over anhydrous MgSO₄, filtered and concentrated under reduced pressure. Purification by reverse phase chromatography provided Compound 87 as a white solid.

Compound 88 was prepared in a similar manner to Compound 87 starting from Intermediate 49-b.

Synthesis of Intermediates 53-b and 53-b'

Scheme 53

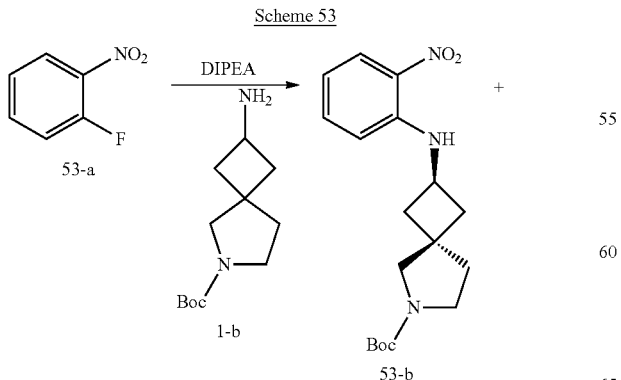

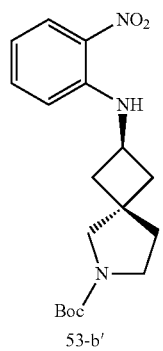

53-b'

To a solution of Intermediate 53-a (405 mg, 2.9 mmol) and DIPEA (2.5 ml, 14.4 mmol) in acetonitrile was added Intermediate 1-b (650 mg, 2.9 mmol). The reaction was stirred at 70° C. overnight and then cooled to room temperature. Volatiles were removed under reduced pressure, a saturated aqueous solution of ammonium chloride and dichloromethane were added to the residue, the organic layer was separated, and the aqueous phase was extracted twice with dichloromethane. The combined organic extracts were washed with a saturated aqueous solution of ammonium chloride and brine, dried over MgSO₄, filtered and concentrated under reduced pressure. Separation by silica gel chromatography eluting with an ethyl acetate/hexane gradient provided Intermediates isomers 53-b as a yellow solid and 53-b' as a yellow solid.

Synthesis of Intermediate 54-b

Scheme 54

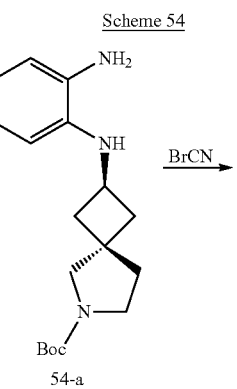

Step 1: Intermediate 54-a

To a solution of Intermediate 53-b' (430 mg, 1.2 mmol) in methanol and stirred under nitrogen was added 10% Pd/C (263 mg, 0.1 mmol). The reaction mixture was purged with H₂ and stirred for 24 hours under H₂. The reaction was then filtered through celite and the filtrate was concentrated under reduced pressure to provide Intermediate 54-a as a beige solid.

Step 2: Intermediate 54-b

To a solution of Intermediate 54-a (400 mg, 1.3 mmol) in EtOH (12.0 ml) was added cyanogen bromide (167 mg, 1.6 mmol) and the reaction was stirred overnight at room temperature. Volatiles were removed under reduced pressure. A saturated aqueous solution of sodium bicarbonate and ethyl acetate were then added to the residue, the organic layer was separated, washed with a saturated aqueous solution of NaHCO$_3$ and brine, dried over MgSO$_4$, filtered and concentrated under reduced pressure to provide Intermediate 54-b as a purple solid.

Synthesis of Intermediate 55-c

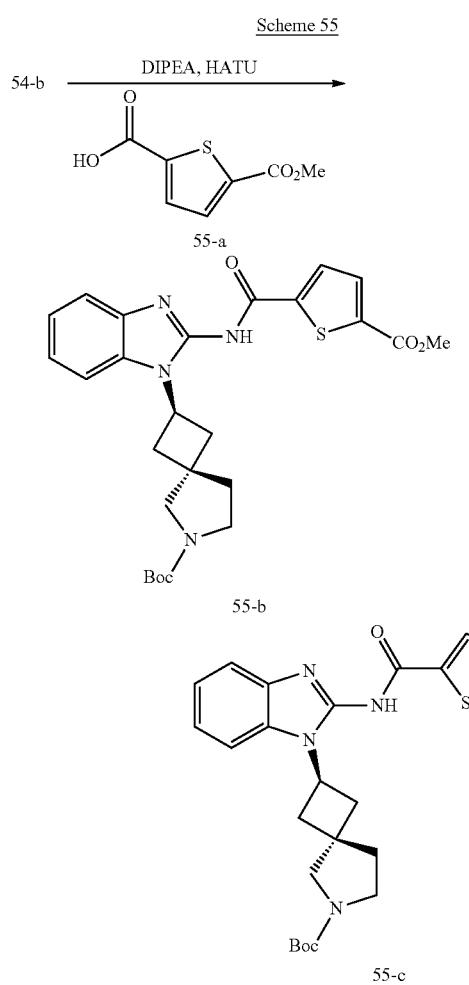

Step 1: Intermediate 55-b

To a solution of Intermediate 55-a (371 mg, 2.0 mmol) in DMF (9.0 ml) was added HATU (1.0 g, 2.7 mmol) and after stirring for 30 minutes a solution of intermediate 54-b (620 mg, 1.8 mmol) and DIPEA (949 µl, 5.4 mmol) in DMF was added. The reaction was then stirred at room temperature overnight. A saturated aqueous solution of ammonium chloride and ethyl acetate were then added, the organic layer was separated, washed with a saturated aqueous solution of NaHCO$_3$ and brine, dried over MgSO$_4$, filtered and concentrated under reduced pressure. Purification by silica gel chromatography provided Intermediate 55-b as a beige solid.

Step 2: Intermediate 55-c

To a solution of Intermediate 55-b (533 mg, 1.0 mmol) in 1,4-dioxane (5 ml) was added a 1N aqueous solution of NaOH (2.0 ml, 2 mmol), the reaction was stirred overnight at room temperature and then acidified with a 1N aqueous solution of HCl. A precipitate formed and was collected by filtration, dried under vacuum to provide Intermediate 55-c as a yellow solid.

Synthesis of Compound 101

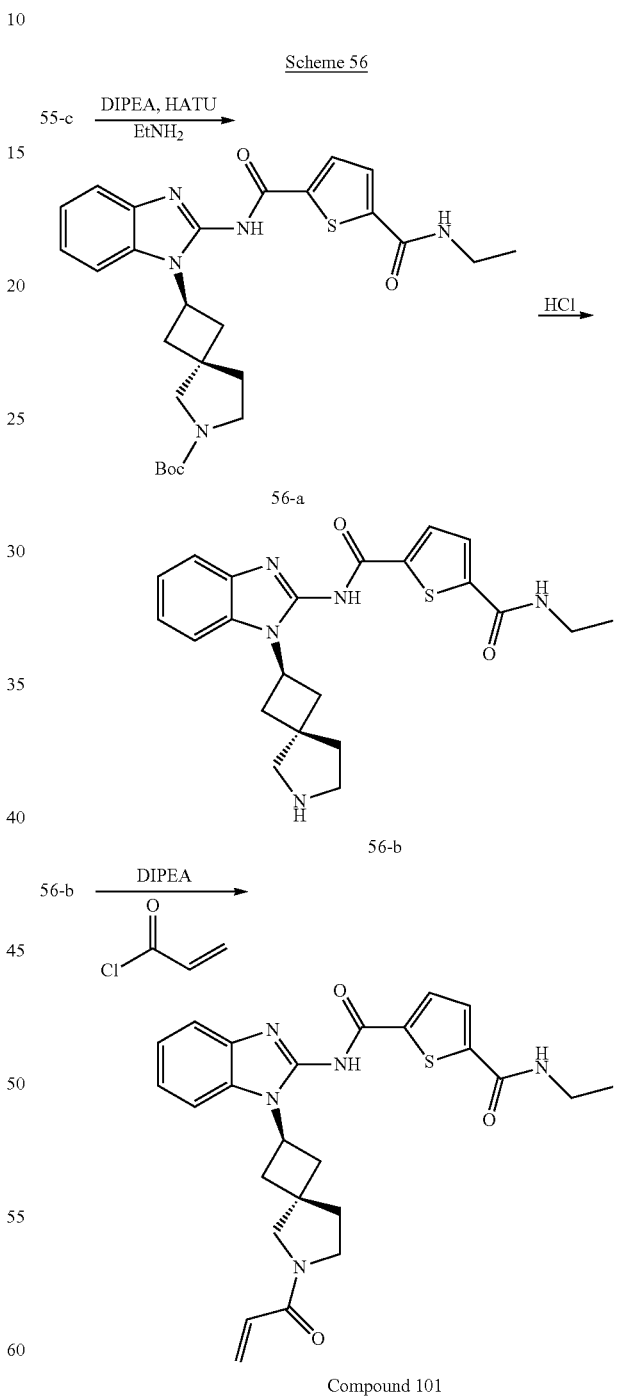

Step 1: Intermediate 56-a

To a solution of Intermediate 55-c (80 mg, 0.2 mmol) in DMF (1 ml) was added HATU (92 mg, 0.2 mmol) and after stirring for 30 minutes DIPEA (84 µl, 0.5 mmol) and ethyl amine (97 µl, 0.2 mmol) were added. The reaction was then stirred at room temperature overnight. A saturated aqueous solution of ammonium chloride and ethyl acetate were then added, the organic layer was separated, washed with a saturated aqueous solution of NaHCO₃ and brine, dried over MgSO₄, filtered and concentrated under reduced pressure. Purification by silica gel chromatography provided Intermediate 56-a as a beige solid.

Step 2: Intermediate 56-b

To a solution of Intermediate 56-a (82 mg, 0.2 mmol) in MeOH (1.0 ml), was added a solution of 4N hydrogen chloride in 1,4-dioxane (3.0 ml, 12.0 mmol). The reaction was stirred for 2 hours. Volatiles were removed under reduced pressure, diethyl ether was added, a precipitate formed and was collected by filtration, dried under vacuum to provide Intermediate 56-b.HCl as a beige solid.

Step 3: Compound 101

To a solution of Intermediate 56-b.HCl (70 mg, 0.1 mmol) in DMF (3.0 ml) cooled to 0° C. were sequentially added DIPEA (80 µl, 0.5 mmol) and acryloyl chloride (15 µl, 0.2 mmol) and the reaction was stirred at 0° C. for 30 minutes. A saturated aqueous solution of ammonium chloride and ethyl acetate were added; the organic layer was separated, washed with a saturated aqueous solution of NaHCO₃ and brine, dried over anhydrous MgSO₄, filtered and concentrated under reduced pressure. Purification by reverse phase chromatography provided Compound 101 as an off-white solid.

Compounds 85, 91, and 102 were prepared, starting from Intermediate 55-c, in a similar manner to Compound 101 by replacing

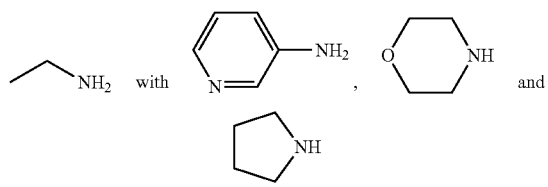

respectively.

Synthesis of Compound 98

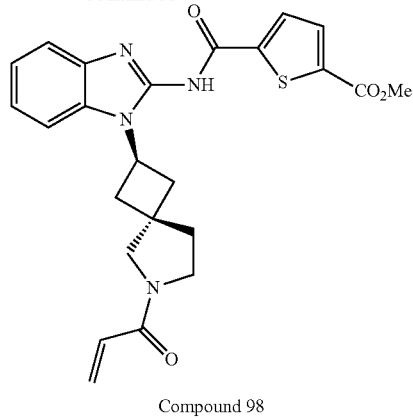

Compound 98

Step 1: Intermediate 57-a

To a solution of Intermediate 55-b (100 mg, 0.2 mmol) in MeOH (1.0 ml), was added a solution of 4N hydrogen chloride in 1,4-dioxane (3.0 ml, 12.0 mmol). The reaction was stirred for 2 hours. Volatiles were removed under reduced pressure, diethyl ether was added, a precipitate formed and was collected by filtration, dried under vacuum to provide Intermediate 57-a.HCl as a beige solid.

Step 2: Compound 98

To a solution of Intermediate 57-a.HCl (88 mg, 0.2 mmol) in DMF (3.0 ml) cooled to 0° C. were sequentially added DIPEA (103 µl, 0.6 mmol) and acryloyl chloride (19 µl, 0.2 mmol) and the reaction was stirred at 0° C. for 30 minutes. A saturated aqueous solution of ammonium chloride and ethyl acetate were added; the organic layer was separated, washed with a saturated aqueous solution of NaHCO₃ and brine, dried over anhydrous MgSO₄, filtered and concentrated under reduced pressure. Purification by reverse phase chromatography provided Compound 98 as a beige solid.

Compound 100 was prepared in a similar manner to Compound 98 starting from Intermediate 55-c.

Synthesis of Intermediate 58-c

Scheme 57

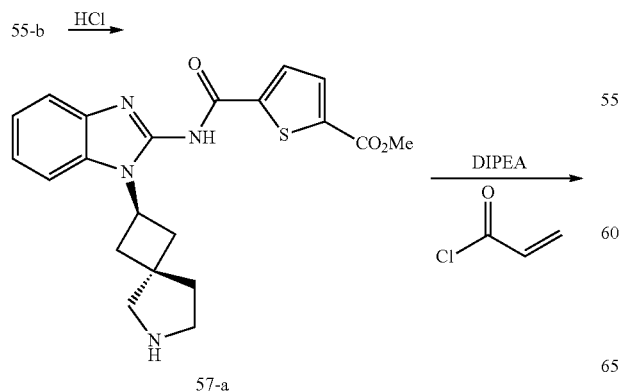

Scheme 58

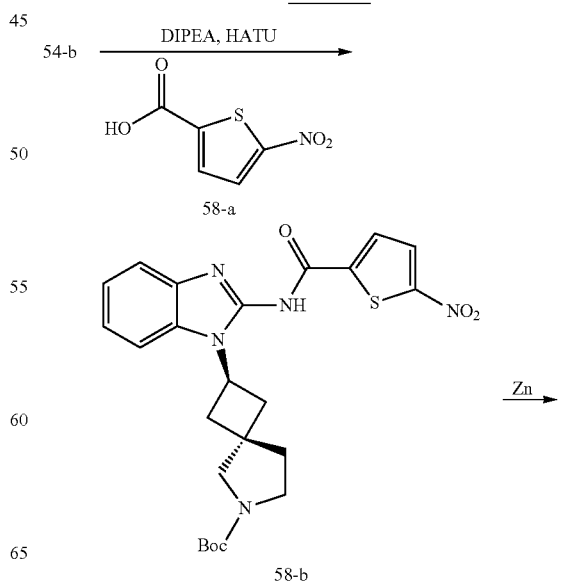

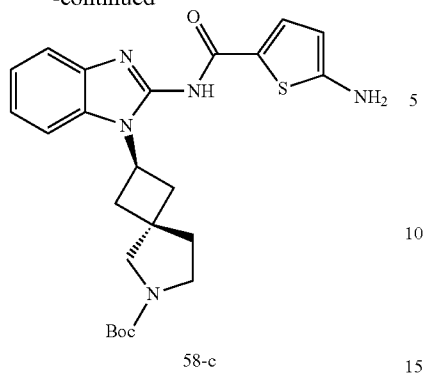

58-c

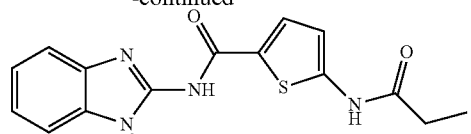

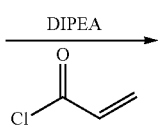

Step 1: Intermediate 58-b

To a solution of Intermediate 58-a (445 mg, 2.6 mmol) in DMF (5.0 ml) was added HATU (1.3 g, 3.5 mmol) and after stirring for 30 minutes a solution of intermediate 54-b (800 mg, 2.4 mmol) and DIPEA (1.2 ml, 7.0 mmol) in DMF was added. The reaction was then stirred at room temperature overnight. A saturated aqueous solution of ammonium chloride and ethyl acetate were then added, the organic layer was separated, washed with a saturated aqueous solution of NaHCO$_3$ and brine, dried over MgSO$_4$, filtered and concentrated under reduced pressure to provide Intermediate 58-b as a beige solid.

Step 2: Intermediate 58-c

To a solution of Intermediate 58-b (1.1 g, 2.3 mmol) in methanol (10.0 ml) and water (1 ml) were sequentially added ammonium chloride (1.2 g) and zinc dust (453 mg, 6.9 mmol) and the reaction was stirred at room temperature overnight. Volatiles were removed under reduced pressure. A saturated aqueous solution of sodium bicarbonate and ethyl acetate were added to the residue, the organic layer was separated, and the aqueous phase was extracted twice with ethyl acetate. The combined organic extracts were washed with a saturated aqueous solution of ammonium chloride and brine, dried over MgSO$_4$, filtered and concentrated under reduced pressure to provide Intermediate 58-c as a beige solid.

Synthesis of Compound 105

Scheme 59

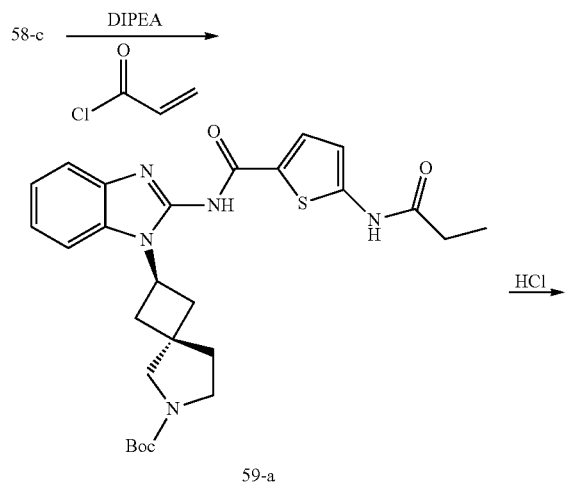

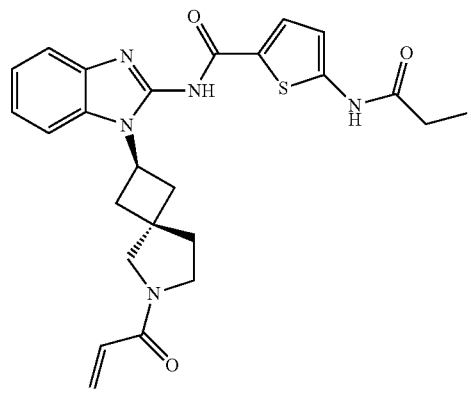

Compound 105

Step 1: Intermediate 59-a

To a solution of Intermediate 58-c (150 mg, 0.3 mmol) in dichloromethane (4.0 ml) cooled to 0° C. were sequentially added DIPEA (103 μl, 0.6 mmol) and propionyl chloride (34 μl, 0.4 mmol) and the reaction was stirred at room temperature overnight. A saturated aqueous solution of ammonium chloride and ethyl acetate were added; the organic layer was separated, washed with a saturated aqueous solution of NaHCO$_3$ and brine, dried over anhydrous MgSO$_4$, filtered and concentrated under reduced pressure. Purification by silica gel chromatography provided Intermediate 59-a as a beige solid.

Step 2: Intermediate 59-b

To a solution of Intermediate 59-a (149 mg, 0.3 mmol) in MeOH (1.0 ml), was added a solution of 4N hydrogen chloride in 1,4-dioxane (2.0 ml, 8.0 mmol). The reaction was stirred for 2 hours. Volatiles were removed under reduced pressure, diethyl ether was added, a precipitate formed and was collected by filtration, dried under vacuum to provide Intermediate 59-b.HCl as a beige solid.

Step 3: Compound 105

To a solution of Intermediate 59-b.HCl (121 mg, 0.3 mmol) in DMF (3.0 ml) cooled to −78° C. were sequentially added DIPEA (138 μl, 0.8 mmol) and acryloyl chloride (26 μl, 0.3 mmol) and the reaction was stirred at 0° C. for 30 minutes. A saturated aqueous solution of ammonium chloride and ethyl acetate were added; the organic layer was separated, washed with a saturated aqueous solution of NaHCO$_3$ and brine, dried over MgSO$_4$, filtered and concentrated under reduced pressure. Purification by reverse phase chromatography provided Compound 105 as a white solid.

Compound 106, 111, and 112 were prepared, starting from Intermediate 58-c, in a similar manner to Compound 105 by replacing

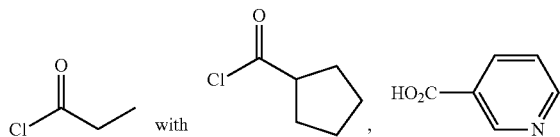

in the presence of HATU and

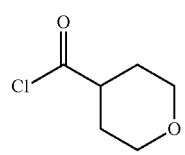

respectively.

Synthesis of Intermediate 60-b

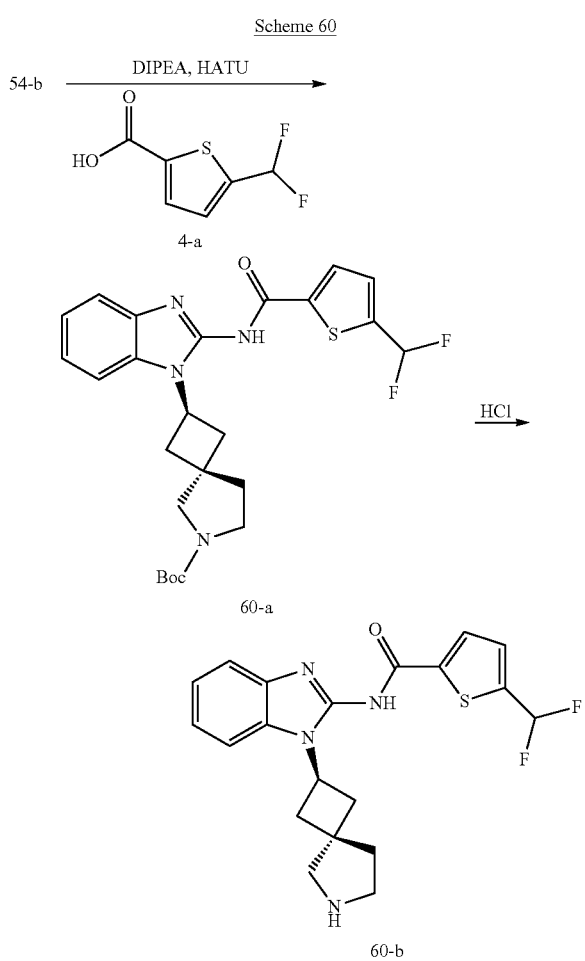

Step 1: Intermediate 60-a

To a solution of Intermediate 4-a (109 mg, 0.6 mmol) in DMF (3.0 ml) was added HATU (274 mg, 0.7 mmol) and after stirring for 30 minutes a solution of intermediate 54-b (190 mg, 0.5 mmol) and DIPEA (291 µl, 1.6 mmol) in DMF was added. The reaction was then stirred at room temperature overnight. A saturated aqueous solution of ammonium chloride and ethyl acetate were then added, the organic layer was separated, washed with a saturated aqueous solution of NaHCO$_3$ and brine, dried over MgSO$_4$, filtered and concentrated under reduced pressure to provide Intermediate 60-a as a beige solid.

Step 2: Intermediate 60-b

To a solution of Intermediate 60-a (170 mg, 0.3 mmol) in MeOH (1.0 ml), was added a solution of 4N hydrogen chloride in 1,4-dioxane (5.0 ml, 20.0 mmol). The reaction was stirred for 2 hours. Volatiles were removed under reduced pressure, diethyl ether was added, a precipitate formed and was collected by filtration, dried under vacuum to provide Intermediate 60-b.HCl as a beige solid.

Synthesis of Compound 15

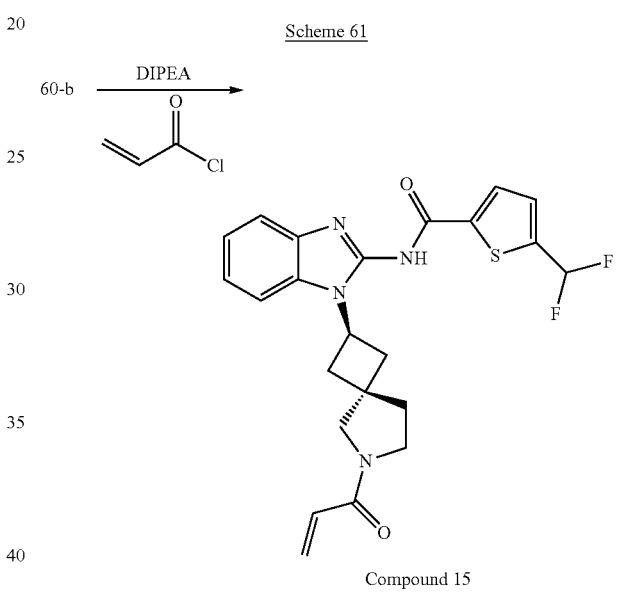

To a solution of Intermediate 60-b.HCl (136 mg, 0.3 mmol) in DMF (2.0 ml) cooled to 0° C. were sequentially added DIPEA (294 µl, 1.7 mmol) and acryloyl chloride (33 µl, 0.4 mmol) and the reaction was stirred at 0° C. for 30 minutes. A saturated aqueous solution of ammonium chloride and ethyl acetate were added; the organic layer was separated, washed with a saturated aqueous solution of NaHCO$_3$ and brine, dried over anhydrous MgSO$_4$, filtered and concentrated under reduced pressure. Purification by reverse phase chromatography provided Compound 15 as a white solid.

Compound 17 was prepared, starting from Intermediate 53-b, in a similar manner to Compound 15.

Compound 18 was prepared, starting from Intermediate 53-b, in a similar manner to Compound 17, by replacing

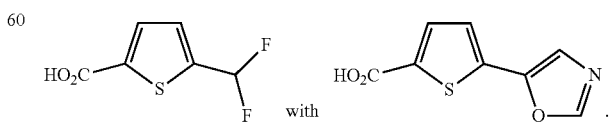

Compounds 16, 29, 30, 45, 46, 47, 48, 49, 55, 66, 79, 80, 81, 82, 83, 84, 92, 93, 94, 103, 104, 107 and 115 were prepared, starting from Intermediate 54-b, in a similar manner to Compound 15, by replacing

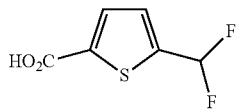 [SMILES: O=C(O)c1ccc(C(F)F)s1]

for the synthesis of Intermediate 60-a with

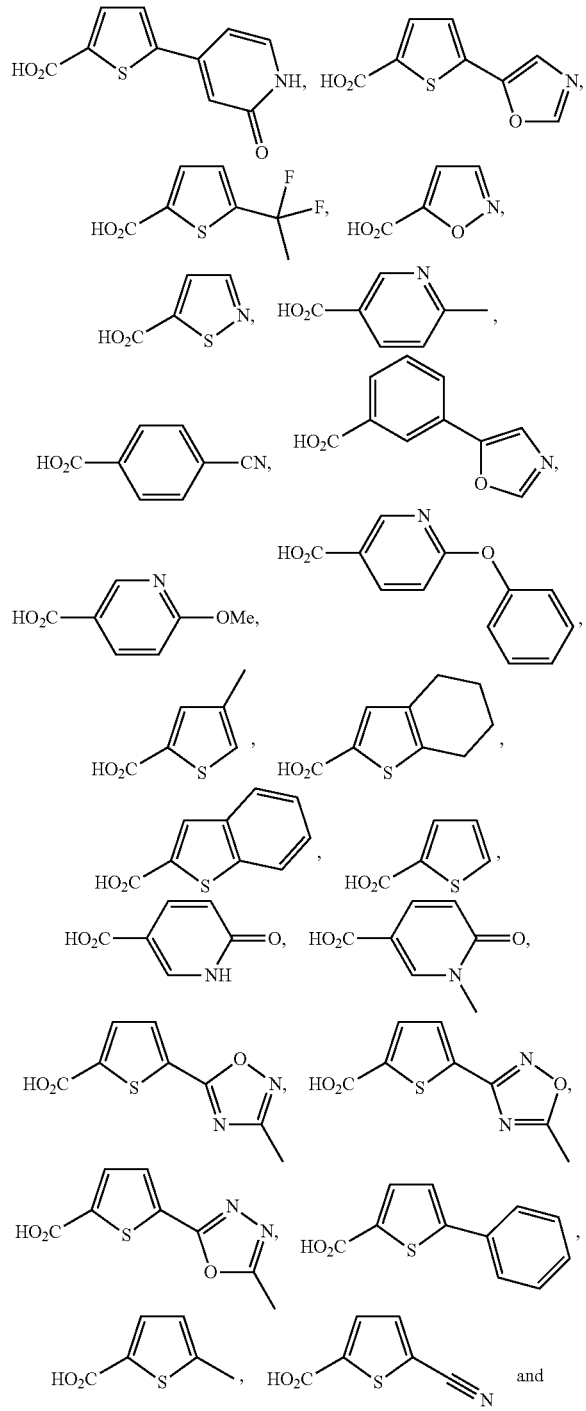

respectively.

Synthesis of Intermediate 62-c

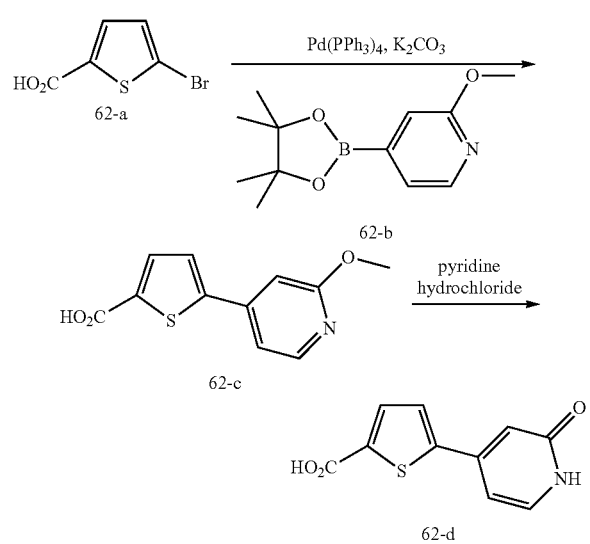

Scheme 62

Step 1: Intermediate 62-c

To a degassed solution of Intermediate 62-a (1.0 g, 4.8 mmol), intermediate 62-b (1.2 g, 5.1 mmol) and potassium carbonate (6.7 g, 48.3 mmol) in 1,4-dioxane (40.2 ml) and water (8.0 ml) was added Pd(PPh$_3$)$_4$ (279 mg, 0.2 mmol) and the reaction was heated at 80° C. overnight and then cooled to room temperature. Dichloromethane was added, the organic layer was separated and the aqueous phase was acidified to PH 3-4 with 6N HCl. A precipitate formed and was collected by filtration, dried under vacuum to provide Intermediate 62-c as a beige solid.

Step 2: Intermediate 62-d

To a solution of Intermediate 62-c (790 mg, 3.4 mmol) in DMSO (2.0 ml) was added pyridine hydrochloride (1.9 g, 16.8 mmol) and the reaction was stirred at 160° C. for 15 minutes and then cooled to room temperature. Water was added; a precipitate formed and was collected by filtration, dried under vacuum to provide Intermediate 62-d as a beige solid.

Synthesis of Intermediate 63-b

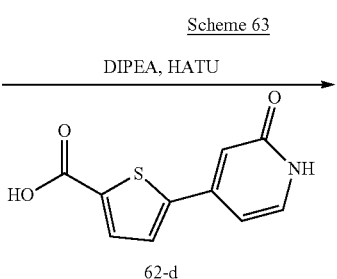

Scheme 63

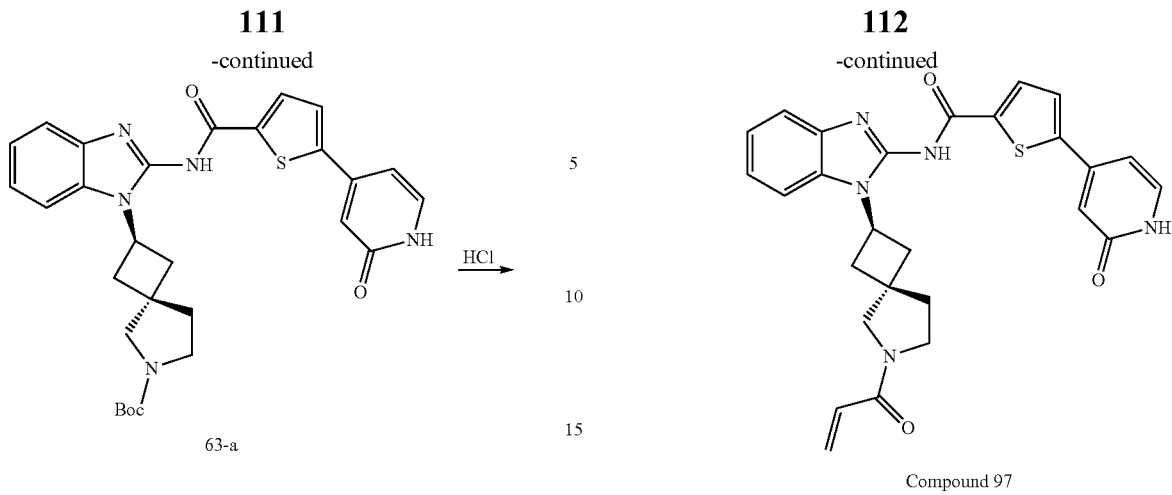

63-a

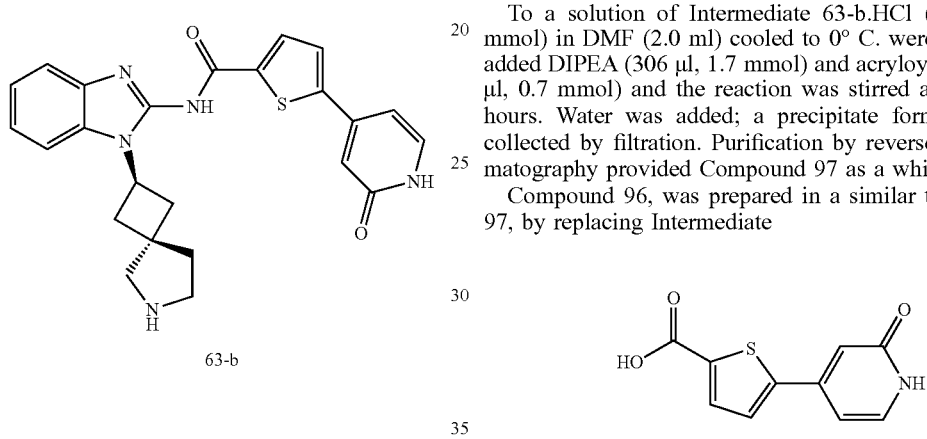

63-b

Step 1: Intermediate 63-a

To a solution of Intermediate 62-d (194 mg, 0.9 mmol) in DMF (1.0 ml) was added HATU (333 mg, 0.9 mmol) and after stirring for 30 minutes a solution of intermediate 54-b (200 mg, 0.6 mmol) and DIPEA (408 µl, 2.3 mmol) in DMF was added. The reaction was then stirred at room temperature overnight. Water was added, a precipitate formed and was collected by filtration, dried under vacuum to provide Intermediate 63-a as a beige solid.

Step 2: Intermediate 63-b

To a solution of Intermediate 63-a (319 mg, 0.6 mmol) in MeOH (2.0 ml), was added a solution of 4N hydrogen chloride in 1,4-dioxane (3.5 ml, 14.0 mmol). The reaction was stirred for 2 hours. Volatiles were removed under reduced pressure, diethyl ether was added, a precipitate formed and was collected by filtration, dried under vacuum to provide Intermediate 63-b.HCl as a beige solid.

Synthesis of Compound 97

Scheme 64

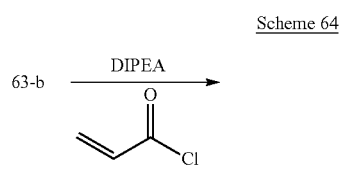

Compound 97

To a solution of Intermediate 63-b.HCl (281 mg, 0.6 mmol) in DMF (2.0 ml) cooled to 0° C. were sequentially added DIPEA (306 µl, 1.7 mmol) and acryloyl chloride (57 µl, 0.7 mmol) and the reaction was stirred at 0° C. for 2 hours. Water was added; a precipitate formed and was collected by filtration. Purification by reverse phase chromatography provided Compound 97 as a white solid.

Compound 96, was prepared in a similar to Compound 97, by replacing Intermediate

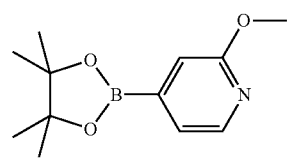

for the synthesis of Intermediate 63-a with

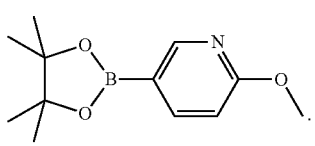

Compounds 95 and 99, were prepared in a similar manner to Compounds 96 and 97, by replacing for the synthesis of Intermediates 62-c and 62-d with Compounds 108 and 109, were prepared in a similar manner to Compound 95, by replacing

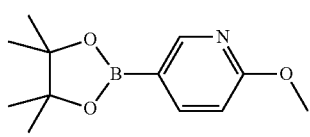

for the synthesis of Intermediate 62-c with

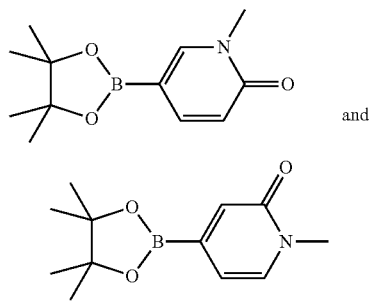

respectively.

Compounds 75 and 113, were prepared in a similar manner to Compound 95, by replacing

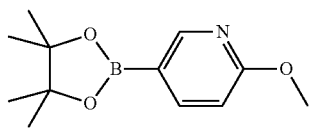

for the synthesis of Intermediate 62-c with

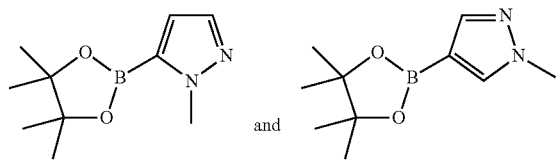

respectively.

Synthesis of Intermediate 65-d

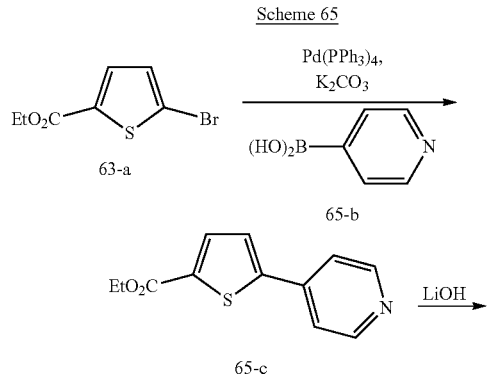

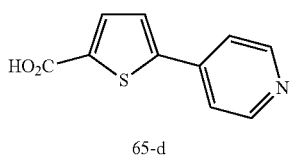

Step 1: Intermediate 65-c

To a degassed solution of Intermediate 63-a (1.0 g, 4.2 mmol), intermediate 65-b (575 mg, 4.7 mmol) and potassium carbonate (1.2 g, 8.5 mmol) in 1,4-dioxane (35.4 ml) and water (7.1 ml) was added Pd(PPh$_3$)$_4$ (246 mg, 0.2 mmol) and the reaction was heated in at 80° C. overnight and then cooled to room temperature. Water and ethyl acetate were added, the organic layer was separated, the aqueous phase was extracted with ethyl acetate, the combined organic extracts were washed with brine, dried over anhydrous MgSO$_4$, filtered and concentrated under reduced pressure to provide Intermediate 65-c as a beige solid.

Step 2: Intermediate 65-d

To a solution of Intermediate 65-c (991 mg, 4.2 mmol) in THF (10.6 ml) and water (10.6 ml) was added LiOH (509 mg, 21.2 mmol) and the reaction was stirred at room temperature overnight. Water and ethyl acetate were added, the organic layer was separated, and the aqueous phase was acidified to PH 3-4 with 6N HCl. A precipitate formed and was collected by filtration, washed with water and diethyl ether, dried under vacuum to provide Intermediate 65-d as a white solid.

Synthesis of Intermediate 66-b

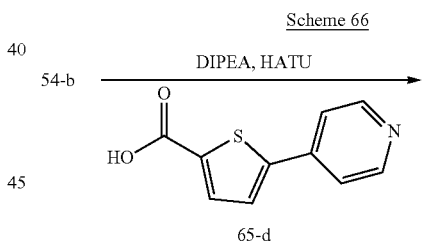

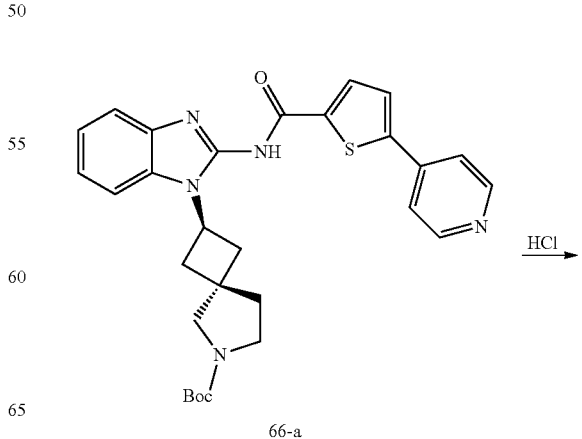

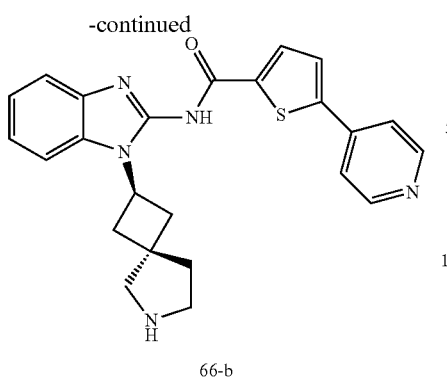

66-b

Step 1: Intermediate 66-a

To a solution of Intermediate 65-d (180 mg, 0.9 mmol) in DMF (1.0 ml) was added HATU (333 mg, 0.9 mmol) and after stirring for 30 minutes a solution of intermediate 54-b (200 mg, 0.6 mmol) and DIPEA (408 µl, 2.3 mmol) in DMF was added. The reaction was then stirred at room temperature overnight. Water was added, a precipitate formed and was collected by filtration, dried under vacuum to provide Intermediate 66-a as a beige solid.

Step 2: Intermediate 66-b

To a solution of Intermediate 66-a (309 mg, 0.6 mmol) in MeOH (2.0 ml), was added a solution of 4N hydrogen chloride in 1,4-dioxane (3.5 ml, 14.0 mmol). The reaction was stirred for 2 hours. Volatiles were removed under reduced pressure, diethyl ether was added, a precipitate formed and was collected by filtration, dried under vacuum to provide Intermediate 66-b.2HCl as a beige solid.

Synthesis of Compound 110

Scheme 67

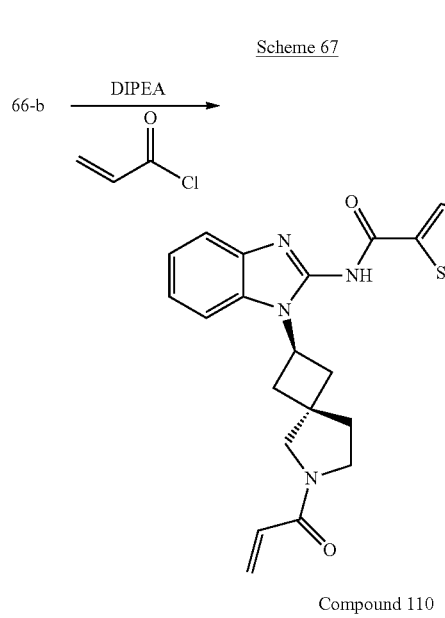

Compound 110

To a solution of Intermediate 66-b.2HCl (272 mg, 0.6 mmol) in DMF (4.0 ml) cooled to 0° C. were sequentially added DIPEA (306 µl, 1.7 mmol) and acryloyl chloride (57 µl, 0.7 mmol) and the reaction was stirred at 0° C. for 2 hours. Water was added; a precipitate formed and was collected by filtration. Purification by reverse phase chromatography provided Compound 110 as a white solid.

Compounds 74, 90 and 125 were prepared in a similar manner to Compound 110, by replacing

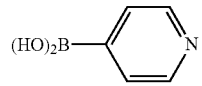

for the synthesis of Intermediate 66-a with

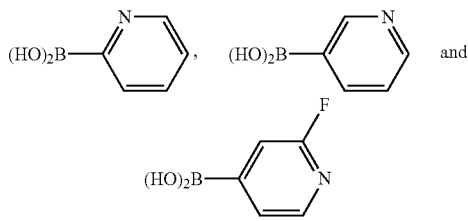

respectively.

Compounds 124 and 126 were prepared in a similar manner to Compound 110, by replacing

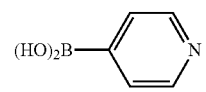

for the synthesis of Intermediate 66-a with

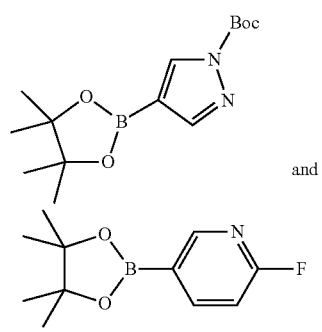

respectively.

Synthesis of Intermediate 68-b

Scheme 68

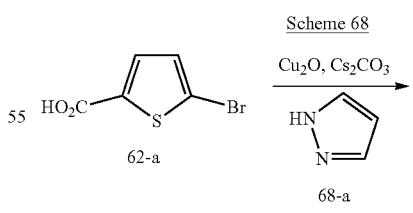

To a degassed solution of Intermediate 62-a (500 mg, 2.4 mmol), Cu₂O (23 mg, 0.2 mmol), cesium carbonate (1.6 g, 4.8 mmol) in DMF was added intermediate 68-a (110 mg, 1.6 mmol) and the reaction was heated in at 110° C. overnight and then cooled to room temperature. A saturated aqueous solution of ammonium chloride was added; a precipitate formed and was collected by filtration to provide Intermediate 68-b as a beige solid.

Synthesis of Intermediate 69-b

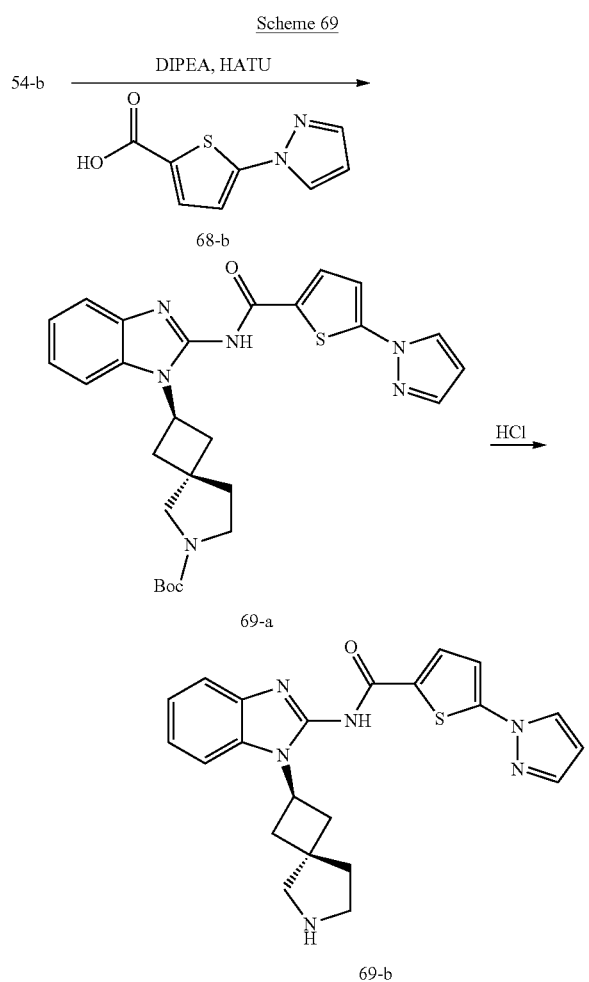

Step 1: Intermediate 69-a

To a solution of Intermediate 68-b (138 mg, 0.7 mmol) in DMF (2.0 ml) was added HATU (269 mg, 0.7 mmol) and after stirring for 30 minutes a solution of intermediate 54-b (200 mg, 0.5 mmol) and DIPEA (248 µl, 1.4 mmol) in DMF was added. The reaction was then stirred at room temperature overnight. Water was added, a precipitate formed and was collected by filtration, dried under vacuum to provide Intermediate 69-a as a beige solid.

Step 2: Intermediate 69-b

To a solution of Intermediate 69-a (90 mg, 0.2 mmol) in MeOH (1.0 ml), was added a solution of 4N hydrogen chloride in 1,4-dioxane (3.0 ml, 12.0 mmol). The reaction was stirred for 2 hours. Volatiles were removed under reduced pressure, diethyl ether was added, a precipitate formed and was collected by filtration, dried under vacuum to provide Intermediate 69-b.2HCl as a beige solid.

Synthesis of Compound 89

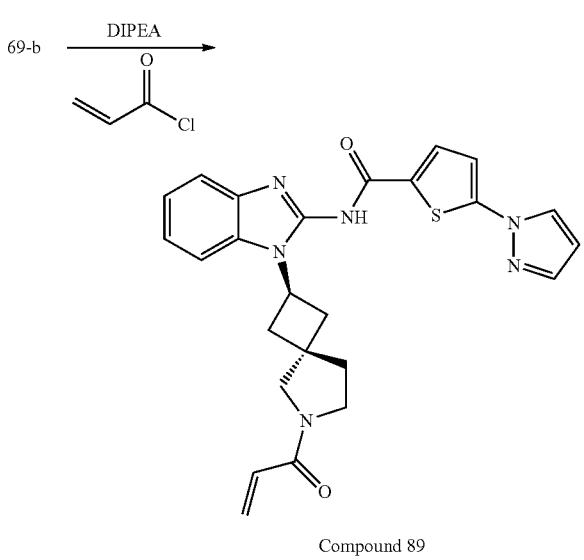

To a solution of Intermediate 69-b.2HCl (90 mg, 0.2 mmol) in DMF (5.0 ml) cooled to 0° C. were sequentially added DIPEA (113 µl, 0.6 mmol) and acryloyl chloride (21 µl, 0.2 mmol) and the reaction was stirred at 0° C. for 2 hours. Water and ethyl acetate were added, the organic layer was separated, the aqueous phase was extracted with ethyl acetate, the combined organic extracts were washed with brine, dried over anhydrous MgSO$_4$, filtered and concentrated under reduced pressure. Purification by reverse phase chromatography provided Compound 89 as a white solid.

Synthesis of Intermediate 71-d

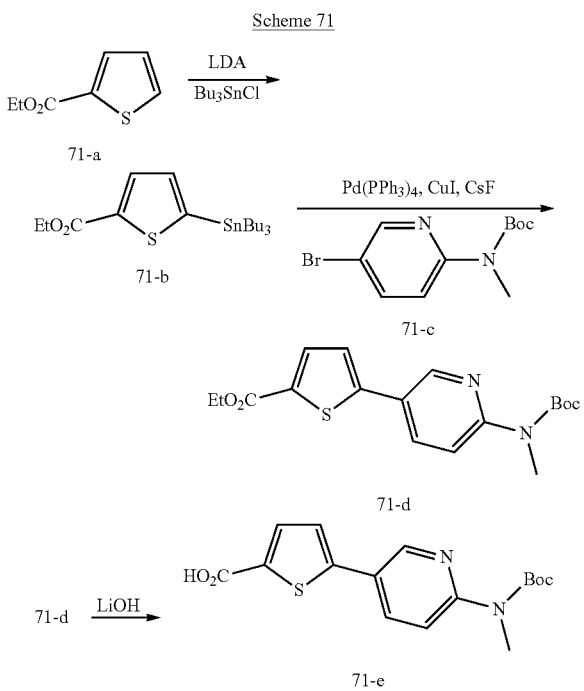

Step 1: Intermediate 71-b

To a solution of ethyl thiophene-2-carboxylate 71-a (2.0 g, 12.8 mmol) in THF (13.0 ml) cooled to −78° C. was added LDA (7.0 ml, 14.1 mmol) and after stirring for 1 hour, Bu₃SnCl (4.4 g, 13.5 mmol) in THF was added drop wise. The reaction was stirred at −70° C. for 1 hour and room temperature overnight. A saturated aqueous solution of ammonium chloride and ethyl acetate were added, the organic layer was separated, dried over anhydrous MgSO₄, filtered and concentrated under reduced pressure. Purification by silica gel chromatography provided Intermediate 71-b as a colorless oil.

Step 2: Intermediate 71-d

To a solution of Intermediate 71-b (500 mg, 1.1 mmol) in DMF (4.0 ml) were sequentially added Intermediate 71-c (269 mg, 0.9 mmol), copper (I) iodide (36 mg, 0.2 mmol) Pd(PPh₃)₄ (108 mg, 0.1 mmol) and CsF (284 mg, 1.9 mmol) and the reaction was stirred at 120° C. overnight and then cooled to room temperature. A saturated aqueous solution of ammonium chloride and ethyl acetate were added, the organic layer was separated, dried over anhydrous MgSO₄, filtered and concentrated under reduced pressure. Purification by silica gel chromatography provided Intermediate 71-d as a white solid.

Step 3: Intermediate 71-e

To a solution of Intermediate 71-d (200 mg, 0.8 mmol) in THF:water 1:1 (8.0 ml) was added LiOH (91 mg, 3.8 mmol) and the reaction was stirred at 60° C. overnight and then cooled to room temperature. Diethyl ether was added; the aqueous phase was separated and acidified to PH ~3 with 2N HCl. A precipitated formed and was collected by filtration, dried under vacuum to provide Intermediate 71-e as a yellow solid.

Synthesis of Intermediate 72-b

Scheme 72

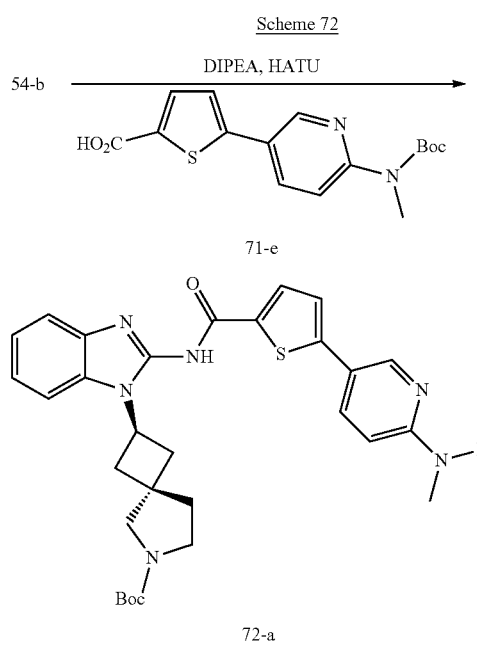

72-a

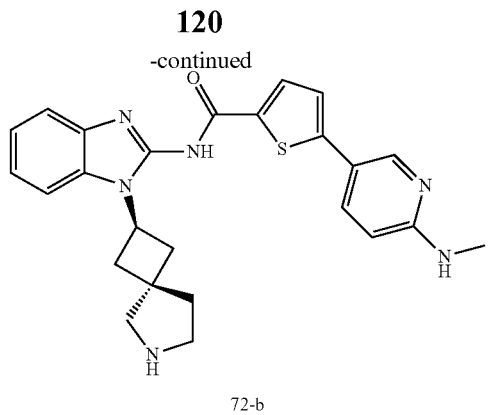

72-b

Step 1: Intermediate 72-a

To a solution of Intermediate 71-e (166 mg, 0.7 mmol) in DMF (2.0 ml) cooled to 0° C. was added HATU (290 mg, 0.8 mmol) and after stirring for 30 minutes a solution of intermediate 54-b (187 mg, 0.5 mmol) and DIPEA (286 µl, 1.6 mmol) in DMF was added. The reaction was then stirred at room temperature overnight. A saturated aqueous solution of ammonium chloride and ethyl acetate were added, the organic layer was separated, dried over anhydrous MgSO₄, filtered and concentrated under reduced pressure. Purification by silica gel chromatography provided Intermediate 72-a as a beige solid.

Step 2: Intermediate 72-b

To a solution of Intermediate 72-a (135 mg, 0.2 mmol) in MeOH (1.0 ml), was added a solution of 4N hydrogen chloride in 1,4-dioxane (4.0 ml, 16.0 mmol). The reaction was stirred for 2 hours. Volatiles were removed under reduced pressure, diethyl ether was added, a precipitate formed and was collected by filtration, dried under vacuum to provide Intermediate 72-b.2HCl as a beige solid.

Synthesis of Compound 117

Scheme 73

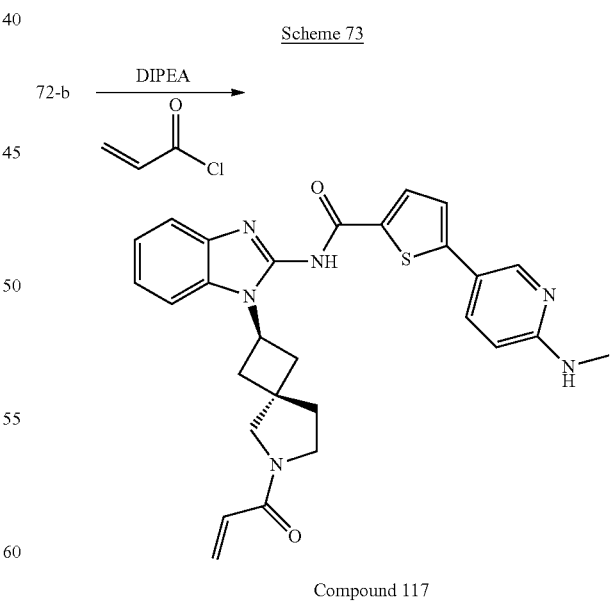

Compound 117

To a solution of Intermediate 72-b.2HCl (120 mg, 0.2 mmol) in DMF (5.0 ml) cooled to −78° C. were sequentially added DIPEA (127 µl, 0.7 mmol) and acryloyl chloride (24 µl, 0.3 mmol) and the reaction was stirred at −78° C. for 15 minutes. A saturated aqueous solution of ammonium chloride and ethyl acetate were added, the organic layer was separated, the aqueous phase was extracted with ethyl acetate, the combined organic extracts were washed with brine, dried over anhydrous MgSO$_4$, filtered and concentrated under reduced pressure. Purification by reverse phase chromatography provided Compound 117 as a white solid.

Compounds 123, 128 and 31 were prepared in a similar manner to Compound 117, by replacing

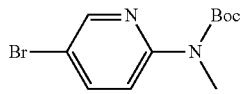

for the synthesis of Intermediate 71-e with

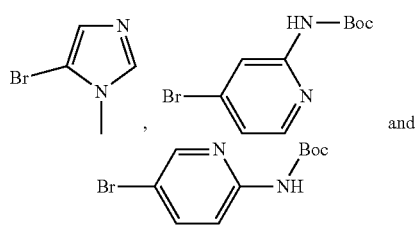

and respectively.

Synthesis of Intermediate 74-c

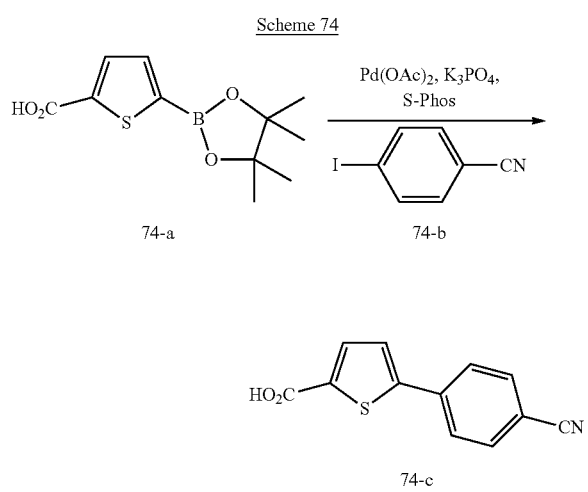

To a degassed solution of Intermediate 74-a (500 mg, 1.9 mmol), intermediate 74-b (239 mg, 1.3 mmol) and potassium phosphate (557 mg, 2.6 mmol) in a 5:1 mixture of 1,4-dioxane:water (5.0 ml) was added Pd(OAc)$_2$ (15 mg, 0.06 mmol), S-Phos (54 mg, 0.1 mmol) and the reaction was heated at 100° C. overnight and then cooled to room temperature. Water and ethyl acetate were added, the organic layer was separated. The aqueous phase was acidified to PH-1, extracted twice with ethyl acetate, the combined organic extracts were washed with brine, dried over anhydrous MgSO$_4$, filtered and concentrated under reduced pressure to provide Intermediate 74-c as a beige solid.

Synthesis of Intermediate 75-b

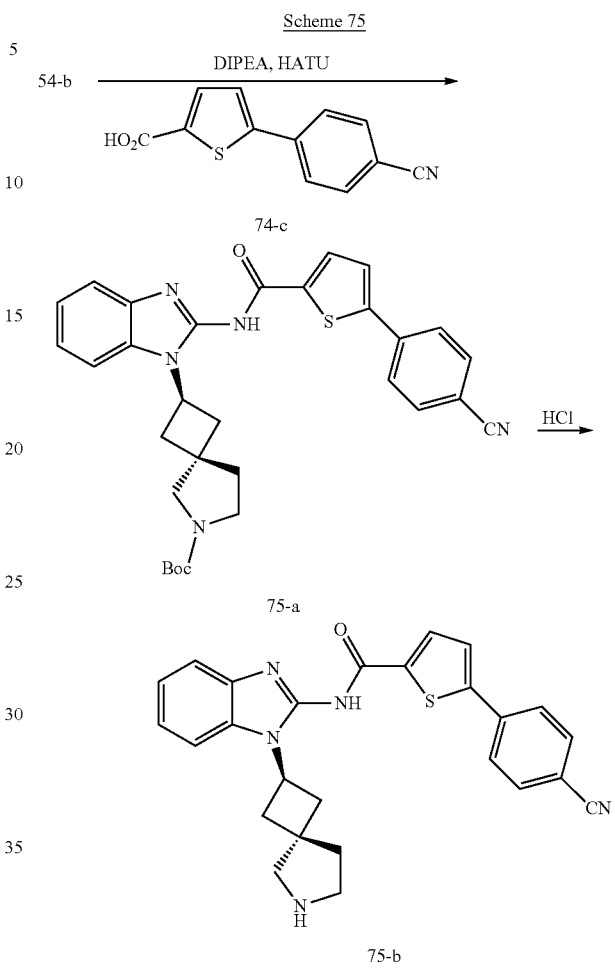

Step 1: Intermediate 75-a

To a solution of Intermediate 74-c (130 mg, 0.6 mmol) in DMF (2.0 ml) was added HATU (232 mg, 0.6 mmol) and after stirring for 30 minutes a solution of intermediate 54-b (149 mg, 0.4 mmol) and DIPEA (229 µl, 1.3 mmol) in DMF was added. The reaction was then stirred at room temperature overnight. A saturated aqueous solution of ammonium chloride and ethyl acetate were added, the organic layer was separated, dried over anhydrous MgSO$_4$, filtered and concentrated under reduced pressure. Purification by silica gel chromatography provided Intermediate 75-a as a beige solid.

Step 2: Intermediate 75-b

To a solution of Intermediate 75-a (135 mg, 0.2 mmol) in MeOH (1.0 ml), was added a solution of 4N hydrogen chloride in 1,4-dioxane (4.0 ml, 16.0 mmol). The reaction was stirred for 2 hours. Volatiles were removed under reduced pressure, diethyl ether was added, a precipitate formed and was collected by filtration, dried under vacuum to provide Intermediate 75-b.HCl as a beige solid.

Synthesis of Compound 118

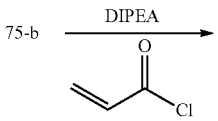

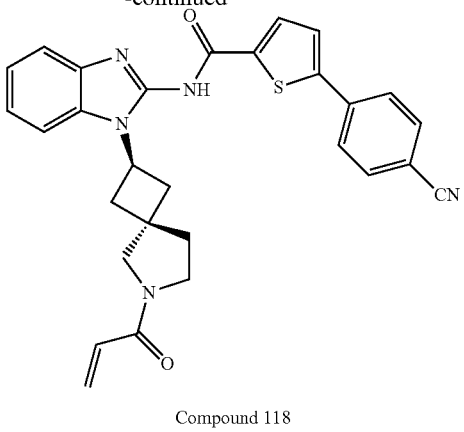

Compound 118

To a solution of Intermediate 75-b.HCl (119 mg, 0.2 mmol) in DMF (5.0 ml) cooled to 0° C. ° C. were sequentially added DIPEA (137 μl, 0.8 mmol) and acryloyl chloride (26 μl, 0.3 mmol) and the reaction was stirred at 0° C. for 15 minutes. A saturated aqueous solution of ammonium chloride and ethyl acetate were added, the organic layer was separated, the aqueous phase was extracted with ethyl acetate, the combined organic extracts were washed with brine, dried over anhydrous MgSO₄, filtered and concentrated under reduced pressure. Purification by reverse phase chromatography provided Compound 118 as a white solid.

Compound 122 was prepared in a similar manner to Compound 118, by replacing

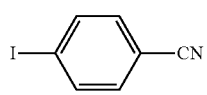

for the synthesis of Intermediate 74-c with

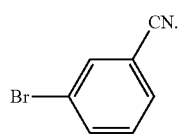

Synthesis of Intermediate 77-d

Scheme 77

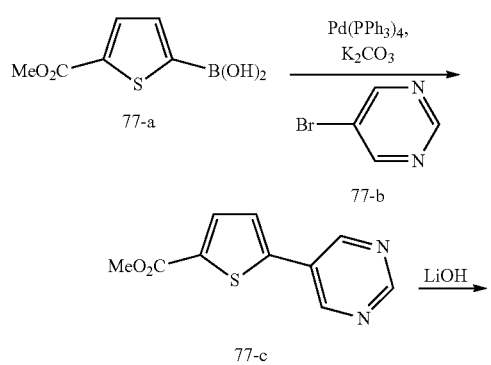

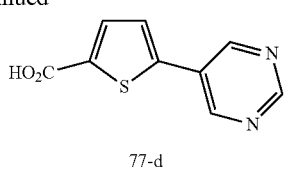

77-d

Step 1: Intermediate 77-c

To a degassed solution of Intermediate 77-a (200 mg, 1.1 mmol), intermediate 77-b (155 mg, 1.0 mmol) and potassium carbonate (270 mg, 1.9 mmol) in 1,4-dioxane (8.1 ml) and water (1.6 ml) was added Pd(PPh₃)₄ (56 mg, 0.05 mmol) and the reaction was heated in at 80° C. for 3 hours and then cooled to room temperature. Water and ethyl acetate were added, the organic layer was separated, the aqueous phase was extracted twice with ethyl acetate, the combined organic extracts were washed with brine, dried over anhydrous MgSO₄, filtered and concentrated under reduced pressure to provide Intermediate 77-c as a beige solid.

Step 2: Intermediate 77-d

To a solution of Intermediate 77-c (215 mg, 1.0 mmol) in THF:water 1:1 (5.0 ml) was added LiOH (117 mg, 4.9 mmol) and the reaction was stirred at room temperature for 3 hours. Water and ethyl acetate were added. The aqueous phase was separated, acidified to PH-1 with 6N HCl and extracted twice with ethyl acetate. The combined organic extracts were dried over anhydrous MgSO₄, filtered and concentrated under reduced pressure to provide Intermediate 77-d as a white solid.

Synthesis of Intermediate 78-b

Scheme 78

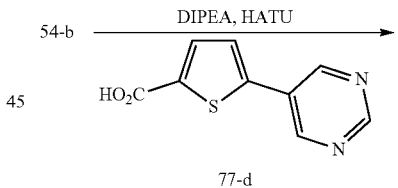

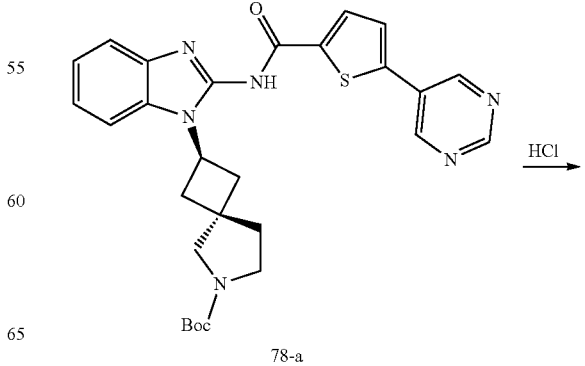

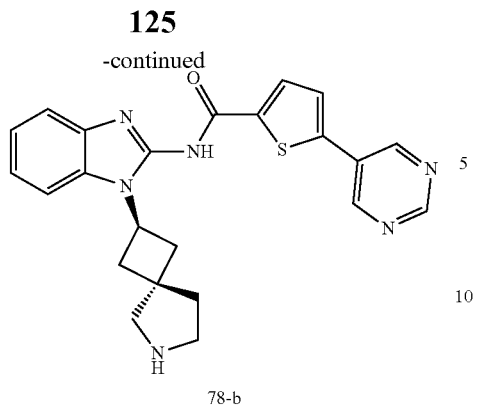

78-b

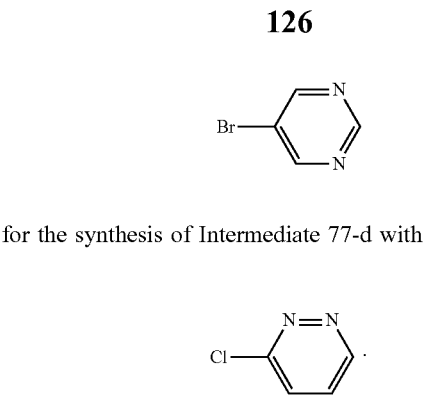

for the synthesis of Intermediate 77-d with

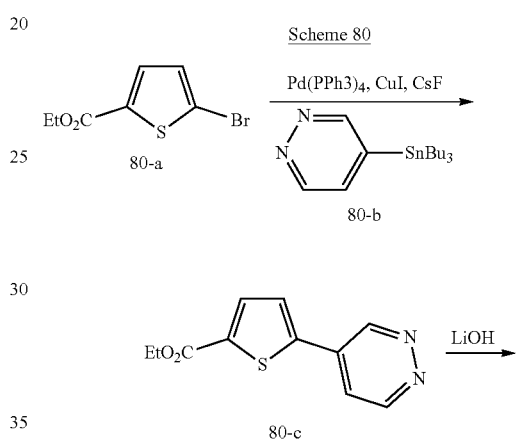

Step 1: Intermediate 78-a

To a solution of Intermediate 77-d (180 mg, 0.9 mmol) in DMF (2.0 ml) was added HATU (453 mg, 1.2 mmol) and after stirring for 30 minutes a solution of intermediate 54-b (272 mg, 0.8 mmol) and DIPEA (416 µl, 2.4 mmol) in DMF was added. The reaction was then stirred at room temperature overnight. Water was added, a precipitate formed and was collected by filtration, dried under vacuum to provide Intermediate 78-a as a beige solid.

Step 2: Intermediate 78-b

To a solution of Intermediate 78-a (420 mg, 0.8 mmol) in MeOH (2.0 ml), was added a solution of 4N hydrogen chloride in 1,4-dioxane (4.75 ml, 19.0 mmol). The reaction was stirred for 1 hour. Volatiles were removed under reduced pressure, diethyl ether was added, a precipitate formed and was collected by filtration, dried under vacuum to provide Intermediate 78-b.2HCl as a beige solid.

Synthesis of Compound 127

Scheme 79

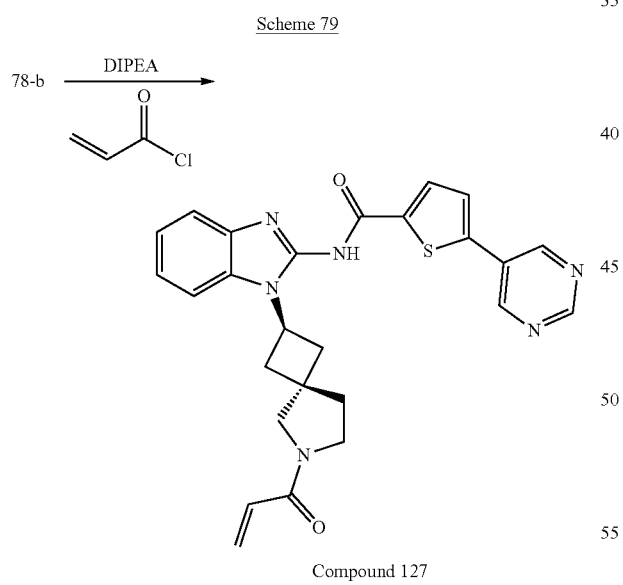

Compound 127

To a solution of Intermediate 78-b.2HCl (370 mg, 0.8 mmol) in DMF (5.0 ml) cooled to 0° C. ° C. were sequentially added DIPEA (415 µl, 2.4 mmol) and acryloyl chloride (71 µl, 0.9 mmol) and the reaction was stirred at 0° C. for 1 hour. Water was added; a precipitate formed and was collected by filtration. Purification by reverse phase chromatography provided Compound 127 as a white solid.

Compound 76 was prepared in a similar manner to Compound 127, by replacing

Synthesis of Intermediate 80-d

Scheme 80

Step 1: Intermediate 80-c

To a solution of Intermediate 80-a (232 mg, 1.0 mmol) in DMF (4.0 ml) were sequentially added Intermediate 80-d (400 mg, 1.1 mmol), copper (I) iodide (38 mg, 0.2 mmol), Pd(PPh$_3$)$_4$ (114 mg, 0.1 mmol) and CsF (284 mg, 1.9 mmol) and the reaction was stirred at 80° C. for 2 hours and then cooled to room temperature. A saturated aqueous solution of ammonium chloride and dichloromethane were added, the organic layer was separated, dried over anhydrous MgSO$_4$, filtered and concentrated under reduced pressure. Diethyl ether was added to the residue; a precipitate formed and was collected by filtration, dried under vacuum to provide Intermediate 80-c as a beige solid.

Step 2: Intermediate 80-d

To a solution of Intermediate 80-c (230 mg, 1.0 mmol) in THF:water 1:1 (10.0 ml) was added LiOH (71 mg, 3.8 mmol) and the reaction was stirred at room temperature overnight. Volatiles were removed by reduced pressure. A precipitated formed and was collected by filtration, dried under vacuum to provide Intermediate 80-d as a white solid.

Synthesis of Intermediate 81-b

Scheme 81

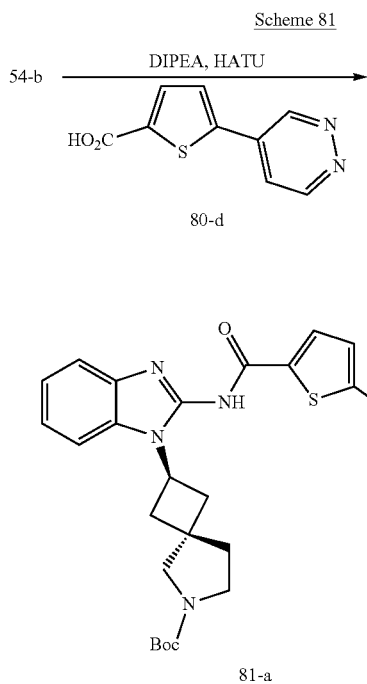

Step 1: Intermediate 81-a

To a solution of Intermediate 80-d (106 mg, 0.4 mmol) in DMF (2.0 ml) was added HATU (250 mg, 0.6 mmol) and after stirring for 30 minutes a solution of intermediate 54-b (150 mg, 0.4 mmol) and DIPEA (230 µl, 1.3 mmol) in DMF was added. The reaction was then stirred at room temperature overnight. A saturated aqueous solution of ammonium chloride and ethyl acetate were added, the organic layer was separated, dried over anhydrous MgSO$_4$, filtered and concentrated under reduced pressure. Purification by silica gel chromatography provided Intermediate 81-a as a beige solid.

Step 2: Intermediate 81-b

To a solution of Intermediate 81-a (200 mg, 0.4 mmol) in MeOH (1.0 ml), was added a solution of 4N hydrogen chloride in 1,4-dioxane (3.0 ml, 12.0 mmol). The reaction was stirred for 2 hours. Volatiles were removed under reduced pressure, diethyl ether was added, a precipitate formed and was collected by filtration, dried under vacuum to provide Intermediate 81-b.2HCl as a beige solid.

Synthesis of Compound 114

Scheme 82

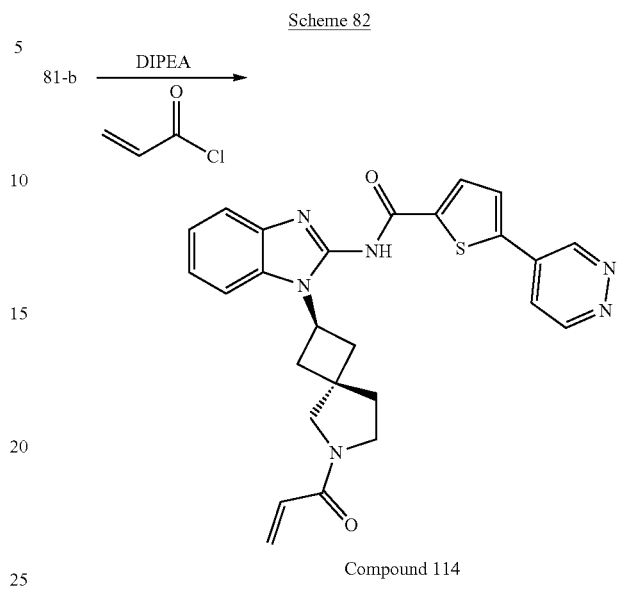

To a solution of Intermediate 81-b.2HCl (200 mg, 0.4 mmol) in DMF (5.0 ml) cooled to 0° C. ° C. were sequentially added DIPEA (69 µl, 0.4 mmol) and acryloyl chloride (33 µl, 0.4 mmol) and the reaction was stirred at 0° C. for 15 minutes. A saturated aqueous solution of ammonium chloride and ethyl acetate were added, the organic layer was separated, the aqueous phase was extracted with ethyl acetate, the combined organic extracts were washed with brine, dried over anhydrous MgSO$_4$, filtered and concentrated under reduced pressure. Purification by reverse phase chromatography provided Compound 114 as a yellow solid.

Synthesis of Intermediate 83-c

Scheme 83

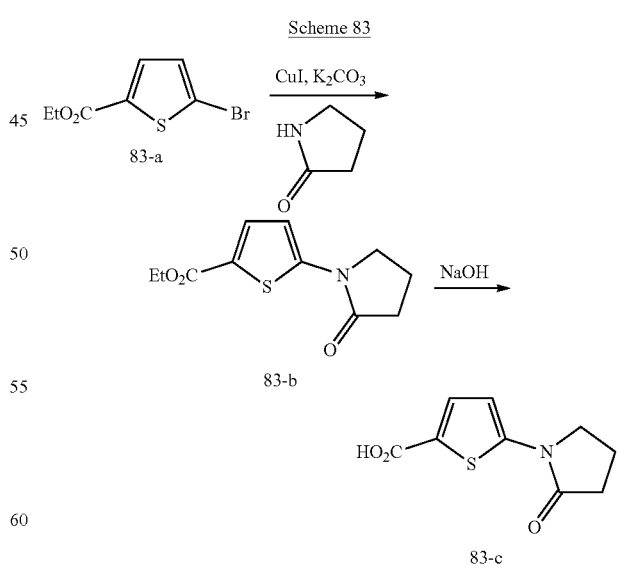

Step 1: Intermediate 83-b

To a solution of Intermediate 83-a (500 mg, 2.1 mmol) in 1,4-dioxane (10.0 ml) were sequentially added pyrrolidin-2-one (217 mg, 2.6 mmol), copper (I) iodide (81 mg, 0.4 mmol), N1,N2-dimethylethane-1,2-diamine (94 mg, 1.1 mmol) and potassium carbonate (882 mg, 6.4 mmol) and the reaction was stirred at 120° C. overnight and then cooled to room temperature. A saturated aqueous solution of ammonium chloride and ethyl acetate were added, the organic layer was separated, dried over anhydrous MgSO$_4$, filtered and concentrated under reduced pressure. Purification by silica gel chromatography provided Intermediate 83-b as a white solid.

Step 2: Intermediate 83-c

To a solution of Intermediate 83-b (440 mg, 1.8 mmol) in 1,4-dioxane (5.0 ml) and MeOH (1.0 ml) was added a 1.0 N aqueous solution of NaOH (3.7 ml, 3.7 mmol) and the reaction was stirred at room temperature overnight. 10% aqueous citric acid and ethyl acetate were added, the organic layer was separated, washed with brine, dried over anhydrous MgSO$_4$, filtered and concentrated under reduced pressure to provide Intermediate 83-c as a beige solid.

Synthesis of Intermediate 84-b

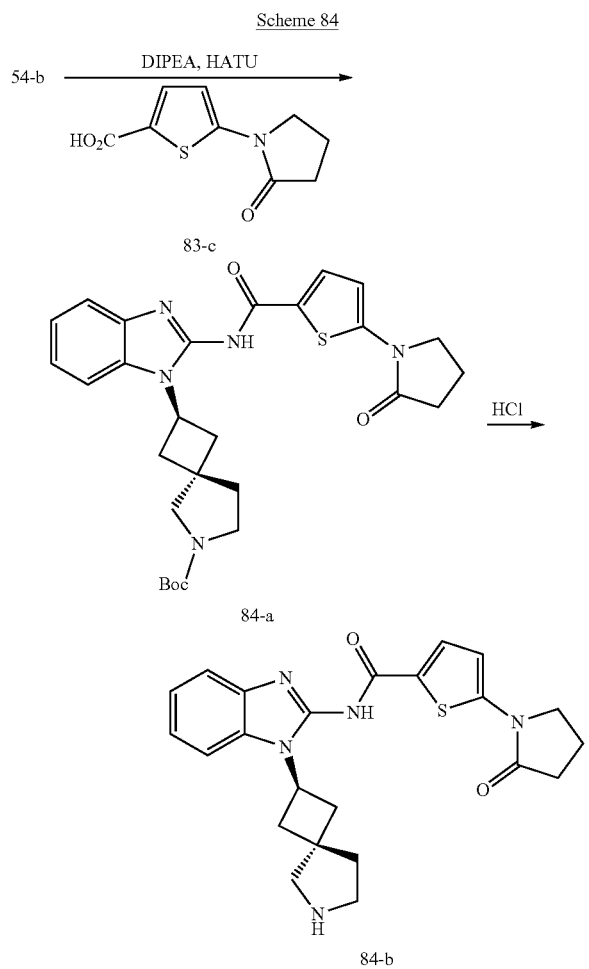

Step 1: Intermediate 84-a

To a solution of Intermediate 83-c (100 mg, 0.5 mmol) in DMF (2.0 ml) was added HATU (195 mg, 0.5 mmol) and after stirring for 30 minutes a solution of intermediate 54-b (135 mg, 0.4 mmol) and DIPEA (207 µl, 1.2 mmol) in DMF was added. The reaction was then stirred at room temperature overnight. A saturated aqueous solution of ammonium chloride and ethyl acetate were added, the organic layer was separated, dried over anhydrous MgSO$_4$, filtered and concentrated under reduced pressure. Purification by silica gel chromatography provided Intermediate 84-a as a white solid.

Step 2: Intermediate 84-b

To a solution of Intermediate 84-a (110 mg, 0.2 mmol) in MeOH (1.0 ml), was added a solution of 4N hydrogen chloride in 1,4-dioxane (3.0 ml, 12.0 mmol). The reaction was stirred for 2 hours. Volatiles were removed under reduced pressure, diethyl ether was added, a precipitate formed and was collected by filtration, dried under vacuum to provide Intermediate 84-b.HCl as a yellow solid.

Synthesis of Compound 121

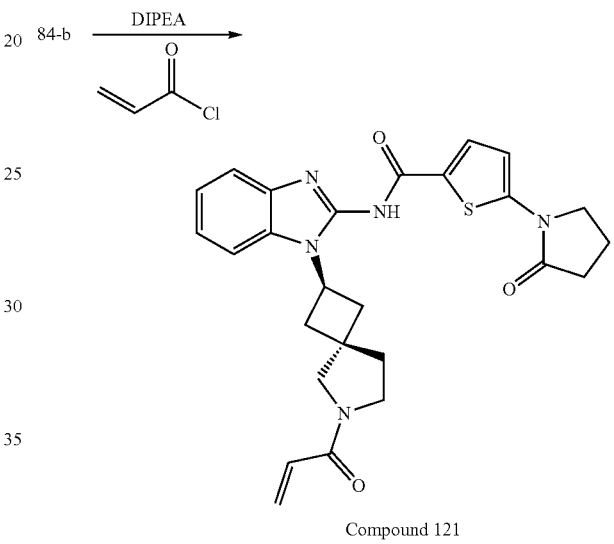

To a solution of Intermediate 84-b.HCl (66 mg, 0.1 mmol) in DMF (3.0 ml) cooled to 0° C. were sequentially added DIPEA (98 µl, 0.6 mmol) and acryloyl chloride (14 µl, 0.1 mmol) and the reaction was stirred at 0° C. for 15 minutes. Volatiles were removed under reduced pressure. Purification by reverse phase chromatography provided Compound 121 as a yellow solid.

Synthesis of Intermediate 86-c

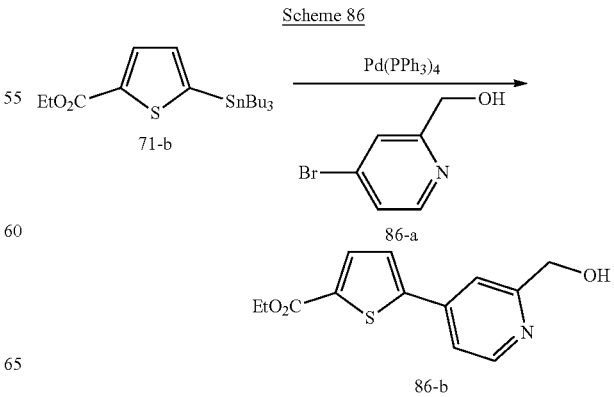

-continued

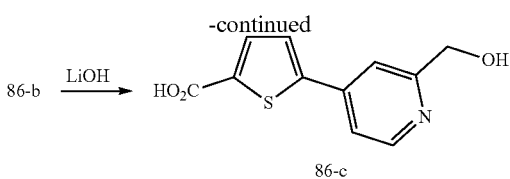

86-b → (LiOH) → 86-c

Step 1: Intermediate 86-b

To a solution of Intermediate 71-b (600 mg, 1.4 mmol) in DMF (5.0 ml) were sequentially added Intermediate 86-a (241 mg, 1.3 mmol) and Pd(PPh$_3$)$_4$ (108 mg, 0.1 mmol) (148 mg, 0.1 mmol) and the reaction was stirred at 120° C. overnight and then cooled to room temperature. A saturated aqueous solution of ammonium chloride and ethyl acetate were added, the organic layer was separated, the aqueous phase was extracted twice with ethyl acetate, the combined organic extracts were washed with brine, dried over anhydrous MgSO$_4$, filtered and concentrated under reduced pressure to provide Intermediate 86-b as a beige solid.

Step 2: Intermediate 86-c

To a solution of Intermediate 86-b (280 mg, 1.1 mmol) in THF:water 1:1 (6.2 ml) was added LiOH (102 mg, 4.2 mmol) and the reaction was stirred at room temperature for 1 hour. Ethyl acetate was added; the aqueous phase was separated and acidified to PH ~3 with 2N HCl. A precipitated formed and was collected by filtration, dried under vacuum to provide Intermediate 86-c as a beige solid.

Synthesis of Intermediate 87-b

Scheme 87

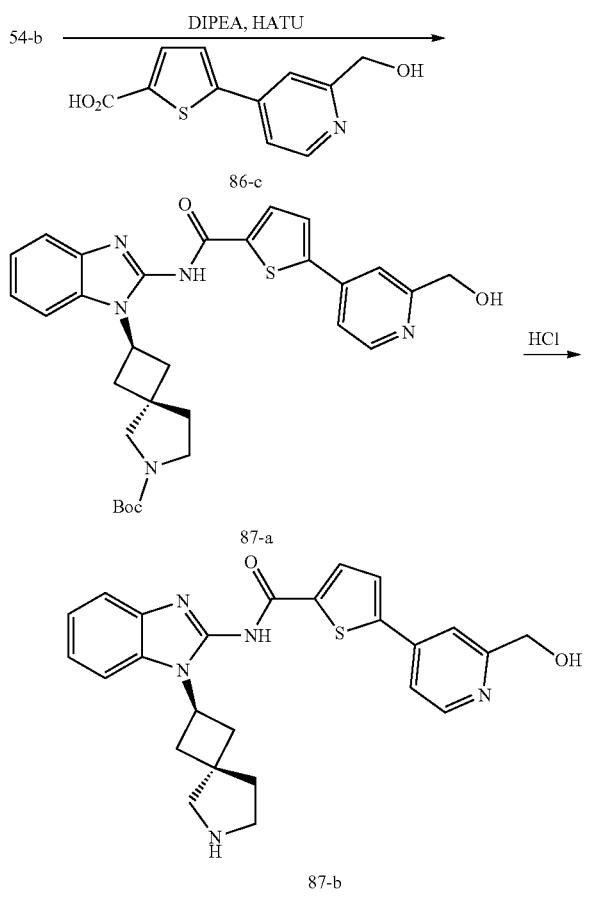

Step 1: Intermediate 87-a

To a solution of Intermediate 86-c (103 mg, 0.4 mmol) in DMF (1.0 ml) cooled to 0° C. was added HATU (250 mg, 0.7 mmol) and after stirring for 30 minutes a solution of intermediate 54-b (150 mg, 0.4 mmol) and DIPEA (230 µl, 1.3 mmol) in DMF was added. The reaction was then stirred at room temperature overnight. A saturated aqueous solution of ammonium chloride was added, a precipitate formed and was collected by filtration, washed with water and dried under vacuum to provide Intermediate 87-a as a beige solid.

Step 2: Intermediate 87-b

To a solution of Intermediate 87-a (52 mg, 0.1 mmol) in MeOH (0.3 ml), was added a solution of 4N hydrogen chloride in 1,4-dioxane (557 µl, 2.2 mmol). The reaction was stirred for 1 hour. Volatiles were removed under reduced pressure, diethyl ether was added, a precipitate formed and was collected by filtration, dried under vacuum to provide Intermediate 87-b.2HCl as a beige solid.

Synthesis of Compound 146

Scheme 88

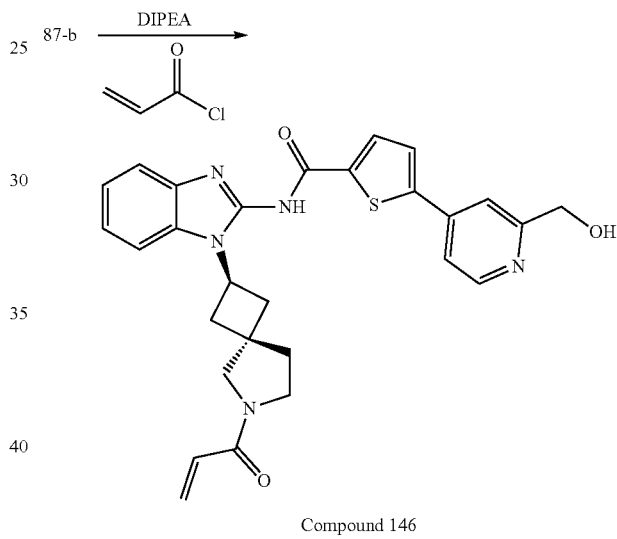

Compound 146

To a solution of Intermediate 87-b.2HCl (50 mg, 0.1 mmol) in DMF (0.6 ml) cooled to 0° C. were sequentially added DIPEA (53 µl, 0.3 mmol) and acryloyl chloride (9 µl, 0.1 mmol) and the reaction was stirred at 0° C. for 30 minutes. A saturated aqueous solution of ammonium chloride and ethyl acetate were added, the organic layer was separated, the aqueous phase was extracted twice with ethyl acetate, the combined organic extracts were washed with brine, dried over anhydrous MgSO$_4$, filtered and concentrated under reduced pressure. Purification by reverse phase chromatography provided Compound 146 as a white solid.

Compounds 132, 133, 136, 137, 138, 139, 140, 141, 142, 143, 144, 145, 147, 149, 150, 151, 153 and 154 were prepared in a similar manner to Compound 146, by replacing

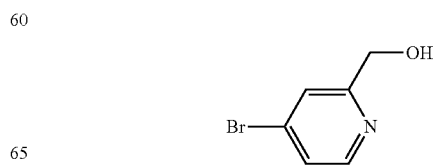

for the synthesis of Intermediate 86-c with

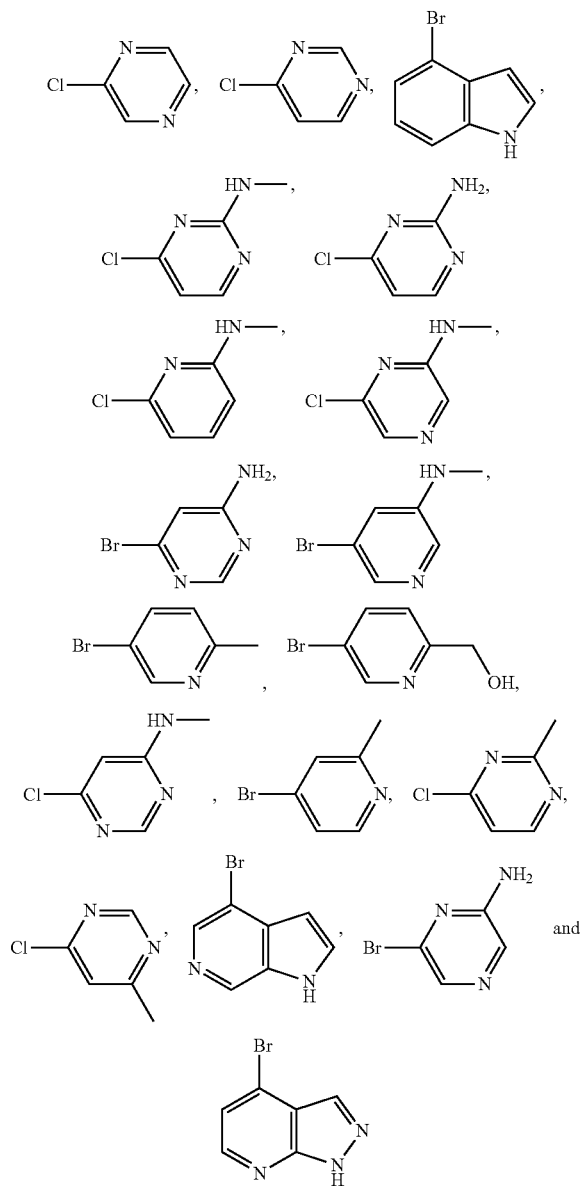

respectively.

Synthesis of Intermediate 89-c

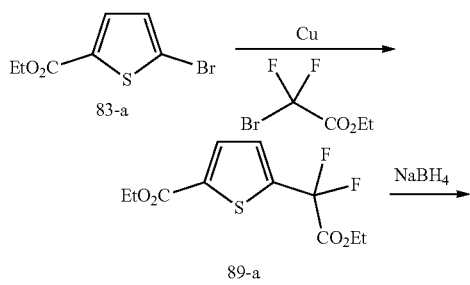

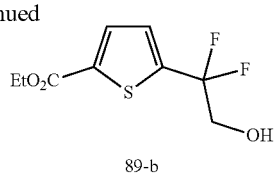

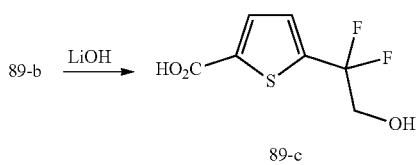

Step 1: Intermediate 89-a

A suspension of copper (1.1 g, 17.0 mmol) and ethyl 2-bromo-2,2-difluoroacetate (1.7 g, 8.5 mmol) in DMSO was stirred for 1 hour at room temperature, intermediate 83-a (1.0 g, 4.2 mmol) was added and the reaction was then stirred at room temperature overnight. A saturated aqueous solution of ammonium chloride and ethyl acetate were added, the organic layer was separated, the aqueous phase was extracted with ethyl acetate, the combined organic extracts were washed with brine, dried over anhydrous $MgSO_4$, filtered and concentrated under reduced pressure. Purification by silica gel chromatography provided Intermediate 89-a as a colorless oil.

Step 2: Intermediate 89-b

To a solution of Intermediate 89-a (1.0 g, 3.6 mmol) in MeOH (5.0 ml) cooled to 0° C. was added sodium borohydride (68 mg, 1.8 mmol) and the reaction was then stirred at room temperature for 2.5 hours. A saturated aqueous solution of $NaHCO_3$ and ethyl acetate were added, the organic layer was separated, the aqueous phase was extracted with ethyl acetate, the combined organic extracts were washed with brine, dried over anhydrous $MgSO_4$, filtered and concentrated under reduced pressure. The residue was dissolved in THF (5 ml) and water (0.1 ml), the solution was cooled to 0° C. and sodium borohydride (18 mg, 0.5 mmol) was added. After stirring for 2.5 hours at room temperature a saturated aqueous solution of $NaHCO_3$ and ethyl acetate were added, volatiles were removed under reduced pressure, ethyl acetate was added, the organic layer was separated, the aqueous phase was extracted twice with ethyl acetate, the combined organic extracts were washed with brine, dried over anhydrous $MgSO_4$, filtered and concentrated under reduced pressure to provide Intermediate 89-b as a colorless oil.

Step 3: Intermediate 89-c

To a solution of Intermediate 89-b (250 mg, 1.1 mmol) in 1,4-dioxane (8.0 ml) was added an aqueous solution of LiOH 1.0M (2.1 ml, 2.1 mmol) and the reaction was stirred at room temperature overnight. Diethyl ether was added; the aqueous phase was separated and acidified to PH ~3 with 2N HCl and then extracted twice with dichloromethane. The combined organic extracts were washed with brine, dried over anhydrous $MgSO_4$, filtered and concentrated under reduced pressure to provide Intermediate 89-c as a white solid.

Synthesis of Intermediate 90-b

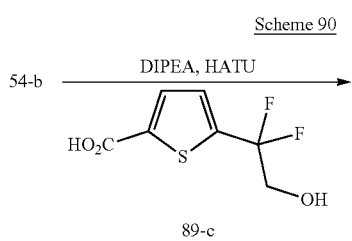

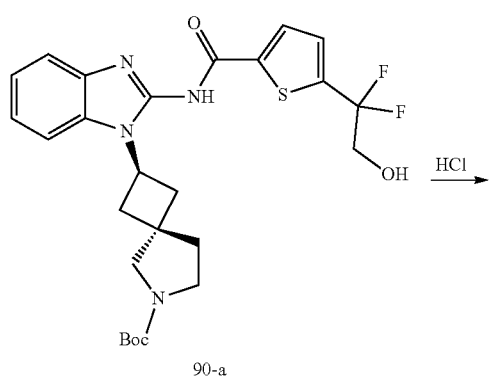

Step 1: Intermediate 90-a

To a solution of Intermediate 89-c (158 mg, 0.7 mmol) in DMF (3.0 ml) cooled to 0° C. was added HATU (333 mg, 0.9 mmol) and after stirring for 30 minutes a solution of intermediate 54-b (200 mg, 0.6 mmol) and DIPEA (306 µl, 1.7 mmol) in DMF was added. The reaction was then stirred at room temperature overnight. A saturated aqueous solution of ammonium chloride and ethyl acetate were added, the organic layer was separated, dried over anhydrous MgSO4, filtered and concentrated under reduced pressure. Purification by silica gel chromatography provided Intermediate 90-a as a beige solid.

Step 2: Intermediate 90-b

To a solution of Intermediate 90-a (40 mg, 0.07 mmol) in MeOH (1.0 ml), was added a solution of 4N hydrogen chloride in 1,4-dioxane (1.0 ml, 4.0 mmol). The reaction was stirred for 30 minutes. Volatiles were removed under reduced pressure, diethyl ether was added, a precipitate formed and was collected by filtration, dried under vacuum to provide Intermediate 90-b.HCl as a white solid.

Synthesis of Compound 130

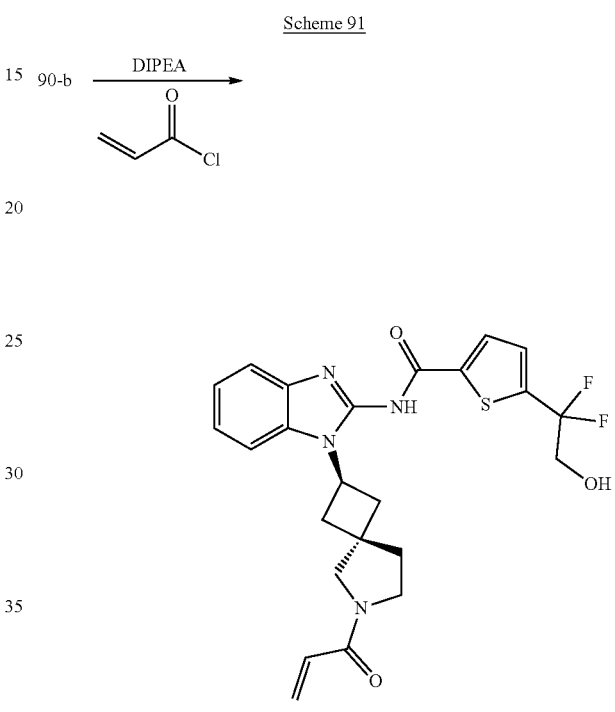

To a solution of Intermediate 90-b.HCl (35 mg, 0.07 mmol) in DMF (5.0 ml) cooled to −78° C. were sequentially added DIPEA (39 µl, 0.2 mmol) and acryloyl chloride (6.7 µl, 0.08 mmol) and the reaction was stirred at −78° C. for 15 minutes. A saturated aqueous solution of ammonium chloride and ethyl acetate were added, the organic layer was separated, the aqueous phase was extracted with ethyl acetate, the combined organic extracts were washed with brine, dried over anhydrous MgSO4, filtered and concentrated under reduced pressure. Purification by reverse phase chromatography provided Compound 130 as a white solid.

Compounds 116, 129, 131, 134, 135, 148, 152, 153, 154, 155 and 156 were prepared in a similar manner to compounds 95, 110, 117, 127 or 146 starting from commercially available starting materials.

TABLE 1

Examples of compounds of Formula I

| Compound | Structure | MS (m/z) |
|---|---|---|
| 1 | 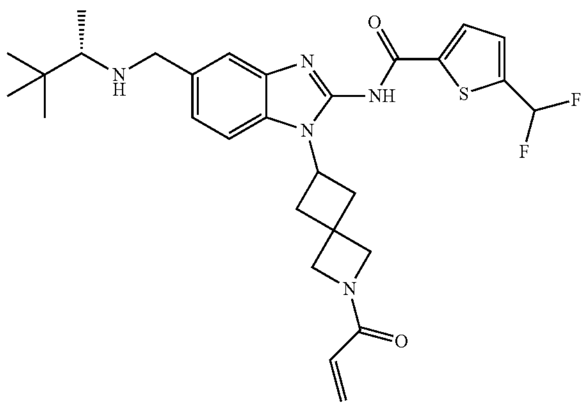 [SMILES: C=CC(=O)N1CC2(CC(n3c(NC(=O)c4ccc(C(F)F)s4)nc4cc(CN[C@@H](C)C(C)(C)C)ccc43)C2)C1] | [M+H]⁺=556.4 |
| 2 | 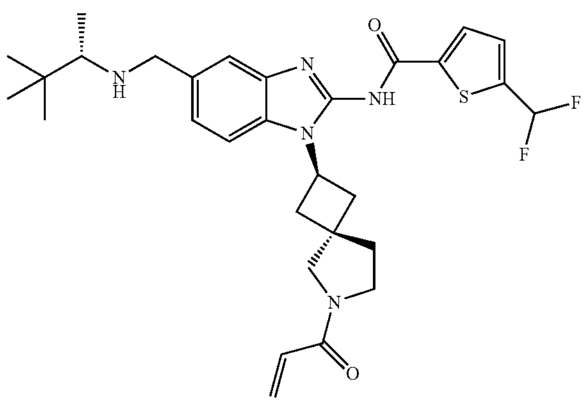 [SMILES: C=CC(=O)N1CC[C@]2(C1)C[C@H](n1c(NC(=O)c3ccc(C(F)F)s3)nc3cc(CN[C@@H](C)C(C)(C)C)ccc31)C2] | [M+H]⁺=570.3 |
| 3 | 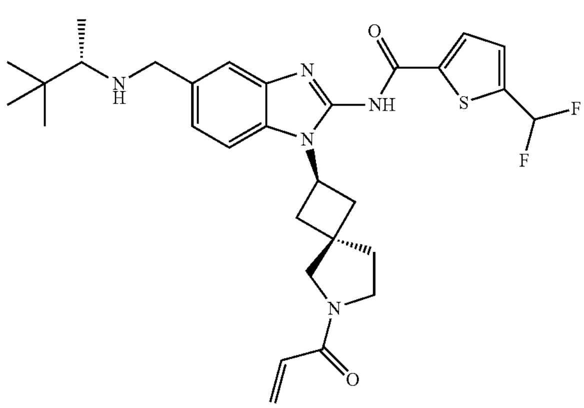 [SMILES: C=CC(=O)N1CC[C@]2(C1)C[C@@H](n1c(NC(=O)c3ccc(C(F)F)s3)nc3cc(CN[C@@H](C)C(C)(C)C)ccc31)C2] | [M+H]⁺=570.4 |

TABLE 1-continued

Examples of compounds of Formula I

| Compound | Structure | MS (m/z) |
|---|---|---|
| 4 | 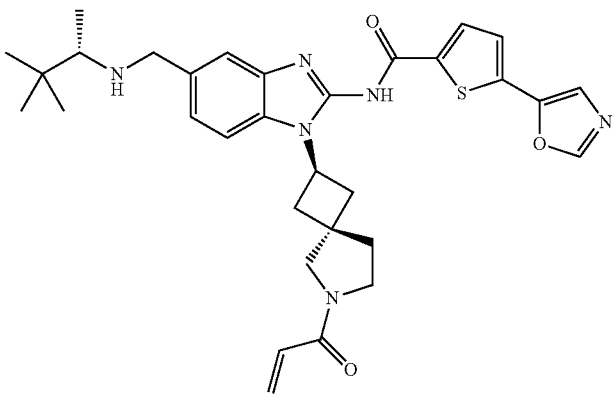 [SMILES: C=CC(=O)N1CC[C@]2(C1)C[C@H](n1c(NC(=O)c3ccc(-c4cnco4)s3)nc3cc(CN[C@@H](C)C(C)(C)C)ccc31)C2] | [M+H]⁺=587.3 |
| 5 | 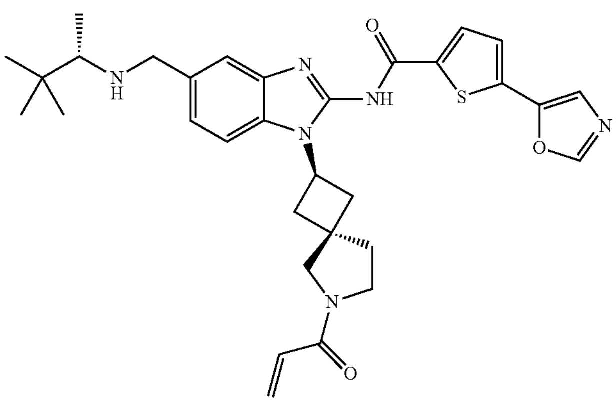 [SMILES: C=CC(=O)N1CC[C@]2(C1)C[C@@H](n1c(NC(=O)c3ccc(-c4cnco4)s3)nc3cc(CN[C@@H](C)C(C)(C)C)ccc31)C2] | [M+H]⁺=587.3 |
| 6 | 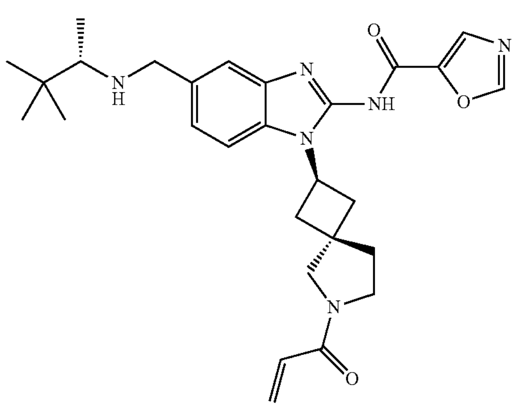 [SMILES: C=CC(=O)N1CC[C@]2(C1)C[C@H](n1c(NC(=O)c3cnco3)nc3cc(CN[C@@H](C)C(C)(C)C)ccc31)C2] | [M+H]⁺=505.3 |

TABLE 1-continued
Examples of compounds of Formula I
| Compound | Structure | MS (m/z) |
|---|---|---|
| 7 | 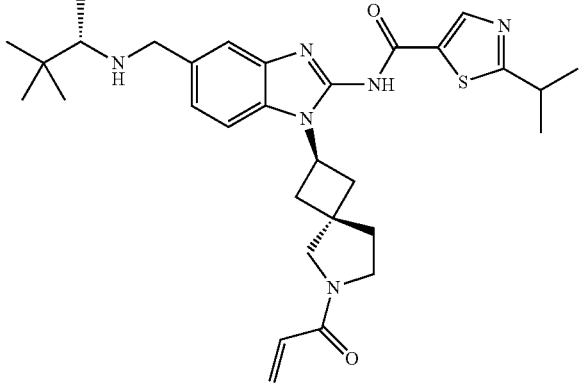 [SMILES: C=CC(=O)N1CC[C@]2(C1)C[C@H](n1c(NC(=O)c3cnc(C(C)C)s3)nc3cc(CN[C@@H](C)C(C)(C)C)ccc31)C2] | [M+H]⁺=563.4 |
| 8 | 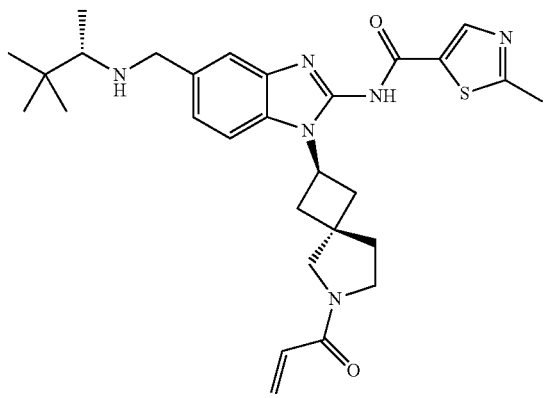 [SMILES: C=CC(=O)N1CC[C@]2(C1)C[C@H](n1c(NC(=O)c3cnc(C)s3)nc3cc(CN[C@@H](C)C(C)(C)C)ccc31)C2] | [M+H]⁺=535.4 |
| 9 | 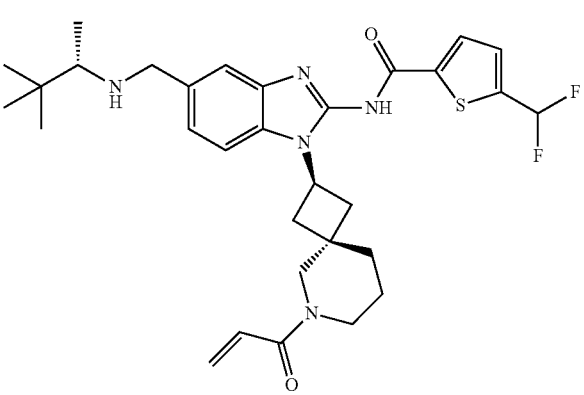 [SMILES: C=CC(=O)N1CCC[C@]2(C1)C[C@H](n1c(NC(=O)c3ccc(C(F)F)s3)nc3cc(CN[C@@H](C)C(C)(C)C)ccc31)C2] | [M+H]⁺=584.4 |
| 10 | 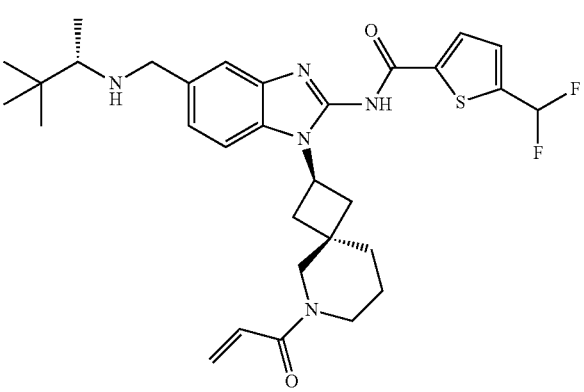 [SMILES: C=CC(=O)N1CCC[C@]2(C1)C[C@@H](n1c(NC(=O)c3ccc(C(F)F)s3)nc3cc(CN[C@@H](C)C(C)(C)C)ccc31)C2] | [M+H]⁺=584.4 |

TABLE 1-continued

Examples of compounds of Formula I

| Compound | Structure | MS (m/z) |
|---|---|---|
| 11 | 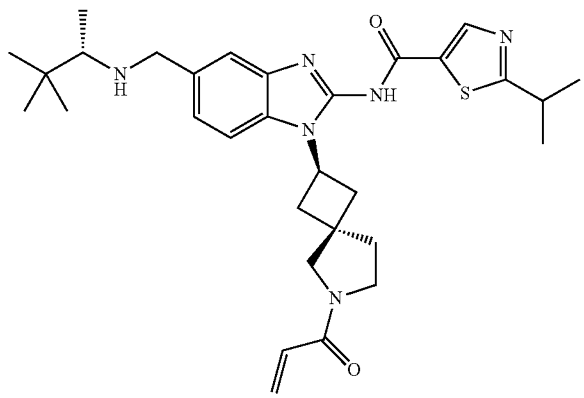 [SMILES: C=CC(=O)N1CC[C@]2(C1)C[C@@H](n1c(NC(=O)c3cnc(C(C)C)s3)nc3cc(CN[C@@H](C)C(C)(C)C)ccc31)C2] | [M+H]⁺=563.3 |
| 12 | 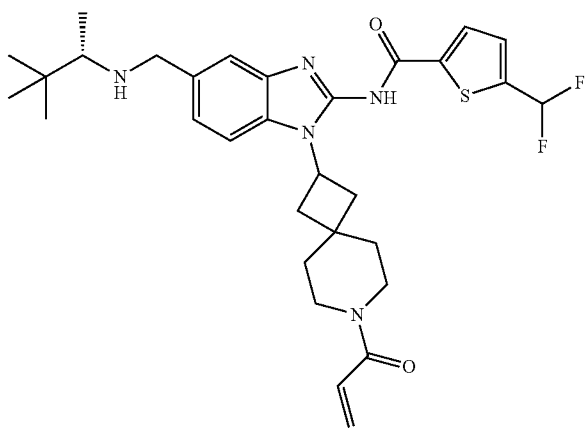 [SMILES: C=CC(=O)N1CCC2(CC1)CC(n1c(NC(=O)c3ccc(C(F)F)s3)nc3cc(CN[C@@H](C)C(C)(C)C)ccc31)C2] | [M+H]⁺=584.4 |
| 13 | 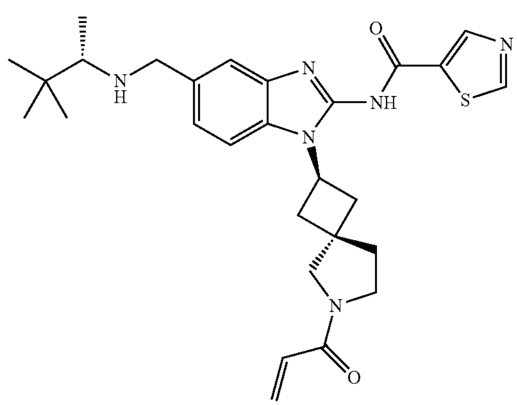 [SMILES: C=CC(=O)N1CC[C@]2(C1)C[C@H](n1c(NC(=O)c3cncs3)nc3cc(CN[C@@H](C)C(C)(C)C)ccc31)C2] | [M+H]⁺=521.3 |

TABLE 1-continued

Examples of compounds of Formula I

| Compound | Structure | MS (m/z) |
|---|---|---|
| 14 | 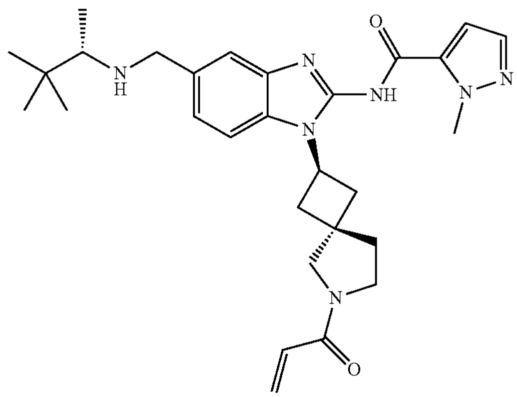 [SMILES: C=CC(=O)N1CC[C@]2(C1)C[C@H](n1c(NC(=O)c3ccnn3C)nc3cc(CN[C@@H](C)C(C)(C)C)ccc31)C2] | [M+H]⁺=518.4 |
| 15 | 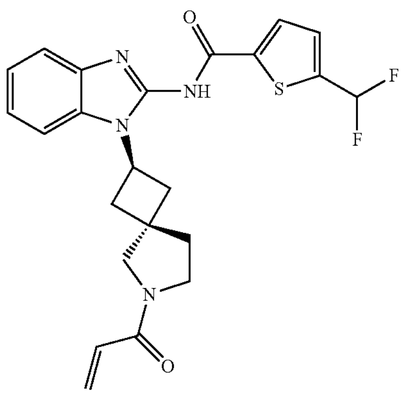 [SMILES: C=CC(=O)N1CC[C@]2(C1)C[C@H](n1c(NC(=O)c3ccc(C(F)F)s3)nc3ccccc31)C2] | [M+H]⁺=457.2 |
| 16 | 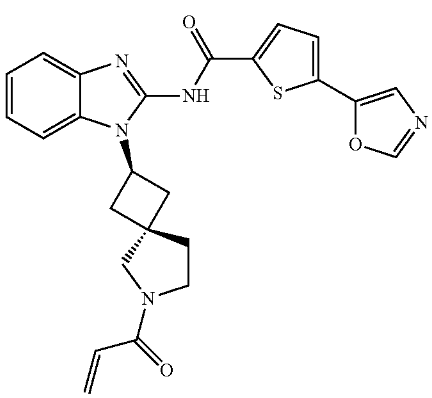 [SMILES: C=CC(=O)N1CC[C@]2(C1)C[C@H](n1c(NC(=O)c3ccc(-c4cnco4)s3)nc3ccccc31)C2] | [M+H]⁺=474.0 |
| 17 | 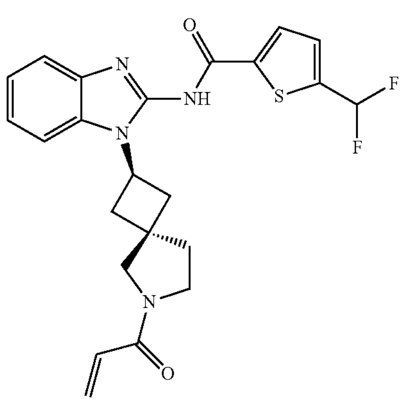 [SMILES: C=CC(=O)N1CC[C@]2(C1)C[C@@H](n1c(NC(=O)c3ccc(C(F)F)s3)nc3ccccc31)C2] | [M+H]⁺=457.2 |

TABLE 1-continued

Examples of compounds of Formula I

| Compound | Structure | MS (m/z) |
|---|---|---|
| 18 | 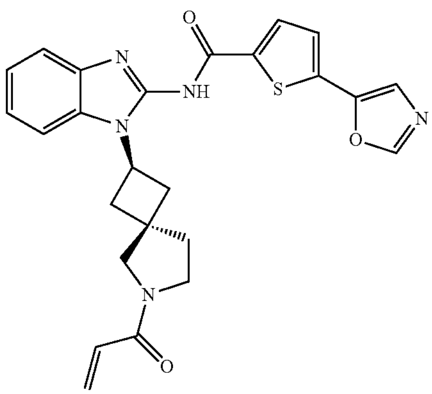 [SMILES: C=CC(=O)N1CC[C@]2(C1)C[C@@H](n1c(NC(=O)c3ccc(-c4cnco4)s3)nc3ccccc31)C2] | [M+H]⁺=474.2 |
| 19 | 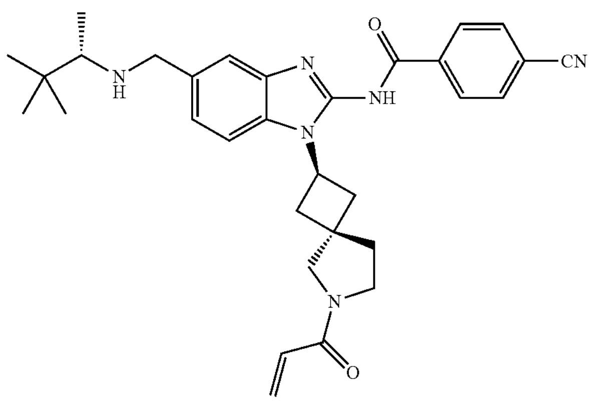 [SMILES: C=CC(=O)N1CC[C@]2(C1)C[C@H](n1c(NC(=O)c3ccc(C#N)cc3)nc3cc(CN[C@@H](C)C(C)(C)C)ccc31)C2] | [M+H]⁺=538.8 |
| 20 | 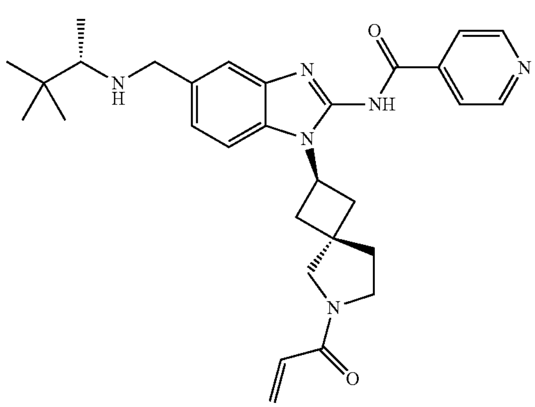 [SMILES: C=CC(=O)N1CC[C@]2(C1)C[C@H](n1c(NC(=O)c3ccncc3)nc3cc(CN[C@@H](C)C(C)(C)C)ccc31)C2] | [M+H]⁺=515.2 |

TABLE 1-continued
Examples of compounds of Formula I
| Compound | Structure | MS (m/z) |
|---|---|---|
| 21 | 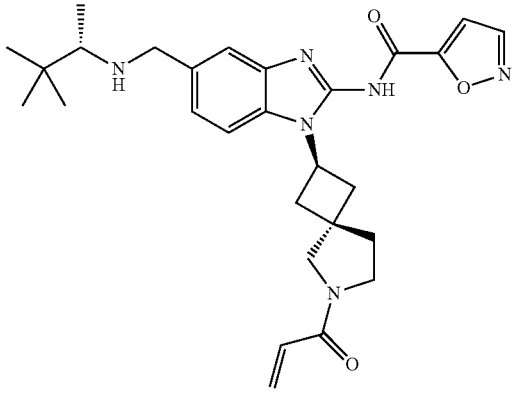 | [M+H]⁺=505.2 |
| 22 | 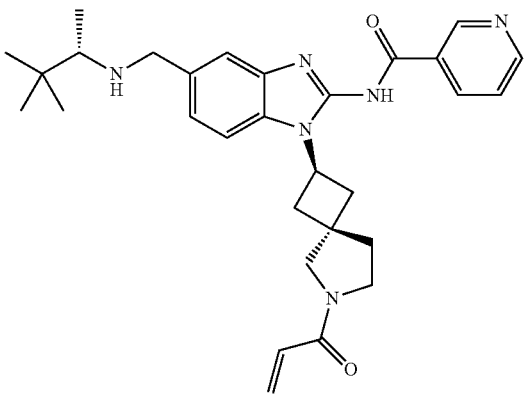 [SMILES: C=CC(=O)N1CC[C@]2(C1)C[C@H](n1c(NC(=O)c3cccnc3)nc3cc(CN[C@@H](C)C(C)(C)C)ccc31)C2] | [M+H]⁺=515.4 |
| 23 | 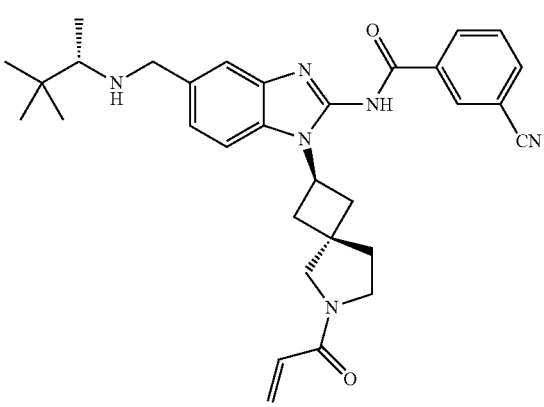 | [M+H]⁺=588.8 |

TABLE 1-continued

Examples of compounds of Formula I

| Compound | Structure | MS (m/z) |
|---|---|---|
| 24 | 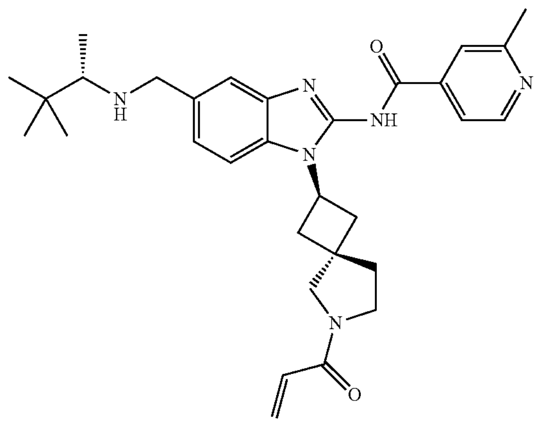 [SMILES: C=CC(=O)N1CC[C@]2(C1)C[C@H](n1c(NC(=O)c3ccnc(C)c3)nc3cc(CN[C@@H](C)C(C)(C)C)ccc31)C2] | [M+H]+=529.2 |
| 25 | 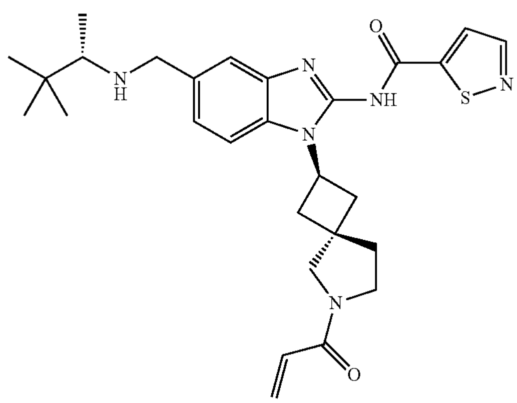 [SMILES: C=CC(=O)N1CC[C@]2(C1)C[C@H](n1c(NC(=O)c3ccns3)nc3cc(CN[C@@H](C)C(C)(C)C)ccc31)C2] | [M+H]+=520.8 |
| 26 | 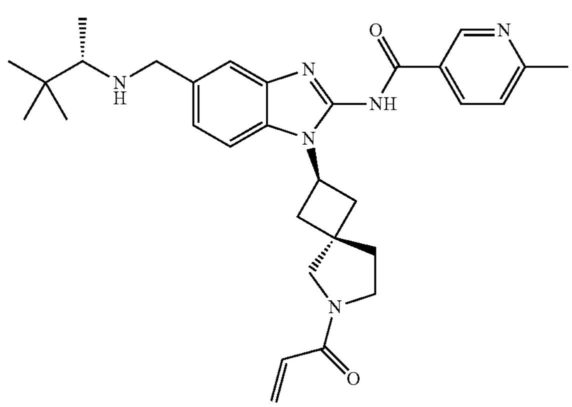 [SMILES: C=CC(=O)N1CC[C@]2(C1)C[C@H](n1c(NC(=O)c3ccc(C)nc3)nc3cc(CN[C@@H](C)C(C)(C)C)ccc31)C2] | [M+H]+=528.8 |

TABLE 1-continued

Examples of compounds of Formula I

| Compound | Structure | MS (m/z) |
|---|---|---|
| 27 | 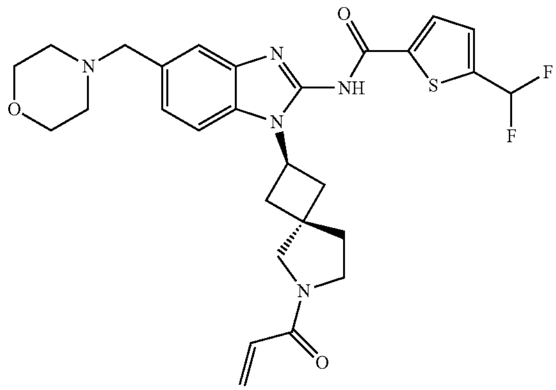 [SMILES: C=CC(=O)N1CC[C@]2(C1)C[C@H](n1c(NC(=O)c3ccc(C(F)F)s3)nc3cc(CN4CCOCC4)ccc31)C2] | [M+H]+=556.0 |
| 28 | 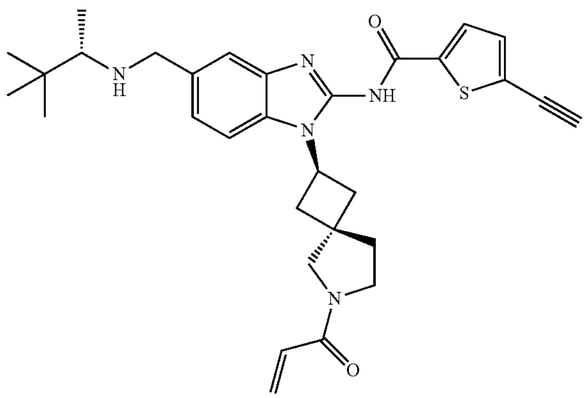 [SMILES: C#Cc1ccc(C(=O)Nc2nc3cc(CN[C@@H](C)C(C)(C)C)ccc3n2[C@H]2C[C@@]3(CCN(C(=O)C=C)C3)C2)s1] | [M+H]+=544.2 |
| 29 | 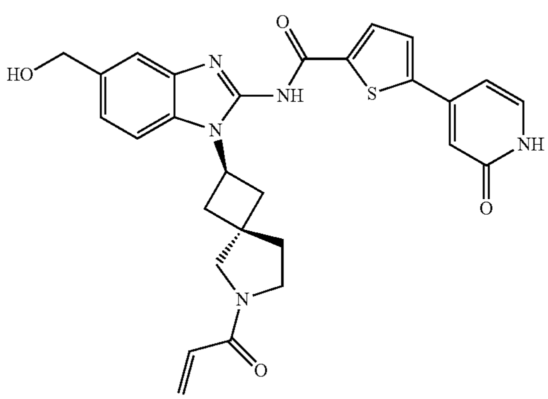 [SMILES: C=CC(=O)N1CC[C@]2(C1)C[C@H](n1c(NC(=O)c3ccc(-c4cc[nH]c(=O)c4)s3)nc3cc(CO)ccc31)C2] | [M+H]+=530.6 |
| 30 | 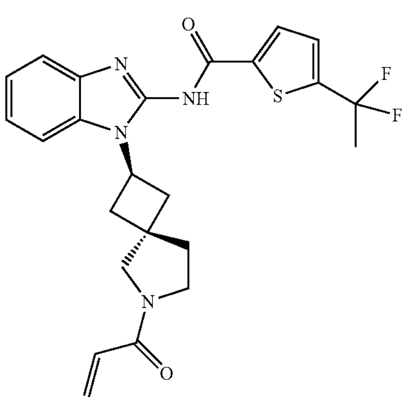 [SMILES: C=CC(=O)N1CC[C@]2(C1)C[C@H](n1c(NC(=O)c3ccc(C(C)(F)F)s3)nc3ccccc31)C2] | [M+H]+=471.0 |

TABLE 1-continued

Examples of compounds of Formula I

| Compound | Structure | MS (m/z) |
|---|---|---|
| 31 | 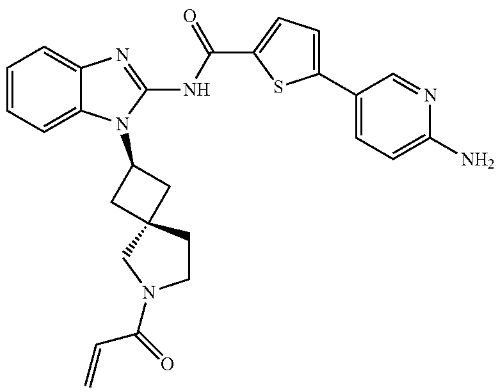 [SMILES: C=CC(=O)N1CC[C@]2(C1)C[C@H](n1c(NC(=O)c3ccc(-c4ccc(N)nc4)s3)nc3ccccc31)C2] | [M+H]+=499.2 |
| 32 | 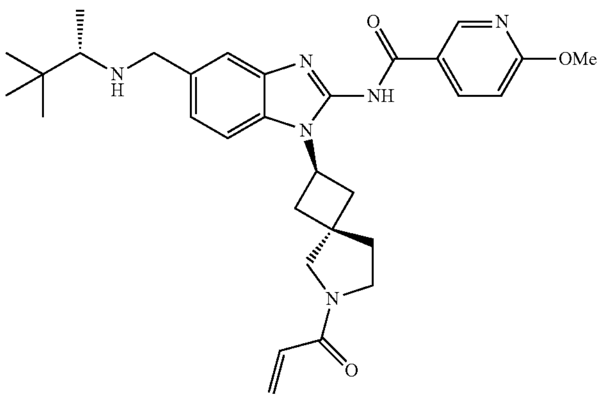 [SMILES: C=CC(=O)N1CC[C@]2(C1)C[C@H](n1c(NC(=O)c3ccc(OC)nc3)nc3cc(CN[C@@H](C)C(C)(C)C)ccc31)C2] | [M+H]+=545.0 |
| 33 | 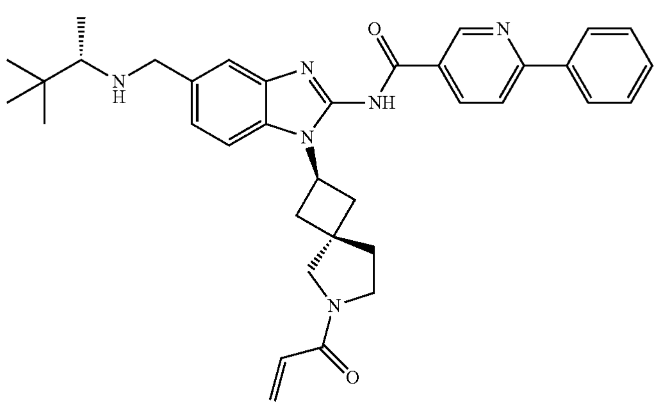 [SMILES: C=CC(=O)N1CC[C@]2(C1)C[C@H](n1c(NC(=O)c3ccc(-c4ccccc4)nc3)nc3cc(CN[C@@H](C)C(C)(C)C)ccc31)C2] | [M+H]+=591.0 |

TABLE 1-continued

Examples of compounds of Formula I

| Compound | Structure | MS (m/z) |
|---|---|---|
| 34 | 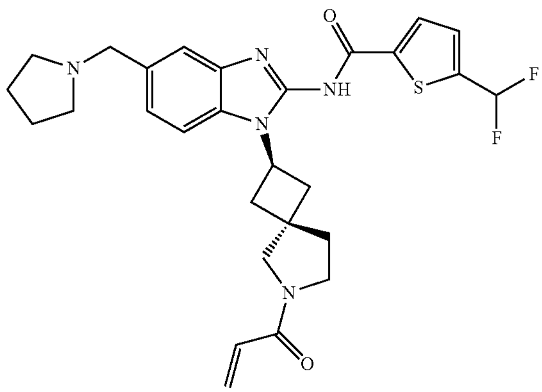 [SMILES: C=CC(=O)N1CC[C@]2(C1)C[C@H](n1c(NC(=O)c3ccc(C(F)F)s3)nc3cc(CN4CCCC4)ccc31)C2] | [M+H]+=540.2 |
| 35 | 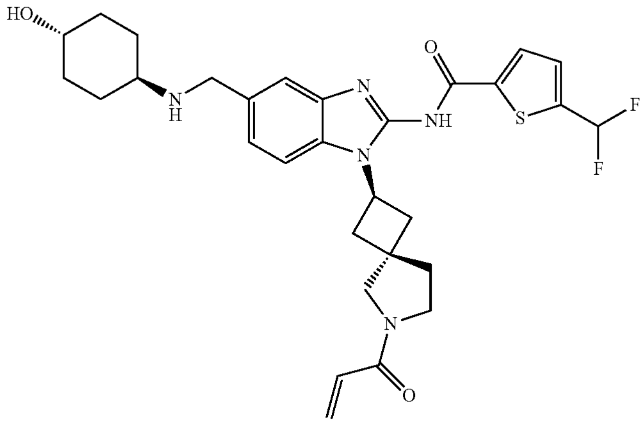 [SMILES: C=CC(=O)N1CC[C@]2(C1)C[C@H](n1c(NC(=O)c3ccc(C(F)F)s3)nc3cc(CN[C@H]4CC[C@H](O)CC4)ccc31)C2] | [M+H]+=584.0 |
| 36 | 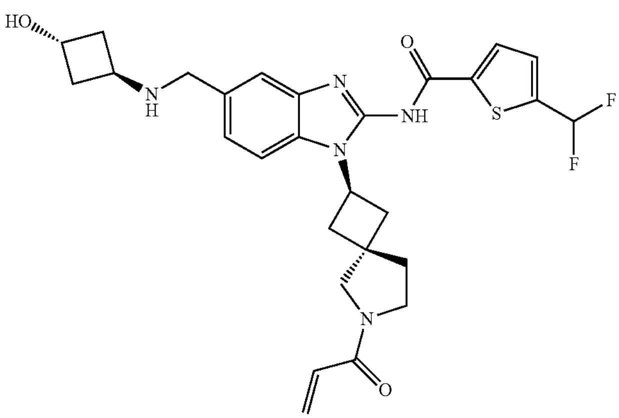 [SMILES: C=CC(=O)N1CC[C@]2(C1)C[C@H](n1c(NC(=O)c3ccc(C(F)F)s3)nc3cc(CN[C@H]4C[C@H](O)C4)ccc31)C2] | [M+H]+=556.2 |

TABLE 1-continued

Examples of compounds of Formula I

| Compound | Structure | MS (m/z) |
|---|---|---|
| 37 | 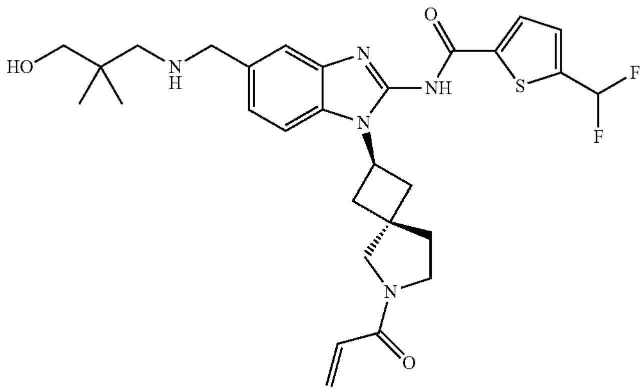 [SMILES: C=CC(=O)N1CC[C@]2(C1)C[C@H](n1c(NC(=O)c3ccc(C(F)F)s3)nc3cc(CNCC(C)(C)CO)ccc31)C2] | [M+H]+=572.0 |
| 38 | 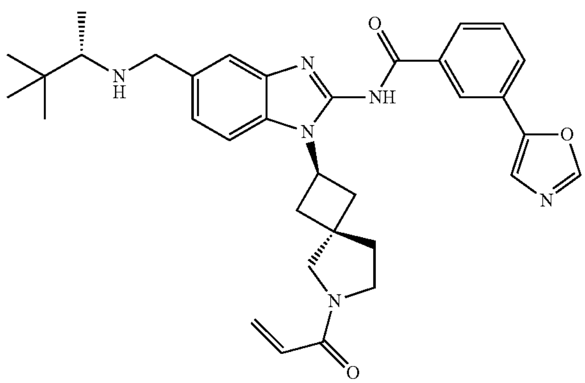 [SMILES: C=CC(=O)N1CC[C@]2(C1)C[C@H](n1c(NC(=O)c3cccc(-c4cnco4)c3)nc3cc(CN[C@@H](C)C(C)(C)C)ccc31)C2] | [M+H]+=581.0 |
| 39 | 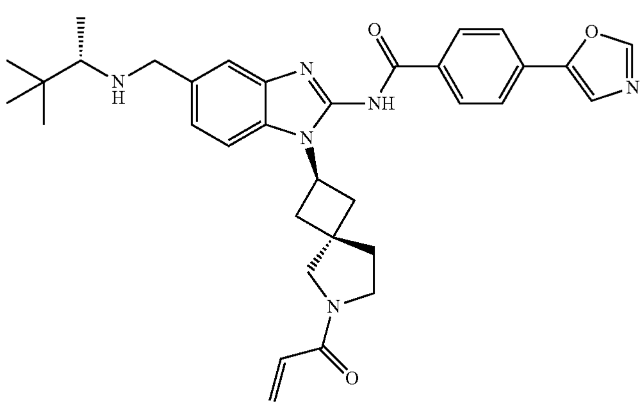 [SMILES: C=CC(=O)N1CC[C@]2(C1)C[C@H](n1c(NC(=O)c3ccc(-c4cnco4)cc3)nc3cc(CN[C@@H](C)C(C)(C)C)ccc31)C2] | [M+H]+=581.0 |
| 40 | 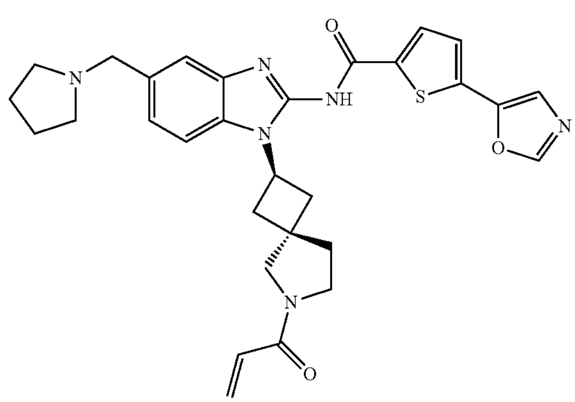 [SMILES: C=CC(=O)N1CC[C@]2(C1)C[C@H](n1c(NC(=O)c3ccc(-c4cnco4)s3)nc3cc(CN4CCCC4)ccc31)C2] | [M+H]+=557.2 |

TABLE 1-continued

Examples of compounds of Formula I

| Compound | Structure | MS (m/z) |
|---|---|---|
| 41 | 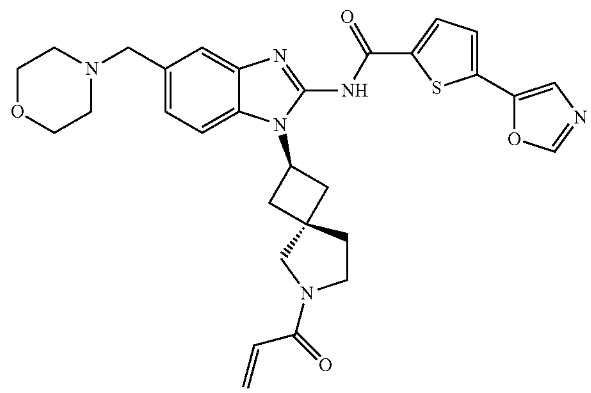 [SMILES: C=CC(=O)N1CC[C@]2(C1)C[C@H](n1c(NC(=O)c3ccc(-c4cnco4)s3)nc3cc(CN4CCOCC4)ccc31)C2] | [M+H]+=573.2 |
| 42 | 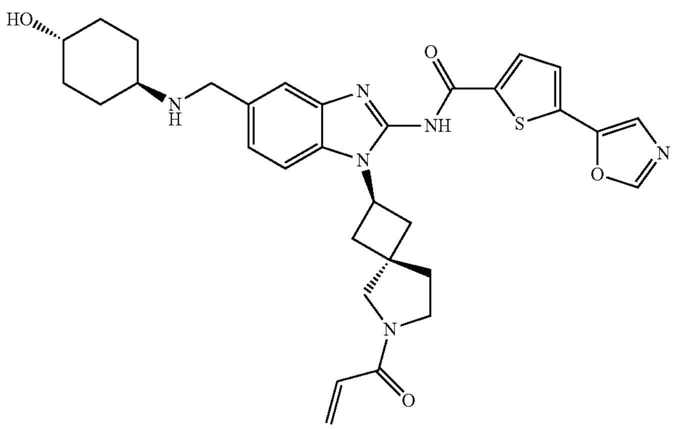 [SMILES: C=CC(=O)N1CC[C@]2(C1)C[C@H](n1c(NC(=O)c3ccc(-c4cnco4)s3)nc3cc(CN[C@H]4CC[C@H](O)CC4)ccc31)C2] | [M+H]+=601.2 |
| 43 | 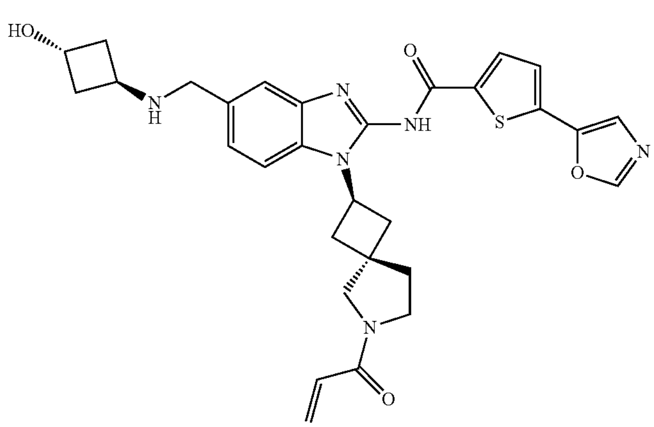 [SMILES: C=CC(=O)N1CC[C@]2(C1)C[C@H](n1c(NC(=O)c3ccc(-c4cnco4)s3)nc3cc(CN[C@H]4C[C@H](O)C4)ccc31)C2] | [M+H]+=573.2 |

TABLE 1-continued

Examples of compounds of Formula I

| Compound | Structure | MS (m/z) |
|---|---|---|
| 44 | 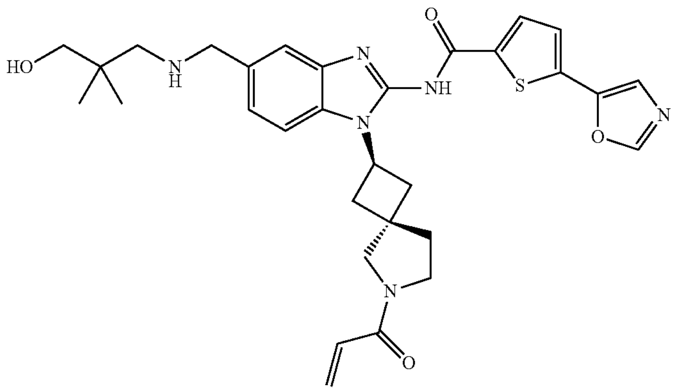 [SMILES: C=CC(=O)N1CC[C@]2(C1)C[C@H](n1c(NC(=O)c3ccc(-c4cnco4)s3)nc3cc(CNCC(C)(C)CO)ccc31)C2] | [M+H]+=589.2 |
| 45 | 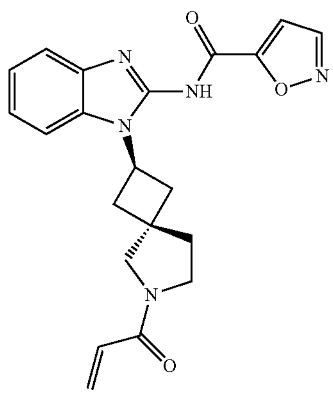 [SMILES: C=CC(=O)N1CC[C@]2(C1)C[C@H](n1c(NC(=O)c3ccno3)nc3ccccc31)C2] | [M+H]+=392.0 |
| 46 | 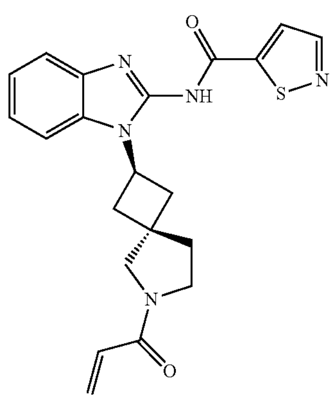 [SMILES: C=CC(=O)N1CC[C@]2(C1)C[C@H](n1c(NC(=O)c3ccns3)nc3ccccc31)C2] | [M+H]+=407.8 |
| 47 | 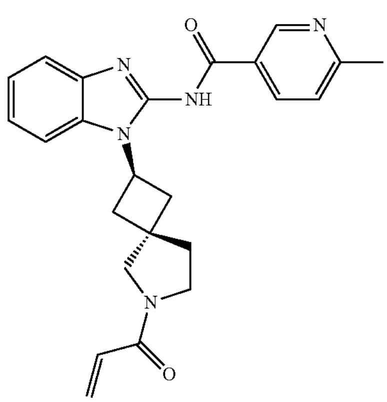 [SMILES: C=CC(=O)N1CC[C@]2(C1)C[C@H](n1c(NC(=O)c3ccc(C)nc3)nc3ccccc31)C2] | [M+H]+=416.0 |

TABLE 1-continued
| Examples of compounds of Formula I | | |
|---|---|---|
| Compound | Structure | MS (m/z) |
| 48 | 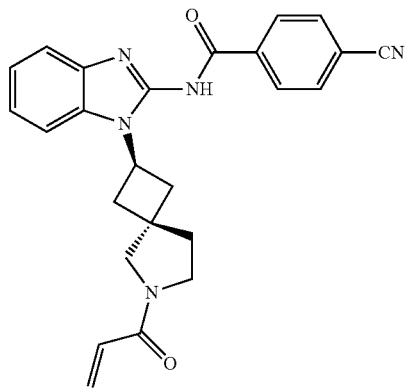 [SMILES: C=CC(=O)N1CC[C@]2(C1)C[C@H](n1c(NC(=O)c3ccc(C#N)cc3)nc3ccccc31)C2] | [M+H]+=426.2 |
| 49 | 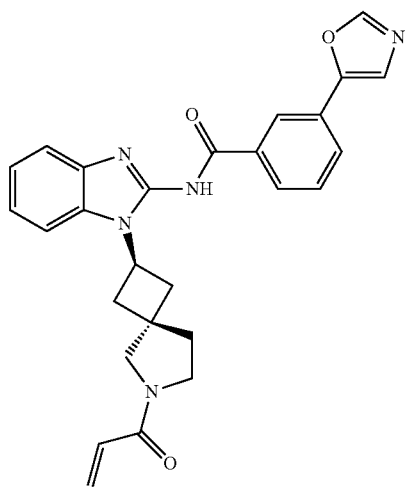 [SMILES: C=CC(=O)N1CC[C@]2(C1)C[C@H](n1c(NC(=O)c3cccc(-c4cnco4)c3)nc3ccccc31)C2] | [M+H]+=468.2 |
| 50 | 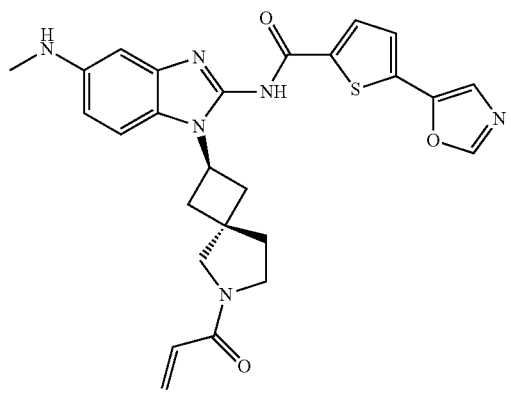 | [M+H]+=508.2 |

TABLE 1-continued

Examples of compounds of Formula I

| Compound | Structure | MS (m/z) |
|---|---|---|
| 51 | 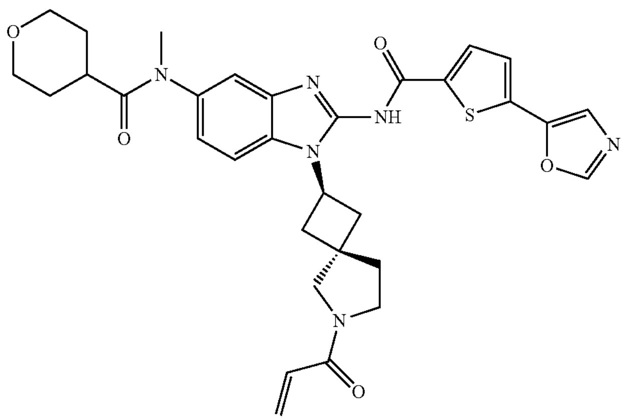 [SMILES: C=CC(=O)N1CC[C@]2(C1)C[C@H](n1c(NC(=O)c3ccc(-c4cnco4)s3)nc3cc(N(C)C(=O)C4CCOCC4)ccc31)C2] | [M+H]+=615.0 |
| 52 | 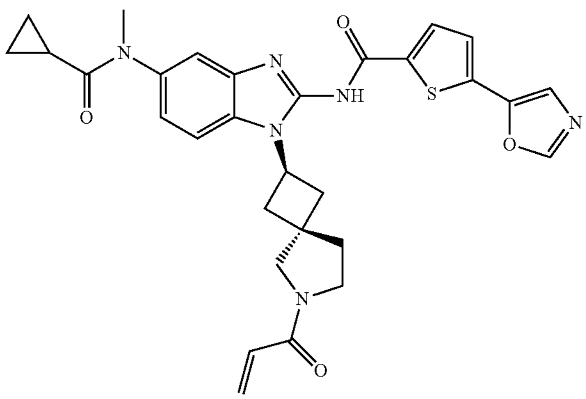 [SMILES: C=CC(=O)N1CC[C@]2(C1)C[C@H](n1c(NC(=O)c3ccc(-c4cnco4)s3)nc3cc(N(C)C(=O)C4CC4)ccc31)C2] | [M+H]+=571.2 |
| 53 | 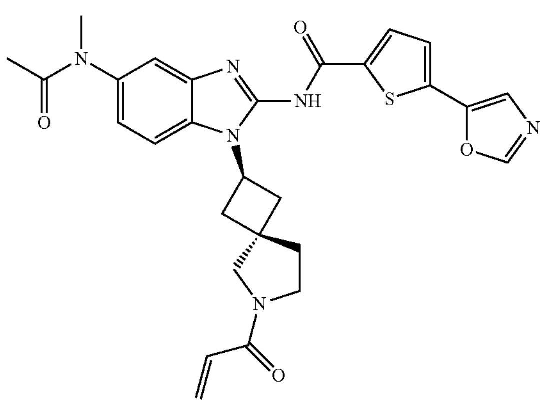 [SMILES: C=CC(=O)N1CC[C@]2(C1)C[C@H](n1c(NC(=O)c3ccc(-c4cnco4)s3)nc3cc(N(C)C(C)=O)ccc31)C2] | [M+H]+=545.2 |

TABLE 1-continued

Examples of compounds of Formula I

| Compound | Structure | MS (m/z) |
|---|---|---|
| 54 | 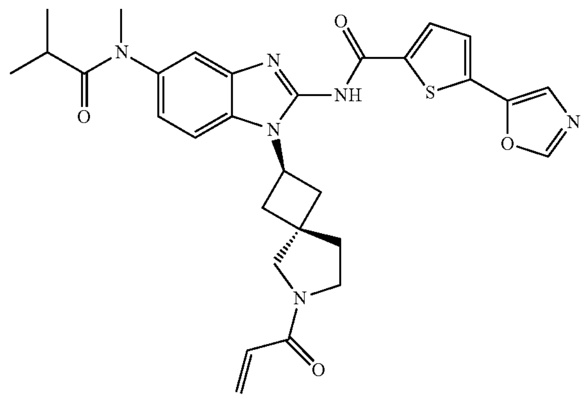 [SMILES: C=CC(=O)N1CC[C@]2(C1)C[C@H](n1c(NC(=O)c3ccc(-c4cnco4)s3)nc3cc(N(C)C(=O)C(C)C)ccc31)C2] | [M+H]+=573.0 |
| 55 | 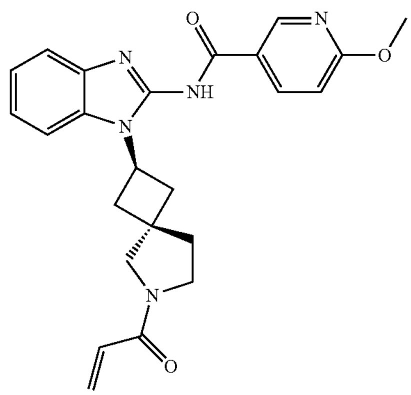 [SMILES: C=CC(=O)N1CC[C@]2(C1)C[C@H](n1c(NC(=O)c3ccc(OC)nc3)nc3ccccc31)C2] | [M+H]+=432.0 |
| 56 | 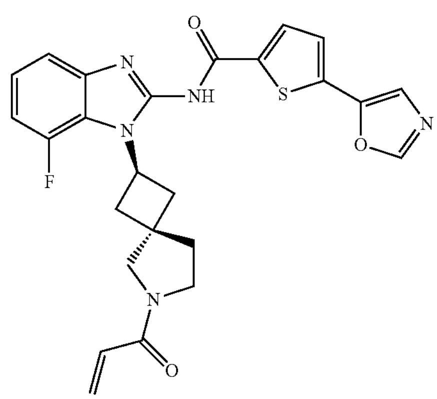 [SMILES: C=CC(=O)N1CC[C@]2(C1)C[C@H](n1c(NC(=O)c3ccc(-c4cnco4)s3)nc3cccc(F)c31)C2] | [M+H]+=492.0 |
| 57 | 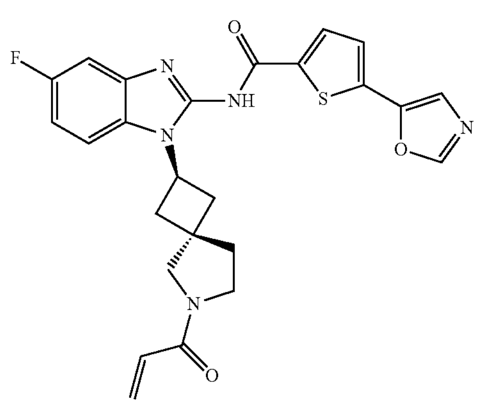 [SMILES: C=CC(=O)N1CC[C@]2(C1)C[C@H](n1c(NC(=O)c3ccc(-c4cnco4)s3)nc3cc(F)ccc31)C2] | [M+H]+=492.0 |

TABLE 1-continued

Examples of compounds of Formula I

| Compound | Structure | MS (m/z) |
|---|---|---|
| 58 | 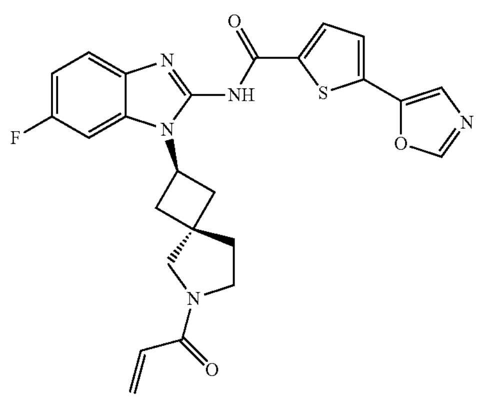 [SMILES: C=CC(=O)N1CC[C@]2(C1)C[C@H](n1c(NC(=O)c3ccc(-c4cnco4)s3)nc3ccc(F)cc31)C2] | [M+H]+=492.0 |
| 59 | 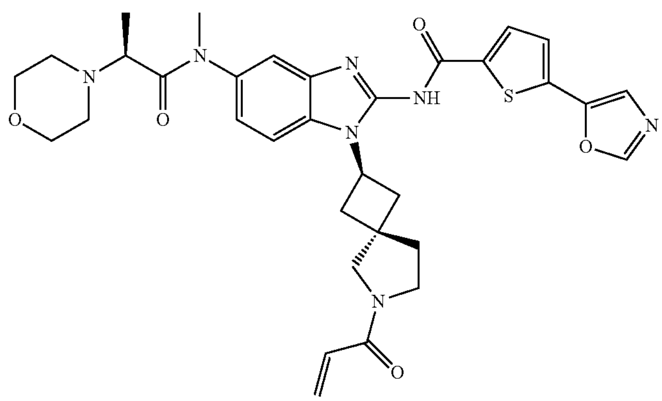 [SMILES: C=CC(=O)N1CC[C@]2(C1)C[C@H](n1c(NC(=O)c3ccc(-c4cnco4)s3)nc3cc(N(C)C(=O)[C@H](C)N4CCOCC4)ccc31)C2] | [M+H]+=643.8 |
| 60 | 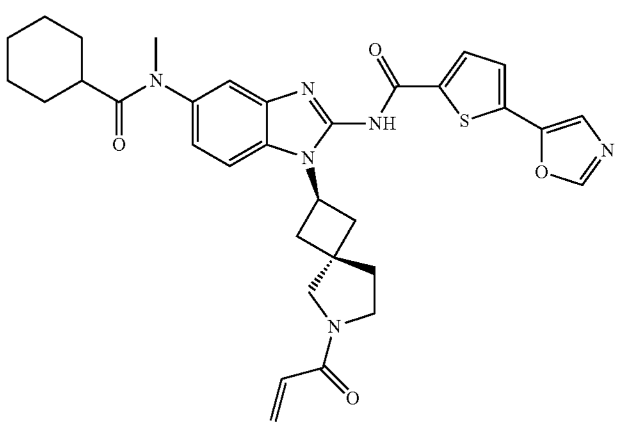 [SMILES: C=CC(=O)N1CC[C@]2(C1)C[C@H](n1c(NC(=O)c3ccc(-c4cnco4)s3)nc3cc(N(C)C(=O)C4CCCCC4)ccc31)C2] | [M+H]+=613.0 |

TABLE 1-continued
Examples of compounds of Formula I
| Compound | Structure | MS (m/z) |
|---|---|---|
| 61 | 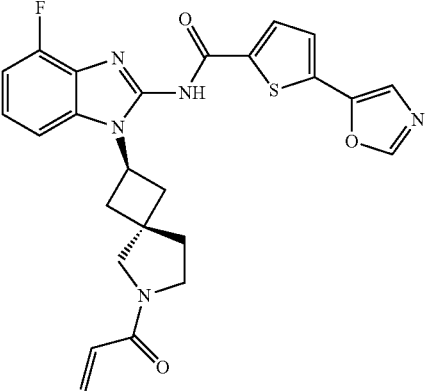 [SMILES: C=CC(=O)N1CC[C@]2(C1)C[C@H](n1c(NC(=O)c3ccc(-c4cnco4)s3)nc3c(F)cccc31)C2] | [M+H]+=491.8 |
| 62 | 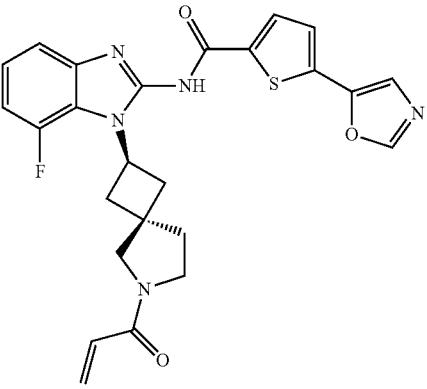 | [M+H]+=492.0 |
| 63 | 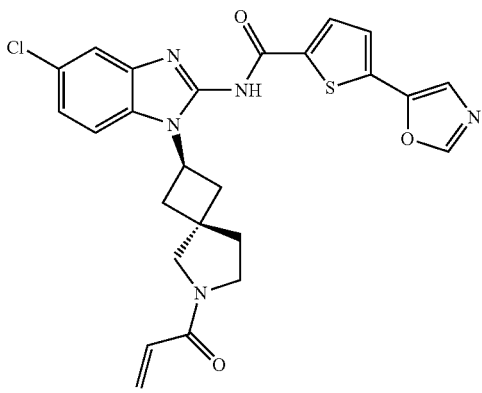 [SMILES: C=CC(=O)N1CC[C@]2(C1)C[C@H](n1c(NC(=O)c3ccc(-c4cnco4)s3)nc3cc(Cl)ccc31)C2] | [M+H]+=508.0 |

TABLE 1-continued
Examples of compounds of Formula I
| Compound | Structure | MS (m/z) |
|---|---|---|
| 64 | 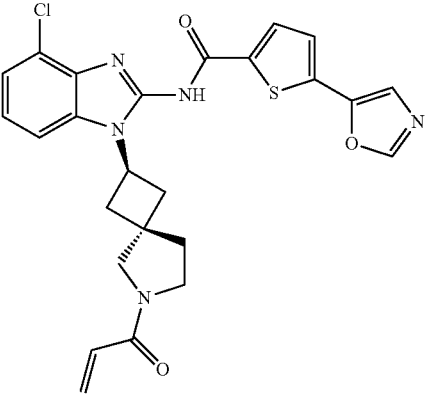 [SMILES: C=CC(=O)N1CC[C@]2(C1)C[C@H](n1c(NC(=O)c3ccc(-c4cnco4)s3)nc3c(Cl)cccc31)C2] | [M+H]+=508.0 |
| 65 | 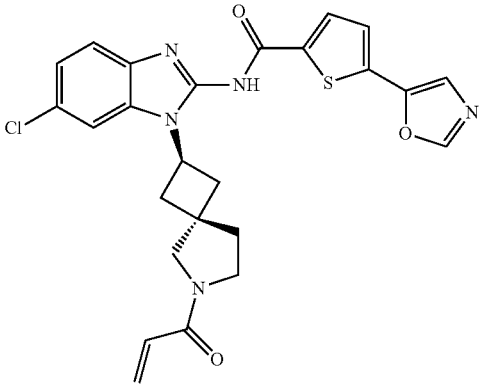 [SMILES: C=CC(=O)N1CC[C@]2(C1)C[C@H](n1c(NC(=O)c3ccc(-c4cnco4)s3)nc3ccc(Cl)cc31)C2] | [M+H]+=508.0 |
| 66 | 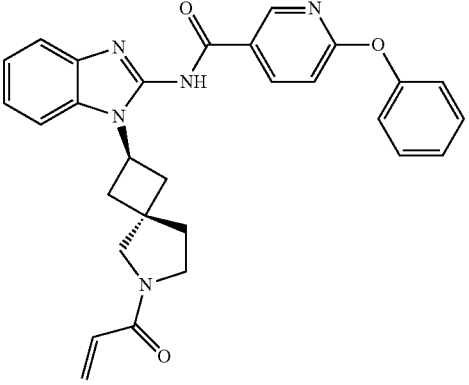 [SMILES: C=CC(=O)N1CC[C@]2(C1)C[C@H](n1c(NC(=O)c3ccc(Oc4ccccc4)nc3)nc3ccccc31)C2] | [M+H]+=494.0 |

TABLE 1-continued

Examples of compounds of Formula I

| Compound | Structure | MS (m/z) |
|---|---|---|
| 67 | 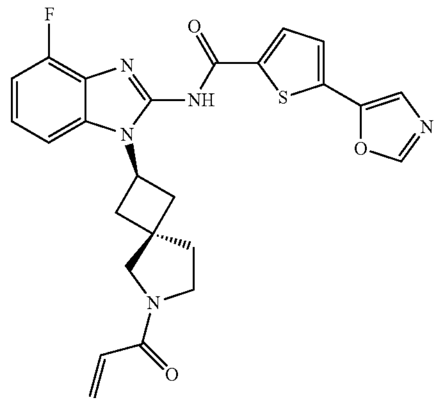 | [M+H]+=492.2 |
| 68 | 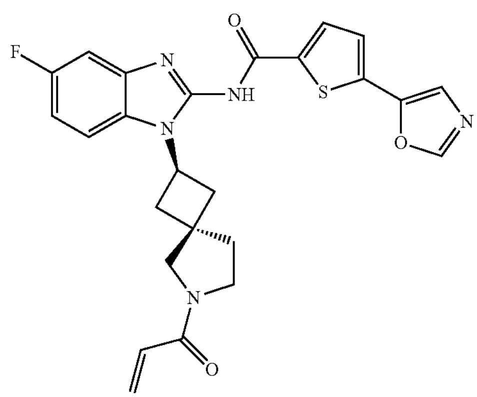 [SMILES: C=CC(=O)N1CC[C@]2(C1)C[C@@H](n1c(NC(=O)c3ccc(-c4cnco4)s3)nc3cc(F)ccc31)C2] | [M+H]+=492.2 |
| 69 | 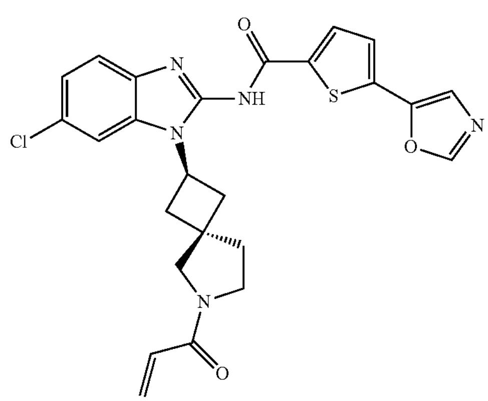 [SMILES: C=CC(=O)N1CC[C@]2(C1)C[C@@H](n1c(NC(=O)c3ccc(-c4cnco4)s3)nc3ccc(Cl)cc31)C2] | [M+H]+=507.6 |
| 70 | 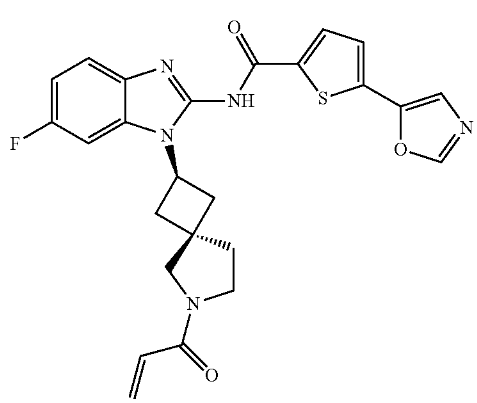 [SMILES: C=CC(=O)N1CC[C@]2(C1)C[C@@H](n1c(NC(=O)c3ccc(-c4cnco4)s3)nc3ccc(F)cc31)C2] | [M+H]+=491.4 |

TABLE 1-continued

Examples of compounds of Formula I

| Compound | Structure | MS (m/z) |
|---|---|---|
| 71 | 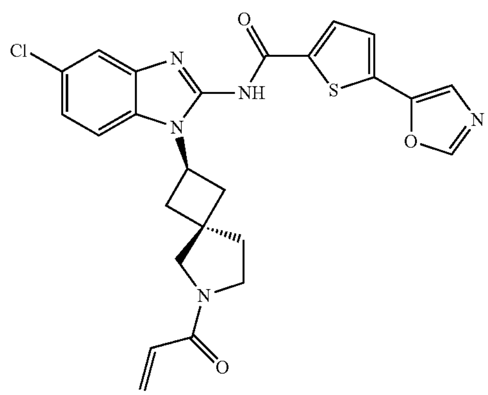 [SMILES: C=CC(=O)N1CC[C@]2(C1)C[C@@H](n1c(NC(=O)c3ccc(-c4cnco4)s3)nc3cc(Cl)ccc31)C2] | [M+H]+=508.0 |
| 72 | 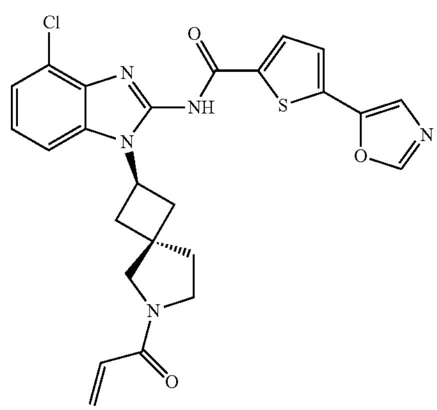 [SMILES: C=CC(=O)N1CC[C@]2(C1)C[C@@H](n1c(NC(=O)c3ccc(-c4cnco4)s3)nc3c(Cl)cccc31)C2] | [M+H]+=508.0 |
| 73 | 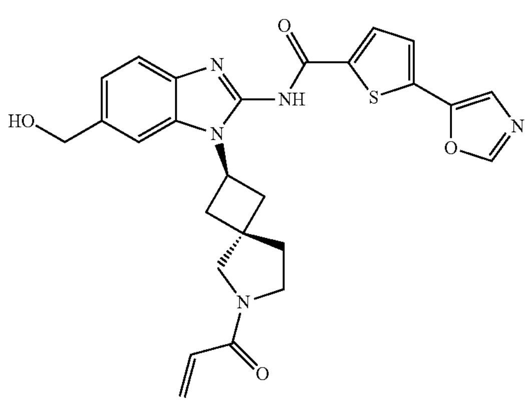 [SMILES: C=CC(=O)N1CC[C@]2(C1)C[C@H](n1c(NC(=O)c3ccc(-c4cnco4)s3)nc3ccc(CO)cc31)C2] | [M+H]+=504.0 |

TABLE 1-continued

Examples of compounds of Formula I

| Compound | Structure | MS (m/z) |
|---|---|---|
| 74 | 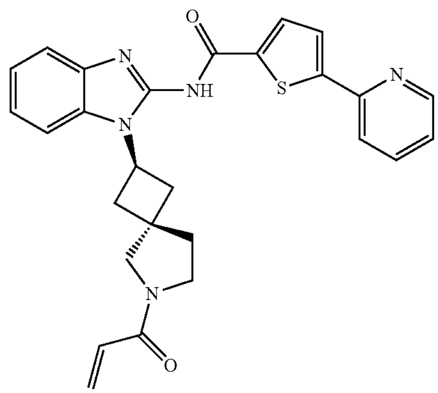 | [M+H]+=484.0 |
| 75 | 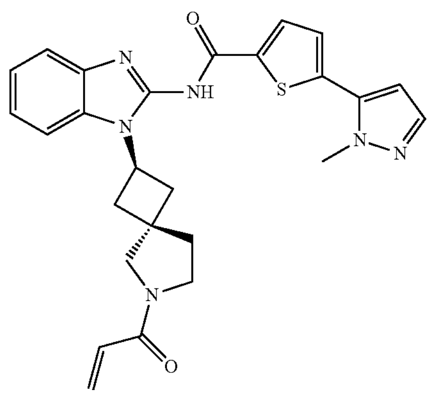 [SMILES: C=CC(=O)N1CC[C@]2(C1)C[C@H](n1c(NC(=O)c3ccc(-c4ccnn4C)s3)nc3ccccc31)C2] | [M+H]+=487.0 |
| 76 | 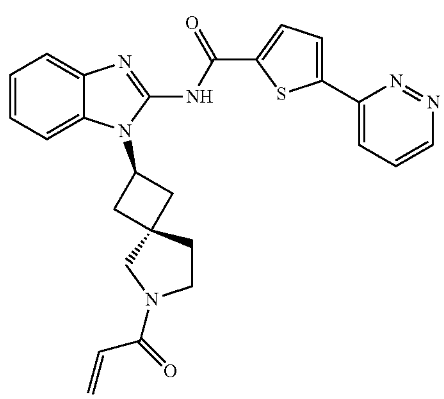 [SMILES: C=CC(=O)N1CC[C@]2(C1)C[C@H](n1c(NC(=O)c3ccc(-c4cccnn4)s3)nc3ccccc31)C2] | [M+H]+=485.0 |
| 77 | 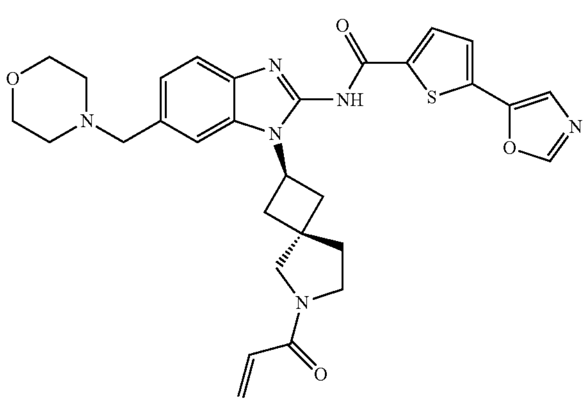 [SMILES: C=CC(=O)N1CC[C@]2(C1)C[C@H](n1c(NC(=O)c3ccc(-c4cnco4)s3)nc3ccc(CN4CCOCC4)cc31)C2] | [M+H]+=573.0 |

TABLE 1-continued
Examples of compounds of Formula I
| Compound | Structure | MS (m/z) |
|---|---|---|
| 78 | 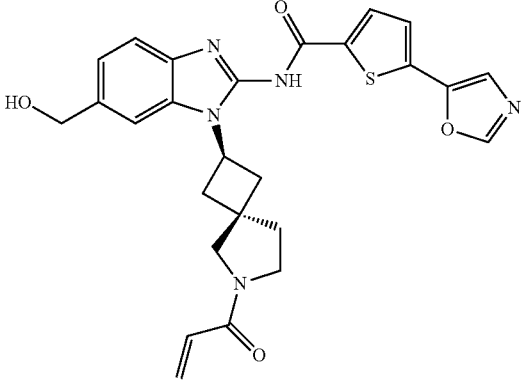 [SMILES: C=CC(=O)N1CC[C@]2(C1)C[C@@H](n1c(NC(=O)c3ccc(-c4cnco4)s3)nc3ccc(CO)cc31)C2] | [M+H]+=504.0 |
| 79 | 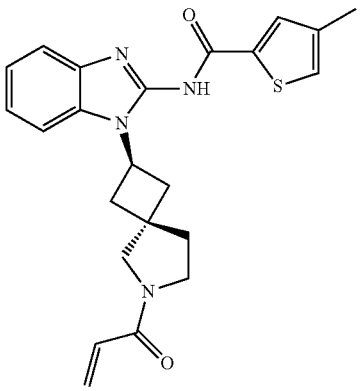 [SMILES: C=CC(=O)N1CC[C@]2(C1)C[C@H](n1c(NC(=O)c3cc(C)cs3)nc3ccccc31)C2] | [M+H]+=421.0 |
| 80 | 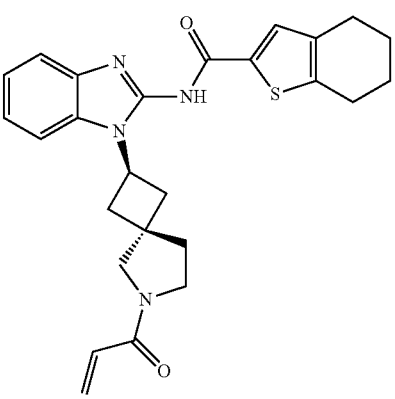 [SMILES: C=CC(=O)N1CC[C@]2(C1)C[C@H](n1c(NC(=O)c3cc4c(s3)CCCC4)nc3ccccc31)C2] | [M+H]+=461.0 |

TABLE 1-continued

Examples of compounds of Formula I

| Compound | Structure | MS (m/z) |
|---|---|---|
| 81 | 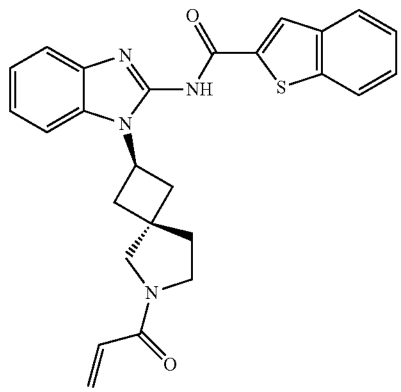 [SMILES: C=CC(=O)N1CC[C@]2(C1)C[C@H](n1c(NC(=O)c3cc4ccccc4s3)nc3ccccc31)C2] | [M+H]+=457.0 |
| 82 | 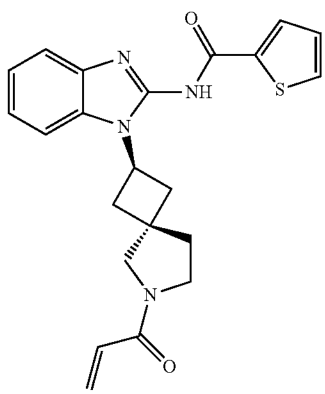 [SMILES: C=CC(=O)N1CC[C@]2(C1)C[C@H](n1c(NC(=O)c3cccs3)nc3ccccc31)C2] | [M+H]+=407.0 |
| 83 | 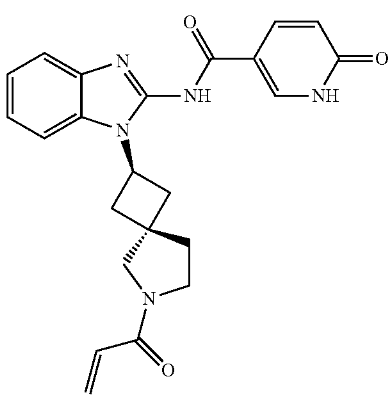 [SMILES: C=CC(=O)N1CC[C@]2(C1)C[C@H](n1c(NC(=O)c3ccc(=O)[nH]c3)nc3ccccc31)C2] | [M+H]+=418.2 |
| 84 | 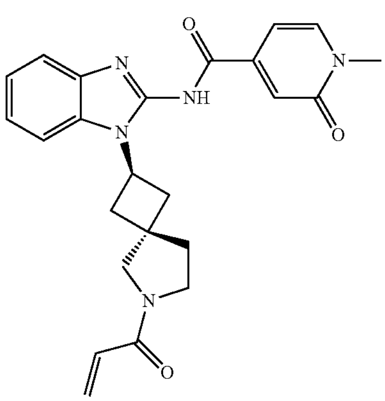 [SMILES: C=CC(=O)N1CC[C@]2(C1)C[C@H](n1c(NC(=O)c3ccn(C)c(=O)c3)nc3ccccc31)C2] | [M+H]+=432.2 |

TABLE 1-continued

Examples of compounds of Formula I

| Compound | Structure | MS (m/z) |
|---|---|---|
| 85 | 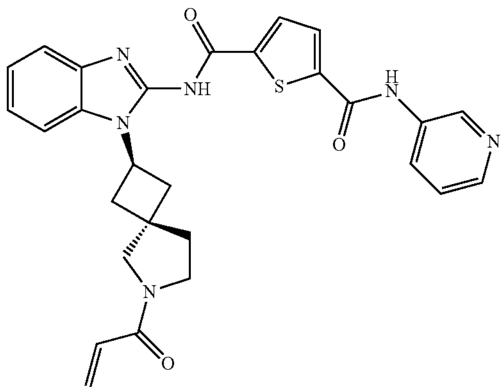 [SMILES: C=CC(=O)N1CC[C@]2(C1)C[C@H](n1c(NC(=O)c3ccc(C(=O)Nc4cccnc4)s3)nc3ccccc31)C2] | [M+H]+=527.2 |
| 86 | 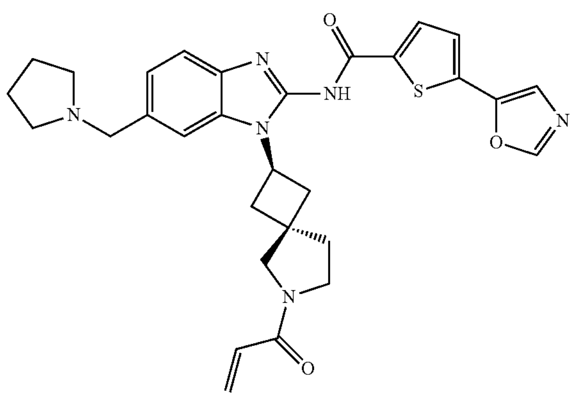 [SMILES: C=CC(=O)N1CC[C@]2(C1)C[C@@H](n1c(NC(=O)c3ccc(-c4cnco4)s3)nc3ccc(CN4CCCC4)cc31)C2] | [M+H]+=557.0 |
| 87 | 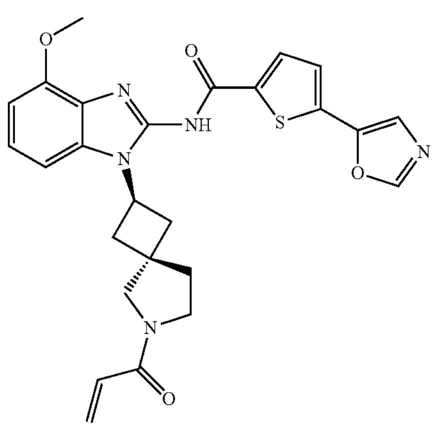 [SMILES: C=CC(=O)N1CC[C@]2(C1)C[C@H](n1c(NC(=O)c3ccc(-c4cnco4)s3)nc3c(OC)cccc31)C2] | [M+H]+=504.0 |

TABLE 1-continued

Examples of compounds of Formula I

| Compound | Structure | MS (m/z) |
|---|---|---|
| 88 | 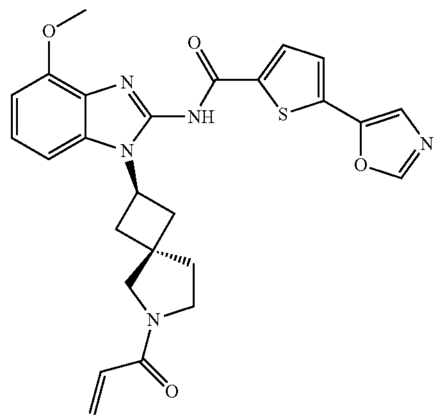 [SMILES: C=CC(=O)N1CC[C@]2(C1)C[C@@H](n1c(NC(=O)c3ccc(-c4cnco4)s3)nc3c(OC)cccc31)C2] | [M+H]+=504.0 |
| 89 | 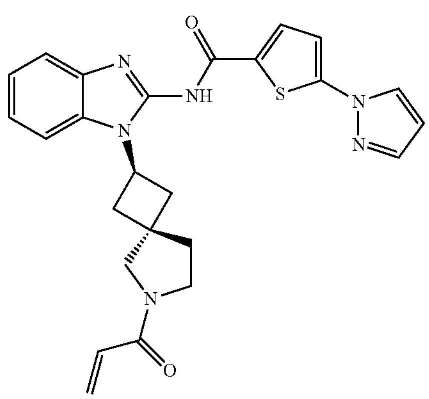 [SMILES: C=CC(=O)N1CC[C@]2(C1)C[C@H](n1c(NC(=O)c3ccc(-n4cccn4)s3)nc3ccccc31)C2] | [M+H]+=473.0 |
| 90 | 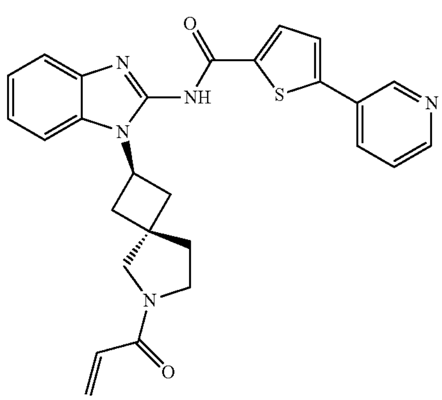 [SMILES: C=CC(=O)N1CC[C@]2(C1)C[C@H](n1c(NC(=O)c3ccc(-c4cccnc4)s3)nc3ccccc31)C2] | [M+H]+=484.5 |

TABLE 1-continued

Examples of compounds of Formula I

| Compound | Structure | MS (m/z) |
|---|---|---|
| 91 | 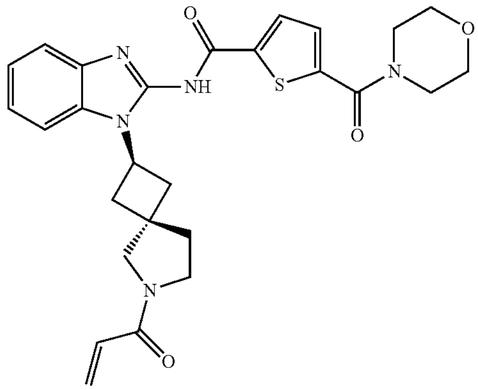 [SMILES: C=CC(=O)N1CC[C@]2(C1)C[C@H](n1c(NC(=O)c3ccc(C(=O)N4CCOCC4)s3)nc3ccccc31)C2] | [M+H]⁺= |
| 92 | 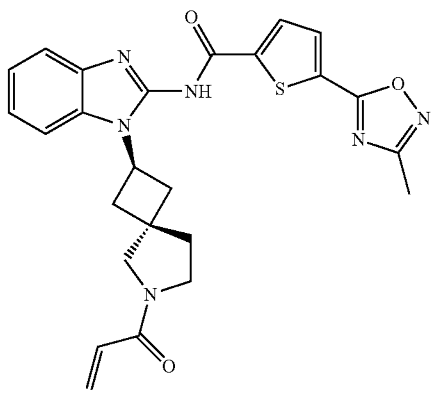 [SMILES: C=CC(=O)N1CC[C@]2(C1)C[C@H](n1c(NC(=O)c3ccc(-c4nc(C)no4)s3)nc3ccccc31)C2] | [M+H]+=489.0 |
| 93 | 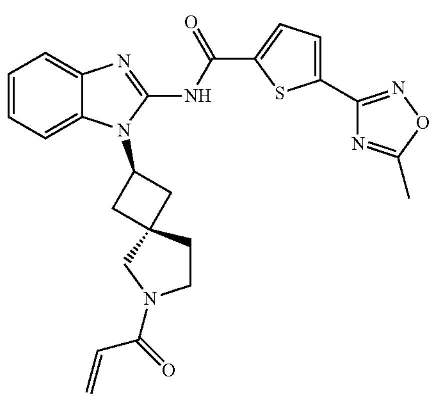 [SMILES: C=CC(=O)N1CC[C@]2(C1)C[C@H](n1c(NC(=O)c3ccc(-c4noc(C)n4)s3)nc3ccccc31)C2] | [M+H]+=489.0 |
| 94 | 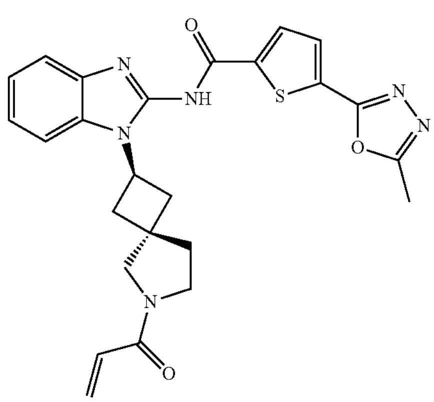 [SMILES: C=CC(=O)N1CC[C@]2(C1)C[C@H](n1c(NC(=O)c3ccc(-c4nnc(C)o4)s3)nc3ccccc31)C2] | [M+H]+=489.0 |

TABLE 1-continued

Examples of compounds of Formula I

| Compound | Structure | MS (m/z) |
|---|---|---|
| 95 | 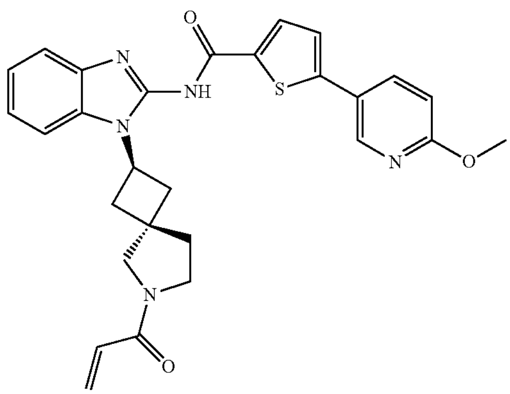 [SMILES: C=CC(=O)N1CC[C@]2(C1)C[C@H](n1c(NC(=O)c3ccc(-c4ccc(OC)nc4)s3)nc3ccccc31)C2] | [M+H]+=514.4 |
| 96 | 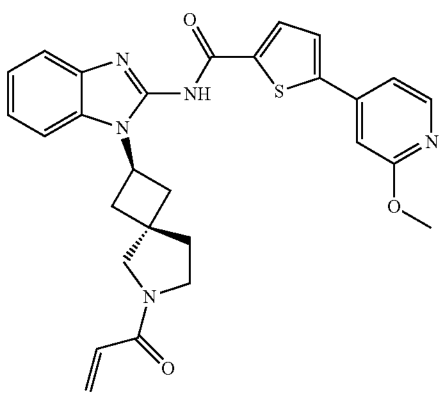 [SMILES: C=CC(=O)N1CC[C@]2(C1)C[C@H](n1c(NC(=O)c3ccc(-c4ccnc(OC)c4)s3)nc3ccccc31)C2] | [M+H]+=514.0 |
| 97 | 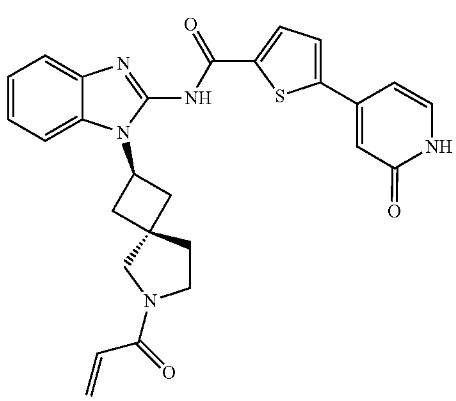 [SMILES: C=CC(=O)N1CC[C@]2(C1)C[C@H](n1c(NC(=O)c3ccc(-c4cc[nH]c(=O)c4)s3)nc3ccccc31)C2] | [M+H]+=500.2 |

TABLE 1-continued

Examples of compounds of Formula I

| Compound | Structure | MS (m/z) |
|---|---|---|
| 98 | 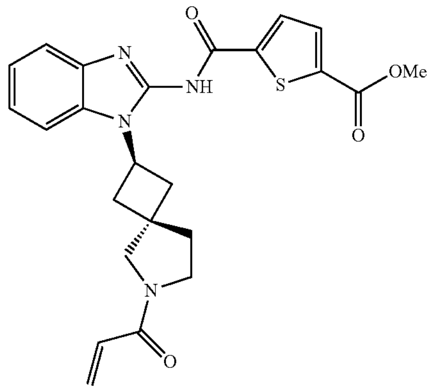 [SMILES: C=CC(=O)N1CC[C@]2(C1)C[C@H](n1c(NC(=O)c3ccc(C(=O)OC)s3)nc3ccccc31)C2] | [M+H]+=465.2 |
| 99 | 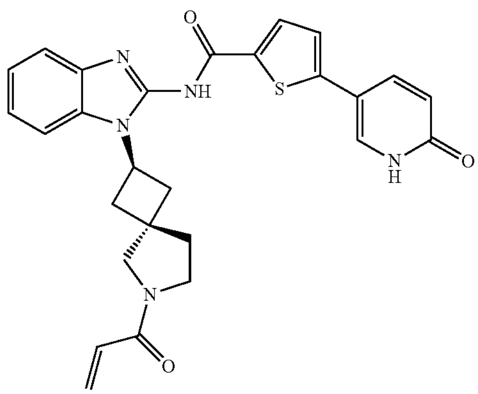 [SMILES: C=CC(=O)N1CC[C@]2(C1)C[C@H](n1c(NC(=O)c3ccc(-c4ccc(=O)[nH]c4)s3)nc3ccccc31)C2] | [M+H]+=500.4 |
| 100 | 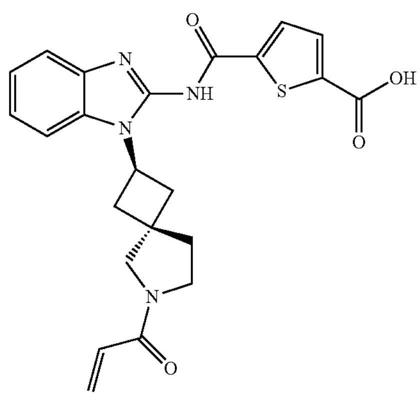 [SMILES: C=CC(=O)N1CC[C@]2(C1)C[C@H](n1c(NC(=O)c3ccc(C(=O)O)s3)nc3ccccc31)C2] | [M+H]+=451.2 |
| 101 | 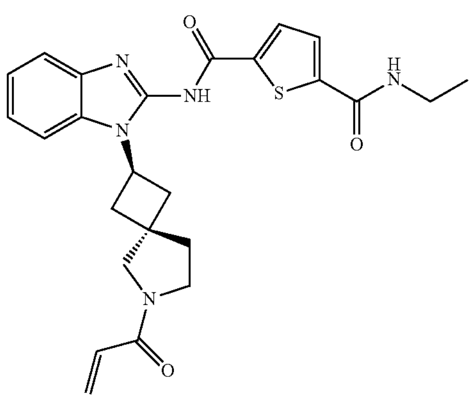 [SMILES: C=CC(=O)N1CC[C@]2(C1)C[C@H](n1c(NC(=O)c3ccc(C(=O)NCC)s3)nc3ccccc31)C2] | [M+H]+=478.4 |

TABLE 1-continued
Examples of compounds of Formula I
| Compound | Structure | MS (m/z) |
|---|---|---|
| 102 | 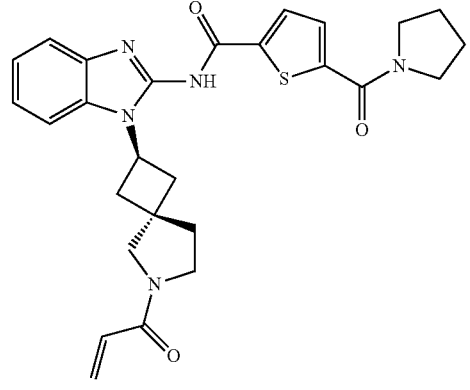 [SMILES: C=CC(=O)N1CC[C@]2(C1)C[C@H](n1c(NC(=O)c3ccc(C(=O)N4CCCC4)s3)nc3ccccc31)C2] | [M+H]+=504.2 |
| 103 | 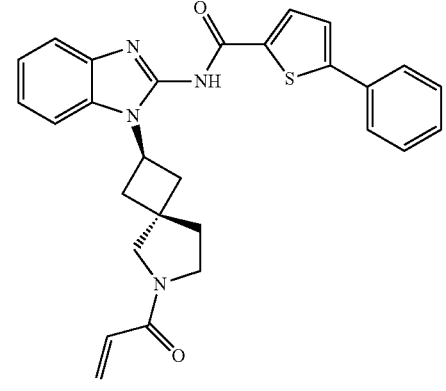 [SMILES: C=CC(=O)N1CC[C@]2(C1)C[C@H](n1c(NC(=O)c3ccc(-c4ccccc4)s3)nc3ccccc31)C2] | [M+H]+=483.0 |
| 104 | 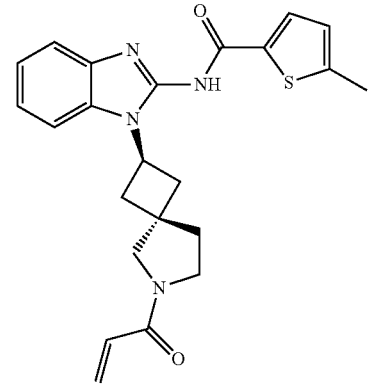 [SMILES: C=CC(=O)N1CC[C@]2(C1)C[C@H](n1c(NC(=O)c3ccc(C)s3)nc3ccccc31)C2] | [M+H]+=421.0 |

TABLE 1-continued
Examples of compounds of Formula I
| Compound | Structure | MS (m/z) |
|---|---|---|
| 105 | 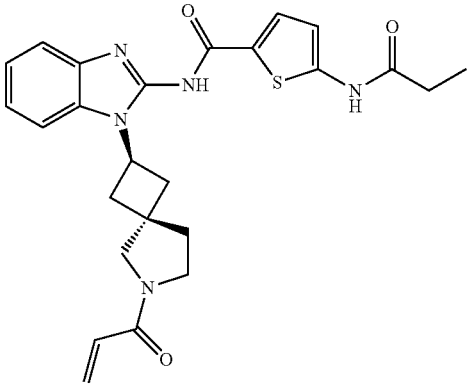 [SMILES: C=CC(=O)N1CC[C@]2(C1)C[C@H](n1c(NC(=O)c3ccc(NC(=O)CC)s3)nc3ccccc31)C2] | [M+H]+=478.2 |
| 106 | 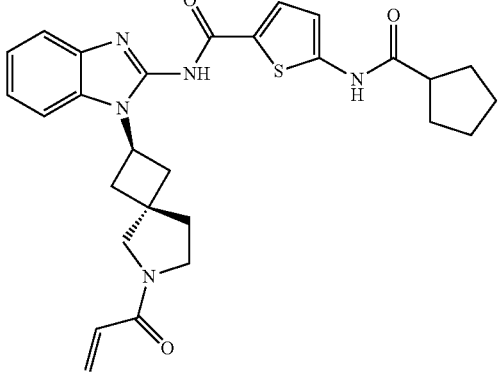 | [M+H]+=518.4 |
| 107 | 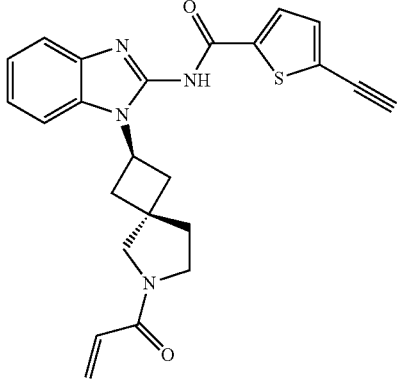 [SMILES: C#Cc1ccc(C(=O)Nc2nc3ccccc3n2[C@H]2C[C@@]3(CCN(C(=O)C=C)C3)C2)s1] | [M+H]+=431.0 |
| 108 | 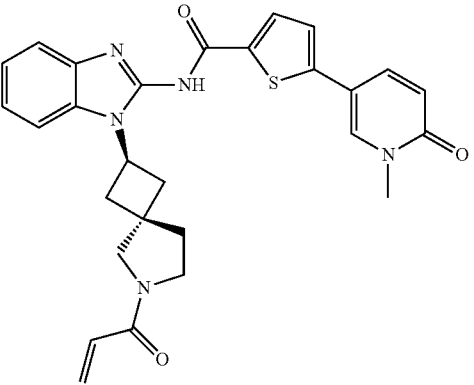 [SMILES: C=CC(=O)N1CC[C@]2(C1)C[C@H](n1c(NC(=O)c3ccc(-c4ccc(=O)n(C)c4)s3)nc3ccccc31)C2] | [M+H]+= |

TABLE 1-continued

| Compound | Structure | MS (m/z) |
|---|---|---|
| 109 | 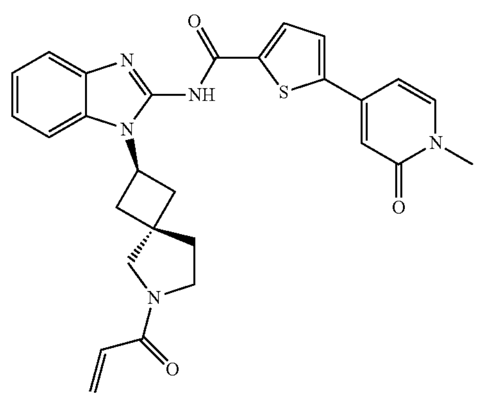 [SMILES: C=CC(=O)N1CC[C@]2(C1)C[C@H](n1c(NC(=O)c3ccc(-c4ccn(C)c(=O)c4)s3)nc3ccccc31)C2] | [M+H]+= |
| 110 | 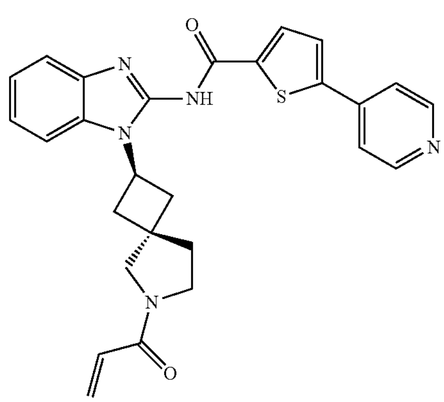 [SMILES: C=CC(=O)N1CC[C@]2(C1)C[C@H](n1c(NC(=O)c3ccc(-c4ccncc4)s3)nc3ccccc31)C2] | [M+H]+= |
| 111 | 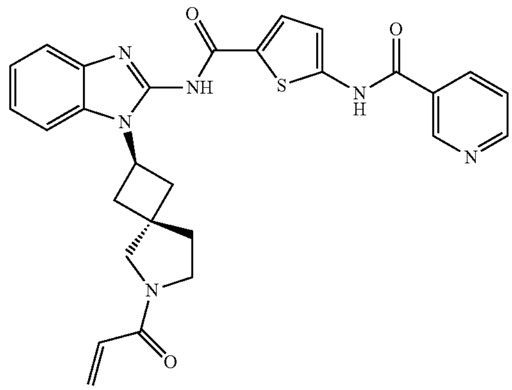 [SMILES: C=CC(=O)N1CC[C@]2(C1)C[C@H](n1c(NC(=O)c3ccc(NC(=O)c4cccnc4)s3)nc3ccccc31)C2] | [M+H]+=527.4 |

TABLE 1-continued

Examples of compounds of Formula I

| Compound | Structure | MS (m/z) |
|---|---|---|
| 112 | 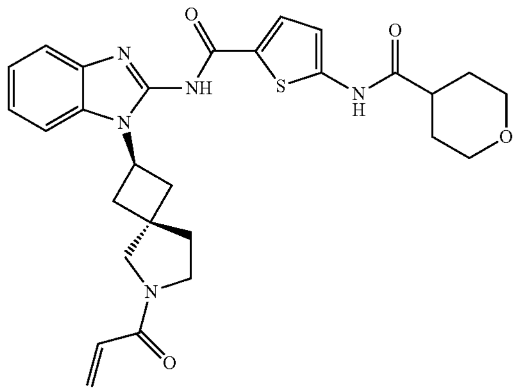 [SMILES: C=CC(=O)N1CC[C@]2(C1)C[C@H](n1c(NC(=O)c3ccc(NC(=O)C4CCOCC4)s3)nc3ccccc31)C2] | [M+H]+=534.4 |
| 113 | 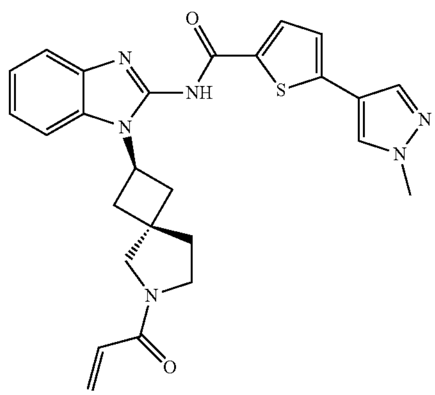 [SMILES: C=CC(=O)N1CC[C@]2(C1)C[C@H](n1c(NC(=O)c3ccc(-c4cnn(C)c4)s3)nc3ccccc31)C2] | [M+H]+=487.2 |
| 114 | 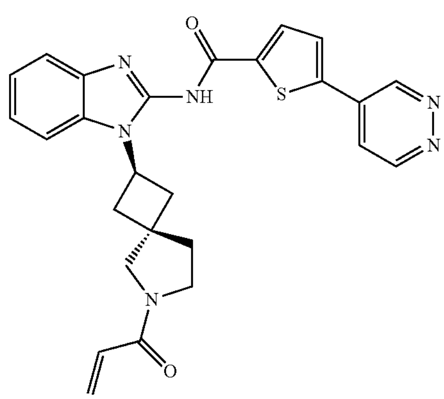 [SMILES: C=CC(=O)N1CC[C@]2(C1)C[C@H](n1c(NC(=O)c3ccc(-c4ccnnc4)s3)nc3ccccc31)C2] | [M+H]+=485.1 |
| 115 | 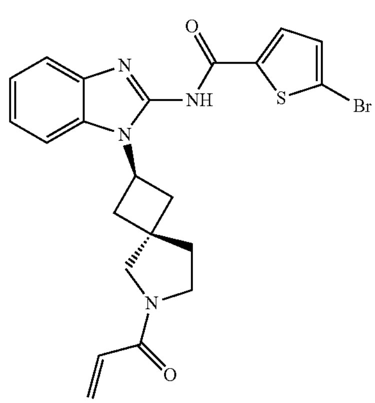 [SMILES: C=CC(=O)N1CC[C@]2(C1)C[C@H](n1c(NC(=O)c3ccc(Br)s3)nc3ccccc31)C2] | [M+H]+=486.0 |

TABLE 1-continued

| Compound | Structure | MS (m/z) |
|---|---|---|
| 116 | 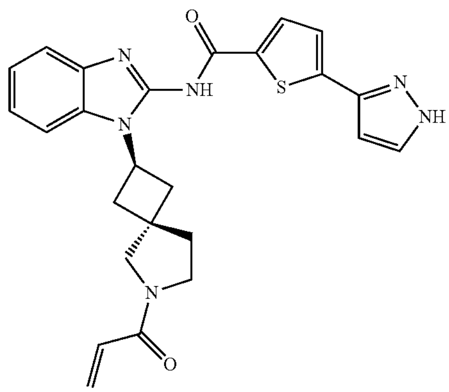 [SMILES: C=CC(=O)N1CC[C@]2(C1)C[C@H](n1c(NC(=O)c3ccc(-c4cc[nH]n4)s3)nc3ccccc31)C2] | [M+H]+=473.0 |
| 117 | 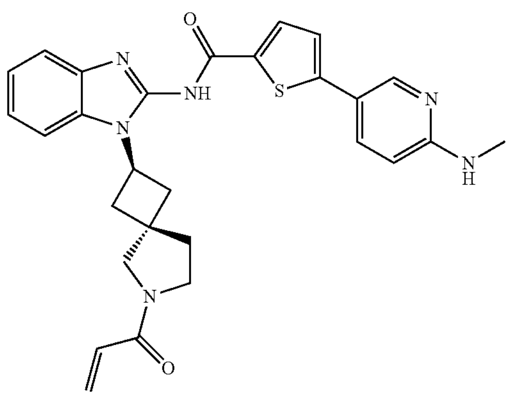 [SMILES: C=CC(=O)N1CC[C@]2(C1)C[C@H](n1c(NC(=O)c3ccc(-c4ccc(NC)nc4)s3)nc3ccccc31)C2] | [M+H]+=513.4 |
| 118 | 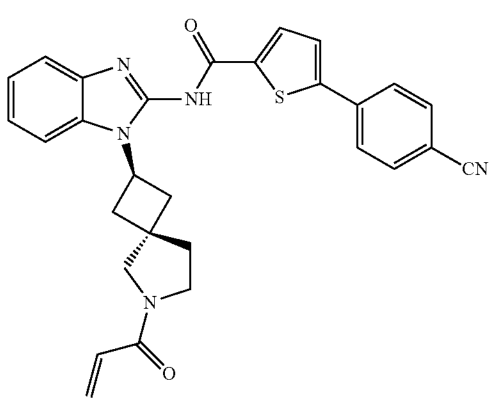 [SMILES: C=CC(=O)N1CC[C@]2(C1)C[C@H](n1c(NC(=O)c3ccc(-c4ccc(C#N)cc4)s3)nc3ccccc31)C2] | [M+H]+=508.6 |

TABLE 1-continued

Examples of compounds of Formula I

| Compound | Structure | MS (m/z) |
|---|---|---|
| 119 | 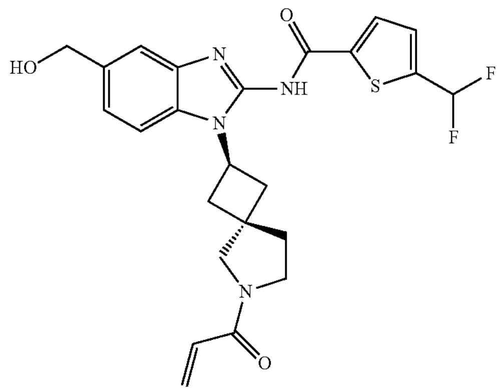 [SMILES: C=CC(=O)N1CC[C@]2(C1)C[C@H](n1c(NC(=O)c3ccc(C(F)F)s3)nc3cc(CO)ccc31)C2] | [M+H]+=486.2 |
| 120 | 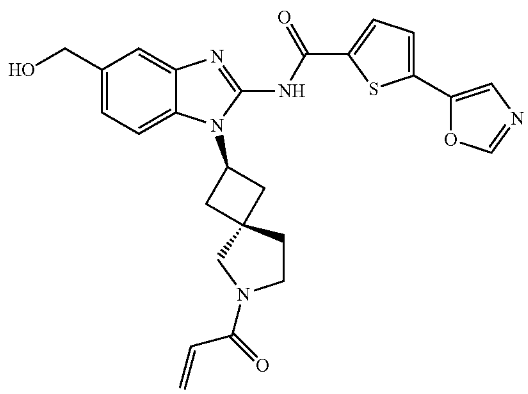 [SMILES: C=CC(=O)N1CC[C@]2(C1)C[C@H](n1c(NC(=O)c3ccc(-c4cnco4)s3)nc3cc(CO)ccc31)C2] | [M+H]+=503.2 |
| 121 | 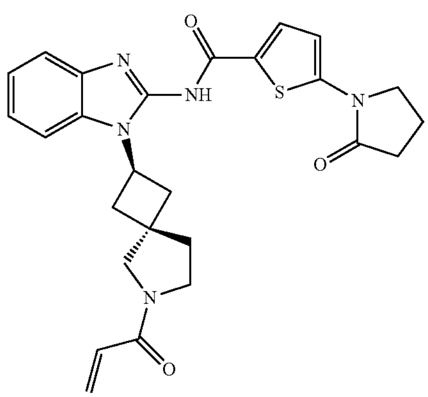 [SMILES: C=CC(=O)N1CC[C@]2(C1)C[C@H](n1c(NC(=O)c3ccc(N4CCCC4=O)s3)nc3ccccc31)C2] | [M+H]+=490.4 |
| 122 | 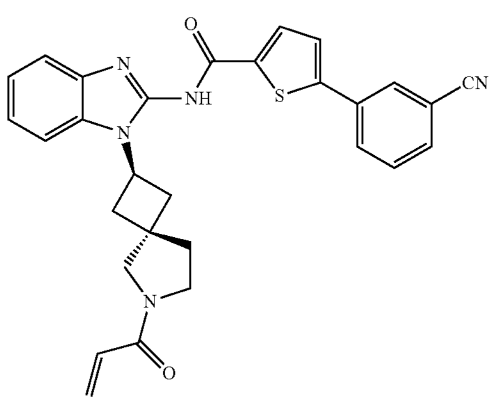 [SMILES: C=CC(=O)N1CC[C@]2(C1)C[C@H](n1c(NC(=O)c3ccc(-c4cccc(C#N)c4)s3)nc3ccccc31)C2] | [M+H]+=508.2 |

TABLE 1-continued

Examples of compounds of Formula I

| Compound | Structure | MS (m/z) |
|---|---|---|
| 123 | 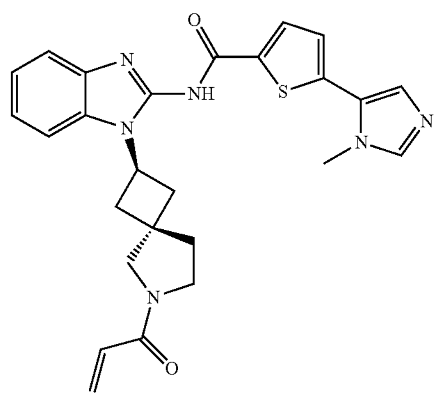 [SMILES: C=CC(=O)N1CC[C@]2(C1)C[C@H](n1c(NC(=O)c3ccc(-c4cncn4C)s3)nc3ccccc31)C2] | [M+H]+=487.4 |
| 124 | 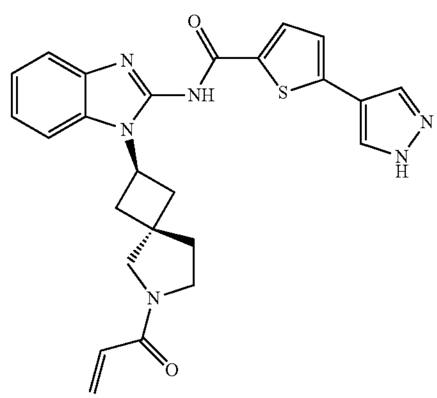 [SMILES: C=CC(=O)N1CC[C@]2(C1)C[C@H](n1c(NC(=O)c3ccc(-c4cn[nH]c4)s3)nc3ccccc31)C2] | [M+H]+=473.0 |
| 125 | 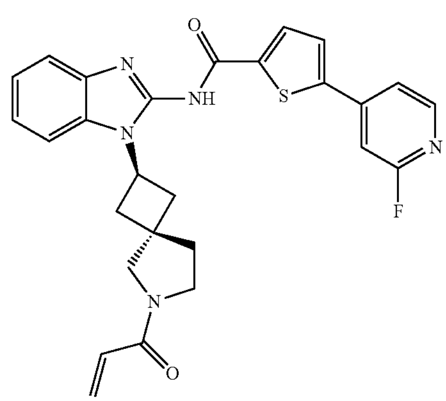 [SMILES: C=CC(=O)N1CC[C@]2(C1)C[C@H](n1c(NC(=O)c3ccc(-c4ccnc(F)c4)s3)nc3ccccc31)C2] | [M+H]+=502.2 |

TABLE 1-continued

Examples of compounds of Formula I

| Compound | Structure | MS (m/z) |
|---|---|---|
| 126 | 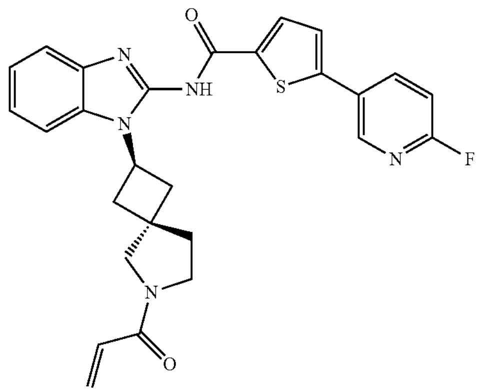 [SMILES: C=CC(=O)N1CC[C@]2(C1)C[C@H](n1c(NC(=O)c3ccc(-c4ccc(F)nc4)s3)nc3ccccc31)C2] | [M+H]+=502.4 |
| 127 | 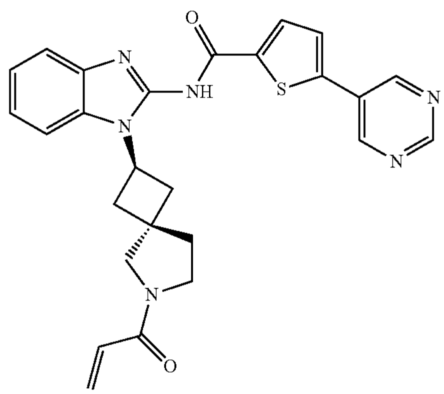 | [M+H]+=484.2 |
| 128 | 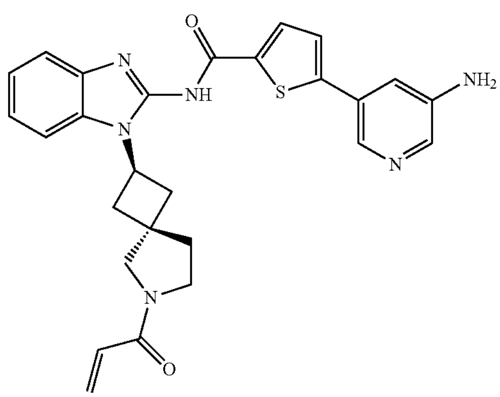 [SMILES: C=CC(=O)N1CC[C@]2(C1)C[C@H](n1c(NC(=O)c3ccc(-c4cncc(N)c4)s3)nc3ccccc31)C2] | [M+H]+=499.4 |
| 129 | 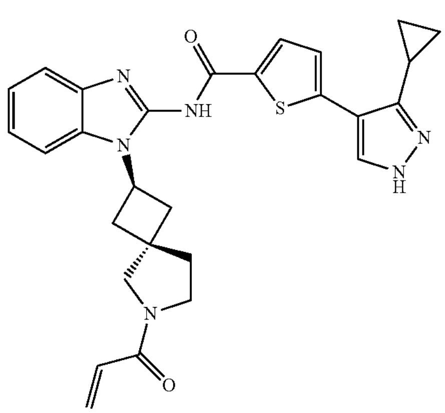 [SMILES: C=CC(=O)N1CC[C@]2(C1)C[C@H](n1c(NC(=O)c3ccc(-c4c[nH]nc4C4CC4)s3)nc3ccccc31)C2] | [M+H]+=513.4 |

TABLE 1-continued

Examples of compounds of Formula I

| Compound | Structure | MS (m/z) |
|---|---|---|
| 130 | 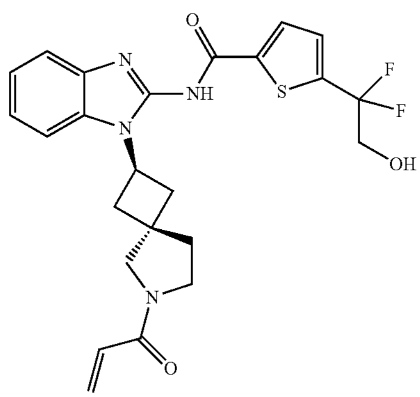 [SMILES: C=CC(=O)N1CC[C@]2(C1)C[C@H](n1c(NC(=O)c3ccc(C(F)(F)CO)s3)nc3ccccc31)C2] | [M+H]+=487.0 |
| 131 | 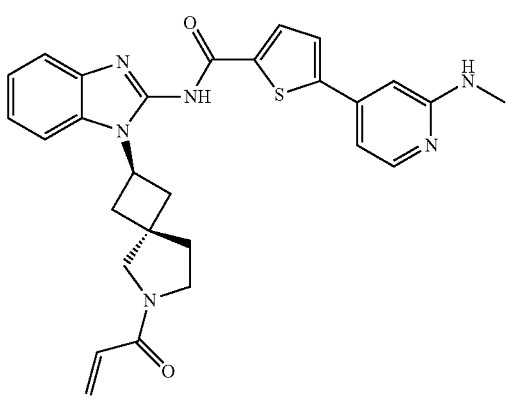 [SMILES: C=CC(=O)N1CC[C@]2(C1)C[C@H](n1c(NC(=O)c3ccc(-c4ccnc(NC)c4)s3)nc3ccccc31)C2] | [M+H]+=513.0 |
| 132 | 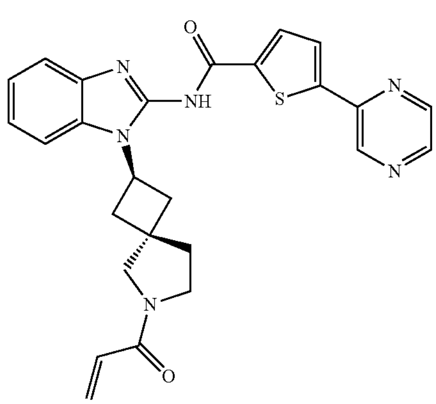 [SMILES: C=CC(=O)N1CC[C@]2(C1)C[C@H](n1c(NC(=O)c3ccc(-c4cnccn4)s3)nc3ccccc31)C2] | [M+H]+=485.2 |

TABLE 1-continued
Examples of compounds of Formula I
| Compound | Structure | MS (m/z) |
|---|---|---|
| 133 | 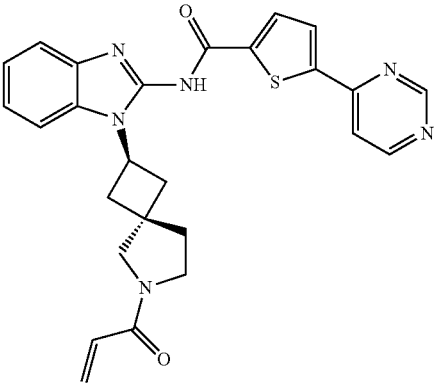 | [M+H]+=485.2 |
| 134 | 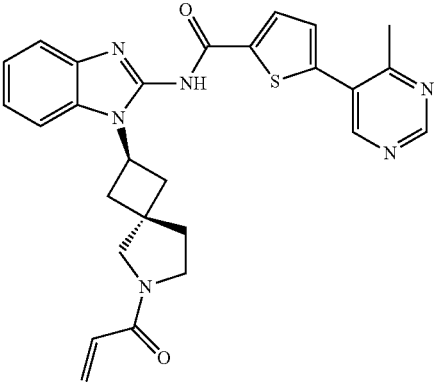 [SMILES: C=CC(=O)N1CC[C@]2(C1)C[C@H](n1c(NC(=O)c3ccc(-c4cncnc4C)s3)nc3ccccc31)C2] | [M+H]+=499.4 |
| 135 | 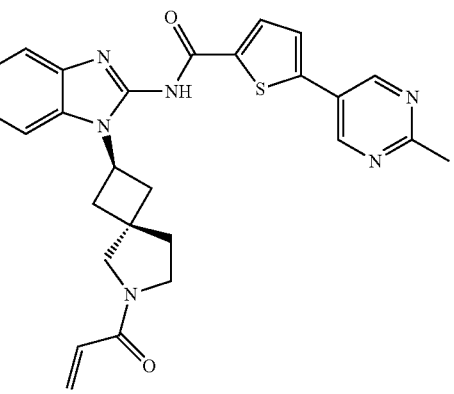 | [M+H]+=499.4 |
| 136 | 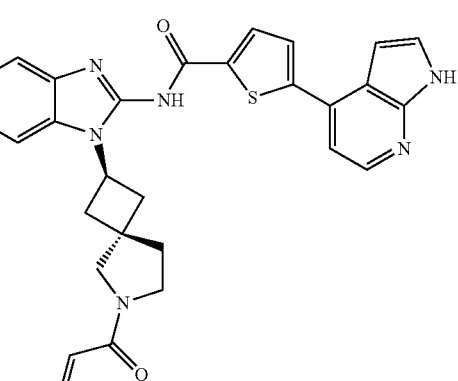 | [M+H]+=533.4 |

TABLE 1-continued

Examples of compounds of Formula I

| Compound | Structure | MS (m/z) |
|---|---|---|
| 137 | 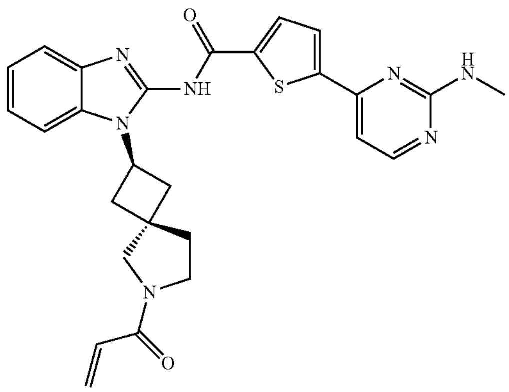 [SMILES: C=CC(=O)N1CC[C@]2(C1)C[C@H](n1c(NC(=O)c3ccc(-c4ccnc(NC)n4)s3)nc3ccccc31)C2] | [M+H]+=514.6 |
| 138 | 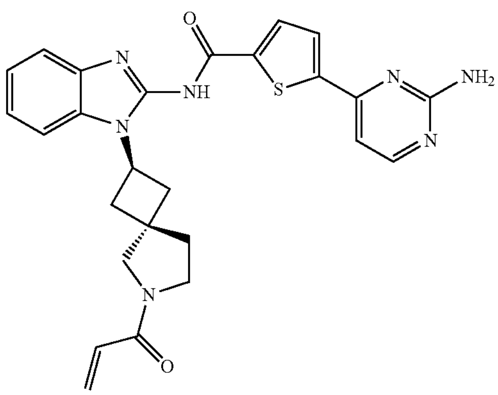 [SMILES: C=CC(=O)N1CC[C@]2(C1)C[C@H](n1c(NC(=O)c3ccc(-c4ccnc(N)n4)s3)nc3ccccc31)C2] | [M+H]+=500.2 |
| 139 | 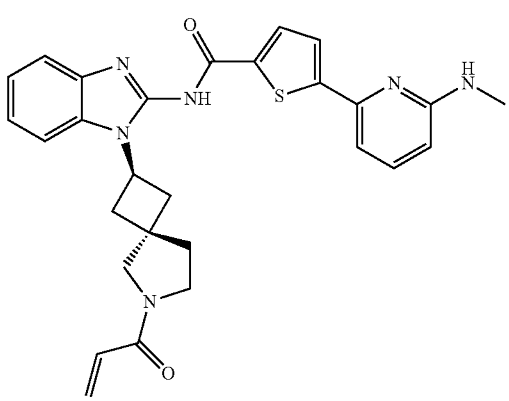 [SMILES: C=CC(=O)N1CC[C@]2(C1)C[C@H](n1c(NC(=O)c3ccc(-c4cccc(NC)n4)s3)nc3ccccc31)C2] | [M+H]+=513.4 |

TABLE 1-continued

Examples of compounds of Formula I

| Compound | Structure | MS (m/z) |
|---|---|---|
| 140 | 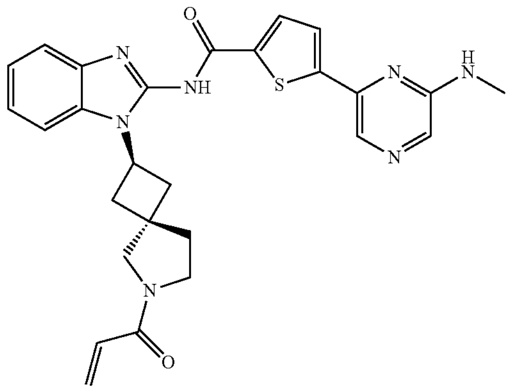 [SMILES: C=CC(=O)N1CC[C@]2(C1)C[C@H](n1c(NC(=O)c3ccc(-c4cncc(NC)n4)s3)nc3ccccc31)C2] | [M+H]+=514.6 |
| 141 | 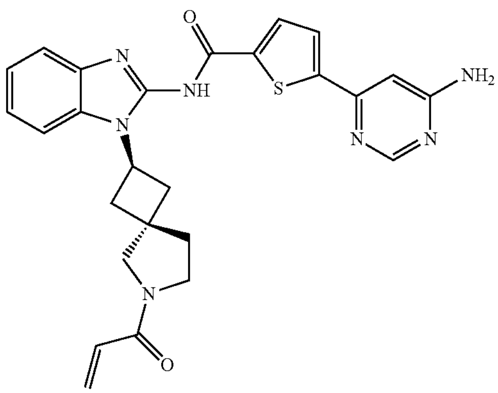 [SMILES: C=CC(=O)N1CC[C@]2(C1)C[C@H](n1c(NC(=O)c3ccc(-c4cc(N)ncn4)s3)nc3ccccc31)C2] | [M+H]+=500.2 |
| 142 | 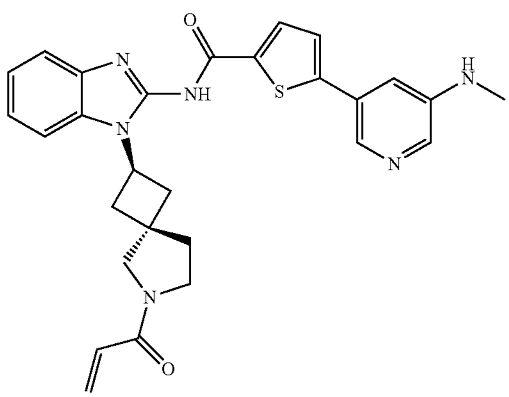 [SMILES: C=CC(=O)N1CC[C@]2(C1)C[C@H](n1c(NC(=O)c3ccc(-c4cncc(NC)c4)s3)nc3ccccc31)C2] | [M+H]+=513.4 |
| 143 | 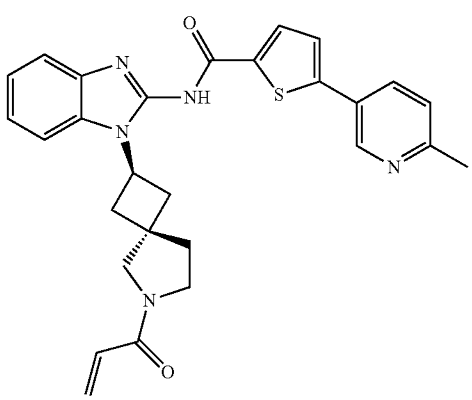 [SMILES: C=CC(=O)N1CC[C@]2(C1)C[C@H](n1c(NC(=O)c3ccc(-c4ccc(C)nc4)s3)nc3ccccc31)C2] | [M+H]+=498.4 |

TABLE 1-continued
Examples of compounds of Formula I
| Compound | Structure | MS (m/z) |
|---|---|---|
| 144 | 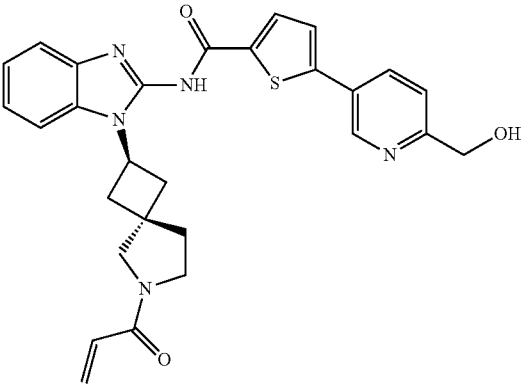 [SMILES: C=CC(=O)N1CC[C@]2(C1)C[C@H](n1c(NC(=O)c3ccc(-c4ccc(CO)nc4)s3)nc3ccccc31)C2] | [M+H]+=514.4 |
| 145 | 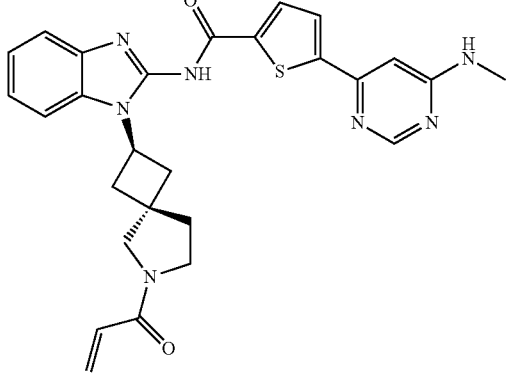 | [M+H]+=514.4 |
| 146 | 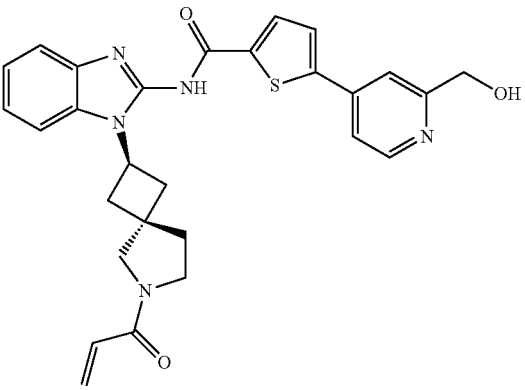 [SMILES: C=CC(=O)N1CC[C@]2(C1)C[C@H](n1c(NC(=O)c3ccc(-c4ccnc(CO)c4)s3)nc3ccccc31)C2] | [M+H]+=514.4 |

TABLE 1-continued

Examples of compounds of Formula I

| Compound | Structure | MS (m/z) |
|----------|-----------|----------|
| 147 | 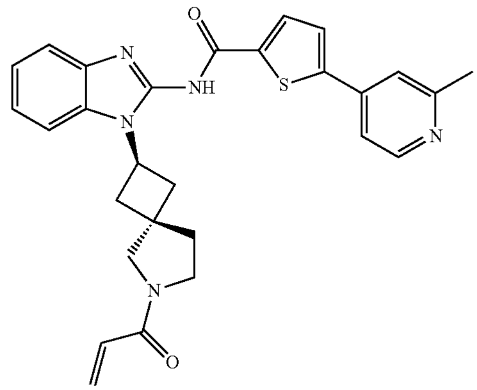 [SMILES: C=CC(=O)N1CC[C@]2(C1)C[C@H](n1c(NC(=O)c3ccc(-c4ccnc(C)c4)s3)nc3ccccc31)C2] | [M+H]+=498.6 |
| 148 | 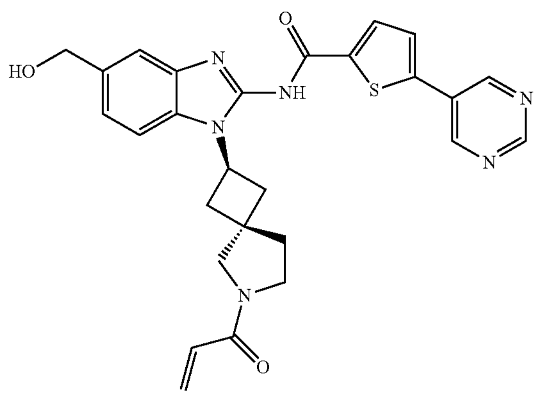 [SMILES: C=CC(=O)N1CC[C@]2(C1)C[C@H](n1c(NC(=O)c3ccc(-c4cncnc4)s3)nc3cc(CO)ccc31)C2] | [M+H]+=515.6 |
| 149 | 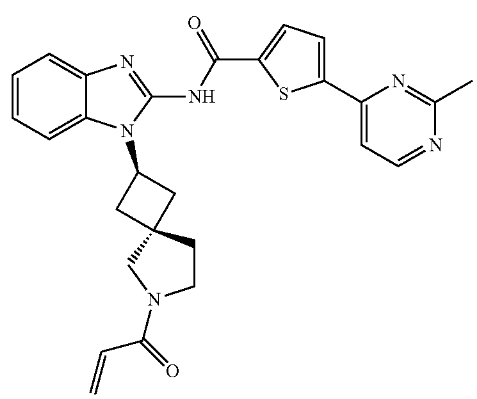 [SMILES: C=CC(=O)N1CC[C@]2(C1)C[C@H](n1c(NC(=O)c3ccc(-c4ccnc(C)n4)s3)nc3ccccc31)C2] | [M+H]+=499.4 |
| 150 | 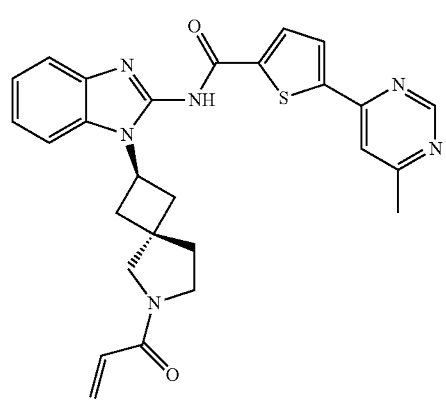 | [M+H]+=523.2 |

TABLE 1-continued
Examples of compounds of Formula I
| Compound | Structure | MS (m/z) |
|---|---|---|
| 151 | 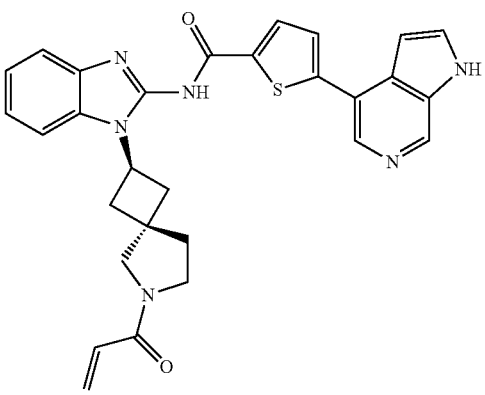 | [M+H]+=554.2 |
| 152 | 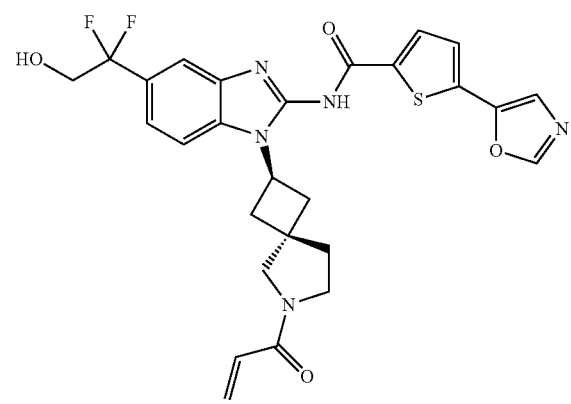 | [M+H]+=500.4 |
| 153 | 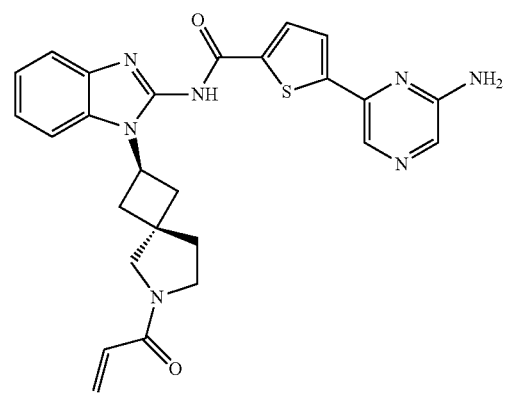 | [M+H]+=524.2 |

TABLE 1-continued

Examples of compounds of Formula I

| Compound | Structure | MS (m/z) |
|---|---|---|
| 154 | 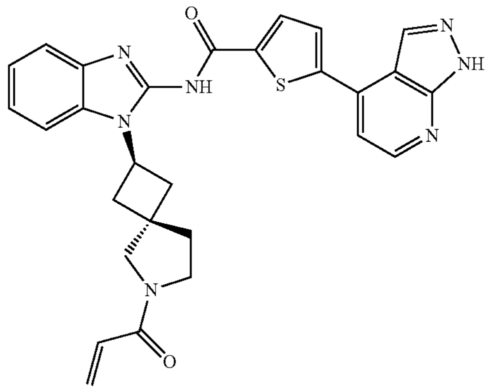 | [M+H]+=554.2 |
| 155 | 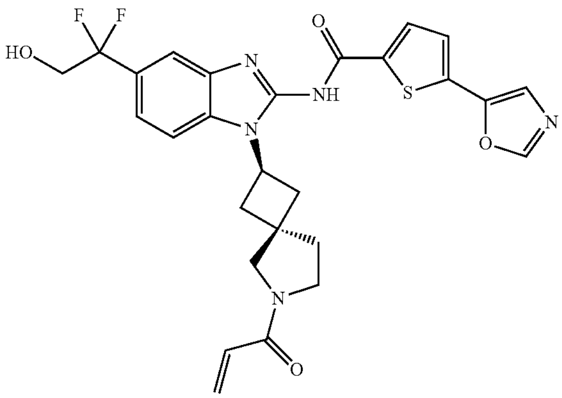 | [M+H]+=523.2 |
| 156 | 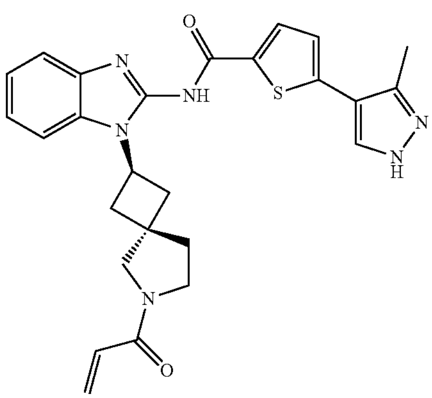 [SMILES: C=CC(=O)N1CC[C@]2(C1)C[C@H](n1c(NC(=O)c3ccc(-c4c[nH]nc4C)s3)nc3ccccc31)C2] | [M+H]+=487.2 |

Example 1: CD3/CD28 Mediated PBMC Proliferation Assay

Inhibition of cellular kinases was assessed by measuring proliferation of PBMC following stimulation with anti-CD3 and anti-CD28 antibodies which is an ITK dependent activity in T cells A (Michel F. et al Immunity; 2001, 15:935-945).

Individual wells of 96 well tissue culture plates were coated with 50 μL of 5 μg/mL anti-CD3 (OKT3, eBiosciences) overnight at 4° C. Human blood was collected in EDTA containing vacutainer tubes. PBMC were isolated on Histopaque 1077 (Sigma) following centrifugation at 400×g. Cells were washed 3 times by resuspension in PBS and centrifugation at 250×g and resuspended in media (RPMI, glutamine, 10% heat inactivated FCS) at a final concentration of 2×10e6 cells/mL. Cells (2×10e5) were added to the washed anti-CD3 coated plates and soluble anti-CD28 (CD28.2 eBiosciences) was added to each well at a final concentration of 2 μg/mL. Finally, compounds were added at various concentrations to each well. The cells were placed in a humidified 37° C. incubator for 72 hours. Controls included unstimulated cells and media alone.

TABLE 2

Results CD3/CD28 assay PBMC proliferation assay

| Compound Number | CD3/CD28 PMBC proliferation IC50 (nM) |
|---|---|
| 1 | >300 |
| 2 | 3 |
| 3 | 35.6 |
| 4 | 1.3 |
| 5 | 7.1 |
| 6 | 23.4 |
| 7 | 227.3 |
| 8 | 26.3 |
| 9 | 2.7 |
| 10 | 30.2 |
| 11 | >300 |
| 12 | >300 |
| 13 | 16.2 |
| 14 | 166 |
| 15 | 6.3 |
| 16 | 1.5 |
| 17 | 151.4 |
| 18 | 91.2 |
| 19 | 4.1 |
| 20 | 6.3 |
| 21 | 3.7 |
| 22 | 4 |
| 23 | 7.3 |
| 24 | 13 |
| 25 | 3.4 |
| 26 | 2.8 |
| 27 | 3 |
| 28 | 6.1 |
| 29 | 15.1 |
| 30 | 2.6 |
| 31 | 38.9 |
| 32 | 4.5 |
| 33 | >300 |
| 34 | 3 |
| 35 | 1.4 |
| 36 | 1.2 |
| 37 | 1 |
| 38 | 19.5 |
| 39 | 64.6 |
| 40 | 3.2 |
| 41 | 4.7 |
| 42 | 3.5 |
| 43 | 3.1 |
| 44 | 1.6 |
| 45 | 60.3 |
| 46 | 37.2 |
| 47 | 20 |
| 48 | 64.6 |
| 49 | 70.8 |
| 50 | 1.4 |
| 51 | 0.5 |
| 52 | 0.7 |
| 53 | 0.8 |
| 54 | 0.8 |
| 55 | 125.9 |
| 56 | 2.1 |
| 57 | 4.2 |
| 58 | 4.2 |
| 59 | 1.2 |
| 60 | 1.2 |
| 61 | 43.6 |
| 62 | 63.1 |
| 63 | 7.6 |
| 64 | 100 |
| 65 | 6.4 |
| 66 | 100 |
| 67 | 300 |
| 68 | 65.3 |
| 69 | 72.4 |
| 70 | 28.8 |
| 71 | 154.9 |
| 72 | >300 |
| 73 | 0.6 |
| 74 | 120.3 |
| 75 | 23.1 |
| 76 | 17.4 |
| 77 | 0.8 |
| 78 | 5.4 |
| 79 | >100 |
| 80 | >300 |
| 81 | >300 |
| 82 | >100 |
| 83 | >300 |
| 84 | >300 |
| 85 | 81.3 |
| 86 | 4.7 |
| 87 | >100 |
| 88 | >300 |
| 89 | 42.7 |
| 90 | 8.6 |
| 91 | 150.5 |
| 92 | >100 |
| 93 | >100 |
| 94 | 21.4 |
| 95 | >300 |
| 96 | 28.6 |
| 97 | 11.5 |
| 98 | 23.4 |
| 99 | >100 |
| 100 | >300 |
| 101 | >300 |
| 102 | >300 |
| 103 | 177.8 |
| 104 | 37.2 |
| 105 | >300 |
| 106 | >300 |
| 107 | 20.9 |
| 108 | 95.5 |
| 109 | 242.7 |
| 110 | 6.4 |
| 111 | >300 |
| 112 | >300 |
| 113 | 17.8 |
| 114 | 3.5 |
| 115 | 7 |
| 116 | 89.1 |
| 117 | 91.2 |
| 118 | >300 |
| 119 | 3 |
| 120 | 0.5 |
| 121 | 24.6 |
| 122 | 239.9 |
| 123 | 15.1 |
| 124 | 1.6 |
| 125 | 8.6 |
| 126 | 47.9 |
| 127 | 7.6 |
| 128 | 1.9 |
| 129 | 6.7 |
| 130 | 2.3 |
| 131 | 4.2 |
| 132 | 24.6 |
| 133 | 7 |
| 134 | 24.6 |
| 135 | 24.6 |
| 136 | 3.2 |
| 137 | 7.6 |
| 138 | 2.8 |
| 139 | 95.5 |
| 140 | 8.6 |
| 141 | 8.7 |
| 142 | 7 |
| 143 | 64.5 |
| 144 | 22.2 |
| 145 | 9.4 |
| 146 | 8.6 |
| 147 | 7.9 |
| 148 | 6.1 |
| 149 | 4.7 |
| 150 | 25 |

TABLE 2-continued

Results CD3/CD28 assay PBMC proliferation assay

| Compound Number | CD3/CD28 PMBC proliferation IC50 (nM) |
|---|---|
| 151 | 220 |
| 152 | 74.1 |
| 153 | 23.4 |
| 154 | 19 |
| 155 | 135 |
| 156 | 8.6 | a-$EC_{50}$ < 1 nM,
b-1 nM < $EC_{50}$ < 10 nM,
c-$EC_{50}$ > 10 nM

Example 2: Kinase Inhibition Assay

The in vitro kinase assays were performed at Nanosyn (Santa Clara, Calif.) utilizing microfluidic detection technology. The test compounds were serially pre-diluted in DMSO and added, by the acoustic dispensing (Labcyte® 550), directly to 384 well assay plates into 10 uL of a buffer with enzyme (ITK, TXK, BTK or TEC) comprising: 100 mM HEPES, pH7.5, 5 mM $MgCl_2$, 0.1% bovine serum albumin, 1 mM DTT, 0.01% Triton X-100 and the enzyme. Final DMSO concentration was maintained at 1% in all samples, including the controls. The reactions were initiated by addition of ATP (1 mM final concentration) and the fluorescently labeled peptide substrate to a final concentration of 1 uM, and incubated for 3 hours at 25° C. Following incubation, the reactions were quenched by addition of 40 µL of termination buffer (100 mM HEPES, pH7.5, 0.01% Triton X-100, 50 mM EDTA). Terminated plates were analyzed using Caliper LabChip® 3000 microfluidic electrophoresis instrument (Caliper Life Sciences/Perkin Elmer). The enzymatic modification of the peptide substrate (phosphorylation) results in a change of net charge enabling electrophoretic separation of product from substrate. As substrate and product are separated by electrophoresis, two peaks of fluorescence are observed. Change in the relative fluorescence intensity of the substrate and product peaks was the parameter measured, reflecting enzyme activity. In the presence of inhibitor, the ratio between product and substrate is altered: signal of the product decreases, while the signal of the substrate increases. Activity in each test sample was determined as the product to sum ratio (PSR): P/(S+P), where P is the peak height of the product and S is the peak height of the FAM-cAMP substrate. For each compound, enzyme activity was measured at 12 concentrations spaced by 3× dilution intervals. Negative control samples (0%-inhibition in the absence of inhibitor, DMSO only) and positive control samples (100%-inhibition, in the absence of enzyme or in the presence of control inhibitor) were assembled in replicates of four and were used to calculate %-inhibition values in the presence of compounds. Percent inhibition ($P_{inh}$) was determined using the following equation: $P_{inh}=(PSR_{0\%}-PSR_{inh})/(PSR_{0\%}-PSR_{100\%})*100$, where $PSR_{inh}$ is the product sum ratio in the presence of inhibitor, $PSR_{0\%}$ is the product sum ratio in the absence of inhibitor and $PSR_{100\%}$ is the product sum ratio in 100%-inhibition control samples. To determine $IC_{50}$ values, the inhibition curves ($P_{inh}$ versus inhibitor concentration) were fitted by 4 parameter sigmoid dose-response model using XLfit software (IDBS).

TABLE 3

Results kinase inhibition

| Compound Number | ITK IC50 (nM) | TXK IC50 (nM) | BTK IC50 (nM) | TEC IC50 (nM) | ITK/TXK Ratio |
|---|---|---|---|---|---|
| 1 | 26.2 | 52.6 | 378 | — | 0.5 |
| 2 | 0.85 | 0.37 | 1.01 | 2.36 | 2.3 |
| 3 | 3.47 | 2.50 | 26.8 | 49.3 | 1.4 |
| 4 | 0.34 | 0.18 | 0.64 | 1.65 | 1.9 |
| 5 | 0.29 | 0.34 | — | 3.24 | 0.9 |
| 6 | 25.6 | 2.86 | 4.28 | 29.6 | 9.0 |
| 7 | 8.26 | 0.60 | 2.20 | 6.03 | 13.9 |
| 8 | 9.11 | 0.67 | 2.36 | 6.03 | 13.6 |
| 9 | 0.69 | 0.20 | — | — | 3.4 |
| 10 | 2.04 | 0.84 | — | — | 2.4 |
| 11 | — | — | — | — | — |
| 12 | — | — | — | — | — |
| 13 | 10.1 | 0.76 | 1.80 | 4.50 | 13.3 |
| 14 | 84.7 | 3.90 | 23.4 | 53.1 | 21.7 |
| 15 | 3.23 | 0.55 | 4.40 | 1.78 | 5.9 |
| 16 | 0.81 | 0.21 | 0.94 | 0.62 | 3.8 |
| 17 | 54.3 | 11.0 | — | 41.0 | 4.9 |
| 18 | 7.70 | 3.75 | — | 5.15 | 2.1 |
| 19 | 1.50 | 0.47 | 1.34 | 4.32 | 3.2 |
| 20 | 6.19 | 1.84 | 4.52 | 21.7 | 3.4 |
| 21 | 5.71 | 1.22 | 1.54 | 10.7 | 4.7 |
| 22 | 4.57 | 1.71 | 4.79 | 18.0 | 2.7 |
| 23 | 1.14 | 0.52 | 2.45 | 5.49 | 2.2 |
| 24 | 5.01 | 0.99 | 5.47 | 14.8 | 5.1 |
| 25 | 1.62 | 0.59 | 0.70 | 3.16 | 2.7 |
| 26 | 2.41 | 0.99 | 2.84 | 10.9 | 2.4 |
| 27 | 1.52 | 0.67 | 2.59 | 2.27 | 2.3 |
| 28 | 0.75 | 0.63 | 1.70 | 4.30 | 1.2 |
| 29 | 0.64 | 0.27 | 0.84 | — | 2.4 |
| 30 | 2.17 | 0.29 | 2.11 | 0.98 | 7.6 |
| 31 | 3.08 | 1.03 | 5.38 | 1.25 | 3.0 |
| 32 | 2.99 | 0.70 | 5.45 | 15.6 | 4.3 |
| 33 | 18.9 | 0.32 | 0.78 | 2.67 | 58.7 |
| 34 | 1.72 | 0.45 | 1.39 | 10.6 | 3.8 |
| 35 | 1.45 | 0.46 | 1.04 | 6.01 | 3.1 |
| 36 | 2.07 | 0.63 | 1.14 | 9.70 | 3.3 |
| 37 | 0.87 | 0.39 | 0.95 | 3.13 | 2.3 |
| 38 | 1.23 | 0.67 | 4.08 | 5.92 | 1.8 |
| 39 | 2.10 | 0.97 | 5.67 | 7.88 | 2.2 |
| 40 | 1.44 | 0.72 | 1.16 | 4.37 | 2.0 |
| 41 | 1.90 | 0.92 | 1.81 | 2.82 | 2.1 |
| 42 | 0.64 | 0.32 | 0.53 | 2.00 | 2.0 |
| 43 | 0.73 | 0.32 | 0.53 | 1.71 | 2.3 |
| 44 | 0.70 | 0.42 | 0.66 | 1.96 | 1.7 |
| 445 | 83.9 | 3.13 | 3.61 | 5.26 | 26.8 |
| 46 | 33.3 | 1.10 | 1.44 | 2.00 | 30.3 |
| 47 | 24.5 | 2.69 | 11.3 | 7.73 | 9.1 |
| 48 | 58.1 | 1.16 | 4.37 | 3.37 | 50.1 |
| 49 | 4.87 | 1.39 | 13.7 | 4.10 | 3.5 |
| 50 | 0.72 | 0.25 | 0.62 | 0.67 | 2.9 |
| 51 | 0.90 | 0.44 | 0.73 | 1.41 | 2.0 |
| 52 | 0.79 | 0.39 | 0.58 | 1.13 | 2.0 |
| 53 | 0.97 | 0.39 | 0.64 | 1.26 | 2.5 |
| 54 | 0.51 | 0.30 | 0.56 | 0.87 | 1.7 |
| 55 | 70.1 | 3.41 | 27.4 | 7.73 | 20.6 |
| 56 | 1.09 | 0.26 | 1.56 | 0.78 | 4.2 |
| 57 | 0.99 | 0.22 | 1.09 | 0.74 | 4.4 |
| 58 | 1.30 | 0.29 | 1.32 | 1.02 | 4.6 |
| 59 | 1.03 | 0.44 | 1.64 | 1.49 | 2.3 |
| 60 | 1.00 | 0.40 | 1.15 | 1.33 | 2.5 |
| 61 | 3.72 | 0.49 | 6.77 | 1.43 | 7.6 |
| 62 | 5.63 | 1.58 | 10.5 | 2.48 | 3.6 |
| 63 | 1.68 | 0.37 | 1.29 | 1.10 | 4.6 |
| 64 | 194 | 39.7 | 124 | 53.1 | 4.9 |
| 65 | 2.03 | 0.42 | 1.99 | 1.42 | 4.8 |
| 66 | 403 | 4.34 | 11.20 | 13.3 | 92.9 |
| 67 | 66.0 | 19.7 | 99.2 | 35.2 | 3.4 |
| 68 | 7.48 | 6.71 | 41.9 | 4.72 | 1.1 |
| 69 | 21.7 | 7.71 | — | — | 2.8 |
| 70 | 8.99 | 3.58 | — | — | 2.5 |
| 71 | 25.6 | 17.90 | — | — | 1.4 |
| 72 | — | — | — | — | — |
| 73 | 1.02 | 0.26 | — | — | 3.9 |
| 74 | 8.25 | 1.62 | 25.8 | 1.73 | 5.1 |
| 75 | 1.12 | 0.12 | 1.03 | — | 9.2 |

TABLE 3-continued

Results kinase inhibition

| Compound Number | ITK IC50 (nM) | TXK IC50 (nM) | BTK IC50 (nM) | TEC IC50 (nM) | ITK/TXK Ratio |
|---|---|---|---|---|---|
| 76 | 5.59 | 2.80 | 22.6 | 4.01 | 2.0 |
| 77 | 0.82 | 0.37 | 0.78 | — | 2.2 |
| 78 | 4.70 | 2.34 | 11.7 | — | 2.0 |
| 79 | 444 | 17.0 | 251 | 60.9 | 26.1 |
| 80 | — | — | — | — | — |
| 81 | — | — | — | — | — |
| 82 | 98.1 | 3.33 | 33.2 | 7.20 | 29.5 |
| 83 | 933 | 1.98 | 7.55 | — | 471.2 |
| 84 | 521 | 19.8 | 65.3 | — | 26.3 |
| 85 | 39.2 | 3.15 | — | — | 12.4 |
| 86 | 1.60 | 2.24 | 8.41 | — | 0.7 |
| 87 | 52.9 | 5.72 | — | — | 9.2 |
| 88 | — | — | — | — | — |
| 89 | 12.0 | 3.17 | 23.7 | — | 3.8 |
| 90 | 2.07 | 0.51 | 5.23 | 0.64 | 4.0 |
| 91 | 239 | 17.6 | — | — | 13.6 |
| 92 | 520 | 64.3 | — | — | 8.1 |
| 93 | 42.6 | 9.88 | — | — | 4.3 |
| 94 | 2.64 | 0.82 | 1.38 | — | 3.2 |
| 95 | 24.3 | 9.12 | 19.4 | 4.97 | 2.7 |
| 96 | 1.71 | 0.35 | 1.55 | 0.15 | 4.9 |
| 97 | 0.53 | 0.14 | 0.33 | 0.09 | 3.9 |
| 98 | 4.96 | 0.31 | — | — | 16.0 |
| 99 | 2.95 | 1.01 | 10.2 | 1.27 | 2.9 |
| 100 | — | — | — | — | — |
| 101 | 62.8 | 0.93 | 9.24 | — | 67.8 |
| 102 | 47.2 | 5.63 | — | — | 8.4 |
| 103 | 7.50 | 0.93 | 6.12 | 2.32 | 8.1 |
| 104 | 17.6 | 2.16 | 26.2 | 10.4 | 8.1 |
| 105 | 128 | 23.2 | 112 | — | 5.5 |
| 106 | 514 | 30.1 | — | — | 17.1 |
| 107 | 18.7 | 5.25 | 21.1 | 8.16 | 3.6 |
| 108 | 5.19 | 1.02 | 10.4 | 1.32 | 5.1 |
| 109 | 24.1 | 14.0 | 43.5 | 8.33 | 1.7 |
| 110 | 1.16 | 0.18 | 1.11 | 0.19 | 6.4 |
| 111 | 502 | 64.1 | — | 166.0 | 7.8 |
| 112 | — | — | — | — | — |
| 113 | 2.10 | 1.32 | 4.63 | — | 1.6 |
| 114 | 1.28 | 0.22 | 3.31 | 0.23 | 5.9 |
| 115 | 11.7 | 1.94 | 12.90 | 5.17 | 6.0 |
| 116 | 25.7 | 3.08 | 15.70 | — | 8.3 |
| 117 | 9.50 | 4.90 | 7.43 | 1.74 | 1.9 |
| 118 | 17.90 | 7.31 | — | — | 2.4 |
| 119 | 3.83 | 0.66 | 2.44 | 1.57 | 5.8 |
| 120 | 1.20 | 0.28 | — | — | 4.3 |
| 121 | 11.6 | 5.48 | — | — | 2.1 |
| 122 | 9.60 | 1.22 | — | — | 7.9 |
| 123 | 1.65 | 0.49 | 5.33 | — | 3.4 |
| 124 | 0.99 | 0.34 | 1.43 | — | 2.9 |
| 125 | 1.05 | 0.24 | 1.06 | 0.23 | 4.4 |
| 126 | 3.14 | 0.80 | 9.21 | 1.42 | 3.9 |
| 127 | 3.38 | 1.13 | 15.9 | 1.59 | 3.0 |
| 128 | 0.67 | 0.20 | 0.63 | 0.20 | 3.4 |
| 129 | 0.59 | 0.21 | 0.84 | — | 2.9 |
| 130 | 0.51 | — | 1.06 | 1.31 | — |
| 131 | 0.41 | 0.18 | 0.46 | 0.16 | 2.3 |
| 132 | 4.90 | 1.99 | 10.30 | 1.59 | 2.5 |
| 133 | 1.92 | 0.37 | 3.27 | 0.28 | 5.3 |
| 134 | 5.88 | 1.01 | 8.36 | 2.35 | 5.8 |
| 135 | 15.7 | 8.67 | 12.7 | 7.41 | 1.8 |
| 136 | 0.89 | 0.16 | 0.20 | 0.08 | 5.5 |
| 137 | 1.37 | 0.76 | 0.98 | 0.37 | 1.8 |
| 138 | 0.92 | 0.16 | 0.41 | 0.10 | 5.7 |
| 139 | 3.95 | 0.75 | 1.54 | 0.38 | 5.2 |
| 140 | 1.60 | 0.20 | 0.54 | 0.19 | 8.1 |
| 141 | 1.57 | 0.29 | 1.83 | 0.26 | 5.4 |
| 142 | 1.17 | 0.48 | 0.62 | 0.35 | 2.4 |
| 143 | 17.3 | 9.08 | 7.92 | 6.99 | 1.9 |
| 144 | 2.29 | 1.51 | 3.45 | 1.72 | 1.5 |
| 145 | 1.28 | 0.20 | 0.49 | 0.18 | 6.5 |
| 146 | 0.88 | 0.22 | 0.57 | 0.16 | 3.9 |
| 147 | 0.79 | 0.21 | 0.41 | 0.12 | 3.8 |
| 148 | 3.19 | 0.69 | — | — | 4.7 |
| 149 | 0.58 | 0.14 | 0.68 | 0.11 | 4.1 |
| 150 | 3.62 | 0.45 | 2.32 | 0.61 | 8.1 |
| 151 | 6.49 | 0.46 | 1.51 | — | 14.1 |
| 152 | 8.17 | 2.11 | 9.50 | — | 3.9 |
| 153 | 2.95 | 2.72 | 9.75 | — | 1.1 |
| 154 | 1.10 | 0.33 | 1.21 | — | 3.4 |
| 155 | 11.7 | 8.17 | 43.9 | — | 1.4 |
| 156 | 0.78 | 0.24 | 0.70 | — | 3.3 | a-$EC_{50} < 1$ nM,
b-1 nM $< EC_{50} < 10$ nM,
c-$EC_{50} > 10$ nM

Example 3: Efficacy in the Experimental Autoimmune Encephalomyelitis Model of Multiple Sclerosis TEC kinases play important roles in immune cells and pathogenic microglia in multiple sclerosis. The efficacy of compound 16 was evaluated in experimental autoimmune encephalomyelitis (EAE), a mouse model of multiple sclerosis. EAE was induced in mice according to a protocol and reagents supplied by Hooke Laboratories (Lawrence, Mass., USA: Kit EK-2110). Briefly, female C57BL/6 mice were immunized with an emulsion of $MOG_{35-55}$ peptide in complete Freund's adjuvant (CFA), followed by administration of pertussis toxin (PTX) in PBS, first on the day of immunization and then again the following day. Mice were observed for signs of paralysis and were enrolled in the study as symptoms occurred. Two groups of ten mice were recruited and treated after onset of symptoms with Compound 16 formulated in polyethylene glycol 400 (PEG) or with PEG alone. A group of ten naïve C57BL/6 mice was maintained as a negative control. Disease symptoms were monitored on days 1, 4, 6, 8, 10 and 12 post symptom onset. Disease was scored according to the Hooke Laboratories protocol; briefly as follows: 0-No obvious changes in motor function compared to non-immunized mice. 0.5—Tip of tail is limp. 1.0—Tail is limp. 1.5—Limp tail and hind leg inhibition. 2.0—Limp tail and weakness of hind legs. 2.5—Limp tail and dragging of hind legs. 3.0—Limp tail and complete paralysis of hind legs. 3.5—Limp tail and complete paralysis of hind legs and difficulty righting or other motion defects. 4.0—Limp tail, complete hind leg and partial front leg paralysis. 4.5—Complete hind and partial front leg paralysis, no movement around the cage. Mouse is not alert. 5.0—Death or severe paralysis resulting in euthanasia.

Data (see FIG. 1) indicate that Compound 16 when administered by oral gavage once daily at a dose of 30 mg/kg greatly attenuated disease severity. Compound 16 treated mice had minimal symptoms of neurological deficit while vehicle treated animals rapidly progressed.

The invention claimed is:

1. A compound of Formula I:

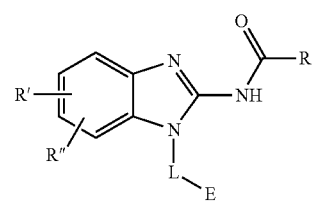

Formula I or a pharmaceutically acceptable salt, solvate, solvate of salt, stereoisomer, tautomer, isotope, or prodrug thereof, wherein
R is selected from substituted or unsubstituted aryl or substituted or unsubstituted heteroaryl;
L is selected from

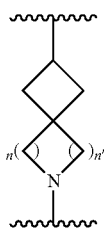

wherein n is an integer from 1 to 3; and n' is an integer from 1 to 3;
E is selected from the group:

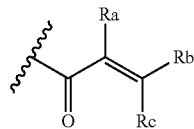

wherein Ra, Rb and Rc are independently selected from hydrogen, halogen, —CN, substituted or unsubstituted alkyl, substituted or unsubstituted heteroalkyl, substituted or unsubstituted cycloalkyl, or substituted or unsubstituted heterocyclyl;
or
Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or
Rb and Rc taken together with the carbon atom to which they are attached form a 3- to 8-membered substituted or unsubstituted cycloalkyl ring or form a 3- to 8-membered heterocyclic ring and Ra is selected as above; or
Ra and Rb taken together with the carbon atoms to which they are attached form a triple bond and Rc is selected as above;
provided L-E is

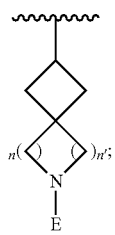

and
R' and R" are independently selected from —X—Y, wherein
X is selected from alkylene, -(alkylene)-NR$^1$—, -(alkylene)-NR$^2$, -(alkylene)-O—, —O—, —S—, —S(O)m-, —NR$^1$—, —NR$^2$—, —C(O)—, —C(O)O—, —C(O)NR$^1$—, —C(O)ONR$^1$—, or —S(O)$_m$NR$^1$—;

wherein
R$^1$ is selected from hydrogen, lower alkyl or lower cycloalkyl;
R$^2$ is selected from —C(O)R$^3$, —C(O)OR$^3$ or —S(O)$_m$R$^3$;
R$^3$ is selected from lower alkyl or lower cycloalkyl;
m is an integer from 1 to 2; or
X is a bond; and
Y is selected from hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or
wherein R' and R" taken together with the carbon atoms to which they are attached form a 3- to 8-membered substituted or unsubstituted cycloalkyl ring, or a 3- to 8-membered substituted or unsubstituted heterocyclyl ring.
2. The compound according to claim 1, or a pharmaceutically acceptable salt, solvate, solvate of salt, stereoisomer, tautomer, isotope, or prodrug thereof, wherein R is a substituted or unsubstituted aryl.
3. The compound according to claim 1, or a pharmaceutically acceptable salt, solvate, solvate of salt, stereoisomer, tautomer, isotope, or prodrug thereof, wherein R is a substituted or unsubstituted heteroaryl.
4. The compound according to any one of claims 1 to 3, or a pharmaceutically acceptable salt, solvate, solvate of salt, stereoisomer, tautomer, isotope, or prodrug thereof, wherein L-E is selected from the group consisting of:

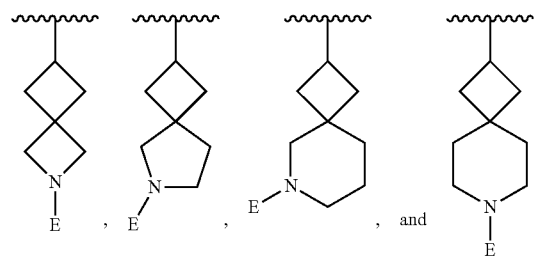

wherein E is selected from the group

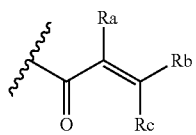

wherein Ra, Rb and Rc are independently selected from hydrogen, halogen, —CN, substituted or unsubstituted alkyl, substituted or unsubstituted heteroalkyl, substituted or unsubstituted cycloalkyl, or substituted or unsubstituted heterocyclyl;
or
Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or
Rb and Rc taken together with the carbon atom to which they are attached form a 3- to 8-membered substituted or unsubstituted cycloalkyl ring or form a 3- to 8-membered heterocyclic ring and Ra is selected as above; or Ra and Rb taken together with the carbon atoms to which they are attached form a triple bond and Rc is selected as above.

5. The compound according to claim 1, or a pharmaceutically acceptable salt, solvate, solvate of salt, stereoisomer, tautomer, isotope, or prodrug thereof, wherein L-E is selected from the group consisting of:

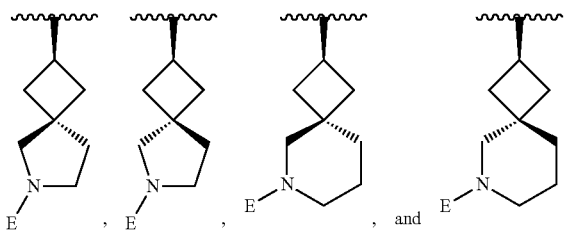

wherein E is selected from the group:

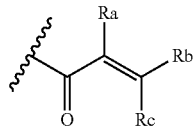

wherein Ra, Rb and Rc are independently selected from hydrogen, halogen, —CN, substituted or unsubstituted alkyl, substituted or unsubstituted heteroalkyl, substituted or unsubstituted cycloalkyl, or substituted or unsubstituted heterocyclyl;

or

Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or Rb and Rc taken together with the carbon atom to which they are attached form a 3- to 8-membered substituted or unsubstituted cycloalkyl ring or form a 3- to 8-membered heterocyclic ring and Ra is selected as above; or Ra and Rb taken together with the carbon atoms to which they are attached form a triple bond and Rc is selected as above.

6. The compound according to claim 1, or a pharmaceutically acceptable salt, solvate, solvate of salt, stereoisomer, tautomer, isotope, or prodrug thereof, wherein L-E is selected from:

wherein E is selected from the group:

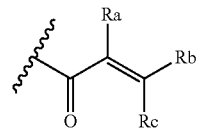

wherein Ra, Rb and Rc are independently selected from hydrogen, halogen, —CN, substituted or unsubstituted alkyl, substituted or unsubstituted heteroalkyl, substituted or unsubstituted cycloalkyl, or substituted or unsubstituted heterocyclyl; or Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or Rb and Rc taken together with the carbon atom to which they are attached form a 3- to 8-membered substituted or unsubstituted cycloalkyl ring or form a 3- to 8-membered heterocyclic ring and Ra is selected as above; or Ra and Rb taken together with the carbon atoms to which they are attached form a triple bond and Rc is selected as above.

7. The compound according to claim 4, or a pharmaceutically acceptable salt, solvate, solvate of salt, stereoisomer, tautomer, isotope, or prodrug thereof, wherein E is

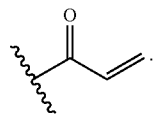

8. The compound according to claim 1, or a pharmaceutically acceptable salt, solvate, solvate of salt, stereoisomer, tautomer, isotope, or prodrug thereof, wherein R' is selected from —CH$_2$—NH—Y, where Y is selected from hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl and; R" is hydrogen.

9. A compound of Formula I:

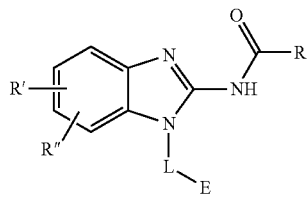

Formula I or a pharmaceutically acceptable salt, solvate, solvate of salt, stereoisomer, tautomer, isotope, or prodrug thereof, wherein R is substituted or unsubstituted aryl or substituted or unsubstituted heteroaryl;

L is

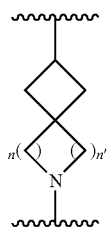

wherein n is an integer from 1 to 3; and n' is an integer from 1 to 3;

E is selected from the group:

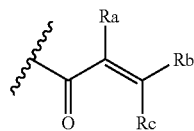

wherein Ra, Rb and Rc are independently hydrogen, halogen, —CN, substituted or unsubstituted alkyl, substituted or unsubstituted heteroalkyl, substituted or unsubstituted cycloalkyl, or substituted or unsubstituted heterocyclyl;

or

Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or Rb and Rc taken together with the carbon atom to which they are attached form a 3- to 8-membered substituted or unsubstituted cycloalkyl ring or form a 3- to 8-membered heterocyclic ring and Ra is selected as above; or Ra and Rb taken together with the carbon atoms to which they are attached form a triple bond and Rc is selected as above;

provided L-E is

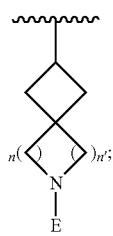

wherein

R' is —NR$^1$C(O)Y;

Y is hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl;

R$^1$ is hydrogen, lower alkyl or lower cycloalkyl and;

R" is hydrogen.

10. A compound selected from the group consisting of:

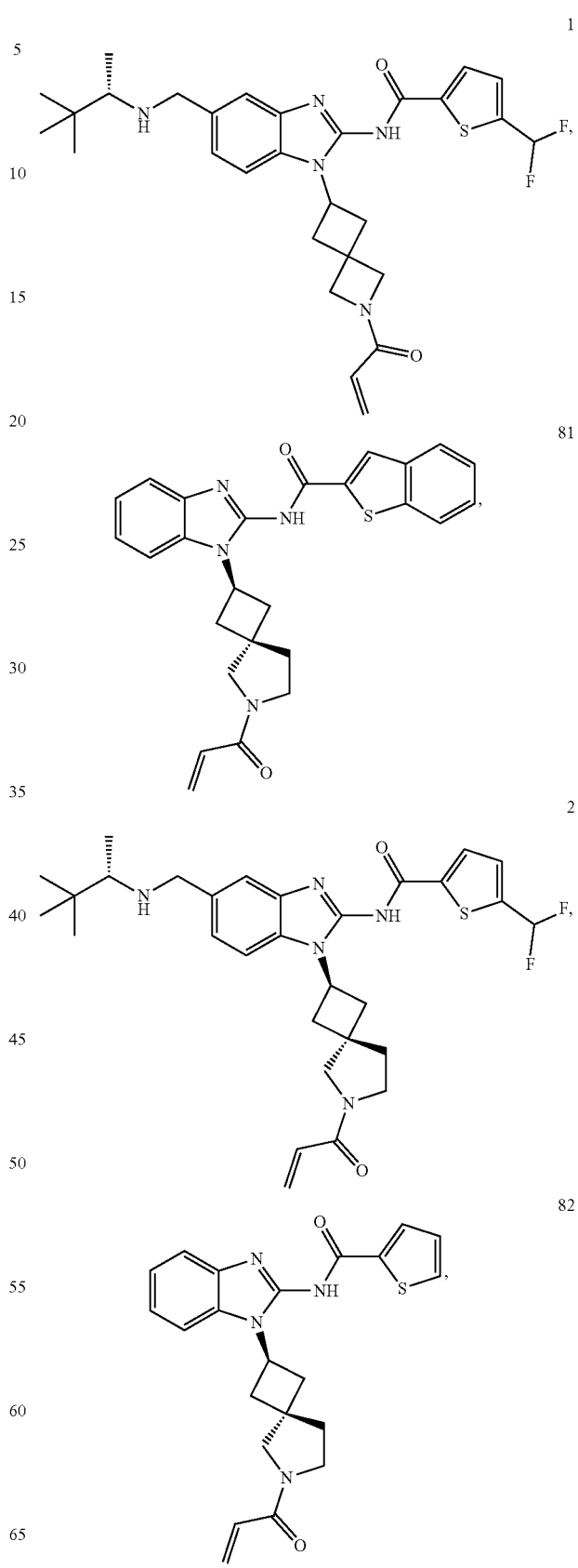

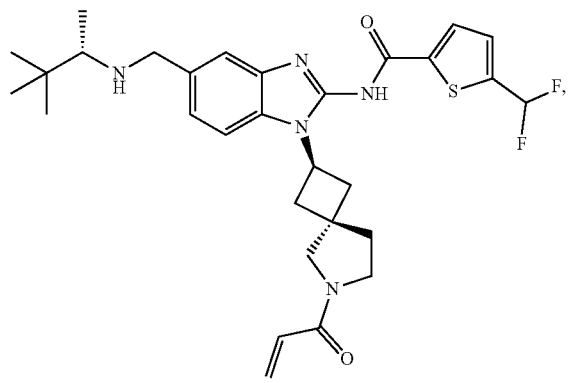
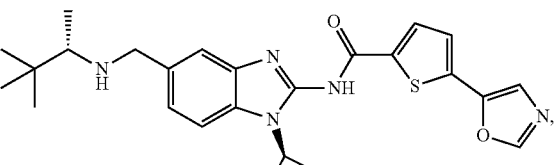
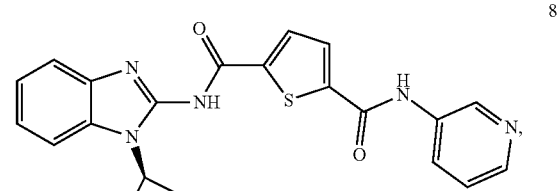
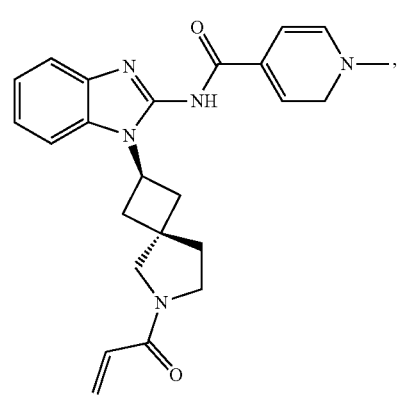
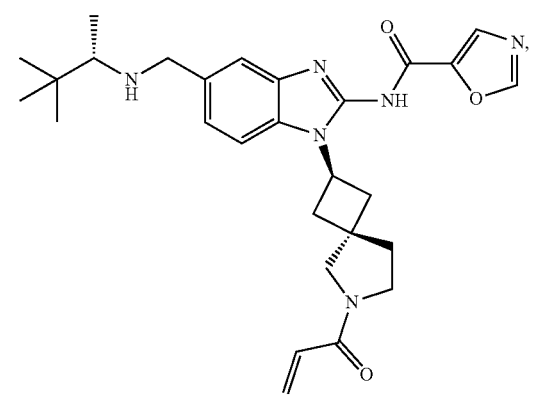
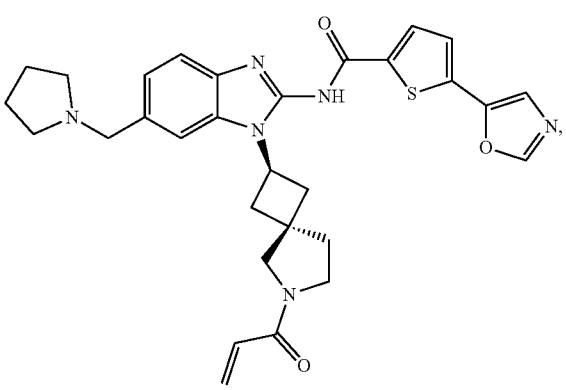

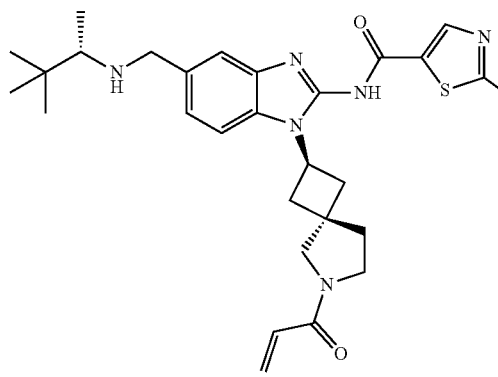
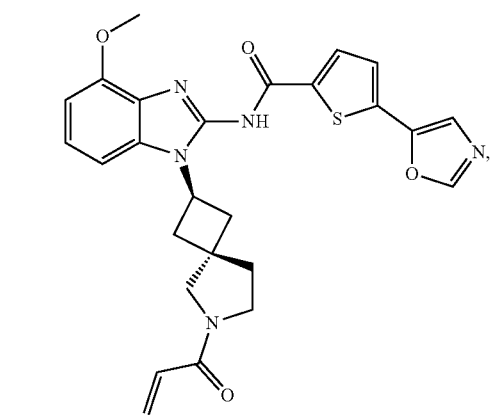
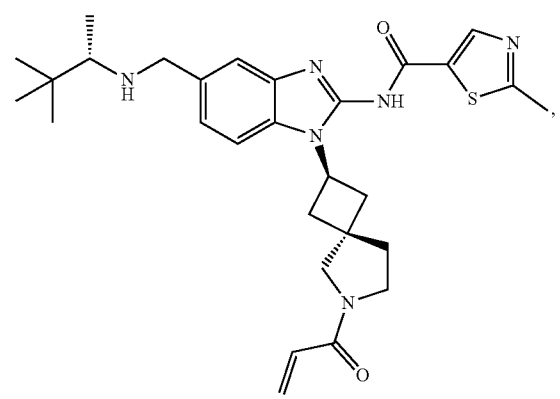
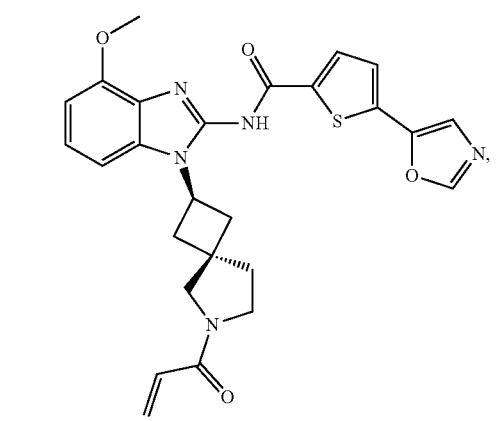
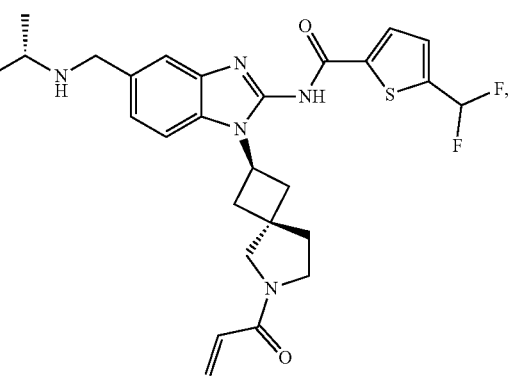
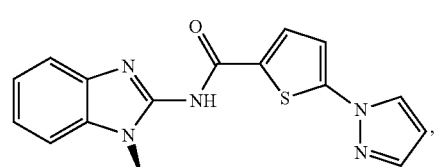

11
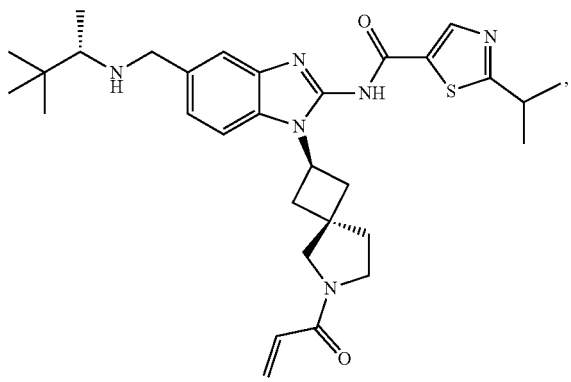
13
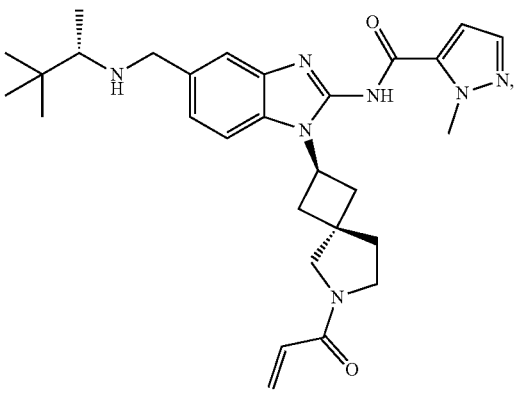
91
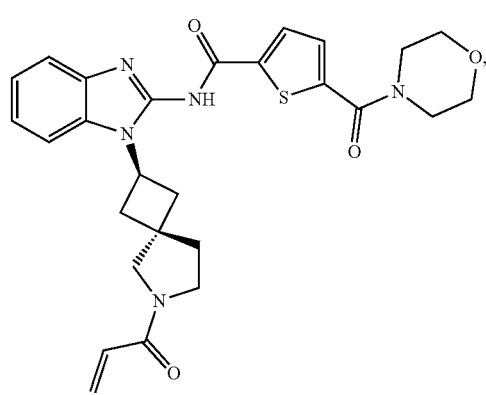
93
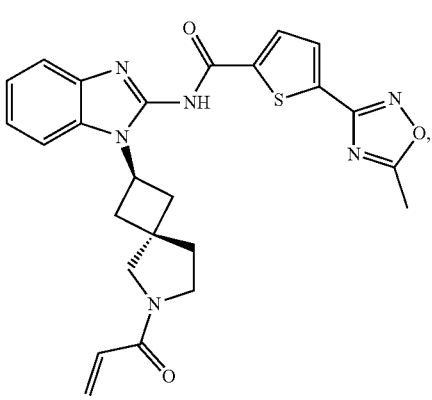
12
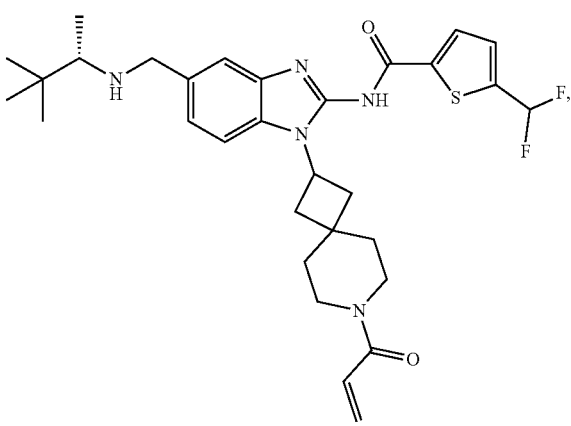
14
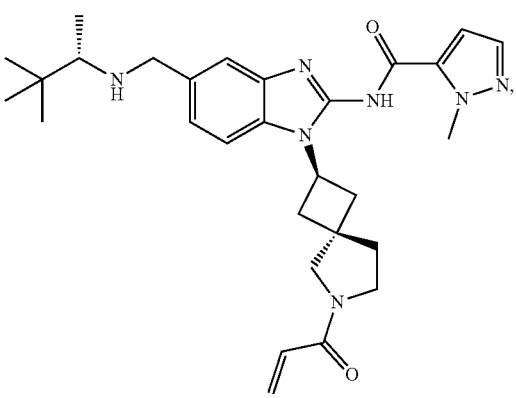
92
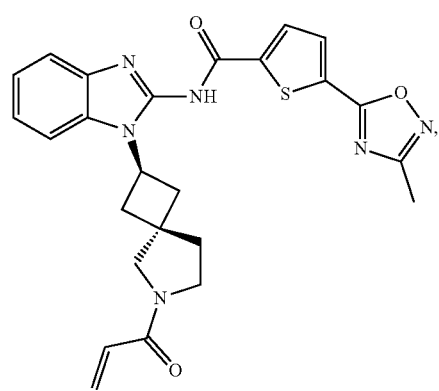
94
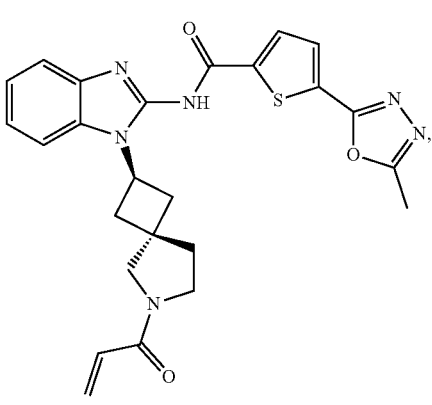

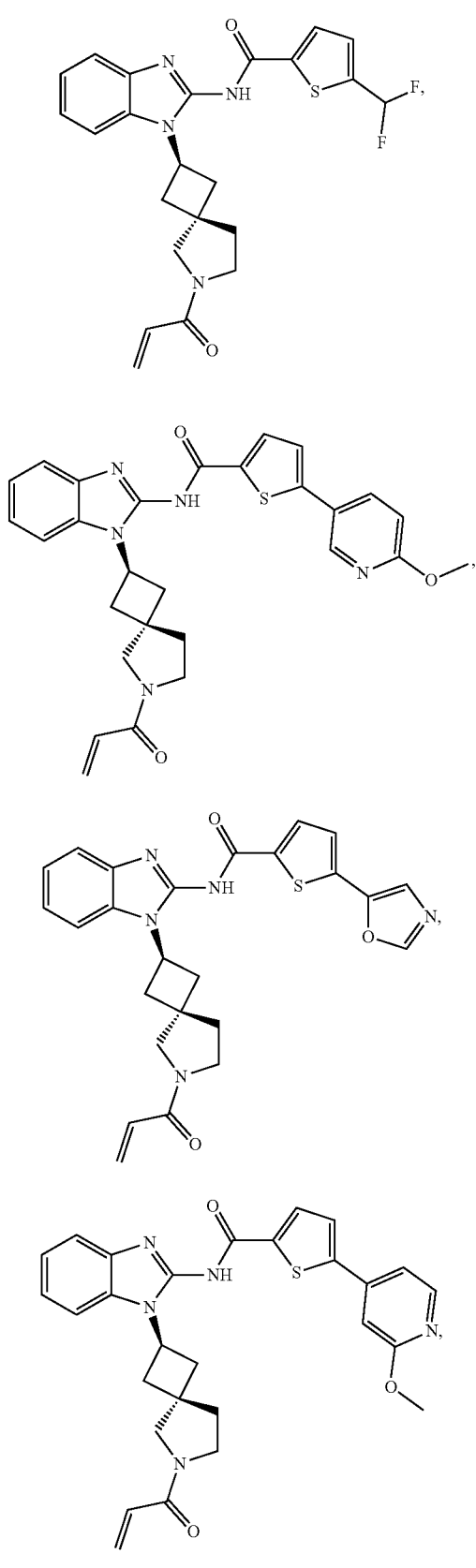
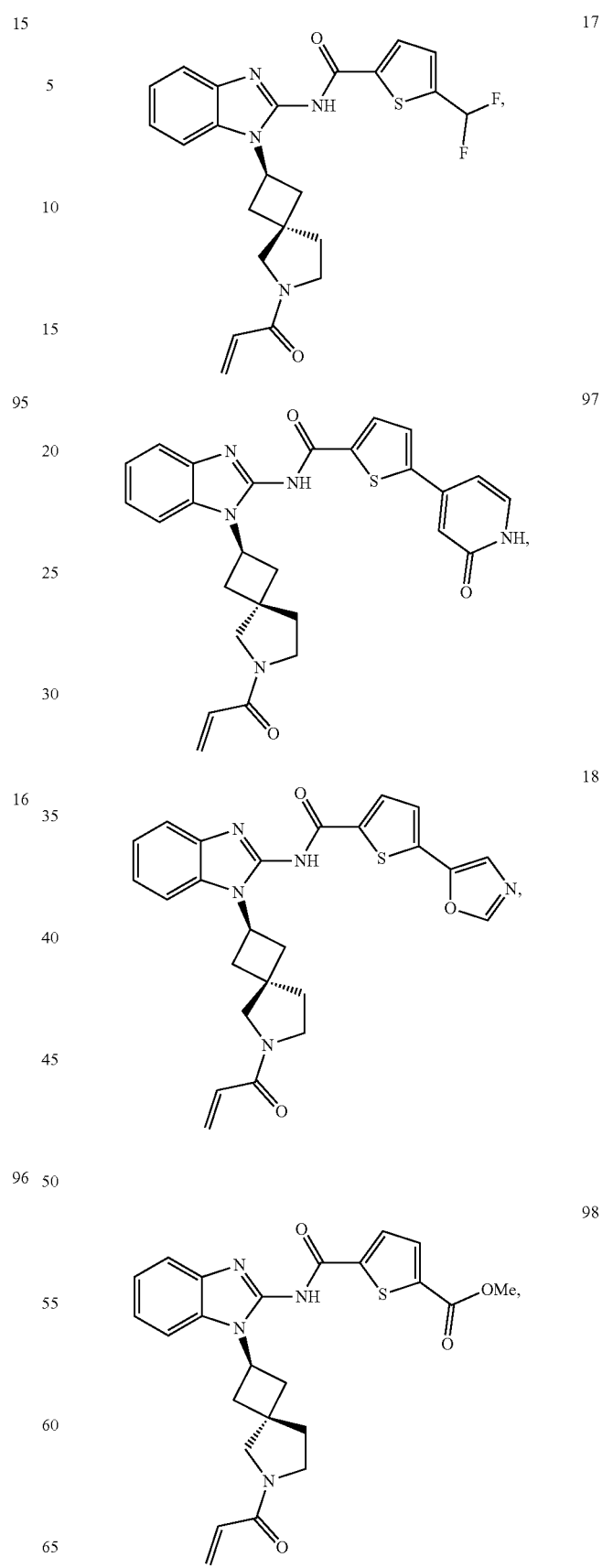

19
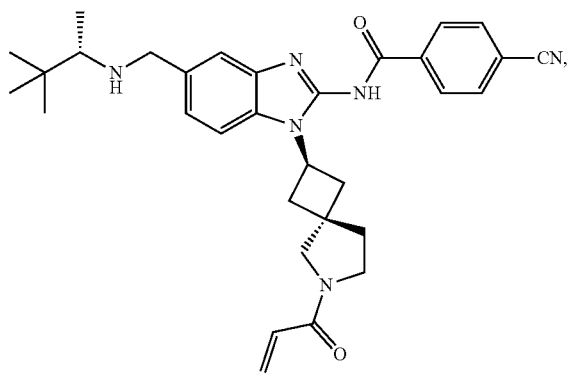
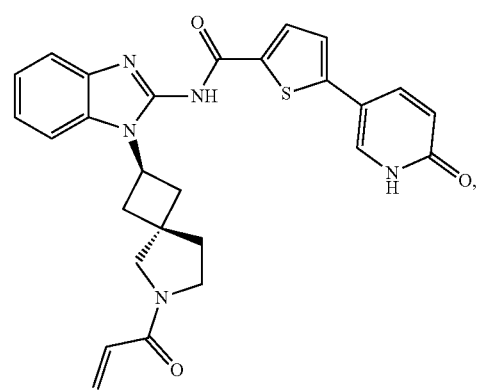
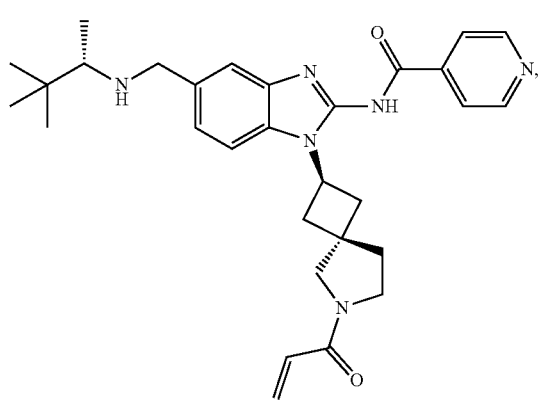
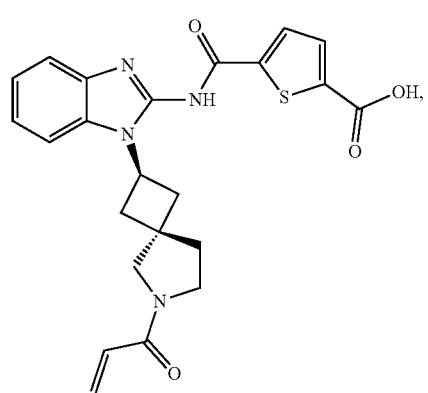
21
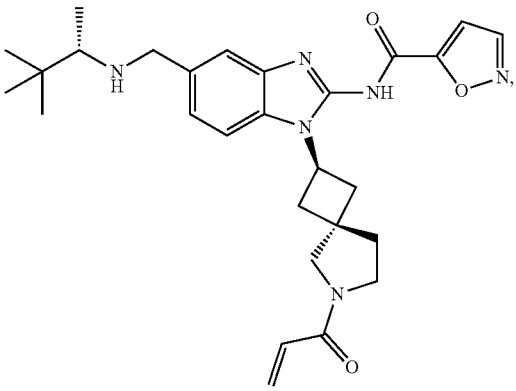
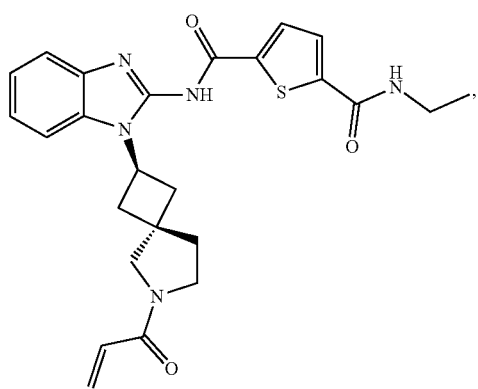
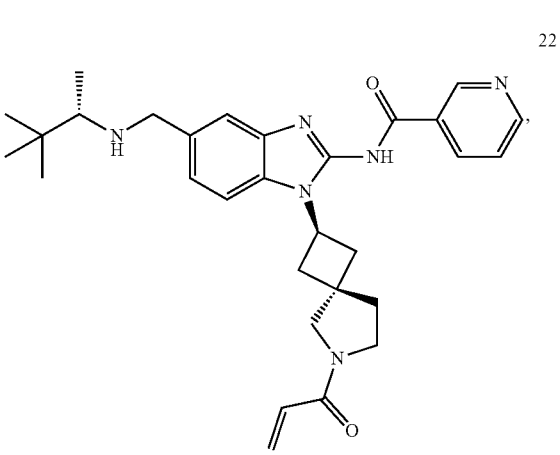
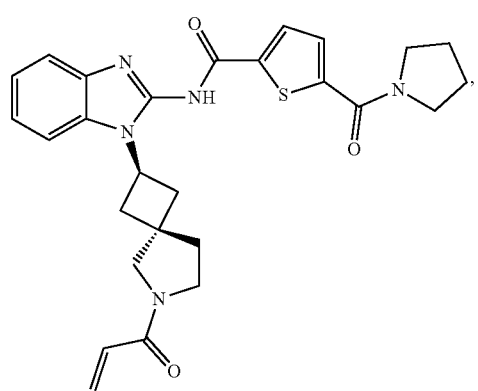

23
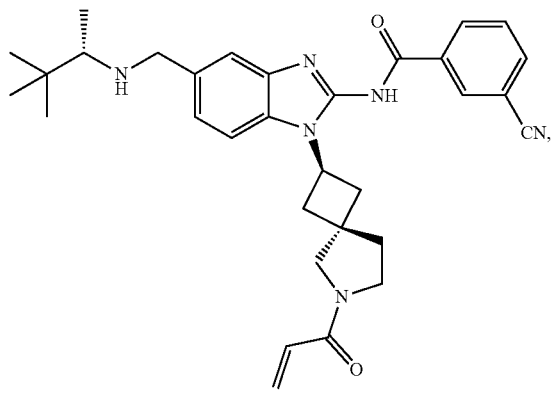
25
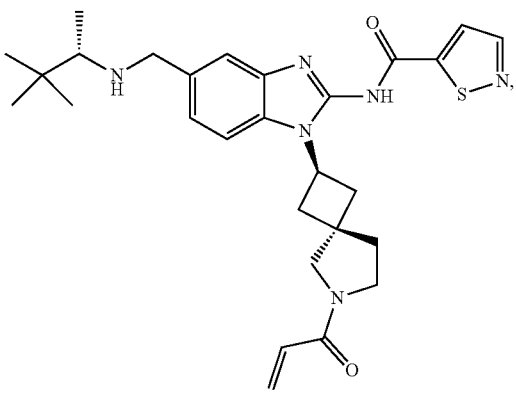
103
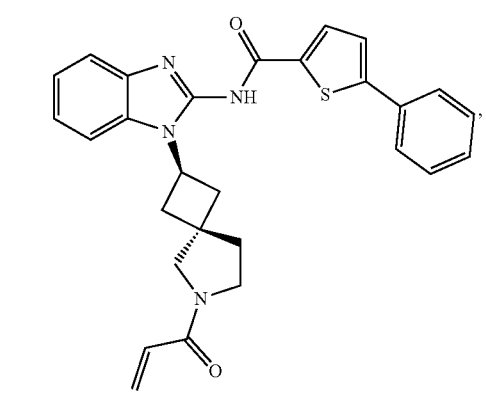
105
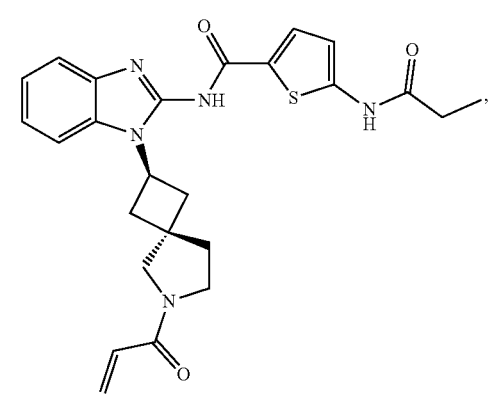
24
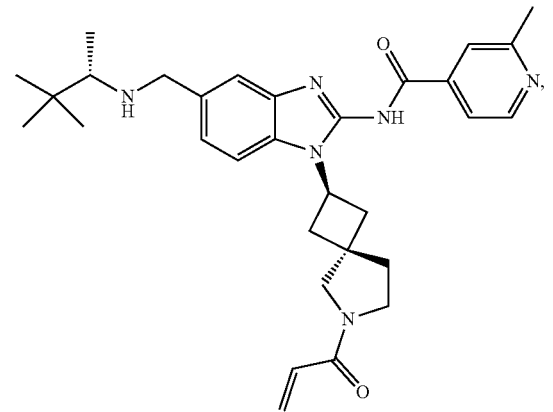
26
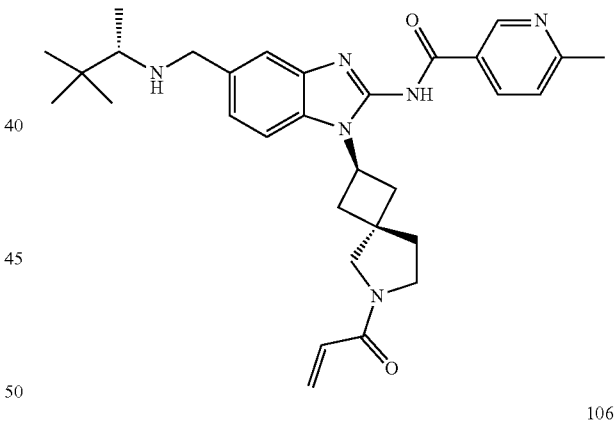
104
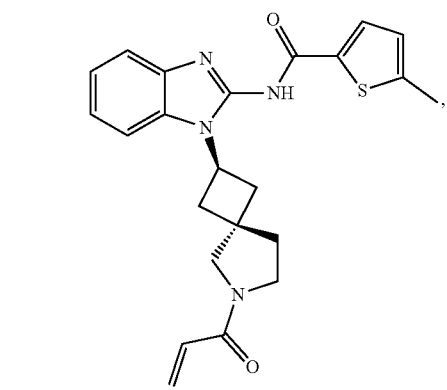
106
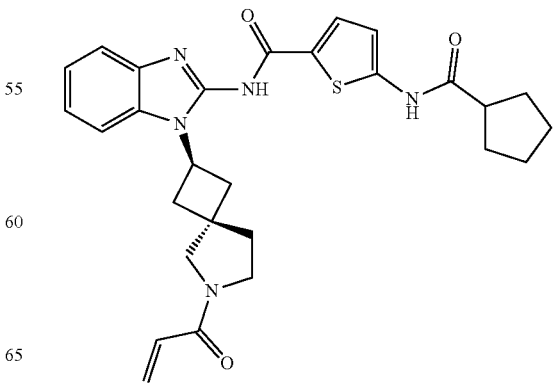

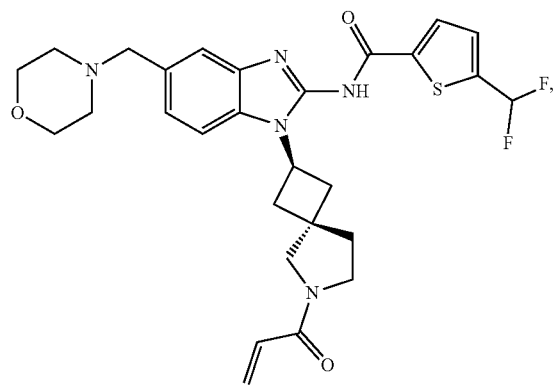
27
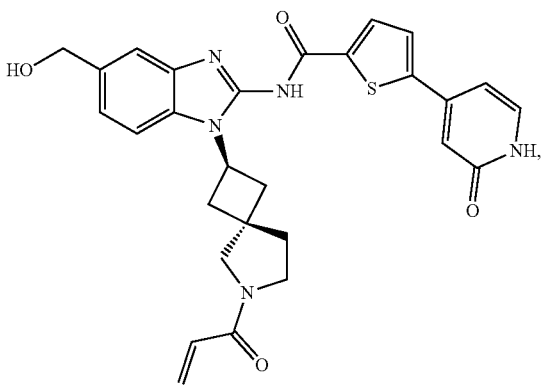
29
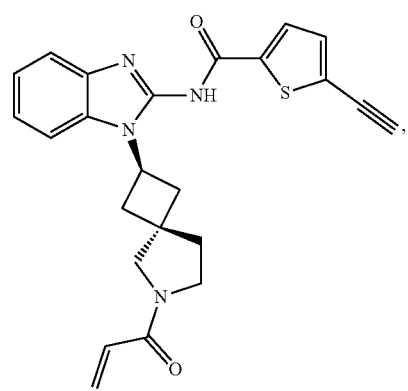
107
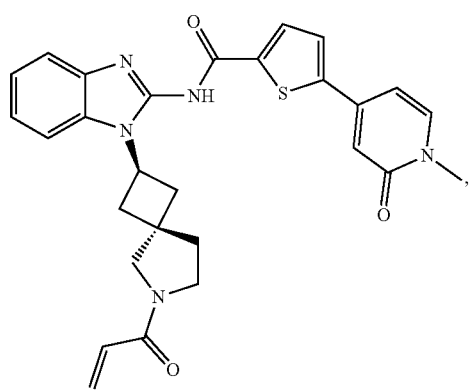
109
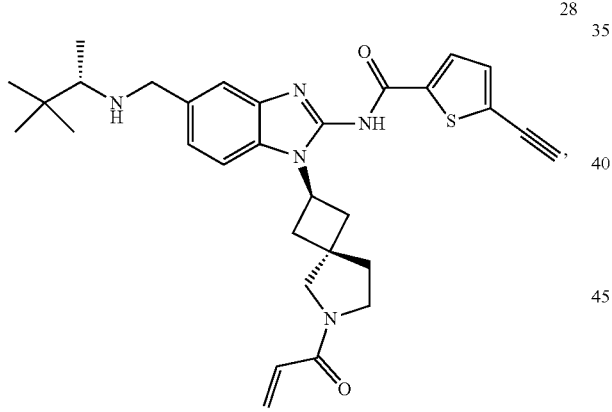
28
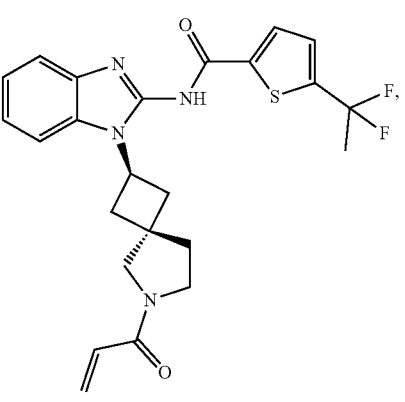
30
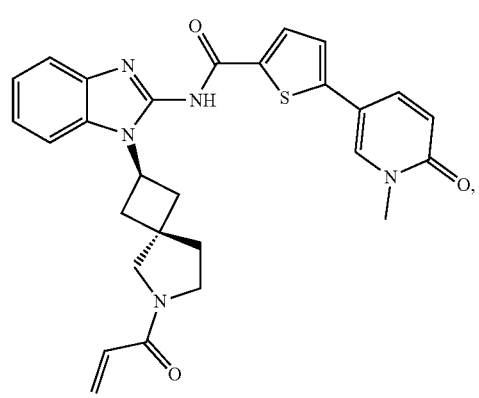
108
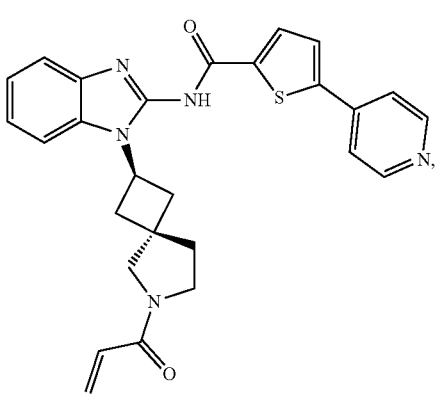
110

31
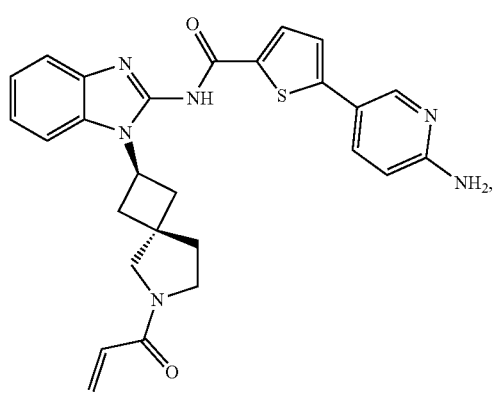
111
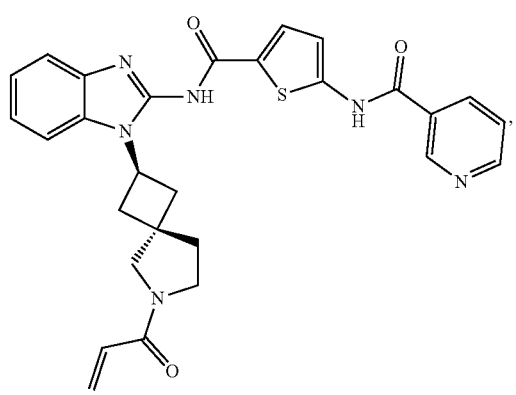
32
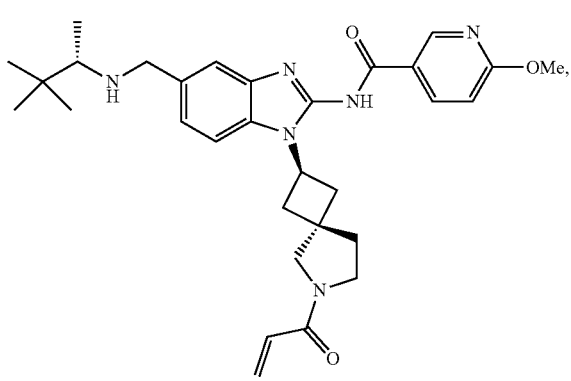
112
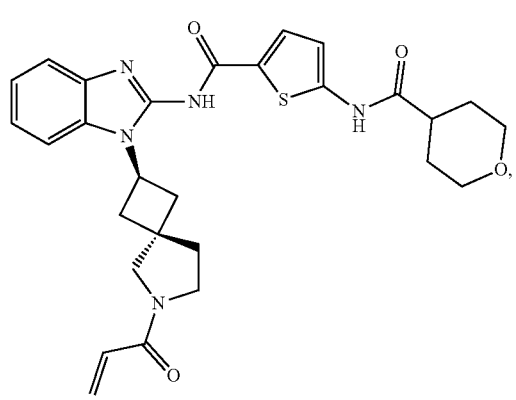
33
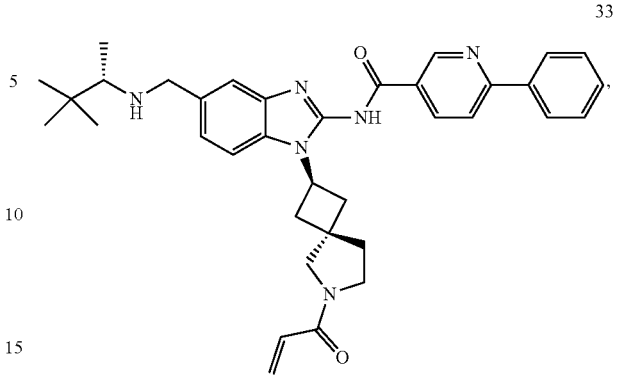
113
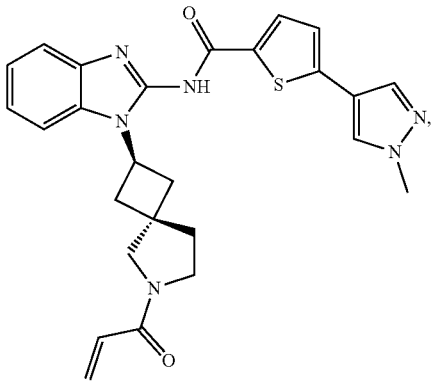
34
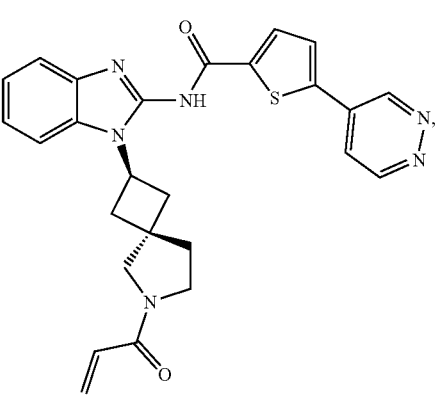
114

| 257 | 258 |
|---|---|
| 35 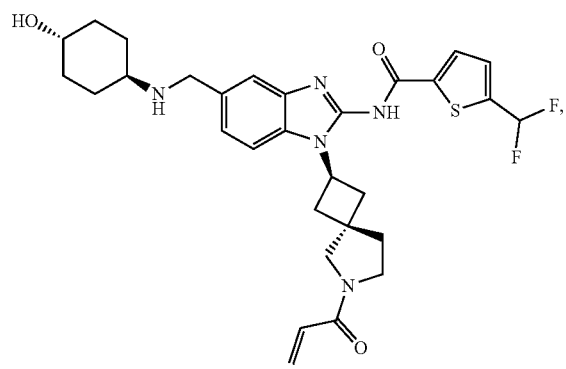 | 37 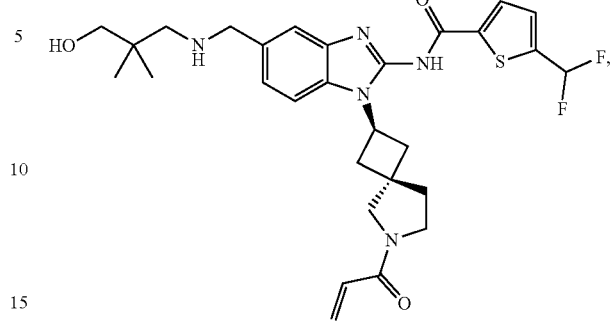 |
| 115 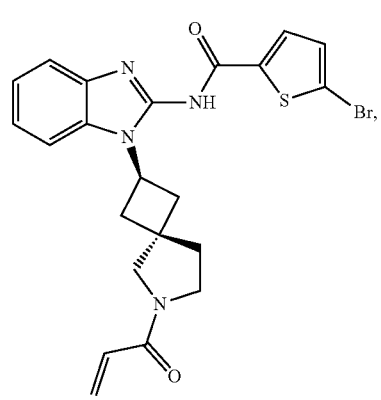 | 117 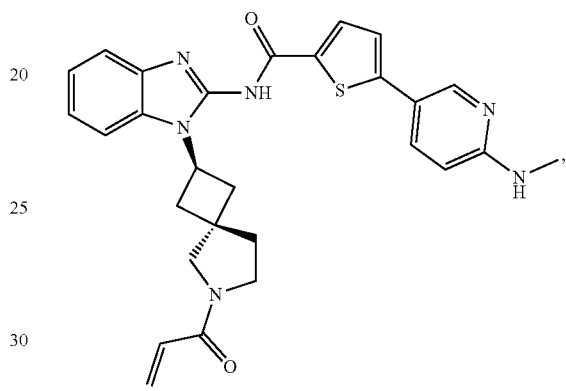 |
| 36 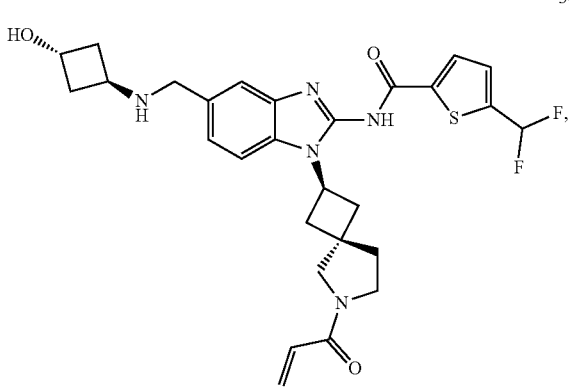 | 38 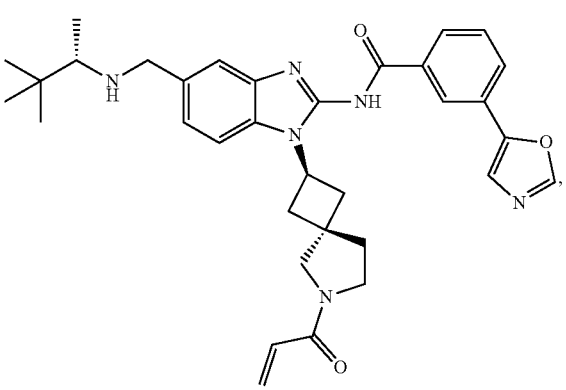 |
| 116 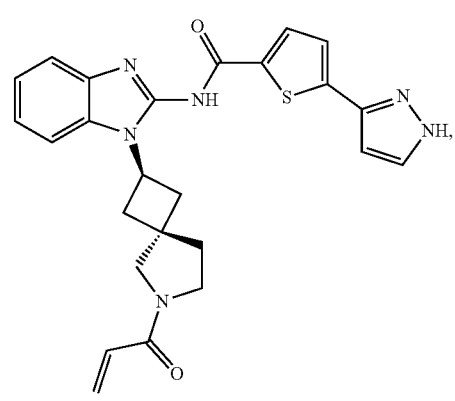 | 118 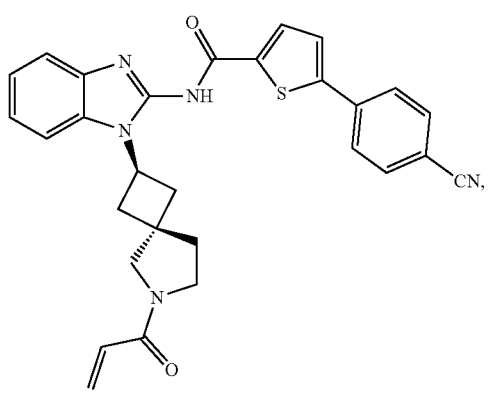 |

39
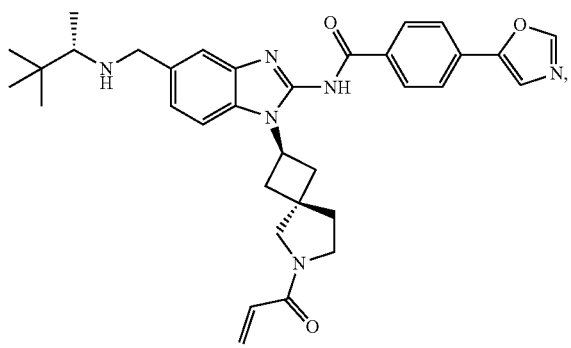
119
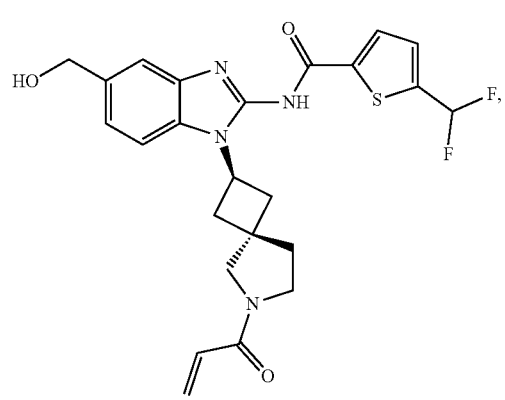
120
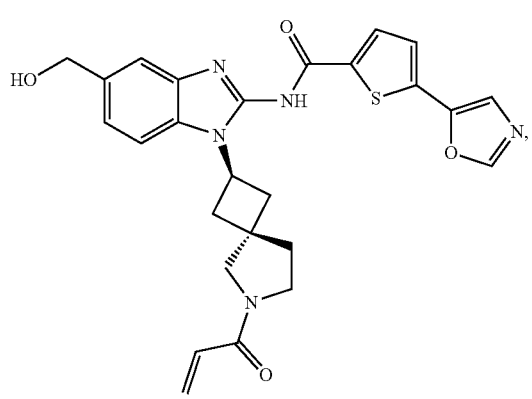
41
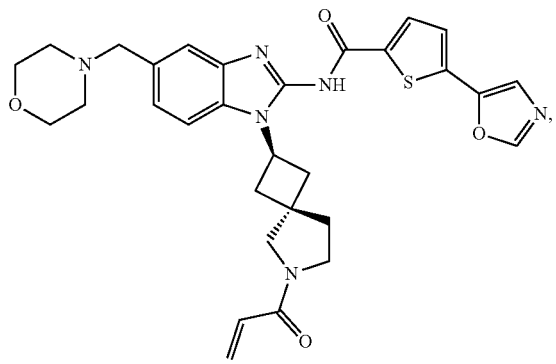
121
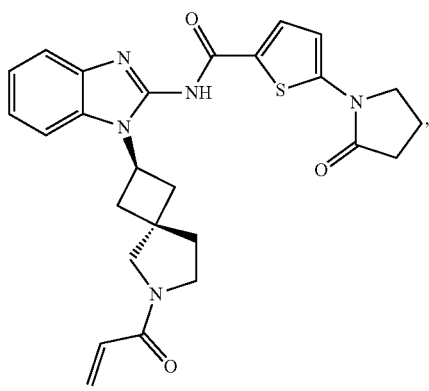
42
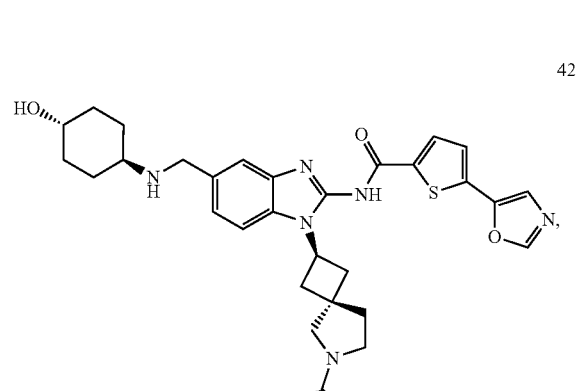
122
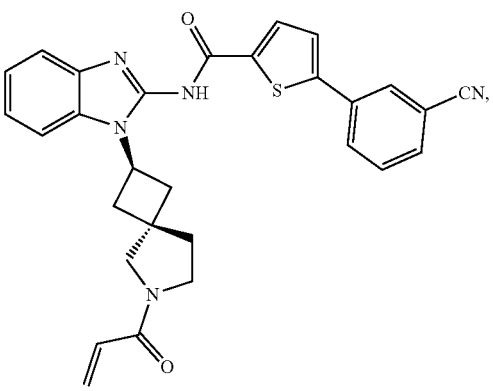

43
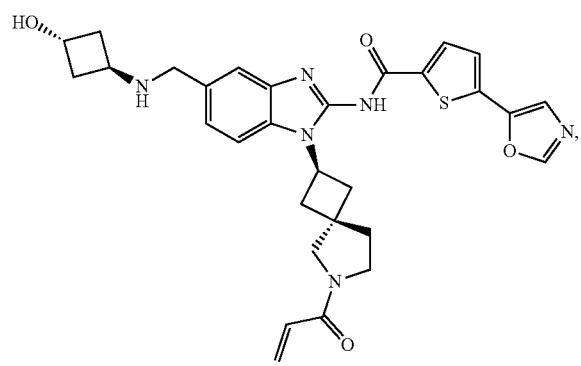
123
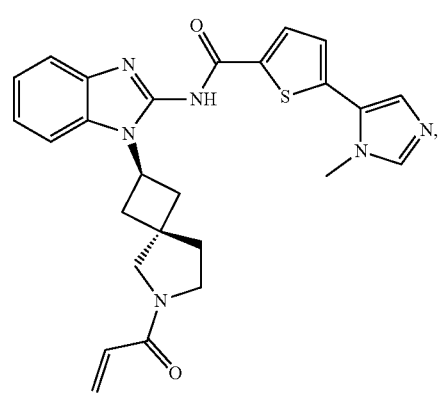
44
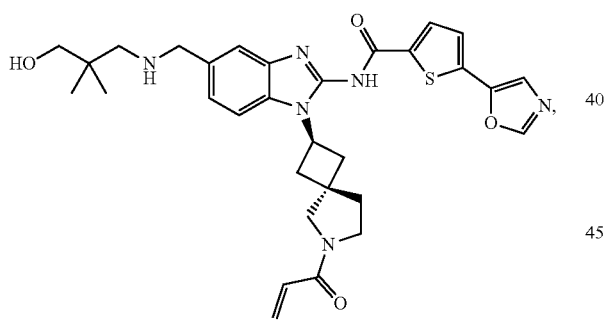
124
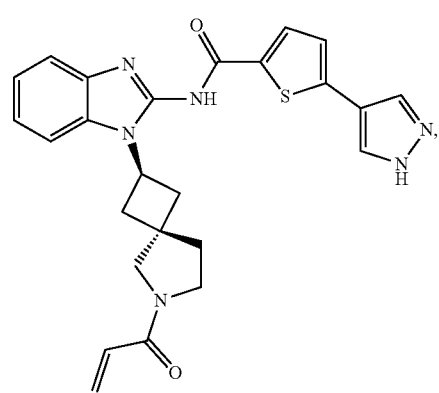
45
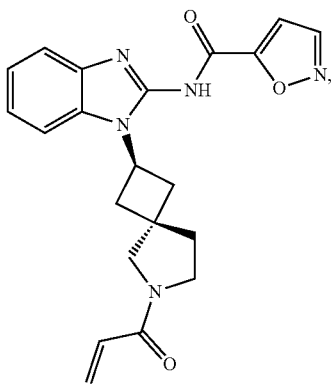
125
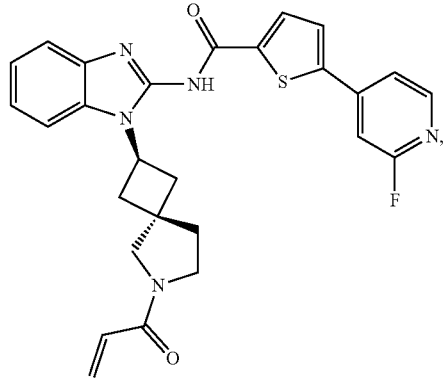
46
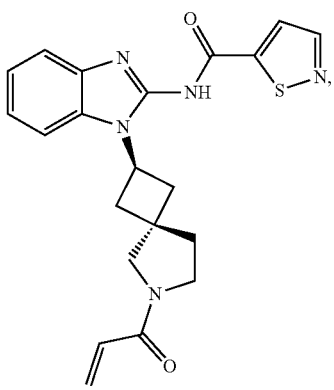
126

47
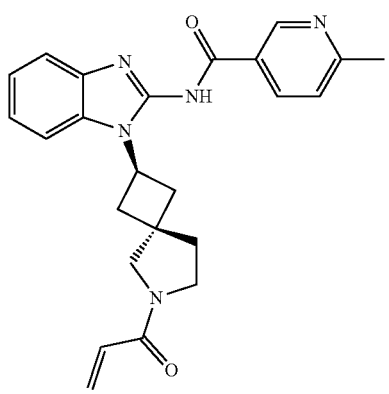
127
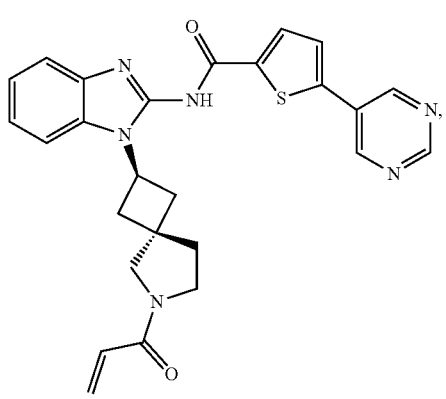
48
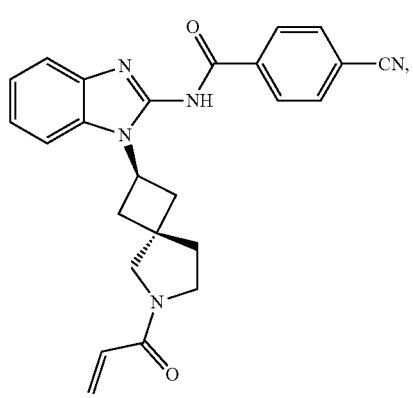
128
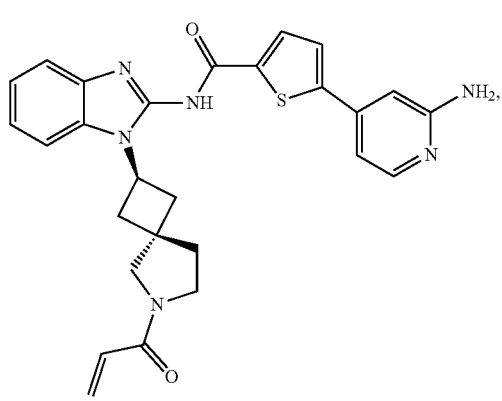
49
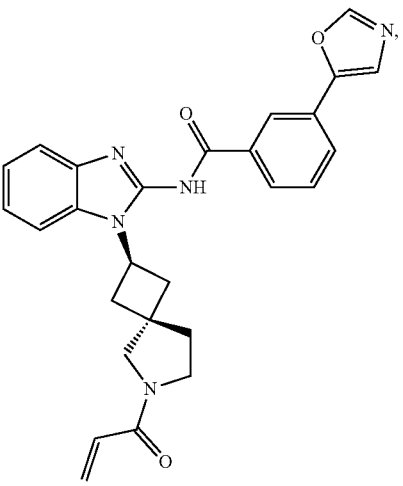
129
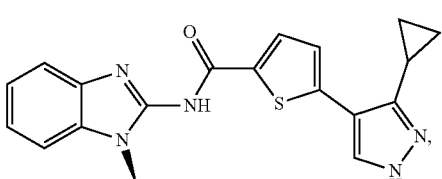
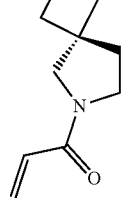
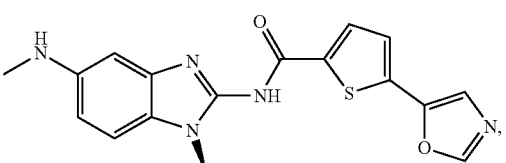
50
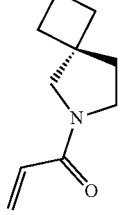
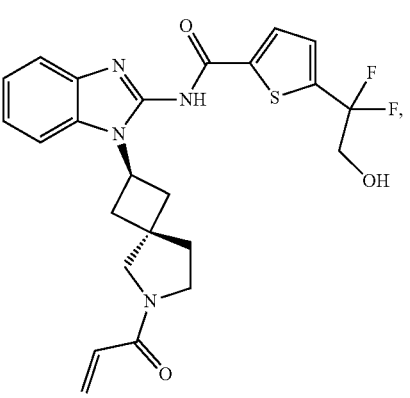
130

51
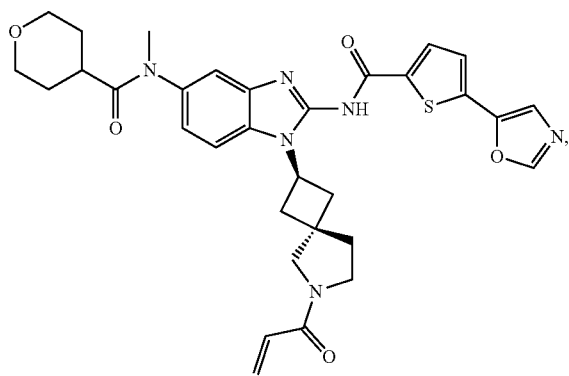
131
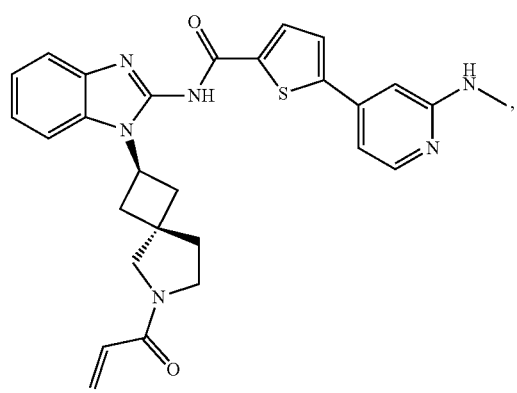
52
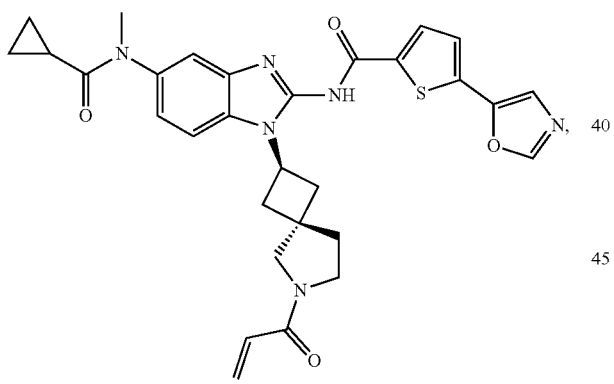
132
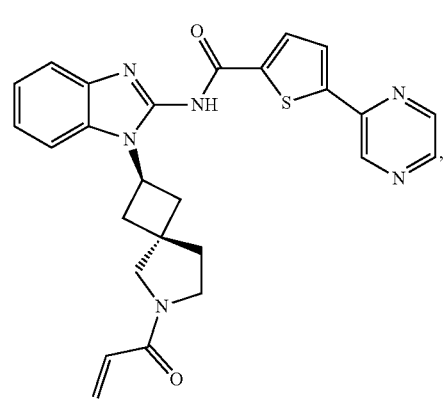
53
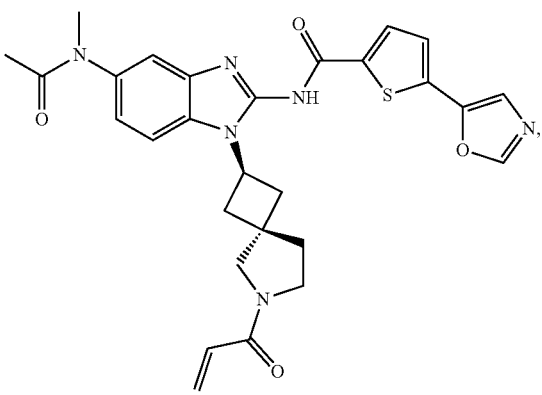
133
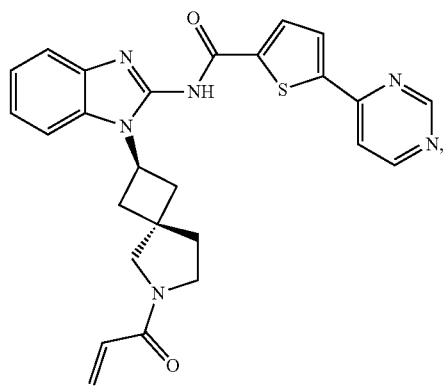
54
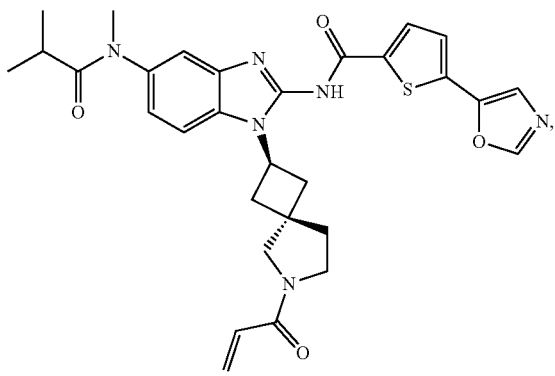
134
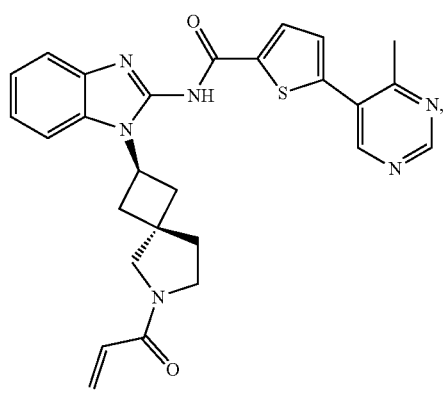

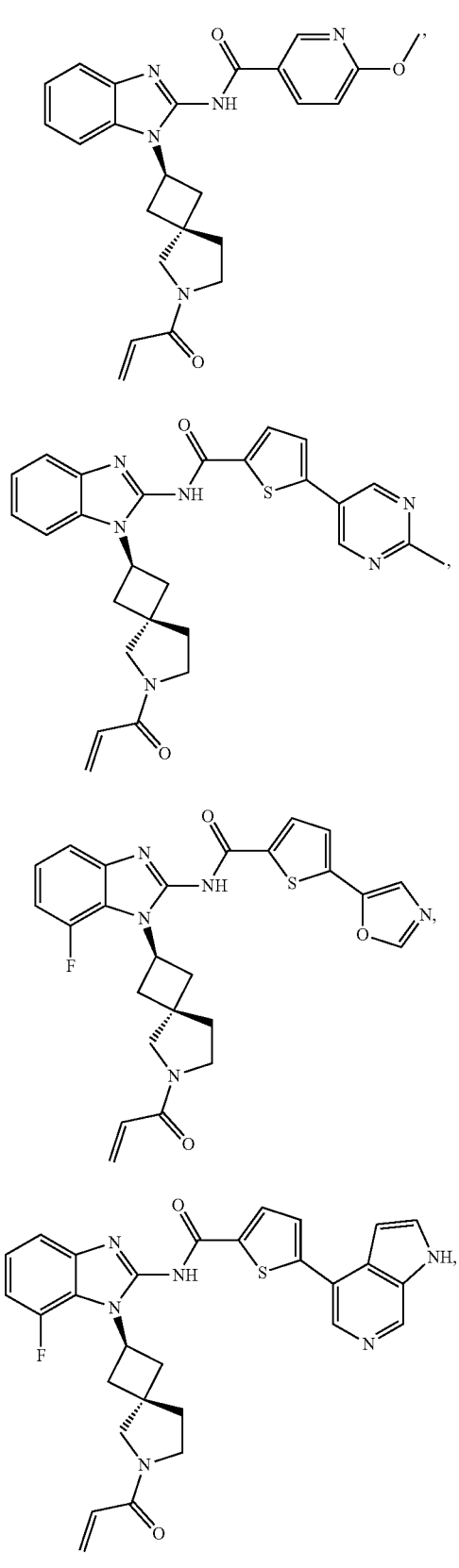
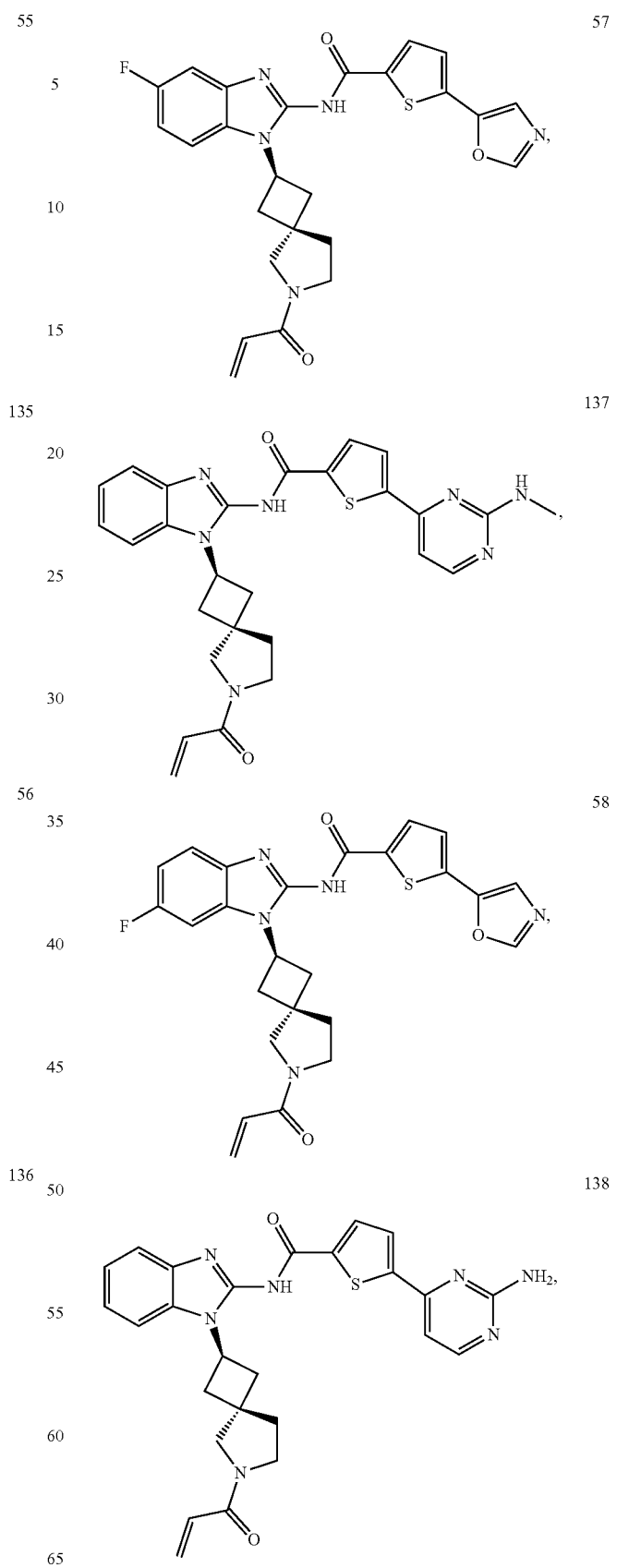

269
-continued
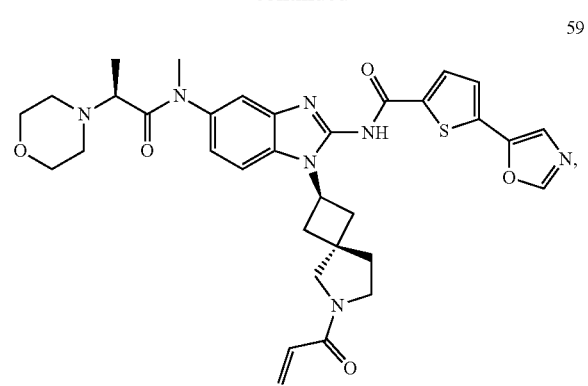
59
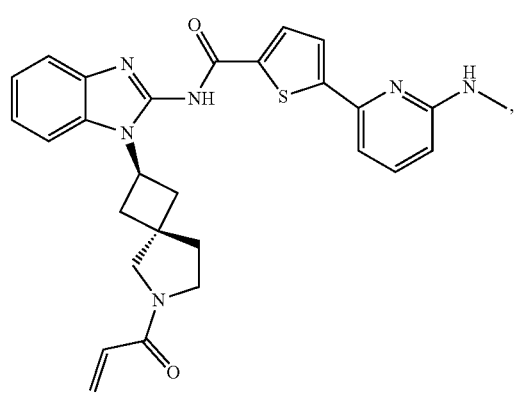
139
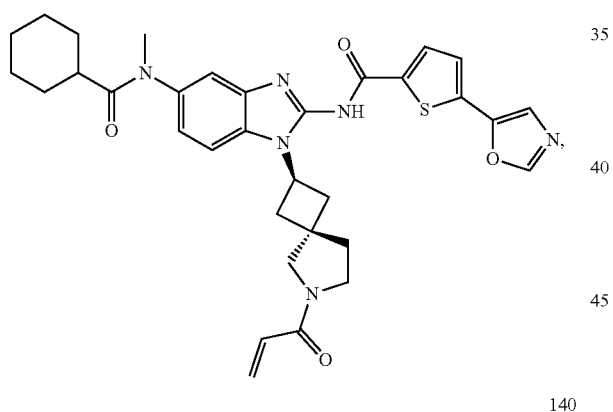
60
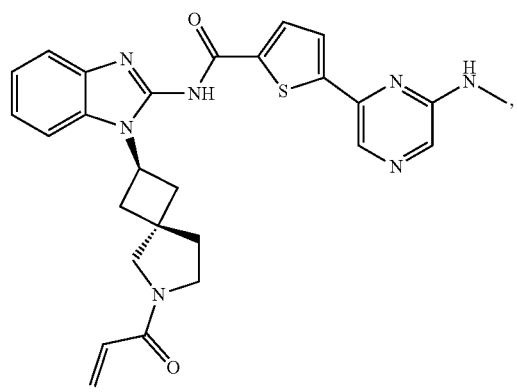
140
270
-continued
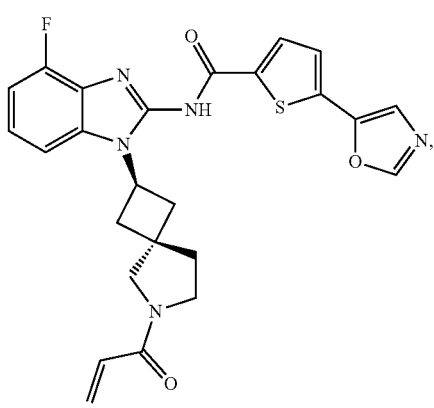
61
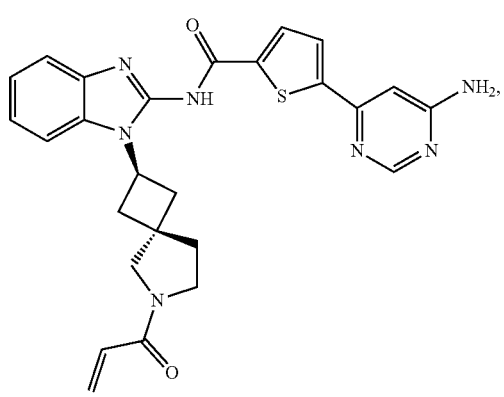
141
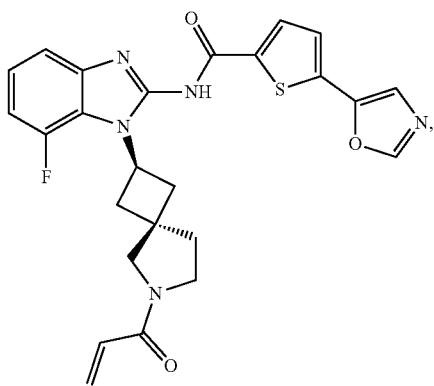
62
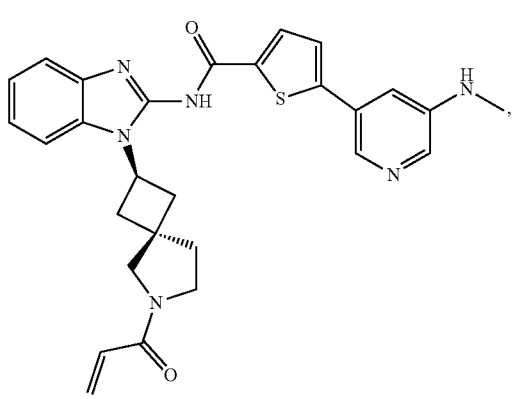
142

63
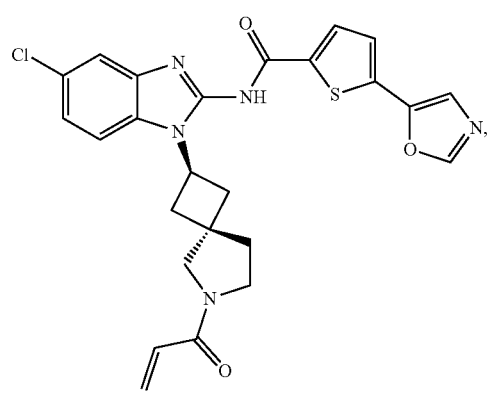
143
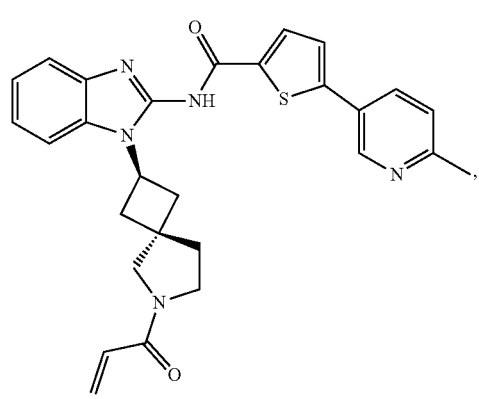
64
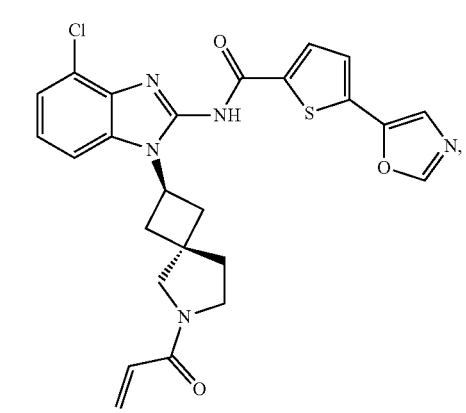
144
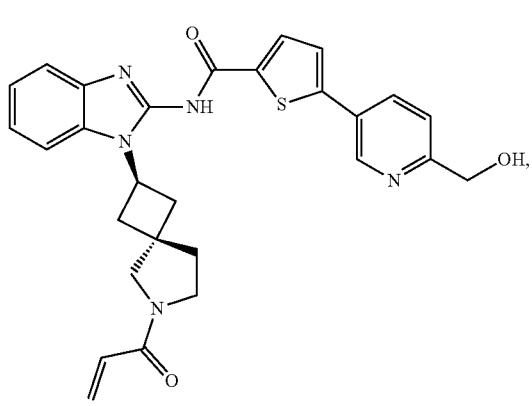
65
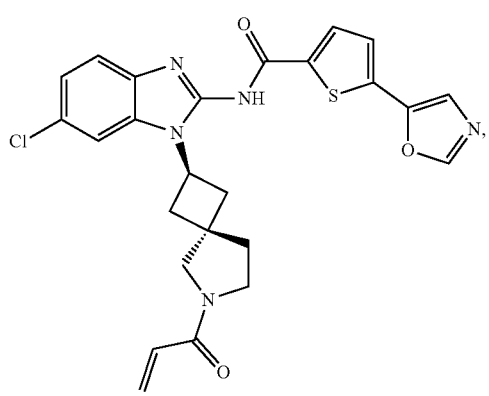
145
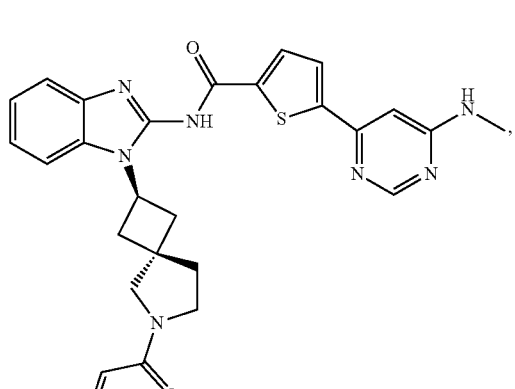
66
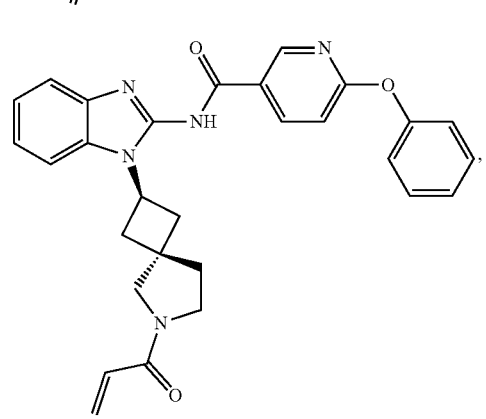
146
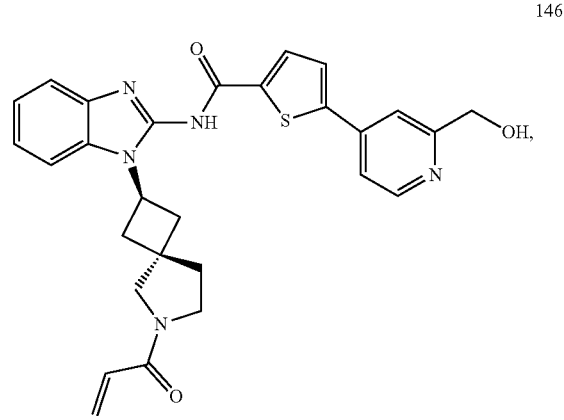

67
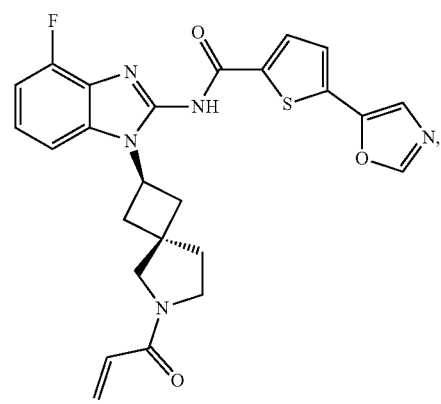
147
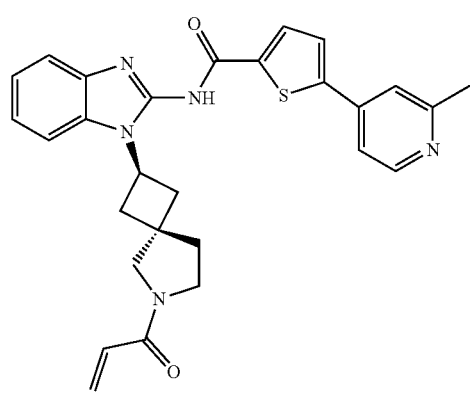
68
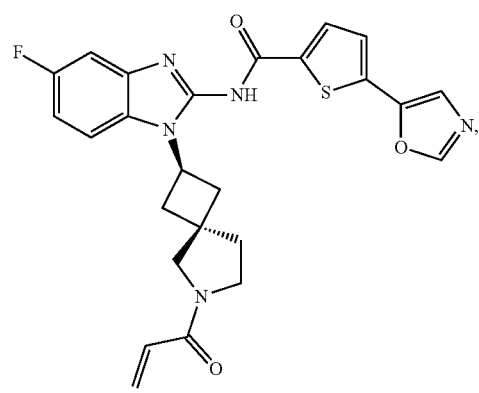
148
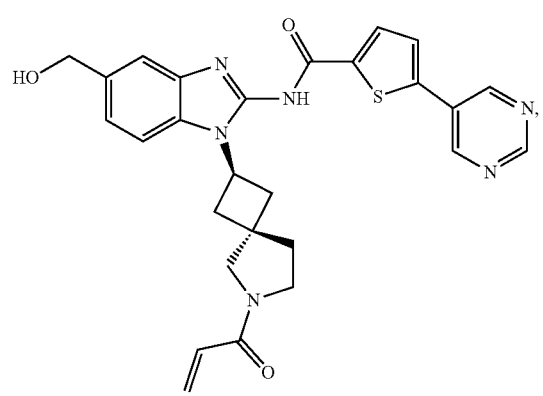
69
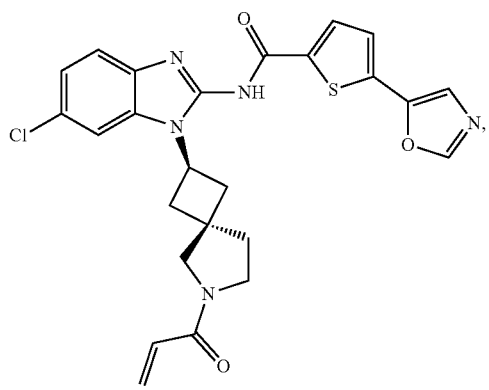
149
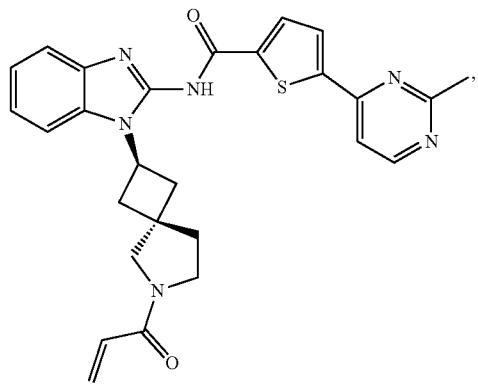
70
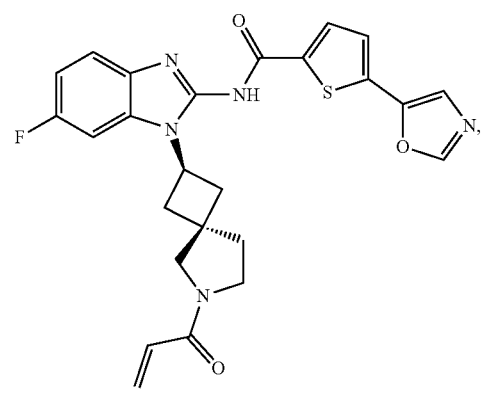
150
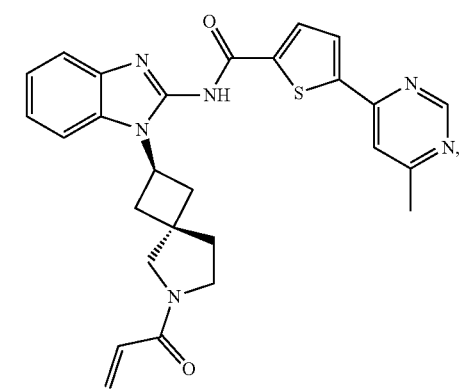

71
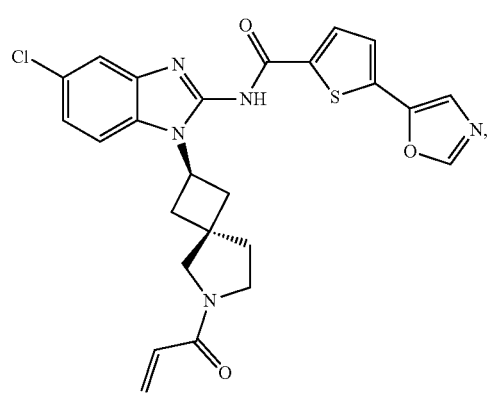
151
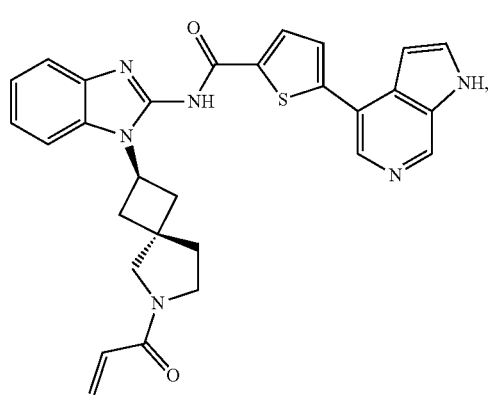
72
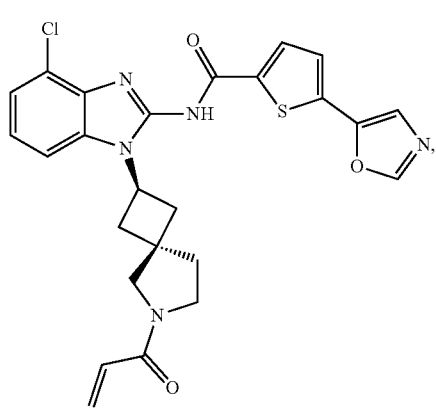
152
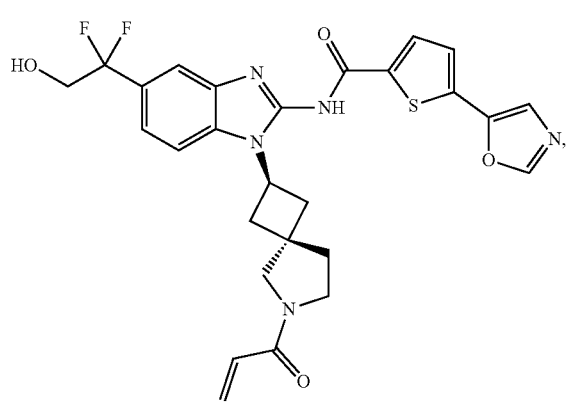
73
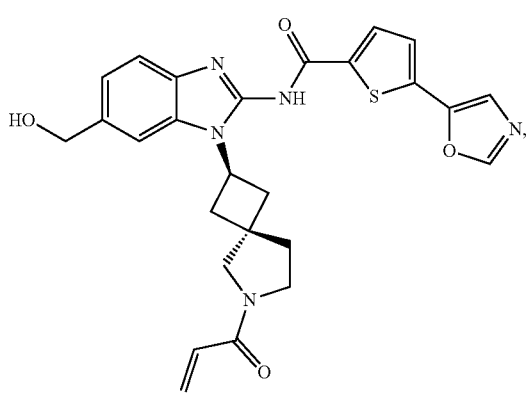
153
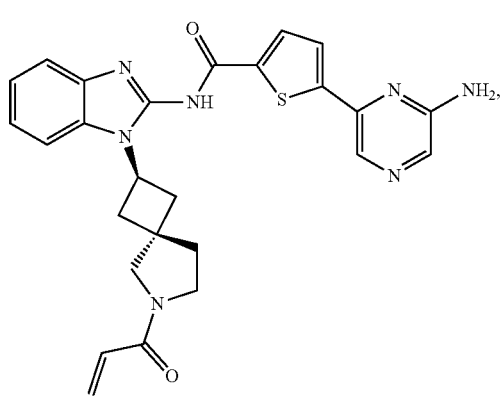
74
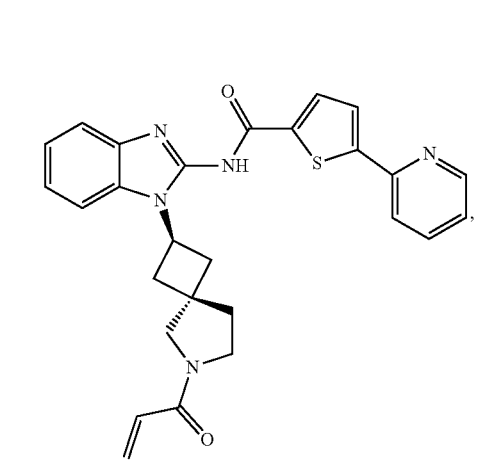
154
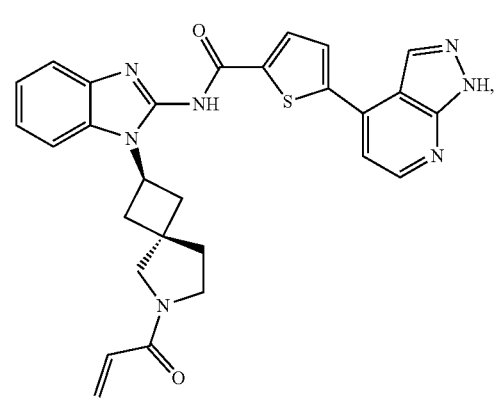

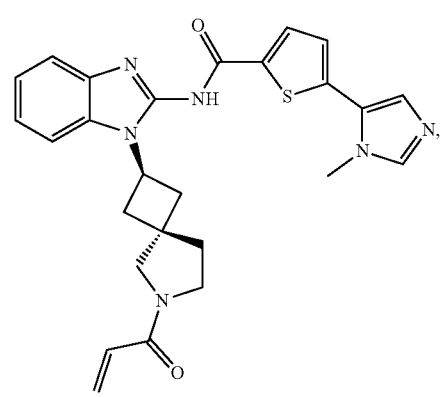
75
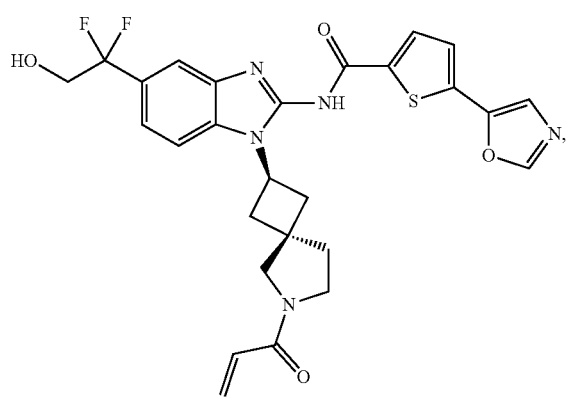
155
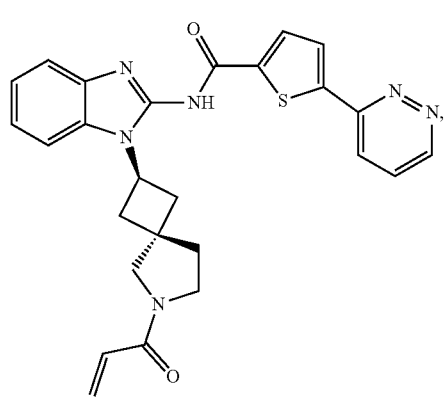
76
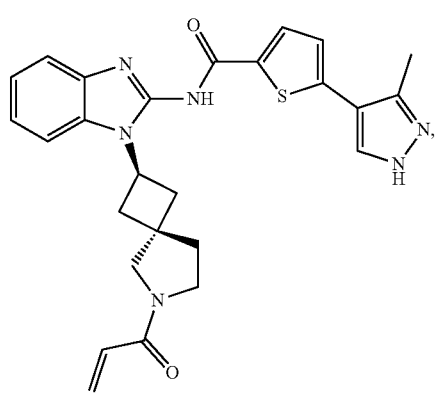
156
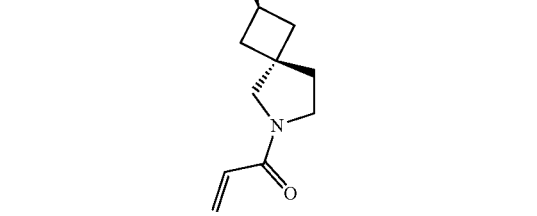
77
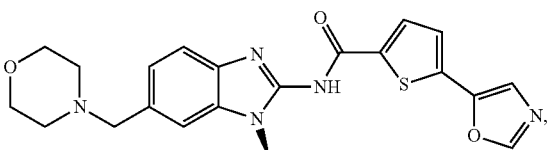
78
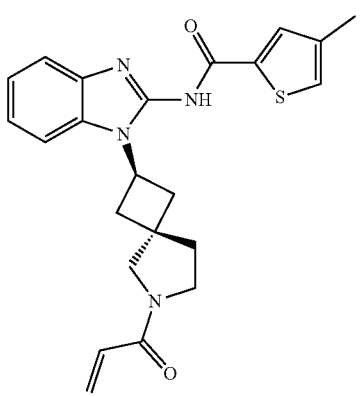
79
and
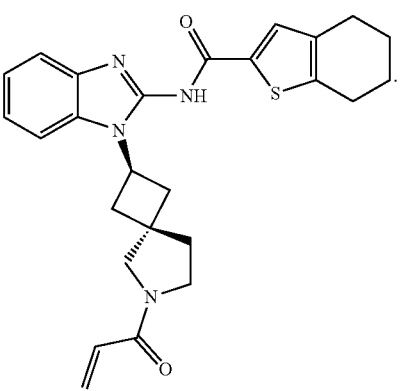
80 or a pharmaceutically acceptable salt, solvate, solvate of salt, stereoisomer, tautomer, isotope, or prodrug thereof.

11. A pharmaceutical composition comprising the compound of claim 1, and/or a pharmaceutically acceptable salt, solvate, solvate of a salt, stereoisomer, tautomer, isotope, or prodrug thereof, and at least one pharmaceutically acceptable carrier or excipient.

12. A method for treating a subject suffering from a protein kinase mediated disease, disorder or condition mediated by a protein kinase, the method comprising administering to a subject in need thereof a compound according to Formula I:

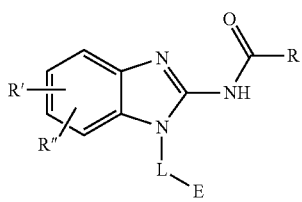

Formula I or a pharmaceutically acceptable salt, solvate, solvate of salt, stereoisomer, tautomer, isotope, or prodrug thereof, wherein R is selected from substituted or unsubstituted aryl or substituted or unsubstituted heteroaryl;

L is selected from

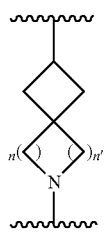

wherein n is an integer from 1 to 3; and n' is an integer from 1 to 3;

E is selected from the group

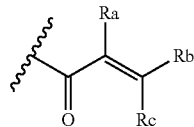

wherein Ra, Rb and Rc are independently selected from hydrogen, halogen, —CN, substituted or unsubstituted alkyl, substituted or unsubstituted heteroalkyl, substituted or unsubstituted cycloalkyl, or substituted or unsubstituted heterocyclyl;

or

Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or Rb and Rc taken together with the carbon atom to which they are attached form a 3- to 8-membered substituted or unsubstituted cycloalkyl ring or form a 3- to 8-membered heterocyclic ring and Ra is selected as above; or Ra and Rb taken together with the carbon atoms to which they are attached form a triple bond and Rc is selected as above;

provided L-E is

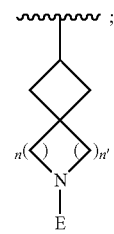

and

R' and R" are independently selected from —X—Y, wherein

X is selected from alkylene, -(alkylene)-NR$^1$—, -(alkylene)-NR$^2$, -(alkylene)-O—, —O—, —S—, —S(O)m-, —NR$^1$—, —NR$^2$—, —C(O)—, —C(O)O—, —C(O)NR$^1$—, —C(O)ONR$^1$—, or —S(O)$_m$NR$^1$—;

wherein

R$^1$ is selected from hydrogen, lower alkyl or lower cycloalkyl;

R$^2$ is selected from —C(O)R$^3$, —C(O)OR$^3$ or —S(O)$_m$R$^3$;

R$^3$ is selected from lower alkyl or lower cycloalkyl;

m is an integer from 1 to 2; or

X is a bond; and

Y is selected from hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl; or wherein R' and R" taken together with the carbon atoms to which they are attached form a 3- to 8-membered substituted or unsubstituted cycloalkyl ring, or a 3- to 8-membered substituted or unsubstituted heterocyclyl ring.

13. A method of inhibiting kinase activity in a subject comprising administering a therapeutically effective amount of the compound of claim 1, or a pharmaceutically acceptable salt solvate, solvates of a salt, stereoisomer, tautomer, isotope, or prodrug thereof.

* * * * *